(12) United States Patent
Mohler et al.

(10) Patent No.: US 12,337,004 B2
(45) Date of Patent: Jun. 24, 2025

(54) COUMARIN-MODIFIED ANDROGENS FOR THE TREATMENT OF PROSTATE CANCER

(71) Applicants: Health Research, Inc., Buffalo, NY (US); University of Kentucky Research Foundation, Lexington, KY (US)

(72) Inventors: James L. Mohler, Buffalo, NY (US); Michael V. Fiandalo, Buffalo, NY (US); David Watt, Lexington, KY (US); Vitaliy Sviripa, Frederick, MD (US)

(73) Assignees: Health Research, Inc., Buffalo, NY (US); University of Kentucky Research Foundation, Lexington, KY (US)

( * ) Notice: Subject to any disclaimer, the term of this patent is extended or adjusted under 35 U.S.C. 154(b) by 190 days.

(21) Appl. No.: 17/606,998

(22) PCT Filed: Apr. 27, 2020

(86) PCT No.: PCT/US2020/030147
§ 371 (c)(1),
(2) Date: Oct. 27, 2021

(87) PCT Pub. No.: WO2020/223174
PCT Pub. Date: Nov. 5, 2020

(65) Prior Publication Data
US 2022/0218722 A1 Jul. 14, 2022

Related U.S. Application Data

(60) Provisional application No. 62/890,292, filed on Aug. 22, 2019, provisional application No. 62/844,062, (Continued)

(51) Int. Cl.
*A61K 31/585* (2006.01)
*A61K 31/167* (2006.01)
(Continued)

(52) U.S. Cl.
CPC .......... *A61K 31/585* (2013.01); *A61K 31/167* (2013.01); *A61K 31/277* (2013.01);
(Continued)

(58) Field of Classification Search
CPC ........................... A61K 31/585; A61K 31/167
(Continued)

(56) References Cited

U.S. PATENT DOCUMENTS 2,226,627 A * 12/1940 Marker ............... C07J 75/00
552/532
4,297,350 A 10/1981 Babcock et al.
(Continued)

FOREIGN PATENT DOCUMENTS

EP 0101162 A2 2/1984
EP 1339129 B1 10/2010
(Continued)

OTHER PUBLICATIONS

Chang et al., "Dihydrotestosterone synthesis bypasses testosterone to drive castration-resistant prostate cancer", 2011, Proceedings of the National Academy of Sciences of the United States of America (PNAS), vol. 108, No. 33, pp. 13728-13733. (Year: 2011).*
(Continued)

*Primary Examiner* — Jeffrey S Lundgren
*Assistant Examiner* — Heather Dahlin
(74) *Attorney, Agent, or Firm* — Hodgson Russ LLP

(57) ABSTRACT

Provided are androstane and dihydrotestosterone compounds functionalized with carbocyclic groups or heterocyclic groups that may be saturated or unsaturated. The compounds may be used in methods of inhibiting cell growth of
(Continued)

malignant cells and/or hyperplastic cells and/or treating individuals having diseases associated with malignant cell growth (e.g., cancer, such as, for example, prostate cancer) and/or hyperplastic cell growth and/or molecular imaging of malignant cells and/or hyperplastic cells and/or inducing degradation of a target protein. Also provided are compositions.

23 Claims, 40 Drawing Sheets

Related U.S. Application Data filed on May 6, 2019, provisional application No. 62/844,073, filed on May 6, 2019, provisional application No. 62/839,676, filed on Apr. 27, 2019.

(51) Int. Cl.

| | |
|---|---|
| *A61K 31/277* | (2006.01) |
| *A61K 31/4155* | (2006.01) |
| *A61K 31/4166* | (2006.01) |
| *A61K 31/4439* | (2006.01) |
| *A61K 31/496* | (2006.01) |
| *A61K 31/58* | (2006.01) |
| *A61K 49/00* | (2006.01) |
| *C07J 43/00* | (2006.01) |

(52) U.S. Cl.
CPC ...... *A61K 31/4155* (2013.01); *A61K 31/4166* (2013.01); *A61K 31/4439* (2013.01); *A61K 31/496* (2013.01); *A61K 31/58* (2013.01); *A61K 49/0002* (2013.01); *C07J 43/003* (2013.01); *C07J 43/006* (2013.01)

(58) Field of Classification Search
USPC ........................................................ 514/171
See application file for complete search history.

(56) References Cited

U.S. PATENT DOCUMENTS

| | | | |
|---|---|---|---|
| 9,156,878 B2* | 10/2015 | Morrison et al. ...... | A61K 31/58 |
| 9,284,345 B2 | 3/2016 | Labrie et al. | |
| 2011/0053902 A1 | 3/2011 | Cerri et al. | |
| 2012/0046291 A1 | 2/2012 | Nitz et al. | |
| 2012/0238488 A1* | 9/2012 | Alevizopoulos et al. .................. | |
| | | | A61K 31/58 |
| | | | 514/1.1 |
| 2013/0171415 A1 | 7/2013 | Sakita et al. | |
| 2013/0252930 A1* | 9/2013 | Chu et al. ................. | C07J 73/00 |
| 2017/0051008 A1 | 2/2017 | Runyon et al. | |
| 2017/0362271 A1 | 12/2017 | Qian | |
| 2018/0036417 A1 | 2/2018 | Lam et al. | |

FOREIGN PATENT DOCUMENTS

| | | |
|---|---|---|
| WO | 98/05337 A | 2/1998 |
| WO | 2017/035501 A1 | 3/2017 |
| WO | 2018013613 A1 | 1/2018 |
| WO | 2018015788 A1 | 1/2018 |
| WO | 2019222272 A1 | 11/2019 |
| WO | 2020232119 A1 | 11/2020 |
| WO | 2021097046 A1 | 5/2021 |

OTHER PUBLICATIONS

Fujimoto N. Novel agents for castration-resistant prostate cancer: early experience and beyond. International Journal of Urology. Feb. 2016;23(2):114-21. (Year: 2016).*

Bastupati, S., Narasu, M., Daddam, J. In silico docking studies of elytraria acaulis gas chromatography-mass spectroscopy derived compound against breast cancer target proteins. World J. Pharm. Pharm. Sci. 2017;10:1053-62. (Year: 2017).*

Shimada K, Oe T, Suzuki M. Effect of derivatization of steroids on their retention behaviour in inclusion chromatography using cyclodextrin as a mobile phase additive. Journal of Chromatography A. Sep. 27, 1991;558(1):306-10. (Year: 1991).*

Spencer TA, Wang P, Li D, Russel JS, Blank DH, Huuskonen J, Fielding PE, Fielding CJ. Benzophenone-containing cholesterol surrogates: synthesis and biological evaluation. Journal of lipid research. Aug. 1, 2004;45(8):1510-8. (Year: 2004).*

CAS RN 851983-85-2, Galeterone, SciFinder, Retrieved 2023 (Year: 2023).*

CAS RN 57305-11-0, Androstane-11,17-dione, 3-[(trimethylsilyl)oxy]-, 17-[O-(phenyl methyl)oxime], (3α,5α)-(9CI, ACI), SciFinder, Retrieved 2023 (Year: 2023).*

CAS RN 136811-32-0, Androstan-17-one, 3-hydroxy-, O-[(4-nitrophenyl)methyl]oxime, (3α,5β)-(9CI), Scifinder, Retrieved 2023 (Year: 2023).*

Desfosses B, Herve F, Moenner M, Urios P, Cittanova N, Dessen P. Interaction between rat alpha1 fetoprotein and fluorescent derivatives of estrone in relation to the position and type of the fluorescent label. Journal of steroid biochemistry. Dec. 1, 1983;19(6):1811-6. (Year: 1983).*

CAS 88859-61-4, Scifinder, retrieved 2024, pp. 1-2 (Year: 2024).*

Purushottamachar P, Kwegyir-Afful AK, Martin MS, Ramamurthy VP, Ramalingam S, Njar VC. Identification of novel steroidal androgen receptor degrading agents inspired by galeterone 3β-Imidazole Carbamate. ACS Medicinal Chemistry Letters. Jul. 14, 2016;7(7):708-13. (Year: 2016).*

Bhadoria, R., et al., Probing Cellular Outcomes Using Heterobivalent Constructs, Biological and Medicinal Chemistry, ChemRxiv, Jan. 22, 2019, pp. 1-9.

Kumar, S., et al., Role of Voluminous Substituents in Controlling the Optical Properties of Disc/Planar-Like Small Organic Molecules: Toward Molecular Emission in Solid State, ACS Omega, Sep. 1, 2017, vol. 2, No. 9, pp. 5348-5356.

Yu, B., et al., Efficient synthesis of new antiproliferative steroidal hybrids using the molecular hybridization approach, European Journal of Medicinal Chemistry, Apr. 12, 2016, vol. 117, pp. 241-255.

Shimada, K., et al., Effect of derivatization of steroids on their retention behaviour in inclusion chromatography using cyclodextrin as a mobile phase additive, Journal of Chromatography, 1991, vol. 558, No. 23, pp. 306-310.

Bodor, A., et al., Struktur und circular-dichroismus einiger steroidoxime, Tetrahedron, 1980, vol. 36, No. 12, pp. 1785-1789.

Chang, H.C., et al., Suppression of delta-5-androstenediol-induced androgen receptor transactivation by selective steroids in human prostate cancer cells, Proc. Natl. Acad. Sci. USA, Sep. 1999, vol. 96, pp. 11173-11177.

Fujimoto, N., Novel agents for castration-resistant prostate cancer: Early experience and beyond, International Journal of Urology, Aug. 27, 2015, vol. 23, pp. 114-121.

* cited by examiner

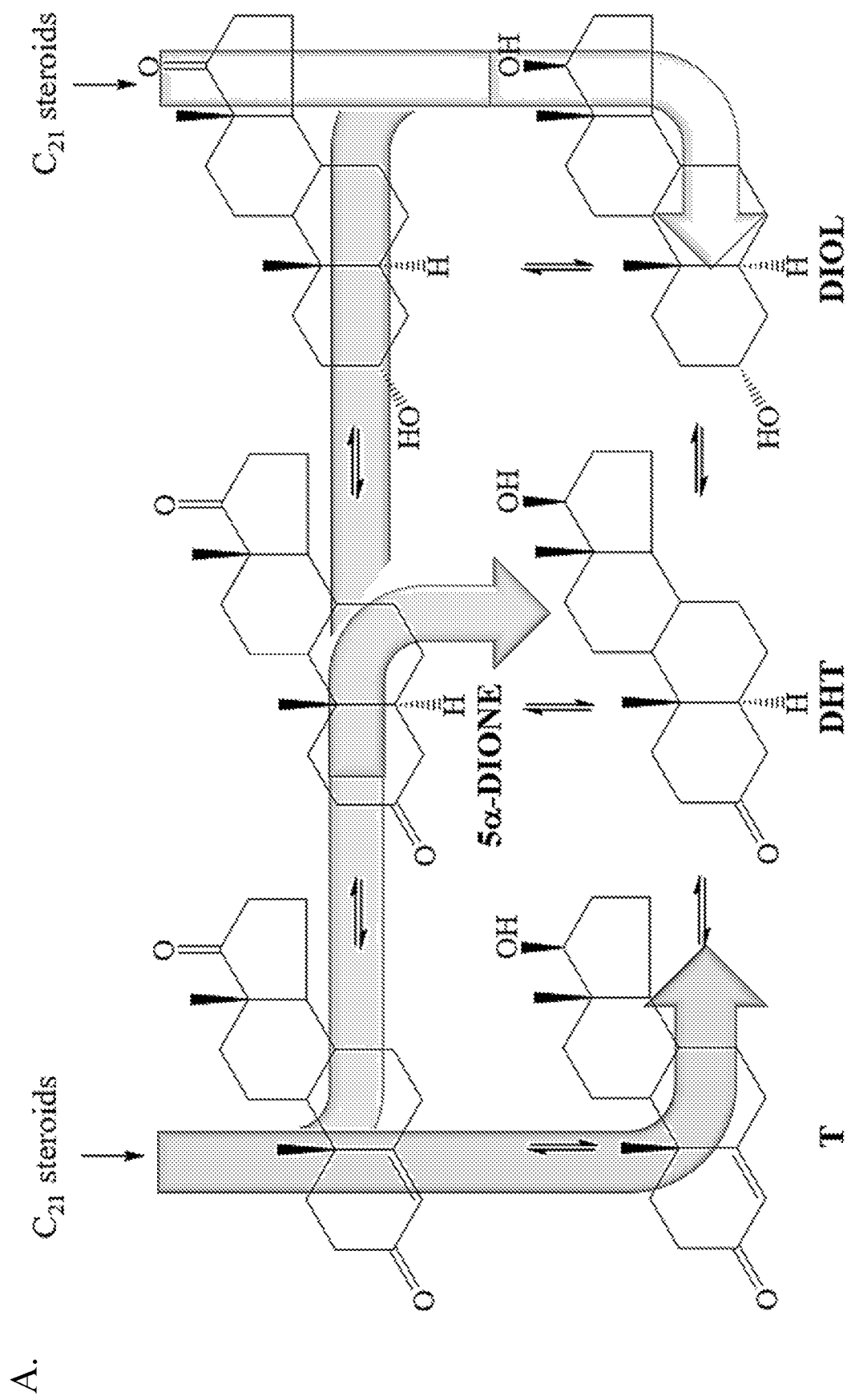
Figure 1 – PRIOR ART

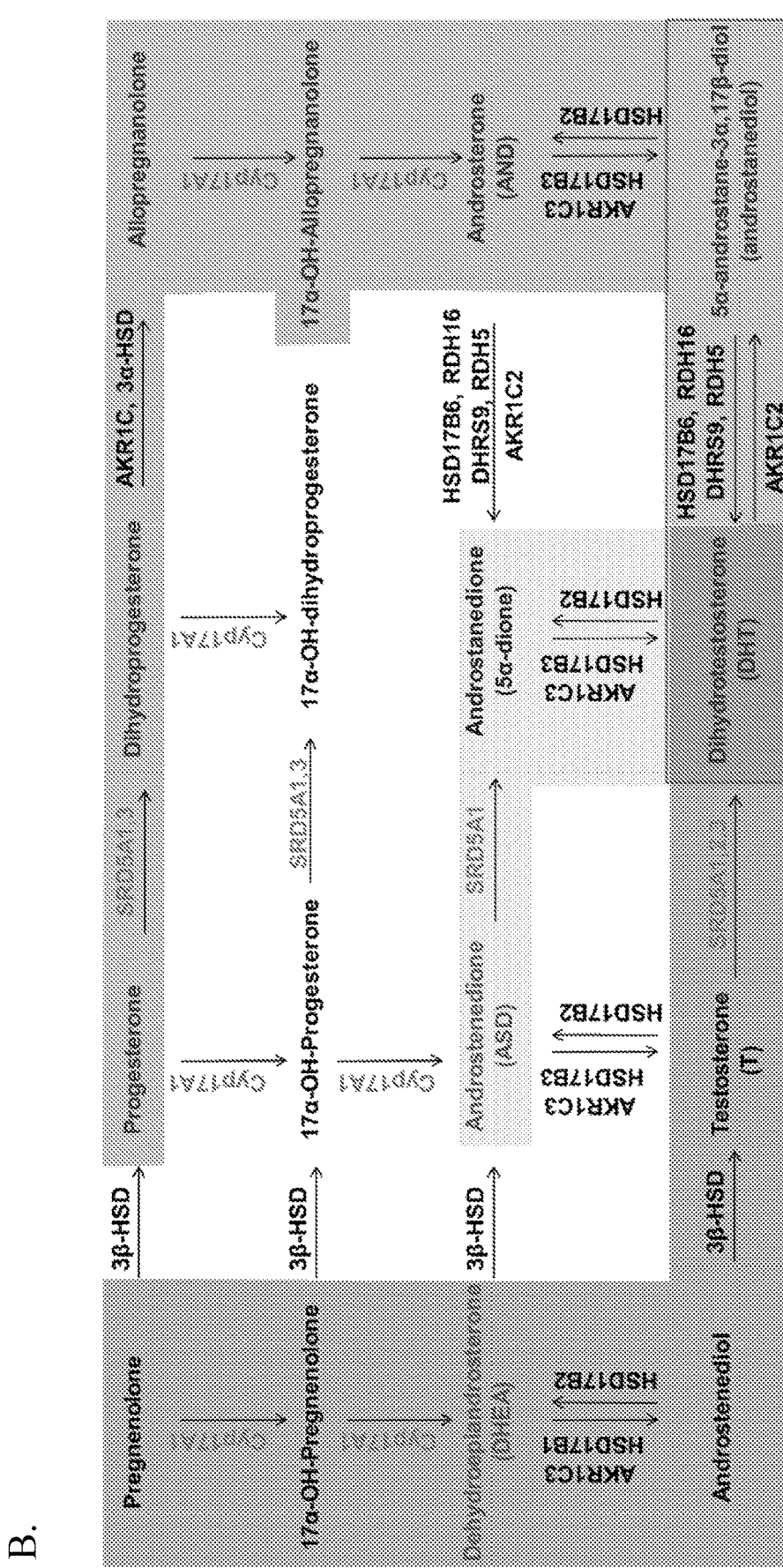
Figure 1 – PRIOR ART (cont.)

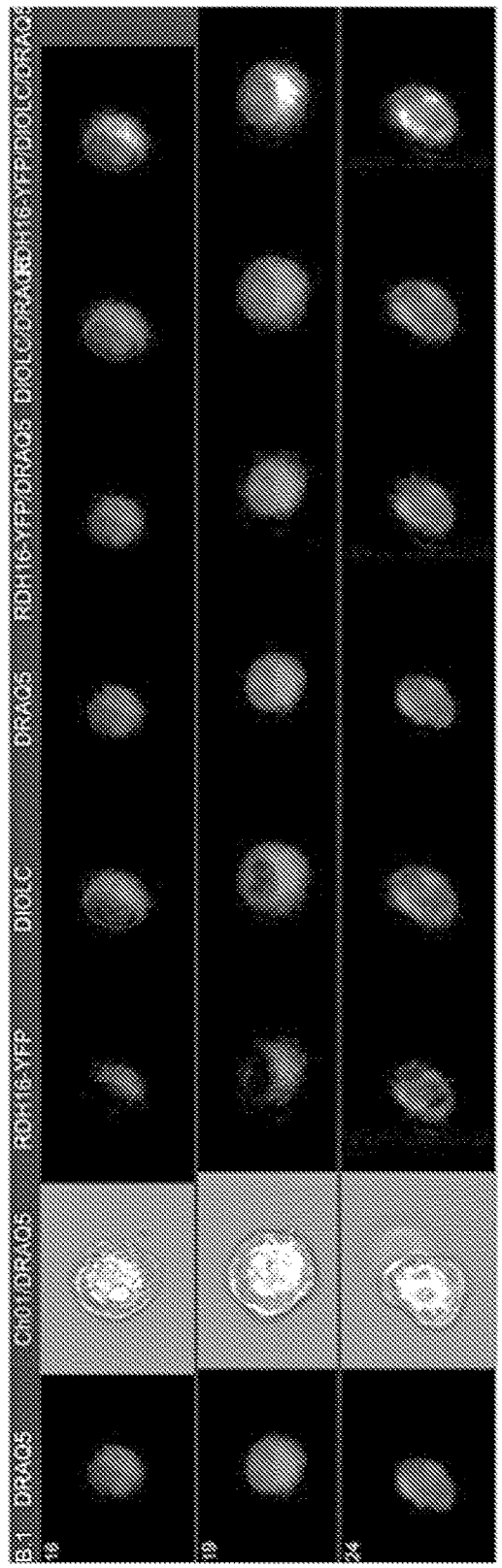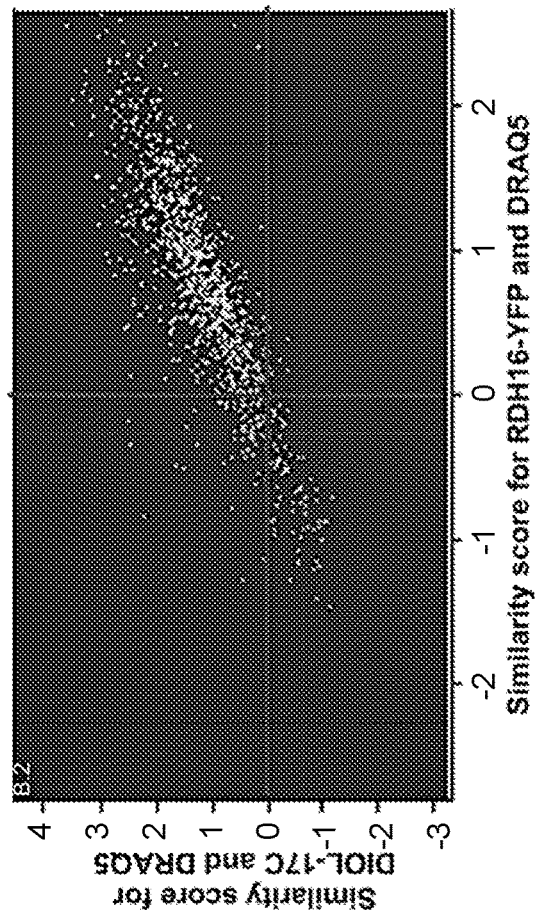
Figure 15 (cont.)

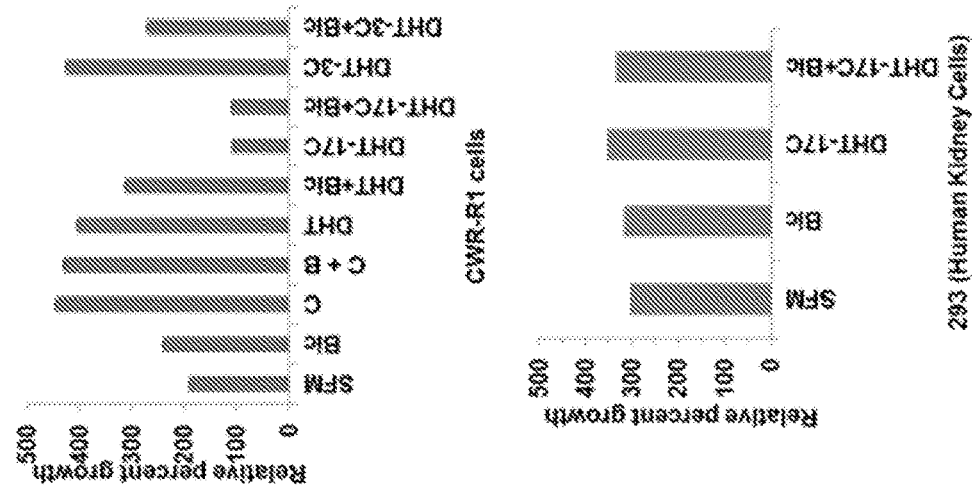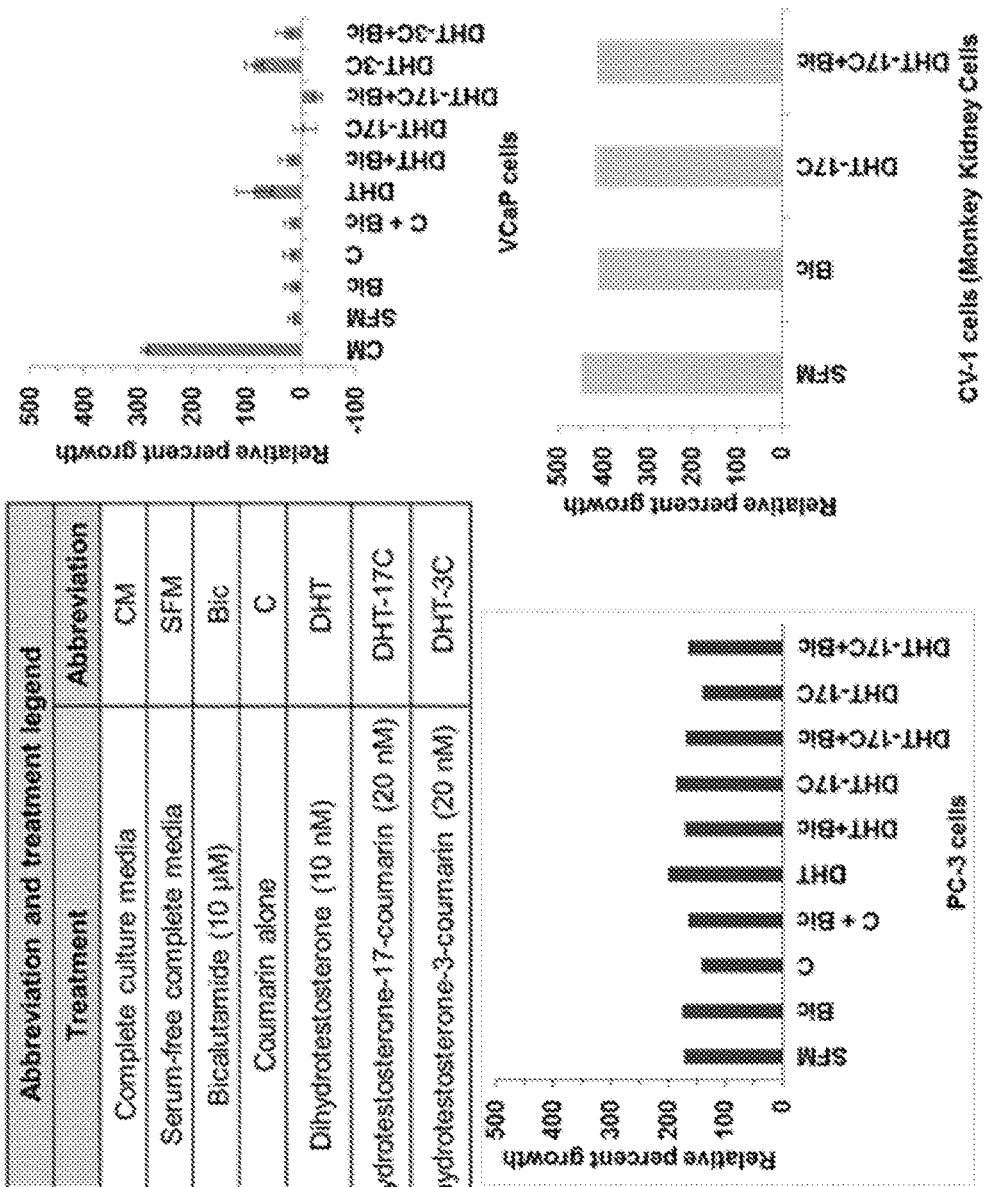
Figure 20

A.

B.

COUMARIN-MODIFIED ANDROGENS FOR THE TREATMENT OF PROSTATE CANCER

CROSS REFERENCE TO RELATED APPLICATIONS

This application claims priority to U.S. Provisional Application No. 62/839,676 filed on Apr. 27, 2019; U.S. Provisional Application No. 62/844,062, filed on May 6, 2019; U.S. Provisional Application No. 62/844,073, filed on May 6, 2019; and U.S. Provisional Application No. 62/890,292, filed on Aug. 22, 2019, the disclosures of which are incorporated herein.

STATEMENT REGARDING FEDERALLY SPONSORED RESEARCH

This invention was made with government support under contract nos. R01 CA077739, P20 RR020171, R21 CA2051, and P30 GM110787 awarded by the National Cancer Institute, grant nos. W81XWH-16-1-0635 and W81XWH-15-1-0409 awarded by the Department of Defense, and grant no. W81XWH-16-1-0633 awarded by the U.S. Army Medical Research and Development Command. The government has certain rights in the invention.

BACKGROUND OF THE DISCLOSURE

Prostate cancer (CaP) growth and progression relies on interaction between the androgen receptor (AR) and the circulating androgen, testosterone (T) that is produced by the testes, and its metabolite, 5α-dihydrotestosterone (DHT) that is produced by 5α-reduction of T in prostatic tissue. T and DHT have similar affinity for the AR at the ligand-binding domain (LBD) but DHT is more potent because it has a slower off rate. The ligand-bound AR dimerizes and translocates to the nucleus, binds androgen response elements (AREs) and initiates transcription of AR-regulated genes that promote CaP cell growth. Most men who present with metastatic disease, or men who have failed potentially curative therapy, are treated with androgen deprivation therapy (ADT) that lowers circulating T levels, impairs AR transactivation and causes CaP regression. However, ADT is palliative and CaP invariably recurs as lethal castration-recurrent/resistant CaP (CRPC). One mechanism that contributes to CaP transition to CRPC is intratumoral androgen metabolism. In the absence of circulating T during ADT, the androgens, dehydroepiandrosterone or 4-androstene-3,17-dione (ASD), undergo conversion to DHT via T by the frontdoor pathway (FIG. 1). CaP cells utilize two other pathways to synthesize DHT that do not require T as an intermediate. In the primary backdoor pathway, 5α-androstan-3α-ol-17-one undergoes enzymatic reduction to 5α-androstane-3α,17β-diol (DIOL) that in turn undergoes enzymatic oxidation to give DHT (FIG. 1). In the secondary backdoor pathway, ASD undergoes enzymatic reduction to 5α-androstane-3,17-dione (5α-DIONE) that in turn undergoes enzymatic reduction to DHT (FIG. 1). In summary, three enzymatically-driven pathways provide CaP tissues access to DHT, and each pathway has enzymes that catalyze critical steps late in the biosynthetic pathway. Finasteride or dutasteride inhibit 5α-reductase (SRD5A) to diminish inhibit the T-to-DHT conversion (i.e., frontdoor pathway in FIG. 1). Both agents fail clinically, in part, because backdoor pathways produce sufficient DHT levels to activate AR and CaP growth. Still other inhibitors, such as the cytochrome P450 17A1 (CYP17A1) inhibitor, abiraterone, inhibit the biosynthesis of pregnanes ($C_{21}$ compounds) to androstanes ($C_{19}$ compounds) well before the terminal portions of the three pathways converging on DHT. Abiraterone (and other CYP17A1 inhibitors) extend survival by only a few months in CRPC because several mechanisms, which include the elevation of CYP17A1 expression levels and accumulation of progesterone that can out-compete abiraterone for CYP17A,25 CYP11A1 or AKR1C3, allow enhanced DHT production and CaP growth.

ASD is metabolized to DHT through a frontdoor and 2 backdoor pathways utilizing the same metabolic steps at C-3 and C-17 in a different order (FIG. 1). ASD either proceeds through T to reach DHT or proceeds to 5α-DIONE that either proceeds directly to DHT or traverses to the primary backdoor pathway through androsterone, then DIOL and finally DHT (FIG. 1). The secondary backdoor pathway, named for its discovery after the primary backdoor pathway, is synonymous with the Sharifi "alternative," Penning "alternate," and Corcoran "5α-DIONE" pathways. A role for HSD17B3 intratumoral metabolism via the frontdoor and secondary backdoor pathways can be isolated using ASD and 5α-DIONE, respectively, as substrates. A pre-clinical study using indomethacin, an AKR1C3 inhibitor, demonstrated proof-of-principle that AKR1C3 inhibition overcame CaP resistance to abiraterone and enzalutamide. The study provided evidence for the necessity for identification and development of AKR1C3 inhibitors. A Phase 1/2 clinical trial that tested the efficacy of ASP9521, an AKR1C3 inhibitor, ended without evidence of clinical response. The authors suggested that insufficient CaP cell expression of AKR1C3 caused therapeutic failure, a problem perhaps not shared by the four 3α-oxidoreductases discussed herein.

Among the methods for achieving ADT, anti-androgens occupy a central position for the chemical castration of men suffering from CaP. The anti-androgens, bicalutamide or enzalutamide, compete with T or DHT for the AR-LBD. Bicalutamide performed poorly clinically because of a lower binding affinity than DHT for the AR-LBD. Furthermore, bicalutamide demonstrated undesired AR agonist, not antagonist, activity after prolonged treatment. Enzalutamide binds the AR-LBD with a higher affinity than bicalutamide, impairs AR nuclear translocation, and inhibits interaction between AR and AREs of AR-regulated genes essential for CaP growth. However, enzalutamide produced modest responses in CRPC and extended survival by only 4.8 months. One mechanism that contributes to abiraterone and anti-androgen resistance is expression of the AR splice-variant 7 (AR-V7) that is constitutively active and lacks an LBD. Lack of an LBD circumvents the need for T or DHT and eliminates the binding site for anti-androgens and thereby renders them ineffective. Small molecule inhibitors that target N-terminal domains of AR rather than the AR-LBD, such as EPI-506, inactivated AR-V7 when studied in vitro. EPI-506 was found safe in Phase I trial but a Phase 2 clinical trial failed. The limited success of current therapies for advanced CaP and especially CRPC warrant the pursuit of novel therapeutics.

SUMMARY OF THE DISCLOSURE

The present disclosure provides androstane and dihydrotestosterone compounds functionalized with carbocyclic groups or heterocyclic groups that may be saturated or unsaturated (e.g., coumarin-containing ring groups (e.g., coumarin groups) and coumarin isostere groups. The compounds may be used in methods of inhibiting cell growth of malignant cells and/or hyperplastic cells and/or treating individuals having diseases associated with malignant cell growth (e.g., cancer, such as, for example, prostate cancer) and/or hyperplastic cell growth and/or molecular imaging of malignant cells and/or hyperplastic cells and/or inducing degradation of a target protein.

The compounds may 1): inhibit oxidoreductase enzymes that appear in the terminal steps of the primary backdoor pathway for DHT biosynthesis and/or 2) function as an anti-androgen by competing for the AR-LBD binding and suppressing cell growth in CaP cell lines expressing high levels of the AR-V7 variant, perhaps by impairing AR-AR-V7 dimerization and/or 3) furnish tools for carrying small-molecules that disrupt AR function or even degrade AR. Compounds that possess one or more than one of these properties would represent a significant clinical advance.

In an aspect, the present disclosure provides functionalized androstane and dihydrotestosterone compounds. The compounds may be modified with coumarin ring groups or coumarin isostere groups.

In various examples, compounds of the present disclosure include 5α-androstane-3α,17β-diol (DIOL), 5α-androstan-3α-ol-17-one, 5α-androstane-3,17-dione (5α-DIONE), and 5α-dihydrotestosterone (DHT) that may be modified with a various carbocyclic or heterocyclic groups that may be saturated or unsaturated. In various examples, the compounds may be modified with a coumarin-containing group or a coumarin isostere group at either the C-3 or the C-17 position in these steroids.

A compound of the present disclosure may have the following structure:

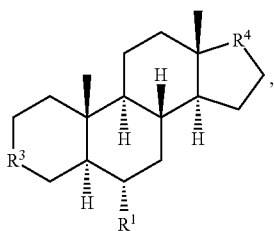

where $R^1$ is hydrogen or an alkyl group (e.g., methyl group, ethyl group, n- and isopropyl group, and the like). $R^3$ is chosen from a carbonyl,

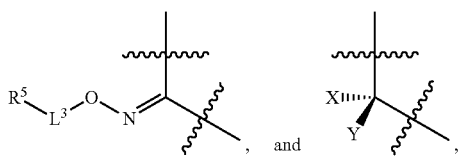

where X is hydroxyl and Y is hydrogen or an alkyl group (e.g., methyl group, ethyl group, n- and isopropyl group, and the like) or X and Y together are a spiro-fused, substituted or unsubstituted coumarin group or coumarin isostere group, and $L^3$ is optional and is a linking group. $R^4$ is chosen from a carbonyl,

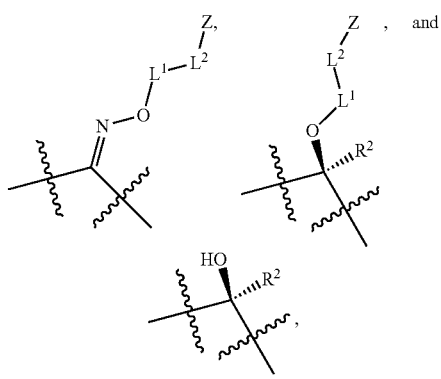

where $L^1$ is a linking group, $L_2$ is optional and is a linking group, Z is an end group comprising a substituted or unsubstituted carbocyclic group or a substituted or unsubstituted heterocyclic group or substituted or unsubstituted coumarin group or substituted or unsubstituted coumarin isostere group, and $R^2$ is an alkyl group (e.g., methyl group, ethyl group, n- and isopropyl group, and the like) or hydrogen. $R^5$ is a photoactive group. When $R^3$ is a carbonyl or

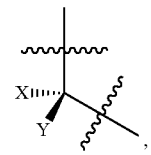

where X is hydroxyl and Y is hydrogen or an alkyl group, $R^4$ is not

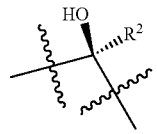

or a carbonyl.

In an aspect, the present disclosure provides compositions comprising compounds of the present disclosure. The compositions further comprise one or more pharmaceutically acceptable carrier.

In an aspect, the present disclosure provides methods of using one or more compound or composition thereof. The compounds are suitable in methods to treat various diseases. For example, one or more compounds of the present disclosure or a composition of the present disclosure can be used to treat cancer, other diseases, or a combination thereof. Methods of the present disclosure may be used to inhibit cell growth of malignant cells and/or hyperplastic cells and/or induce selective degradation of a target protein and/or for molecular imaging. A method can be carried out in combination with one or more known therapies.

In an aspect, the disclosure provides kits. In various examples, a kit comprises a pharmaceutical preparation containing any one or any combination of compounds of the present disclosure. In an example, the instant disclosure includes a closed or sealed package that contains the pharmaceutical preparation. In various examples, the package comprises one or more closed or sealed vials, bottles, blister (bubble) packs, or any other suitable packaging for the sale, distribution, or use of the pharmaceutical compounds and compositions comprising them. The printed material may include printed information. The printed information may be provided on a label, on a paper insert, or printed on packaging material. The printed information may include information that identifies the compound in the package, the amounts and types of other active and/or inactive ingredients in the composition, and instructions for taking the compound and/or composition. The instructions may include information, such as, for example, the number of doses to take over a given period of time, and/or information directed to a pharmacist and/or another health care provider, such as a physician, or a patient. The printed material may include an indication that the pharmaceutical composition and/or any other agent provided therein is for treatment of a subject having prostate cancer (e.g., castration-resistant prostate cancer) and/or other diseases and/or any disorder associated with cancer and/or other diseases. In various examples, the kit includes a label describing the contents of the kit and providing indications and/or instructions regarding use of the contents of the kit to treat a subject having any cancer and/or other diseases.

BRIEF DESCRIPTION OF THE FIGURES

For a fuller understanding of the nature and objects of the disclosure, reference should be made to the following detailed description taken in conjunction with the accompanying figures.

FIG. 1 shows (A and B) biosynthetic pathways to DHT that include the frontdoor pathway, primary backdoor pathway, and secondary backdoor pathway.

FIG. 4 shows a Pictet-Spengler reaction of DHT with 8-(2-aminoethyl)-2,3,4,5-tetrahydro-1H,4H-11-oxa-3α-aza-benzo[de]anthracen-10-one hydrochloride. Legend for the reagents used in the synthesis: a, 1:10 (v/v) conc. HCl-abs. ethanol, reflux.

FIG. 5 shows a 2D ROESY spectrum of DHT-3C (aka compound Ig). Spectrum recorded using Agilent 400 MHz at 25° C. Dotted lines show region expanded that displays the Nuclear Overhauser Effect (NOE) connectivity between $NH_2+$ and ring A protons (i.e., H-5 (with H-1 overlapping), H-4, H-2, and $CH_2$ adjoining $NH_2^+$).

FIG. 20 shows growth data that demonstrated DHT-17C impairs growth of AR and AR-V7 expressing VCaP and CWR-1 cell lines, but not PC-3 (CaP cell line without AR) or non-CaP, non-AR CV-1 or 293 cell lines.

DETAILED DESCRIPTION OF THE DISCLOSURE

Figure 2:
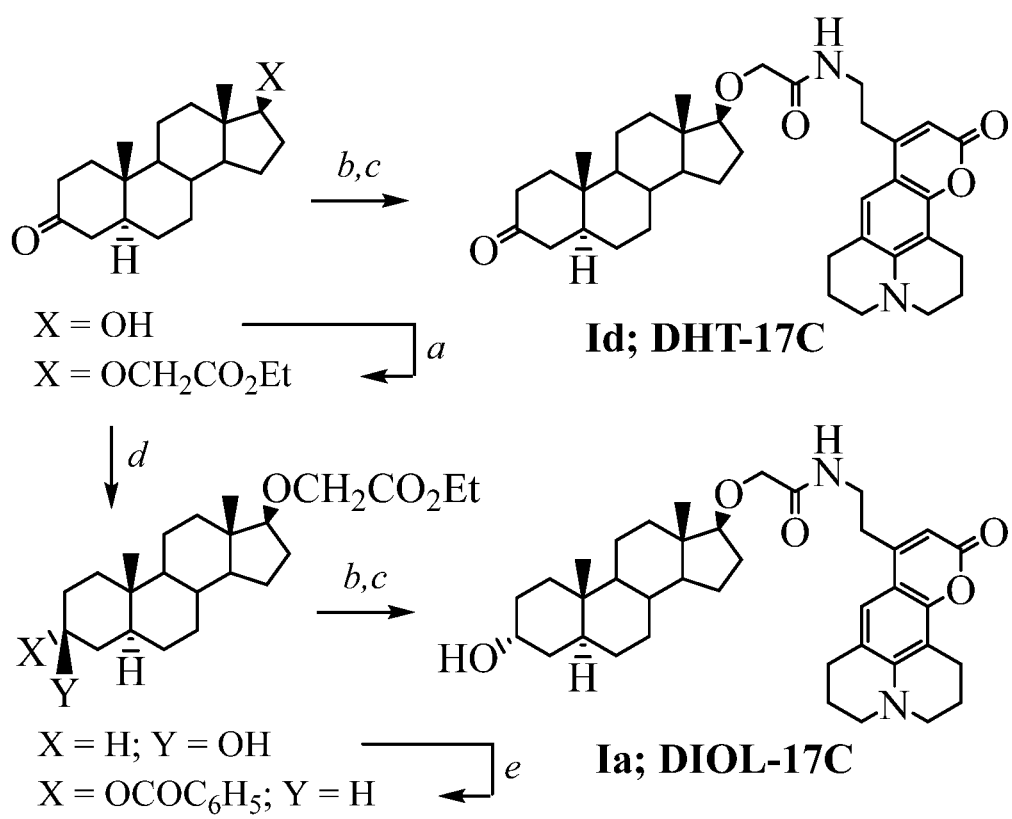
FIG. 2 shows a synthetic route of fluorescent steroids modified at C-17β hydroxyl groups. Legend for the reagents used in the synthesis: a, $N_2CH_2CO_2Et$, $Rh_2(OAc)_4$, $CH_2Cl_2$; b, NaOH, aqueous $CH_3OH$; c, N-(3-dimethylaminopropyl)-N'-ethylcarbodiimide hydrochloride (EDC), 1-hydroxybenzotriazole hydrate (HOBt), and 8-(2-aminoethyl)-2,3,4,5-tetrahydro-1H,4H-11-oxa-3α-aza-benzo[de]anthracen-10-one hydrochloride; d, $LiAlH(OtBu)_3$; e, $C_6H_5CO_2H$, DIAD.

Although the subject matter will be described in terms of certain examples, other examples, including examples that do not provide all of the benefits and features set forth herein, are also within the scope of this disclosure. Various structural, logical, and process steps may be made without departing from the scope of the disclosure.

The present disclosure provides androstane and dihydrotestosterone compounds functionalized with carbocyclic groups or heterocyclic groups that may be saturated or unsaturated (e.g., coumarin-containing ring groups (e.g., coumarin groups) and coumarin isostere groups. The compounds may be used in methods of inhibiting cell growth of malignant cells and/or hyperplastic cells and/or treating individuals having diseases associated with malignant cell growth (e.g., cancer, such as, for example, prostate cancer) and/or hyperplastic cell growth and/or molecular imaging of malignant cells and/or hyperplastic cells and/or inducing degradation of a target protein.

The compounds may 1): inhibit oxidoreductase enzymes that appear in the terminal steps of the primary backdoor pathway for DHT biosynthesis and/or 2) function as an anti-androgen by competing for the AR-LBD binding and suppressing cell growth in CaP cell lines expressing high levels of the AR-V7 variant, perhaps by impairing AR-AR-V7 dimerization and/or 3) furnish tools for carrying small-molecules that disrupt AR function or even degrade AR. Compounds that possess one or more than one of these properties would represent a significant clinical advance.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

As used herein, unless otherwise indicated, the term "group" refers to a chemical entity that is monovalent (i.e., has one terminus that can be covalently bonded to other chemical species as in a methyl or phenyl group), divalent, or polyvalent (i.e., has two or more termini that can be covalently bonded to other chemical species as in a methylene or phenylene group). The term "group" also includes radicals (e.g., monovalent radicals and multivalent radicals, such as, for example, divalent radicals, trivalent radicals, and the like).

As used herein, unless otherwise indicated, the term "alkyl group" refers to branched or unbranched saturated hydrocarbon groups. Examples of alkyl groups include, but are not limited to, methyl groups, ethyl groups, n- and isopropyl groups, n-, sec-, iso- and tert-butyl groups, and the like. The alkyl group can be a $C_1$ to $C_{12}$ alkyl group, including all integer numbers of carbons and ranges of numbers of carbons there between (e.g., $C_1$, $C_2$, $C_3$, $C_4$, $C_5$, $C_6$, $C_7$, $C_8$, $C_9$, $C_{10}$, $C_{11}$, or $C_{12}$). The alkyl group can be unsubstituted or substituted with one or more substituents. Examples of substituents include, but are not limited to, various substituents such as, for example, halogens (e.g., —F, —Cl, —Br, and —I), aliphatic groups (e.g., alkyl groups, alkenyl groups, and alkynyl groups), aryl groups, alkoxide groups, carboxylate groups, carboxylic acids, ether groups, alcohol groups, amine groups, thiol groups, thioether groups, and the like, and combinations thereof.

As used herein, unless otherwise indicated, the term "heteroalkyl group" refers to branched or unbranched, saturated or unsaturated hydrocarbon groups comprising at least one heteroatom. Examples of suitable heteroatoms include, but are not limited to, nitrogen, oxygen, sulfur, phosphorus, and the halogens. The heteroalkyl group can be unsubstituted or substituted with one or more substituents. Examples of substituents include, but are not limited to, various substituents such as, for example, halogens (e.g., —F, —Cl, —Br, and —I), aliphatic groups (e.g., alkyl groups, alkenyl groups, and alkynyl groups), aryl groups, alkoxide groups, carboxylate groups, carboxylic acids, ether groups, alcohol groups, amine groups, thiol groups, thioether groups, and the like, and combinations thereof.

As used herein, unless otherwise indicated, the term "aryl group" refers to $C_5$ to $C_{12}$ aromatic or partially aromatic carbocyclic groups, including all integer numbers of carbons and ranges of numbers of carbons therebetween (e.g., $C_5$, $C_6$, $C_7$, $C_8$, $C_9$, $C_{10}$, $C_{11}$, or $C_{12}$). An aryl group can also be referred to as an aromatic group. The aryl groups can comprise polyaryl groups such as, for example, fused ring or biaryl groups. The aryl group can be unsubstituted or substituted with one or more substituent. Examples of substituents include, but are not limited to, substituents such as, for example, halogens (e.g., —F, —Cl, —Br, and —I), aliphatic groups (e.g., alkyl groups, alkenyl groups, and alkynyl groups), aryl groups, alkoxide groups, carboxylate groups, carboxylic acids, ether groups, alcohol groups, amine groups, thiol groups, thioether groups, and the like, and combinations thereof. Examples of aryl groups include, but are not limited to, phenyl groups, biaryl groups (e.g., biphenyl groups and the like), and fused ring groups (e.g., naphthyl groups and the like).

As used herein, unless otherwise indicated, the terms "carbocyclic" or "heterocyclic" means a carbon-containing ring or a carbon-containing ring in which one or more of the carbon atoms are replaced by a heteroatom, respectively. These groups may be non-aromatic or aromatic. Carbocyclic or heterocyclic groups may be saturated or unsaturated and may have one or more substituent (e.g., hydroxy, alkoxy, thioalkoxy, halogens, and the like), and combinations thereof. Additional examples of substituents include, but are not limited to, halogens (e.g., —F, —Cl, —Br, and —I), aliphatic groups (e.g., alkyl groups, alkenyl groups, and alkynyl groups), aryl groups, alkoxide groups, carboxylate groups, carboxylic acids, ether groups, alcohol groups, amine groups, thiol groups, thioether groups, and the like, and combinations thereof.

As used herein, unless otherwise indicated, the term "heterocyclic group" refers to $C_3$-$C_{20}$ cyclic groups containing one or more heteroatoms (e.g., N, O, S, or the like) as part of the ring structure, including all integer numbers of carbons and ranges of numbers of carbons therebetween ($C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$). The heterocyclic groups may be substituted or unsubstituted and/or have additional degrees of unsaturation. Examples of substituents include, but are not limited to, halogens (e.g., —F, —Cl, —Br, and —I), aliphatic groups (e.g., alkyl groups, alkenyl groups, and alkynyl groups), aryl groups, alkoxide groups, carboxylate groups, carboxylic acids, ether groups, alcohol groups, amine groups, thiol groups, thioether groups, and the like, and combinations thereof. The heterocyclic groups can be fused to carbocyclic groups or to each other. Non-limiting examples of heterocyclic groups include furanyl groups, oxazolyl groups, isothiazolyl groups, thiazolyl groups, tetrahydropyranyl groups, piperazinyl groups, dioxanyl groups, pyrrolidinyl groups, tetrahydrothiophenyl groups, tetrahydrofuranyl groups, quinuclidinyl groups, azaadamantanyl groups, decahydroquinolinyl groups, and the like.

As used herein, unless otherwise indicated, the term "heteroaryl group" means a monovalent monocyclic or polycyclic aromatic group of 5 to 18 ring atoms or a polycyclic aromatic group, containing one or more ring heteroatoms selected from N, O, or S, the remaining ring atoms being C, including all integer number of ring atoms and ranges therebetween (e.g., 5, 6, 7, 8, 9, 10, 11, 12, 13, 14, 15, 16, 17, or 18). Heteroaryl as herein defined also means a polycyclic (e.g., bicyclic) heteroaromatic group where the heteroatom is selected from N, O, or S. The aromatic radical is optionally substituted independently with one or more substituents described herein. The substituents can themselves be optionally substituted. Examples of substituents include, but are not limited to, halogens (e.g., —F, —Cl, —Br, and —I), aliphatic groups (e.g., alkyl groups, alkenyl groups, and alkynyl groups), aryl groups, alkoxide groups, carboxylate groups, carboxylic acids, ether groups, alcohol groups, amine groups, thiol groups, thioether groups, and the like, and combinations thereof. Examples of heteroaryl groups include, but are not limited to, benzothienyl, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, benzoimidazolyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-12-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two fused rings the heteroaryl groups herein defined may have an unsaturated or partially saturated ring fused with a fully saturated ring.

In an aspect, the present disclosure provides functionalized androstane and dihydrotestosterone compounds. The compounds may be functionalized (e.g., modified) with coumarin ring groups or coumarin isostere groups.

In various examples, compounds of the present disclosure include 5α-androstane-3α,17β-diol (DIOL), 5α-androstan-3α-ol-17-one, 5α-androstane-3,17-dione (5α-DIONE), and 5α-dihydrotestosterone (DHT) that may be modified with a various carbocyclic or heterocyclic groups that may be saturated or unsaturated. In various examples, the compounds may be modified (e.g., functionalized) with a coumarin-containing group or a coumarin isostere group at either the C-3 or the C-17 position in these steroids.

A compound of the present disclosure may have the following structure:

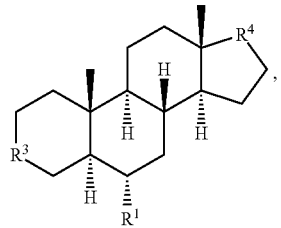

where $R^1$ is hydrogen or an alkyl group (e.g., methyl group, ethyl group, n- and isopropyl group, and the like). $R^3$ is chosen from a carbonyl,

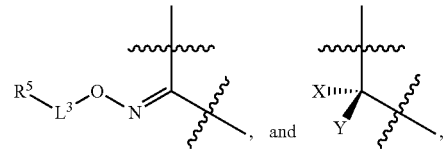

where X is hydroxyl and Y is hydrogen or an alkyl group (e.g., methyl group, ethyl group, n- and isopropyl group, and the like) or X and Y together are a spiro-fused, substituted or unsubstituted coumarin group or coumarin isostere group, and $L^3$ is optional and is a linking group. $R^4$ is chosen from a carbonyl,

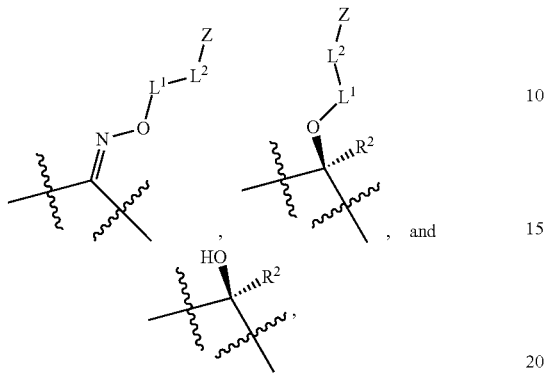

where $L^1$ is a linking group, $L_2$ is optional and is a linking group, Z is an end group comprising a substituted or unsubstituted carbocyclic group or a substituted or unsubstituted heterocyclic group or substituted or unsubstituted coumarin group or substituted or unsubstituted coumarin isostere group, and $R^2$ is an alkyl group (e.g., methyl group, ethyl group, n- and isopropyl group, and the like) or hydrogen. $R^5$ is a photoactive group. When $R^3$ is a carbonyl or

where X is hydroxyl and Y is hydrogen or an alkyl group, $R^4$ is not

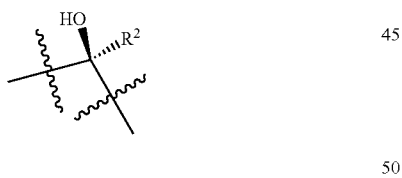

or a carbonyl.

Z can be various end groups. In various examples, Z is a carbocyclic or heterocyclic group that may be saturated or unsaturated and may have one or more substituent (e.g., hydroxy, alkoxy, thioalkoxy, halogens, and the like, and combinations thereof). Non-limiting examples of Z groups include:

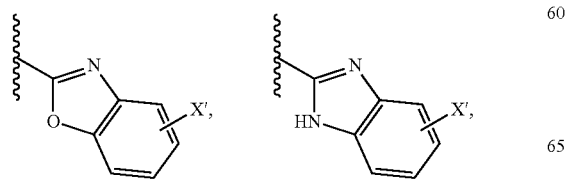

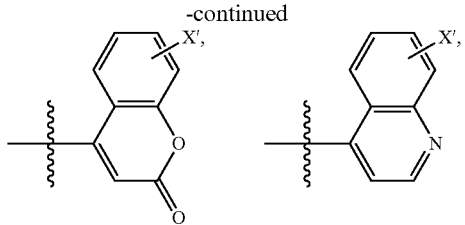

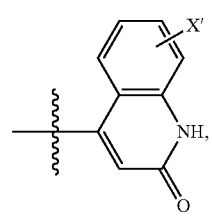

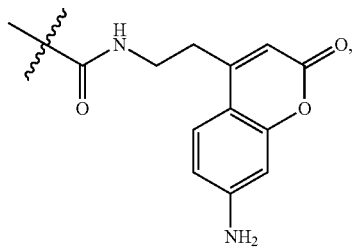

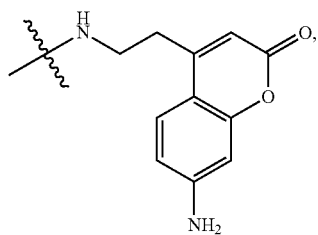

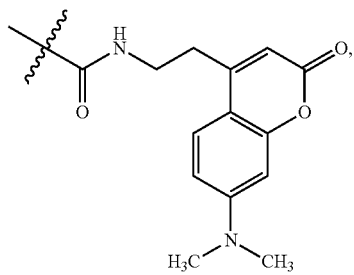

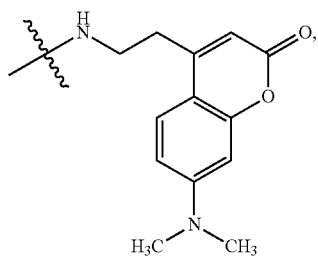

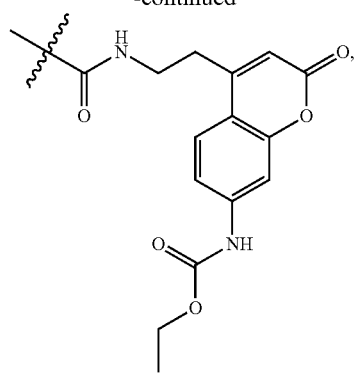
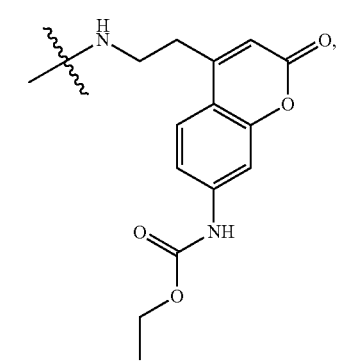
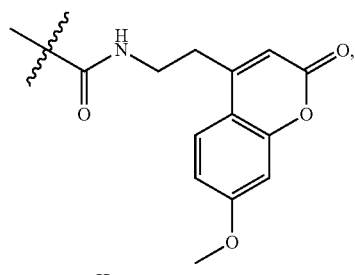
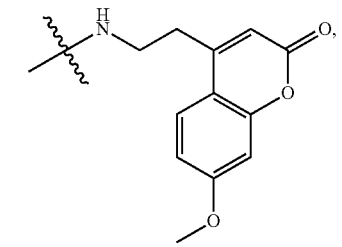
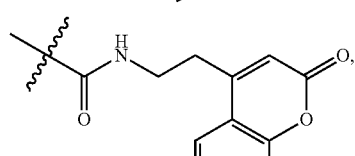
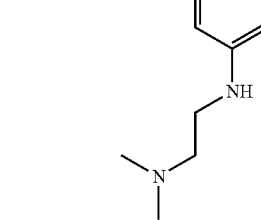
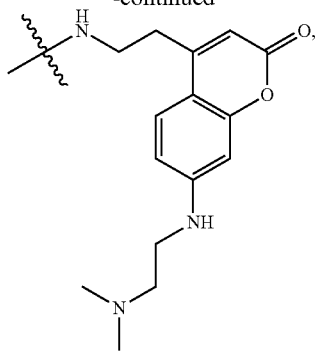
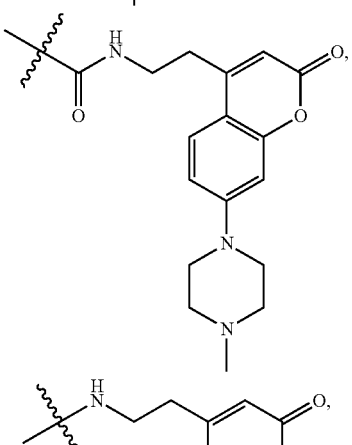
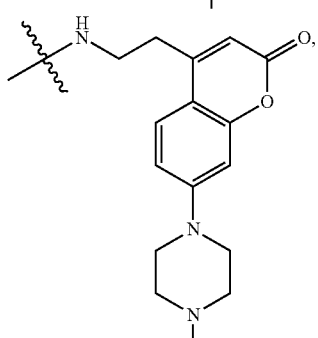
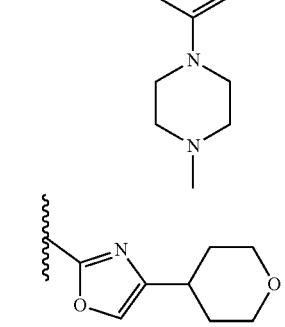
and substituted variants thereof,
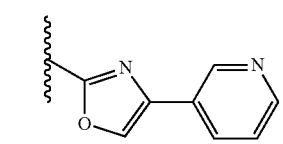 [SMILES: *c1nc(-c2cccnc2)co1]
and substituted variants thereof,
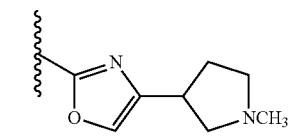 [SMILES: *c1nc(C2CCN(C)C2)co1]
and substituted variants thereof,

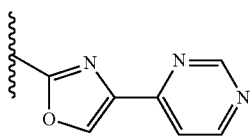

and substituted variants thereof,

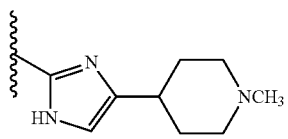 [SMILES: *c1nc(C2CCN(C)CC2)c[nH]1]

and substituted variants thereof,

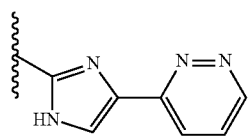 [SMILES: *c1nc(-c2cccnn2)c[nH]1]

and substituted variants thereof,

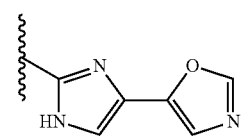 [SMILES: *c1nc(-c2cnco2)c[nH]1]

and substituted variants thereof,

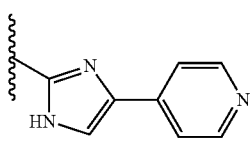 [SMILES: *c1nc(-c2ccncc2)c[nH]1]

and substituted variants thereof, and

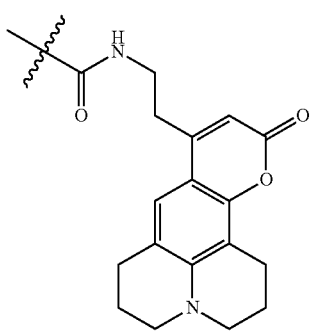 [SMILES: *C(=O)NCCc1cc(=O)oc2c3c4c(cc12)CCCN4CCC3]

and substituted variants thereof, and the like,
where X' is independently at each occurrence chosen from hydrogen, alkyl groups, cycloalkyl groups, alkoxy groups, halogens, and combinations thereof. The Z groups may have various substituents. Non-limiting examples of substituents include halogens (e.g., —F, —Cl, —Br, and —I), aliphatic groups (e.g., alkyl groups, alkenyl groups, and alkynyl groups), aryl groups, alkoxide groups, carboxylate groups, carboxylic acids, ether groups, alcohol groups, amine groups, thiol groups, thioether groups, and the like, and combinations thereof.

Various photoactive groups may be used. Non-limiting examples of photoactive groups ($R^5$) include:

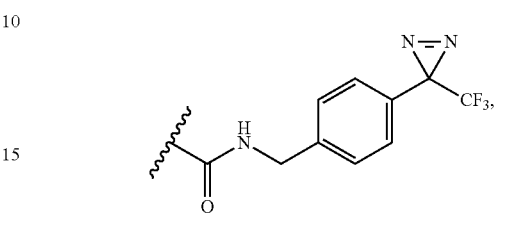

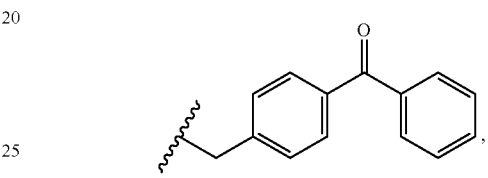

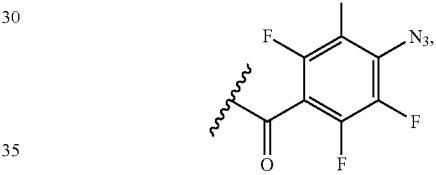

and the like.

General formulas for androgens with substituted coumarin attached at either C-3 or C-17. A compound may have the following structure:

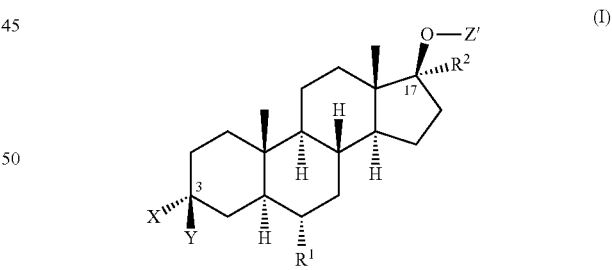

(I)

where $R^1$ and $R^2$ are individually at each occurrence chosen from hydrogen and an alkyl group (e.g., methyl group, ethyl group, n- and isopropyl group, and the like); X and Y are either hydroxyl or hydrogen, respectively, or X and Y comprise a carbonyl group; and Z' is a substituted coumarin ring or coumarin-isostere. In various examples, the $R^1$ and $R^2$ are individually at each occurrence chosen from hydrogen and an alkyl group (e.g., methyl group, ethyl group, n- and isopropyl group, and the like); X and Y are a spiro-fused, substituted coumarin ring or coumarin isostere; and Z' is a hydrogen.

A compound may have the following structure:

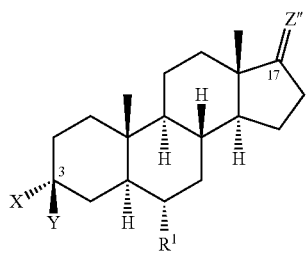
(II)

where R¹ is individually at each occurrence chosen from hydrogen and an alkyl group (e.g., methyl group, ethyl group, n- and isopropyl group, and the like); X and Y are either hydroxyl or hydrogen, respectively; and Z″ is an O-(carboxymethyl)oxime linked to a substituted coumarin or coumarin-isostere. In various examples, the R¹ is individually at each occurrence chosen from hydrogen and an alkyl group (e.g., methyl group, ethyl group, n- and isopropyl group, and the like); X and Y are a spiro-fused, substituted coumarin ring or coumarin isostere; and Z″ is an oxygen.

Representative examples of compounds (I) with substituted coumarins attached at the C-17 position. Non-limiting examples of compounds of the present disclosure include those in which group X in compound (I) is a hydroxyl; Y is a hydrogen and Z′ is a substituted coumarin in which a substituent connects a linker L between the C-17p oxygen of the steroid and the C-4′ position of a coumarin ring or coumarin isostere. Examples of such compounds include, but are not limited to, compounds (Ia), (Ib) and (Ic):

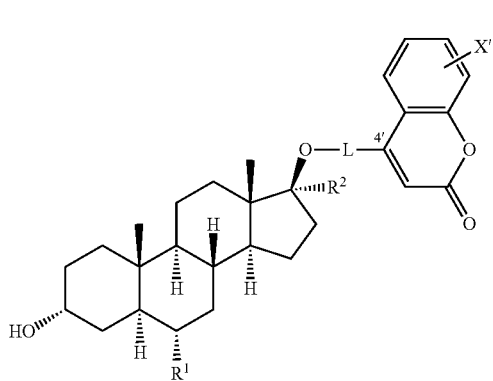
Ia

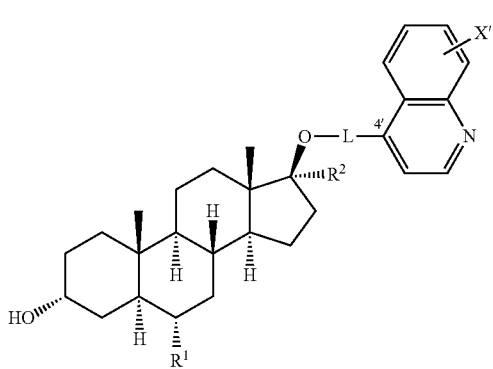
Ib

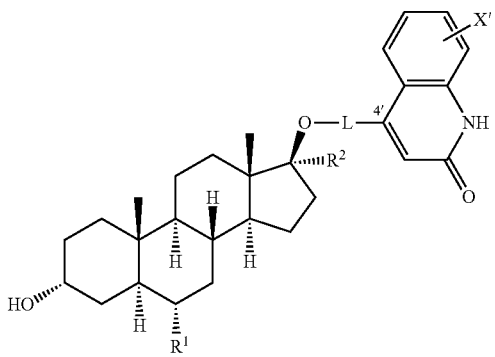
Ic where X′ is independently at each occurrence chosen from hydrogen, alkyl groups (e.g., methyl, ethyl, n and isopropyl, and the like), cycloalkyl groups, alkoxy groups (e.g., —O(CH₂)ₙCH₃ where n is 0, 1, or 2), and/or halogens (i.e., —F, —Cl, —Br, and —I) and L is a linker (e.g., a linker group). Examples of linkers include, but not limited to the following structures where n and m are independently 1, 2, 3, 4, 5, or 6:

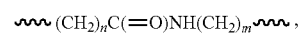
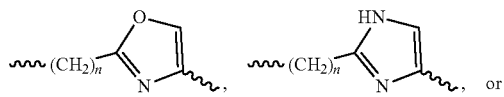
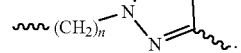
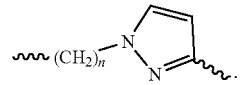

Non-limiting examples of compounds of the present disclosure include those in which groups X and Y in compound (I) are a carbonyl group and Z′ is a substituted coumarin where a substituent connects a linker L between the C-17p oxygen of the steroid and the C-4′ position of a coumarin ring group or coumarin isostere group. Examples of compounds include, but are not limited to, compounds (Id), (Ie) and (If):

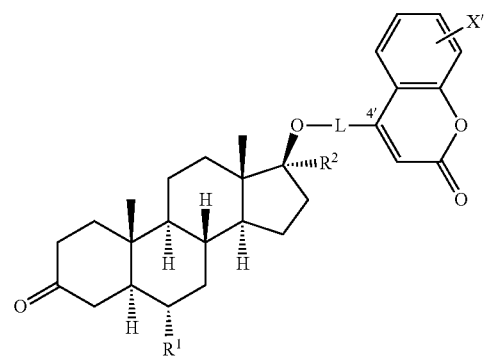
Id

-continued

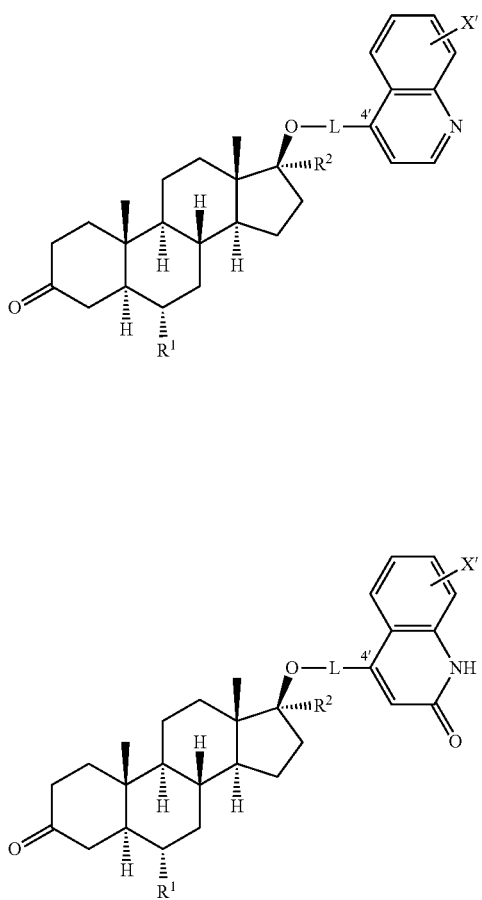

Ie

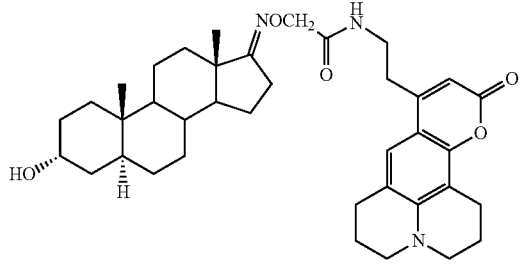

IIa

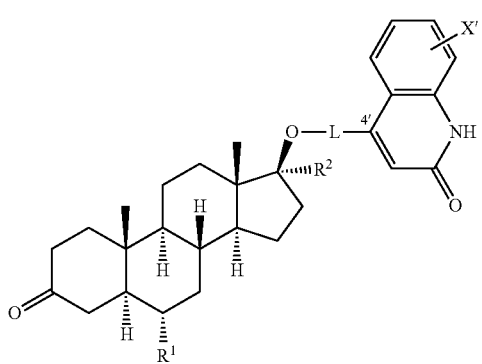

If

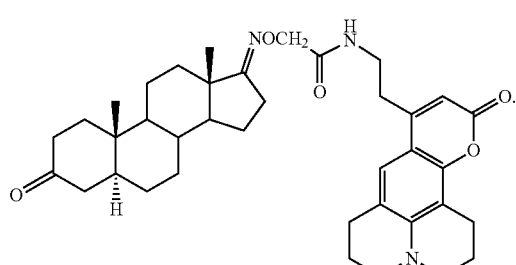

IIb where X' is independently at each occurrence chosen from hydrogen, alkyl groups (e.g., methyl, ethyl, n and isopropyl, and the like), cycloalkyl groups, alkoxy groups (e.g., —O(CH$_2$)$_n$CH$_3$ where n is 0, 1, or 2), and/or halogens (i.e., —F, —Cl, —Br, and —I). and L is a linker (e.g., a linker group). Examples of linkers include, but not limited to the following structures where n and m are independently 1, 2, 3, 4, 5, or 6:

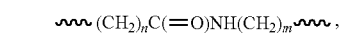
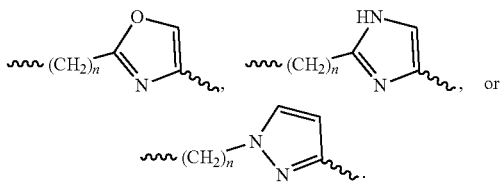

Representative examples of compounds (II) with substituted coumarins attached at the C-17 position. Non-limiting examples of compounds of the present disclosure include those where compound (II) groups X and Y are a hydroxyl group and hydrogen, respectively, or a carbonyl group or an oxime. Examples of groups include, but are not limited to, compounds (IIa) and (IIb):

General, representative examples of compounds (I) with substituted coumarins attached at the C-3 position. Non-limiting examples of compounds of the present disclosure include those where compound (I) groups X and Y are a spiro-fused, substituted coumarin ring group or coumarin isostere group; and Z' is a hydrogen. Examples include, but are not limited to compounds (Ig), (Ih) and (Ii):

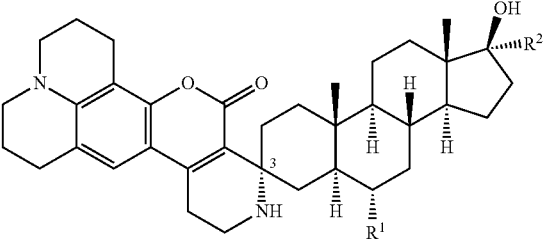

Ig

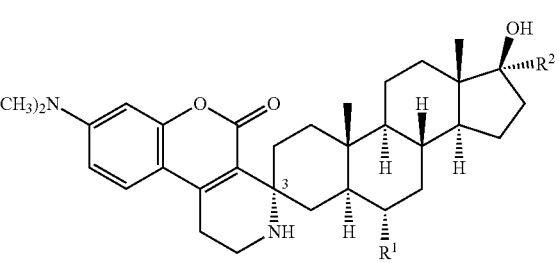

Ih

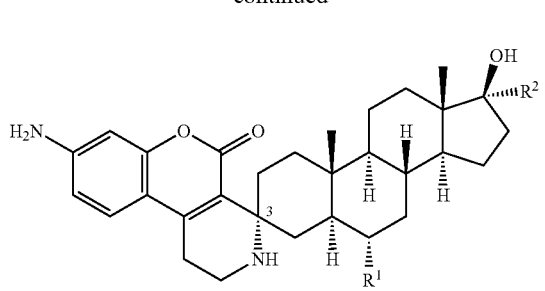

Ii

Non-limiting examples of compounds of the present disclosure include those where compound (II) $R^1$ groups are individually at each occurrence chosen from hydrogen and an alkyl groups (e.g., methyl group, ethyl group, n- and isopropyl group, and the like); groups X and Y are a spiro-fused, substituted coumarin ring or coumarin isostere; and Z″ is an oxygen. Examples include, but are not limited to, compounds (Ij), (Ik) and Il):

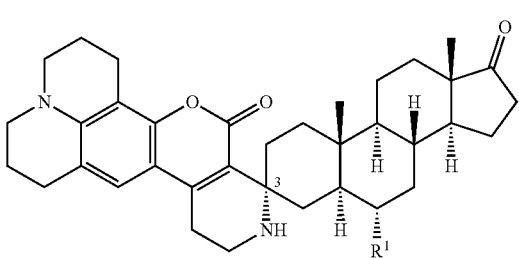

Ij

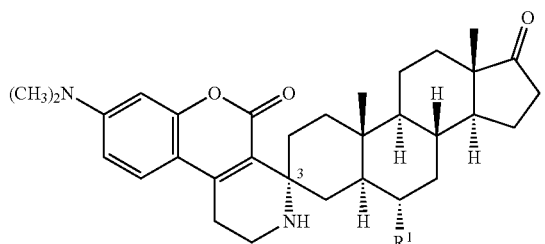

Ik

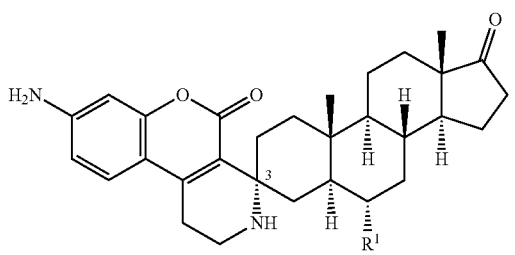

Il

In various examples, a compound of the present disclosure is a PROTAC. A PROTAC may have the following structure: A-L-B, where A is an E3 ligase recruiter, B is a ligand group for a target protein, and L is a linker covalently connecting the E3 ligase recruiter and the ligand group.

In an example, the E3 ligase recruiter can recruit a protein, such as, for example, VHL, CRBN, RNF 114, MDM2, DCAF15, DCAF16, SCF, and the like, which are capable of ubiqutinating the target protein such as AR. Non-limiting examples of E3 ligase recruiter groups include groups formed from:

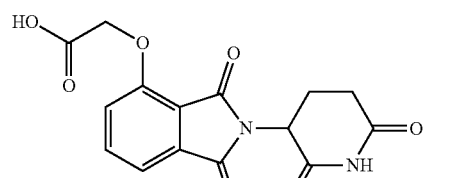

(e.g.,

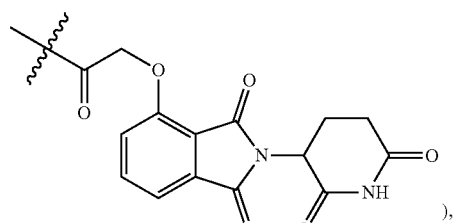

),

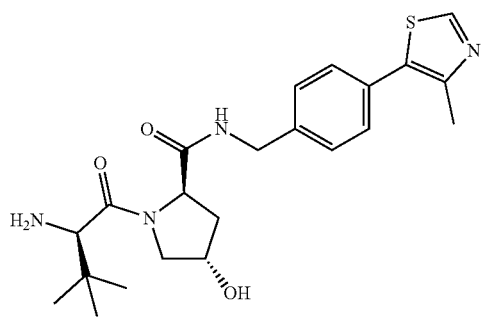

(e.g.,

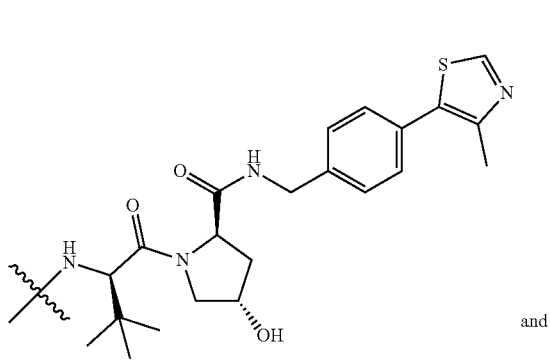

and

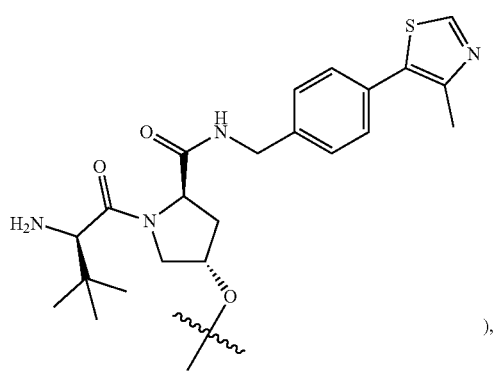

),

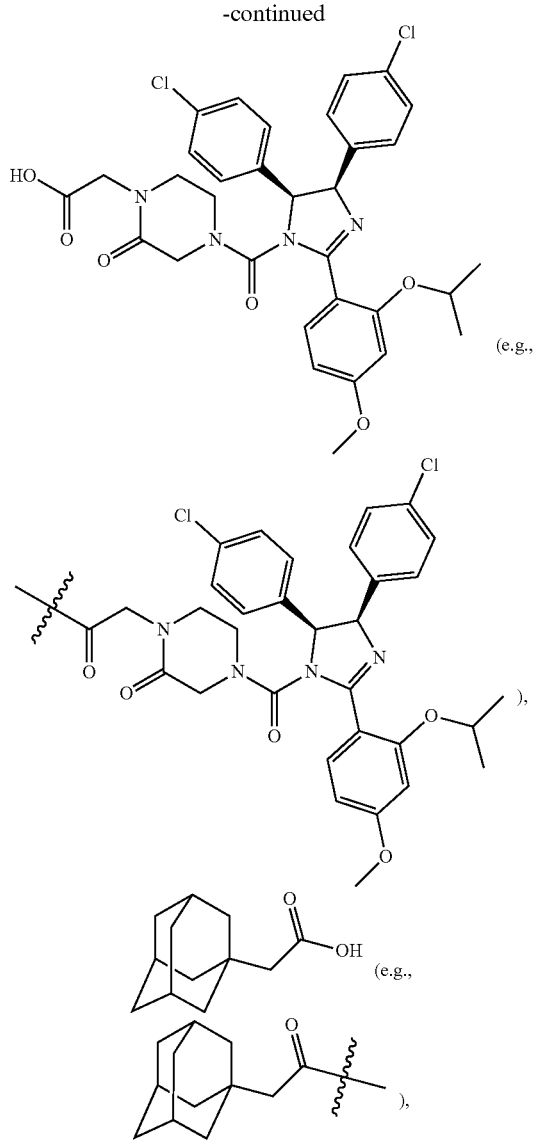

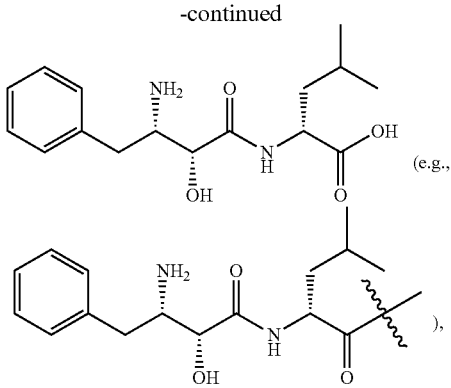

or ligase recruiter groups that bind cereblon, von Hippel-Lindau (VHL), or Mouse-Double-Minute-2.

A compound (e.g., a PROTAC compound) of the present disclosure may comprise various linkers (e.g., a linking group). A linker connects the E3 ligase recruiter and the ligand group for a target protein via covalent bonds (e.g., two or more covalent bonds). Various linkers are known in the art. Non-limiting examples of linkers include: —NH(CH$_2$)$_n$NH—, —C(=O)(CH$_2$)$_n$NH—, —C(=O)(CH$_2$)$_n$C(=O)—, —NH(CH$_2$CH$_2$O)$_n$CH$_2$CH$_2$NH—, —C(=O)(CH$_2$CH$_2$O)$_n$CH$_2$CH$_2$NH—, —C(=O)(CH$_2$CH$_2$O)$_n$CH$_2$CH$_2$C(=O)—, where n is 2-4 (e.g., 2, 3, or 4).

Non-limiting examples of target proteins include proteins associated with cancers (e.g., leukemia, lung cancer (e.g., non-small cell lung cancer), dermatological cancers, premalignant lesions of the upper digestive tract, malignancies of the prostate, malignancies of the brain, malignancies of the breast, solid tumors, and the like), infectious diseases, inflammatory diseases, immune disorders, sleep disorders, neurodegenerative disorders, and the like, and combinations thereof.

A compound of the present disclosure may be used in molecular imaging. Compounds suitable for molecular imaging may comprise an R$^5$ group as described herein or may comprise a spiro-coumarin ring group or both. Non-limiting examples of a compounds suitable for molecular imaging (e.g., imaging hyperplastic cells and/or malignant cells) include:

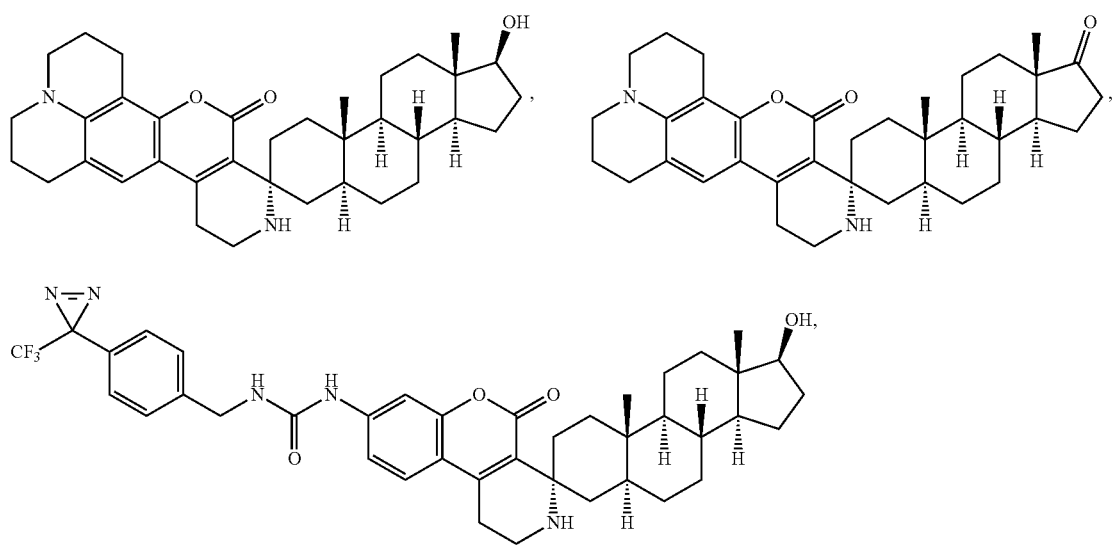

-continued
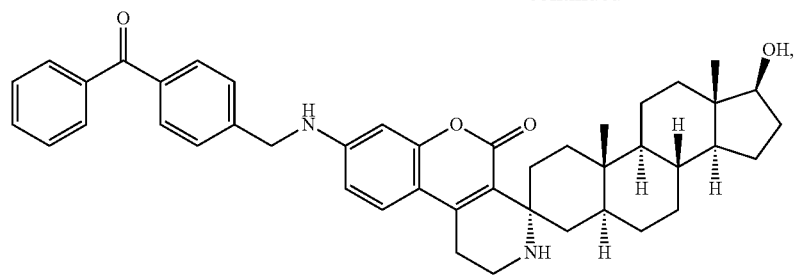
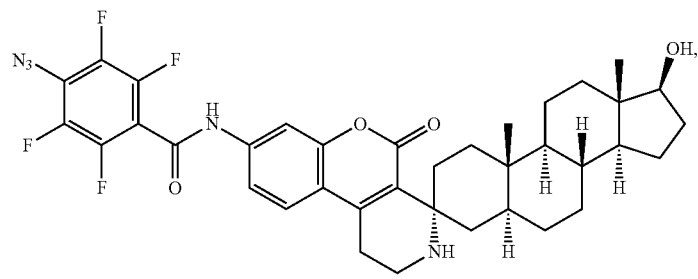
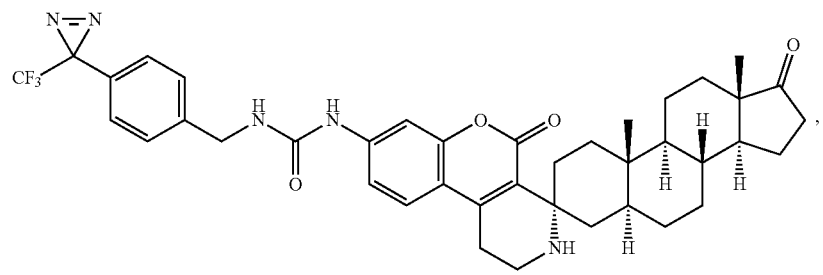
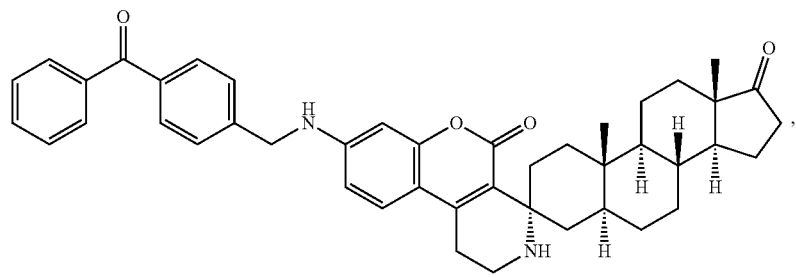
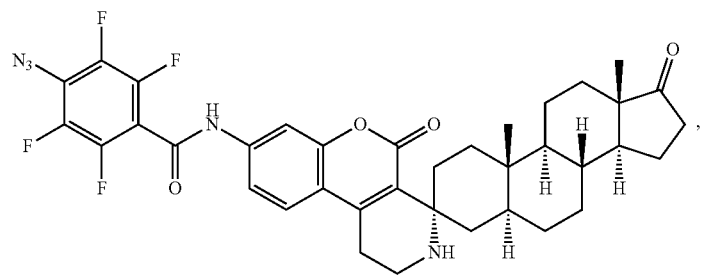
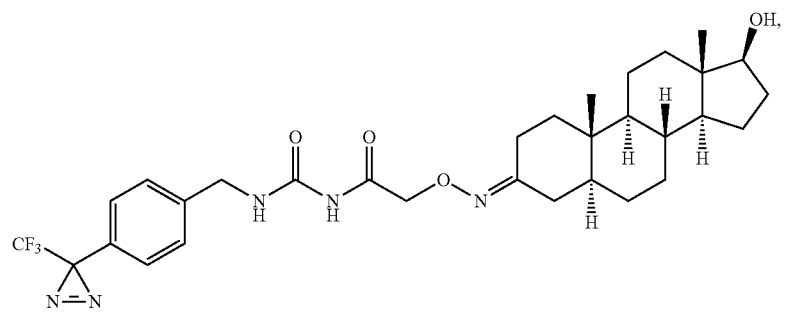

-continued
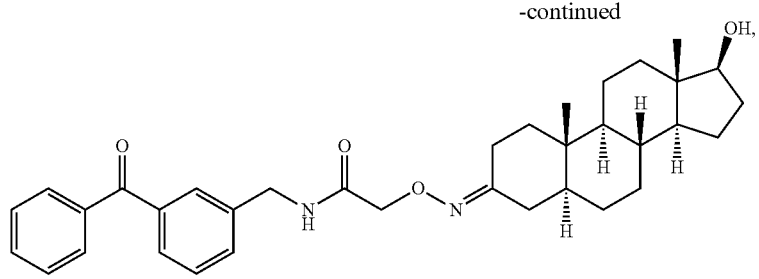
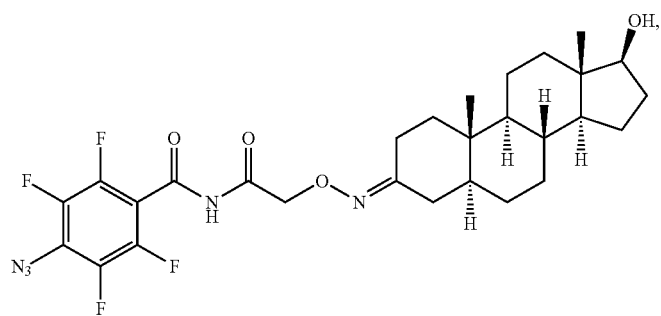
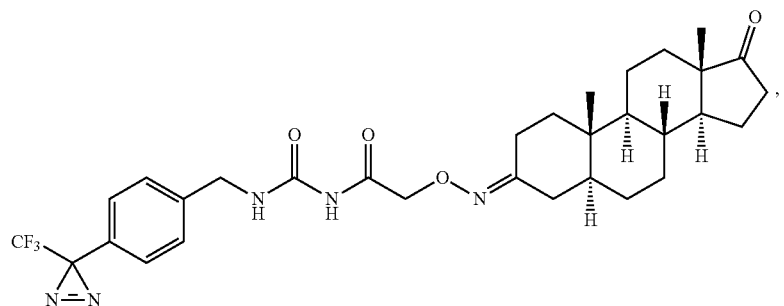
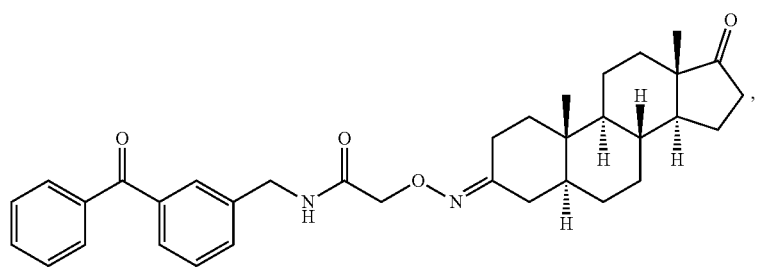
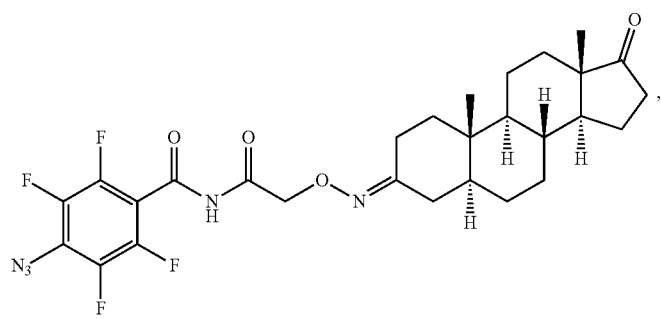
or the like, or a combination thereof.

Specific examples of compounds of the present disclosure include, but are not limited to:
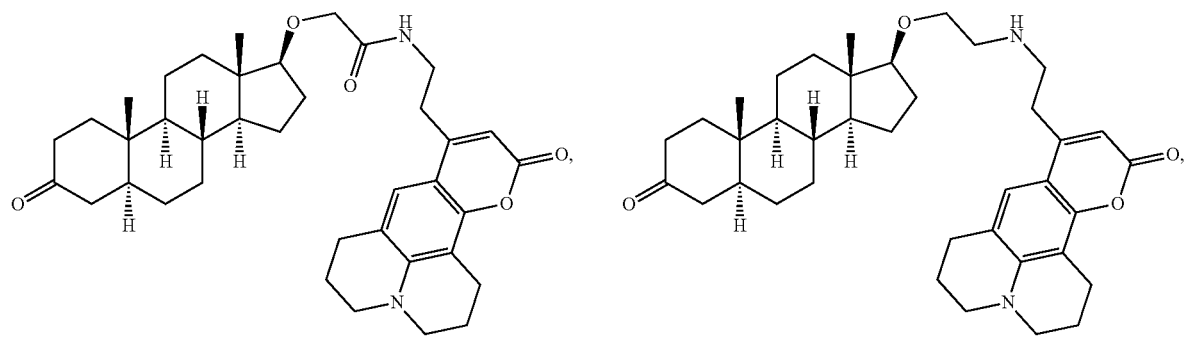
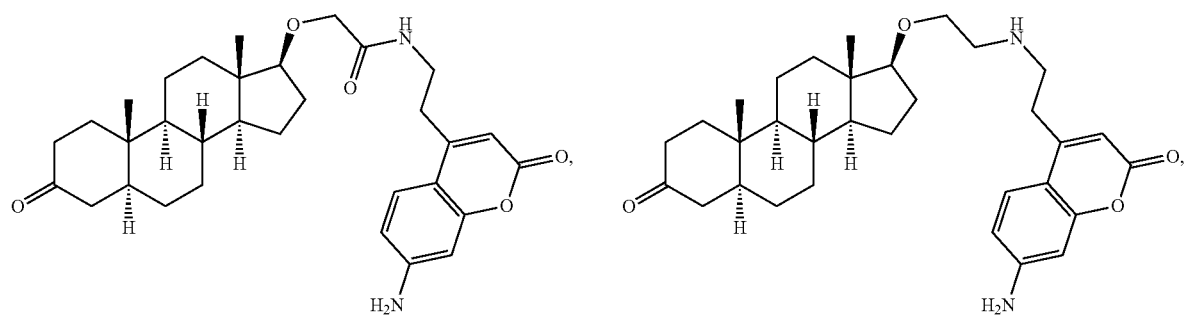
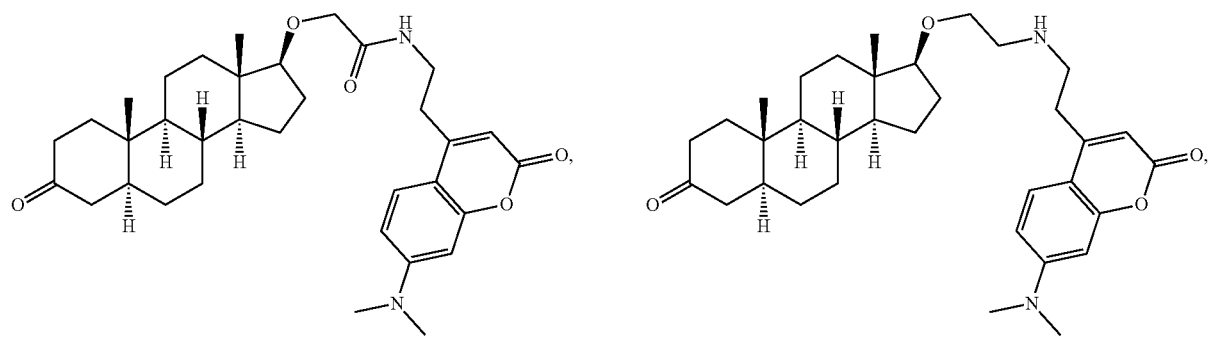
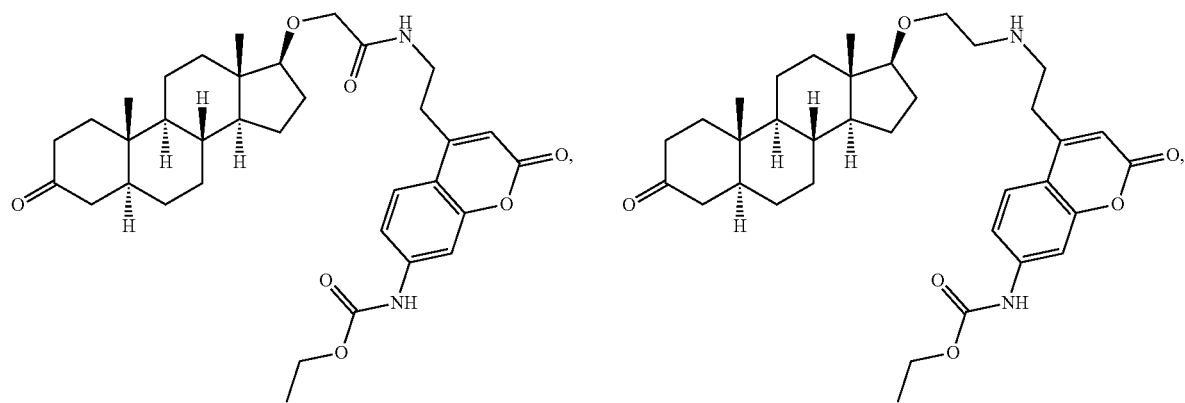

31
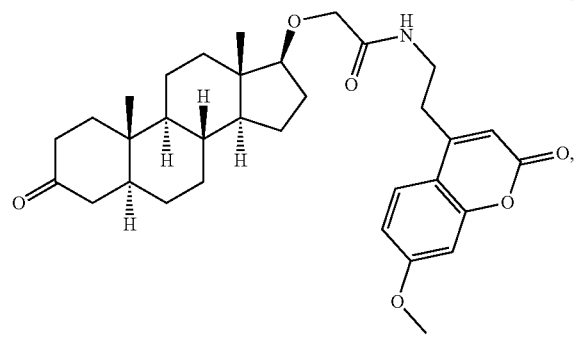
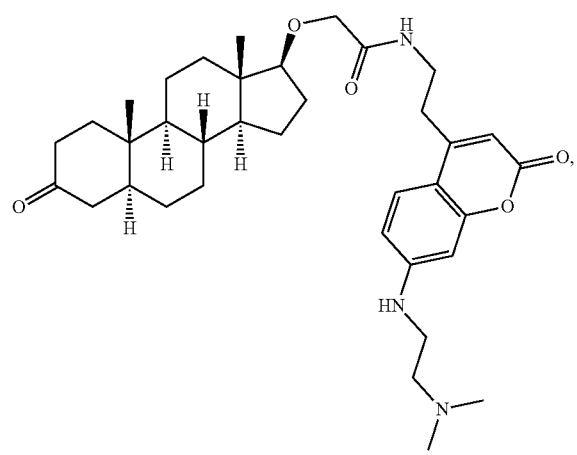
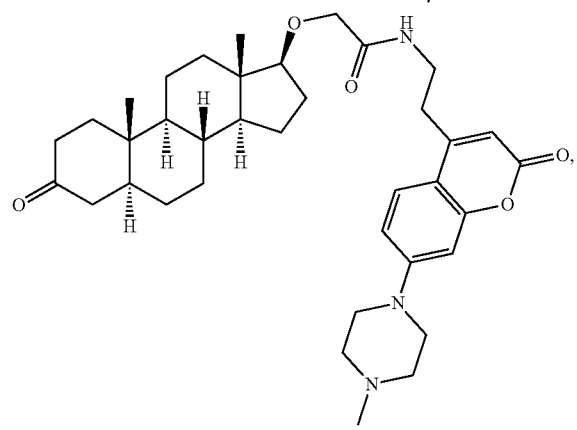
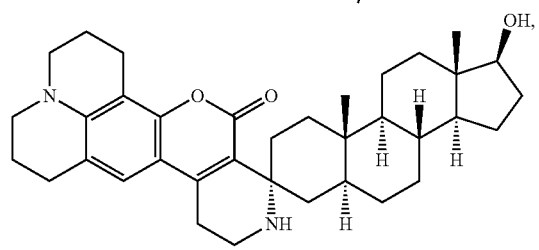
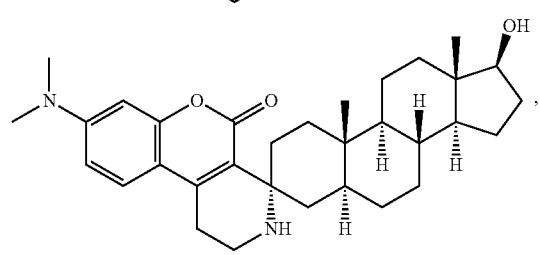
32
-continued
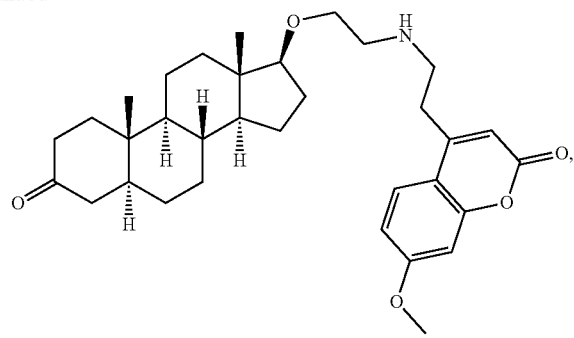
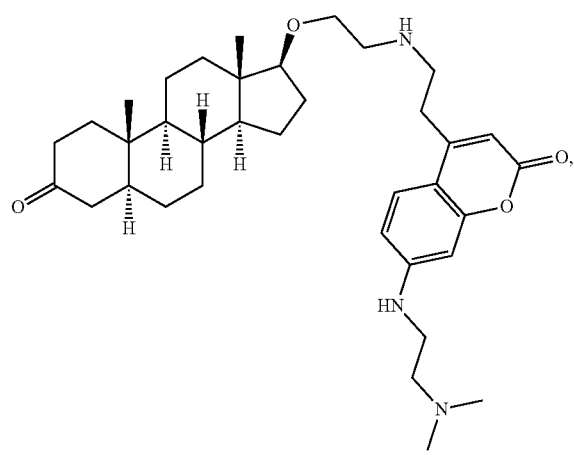
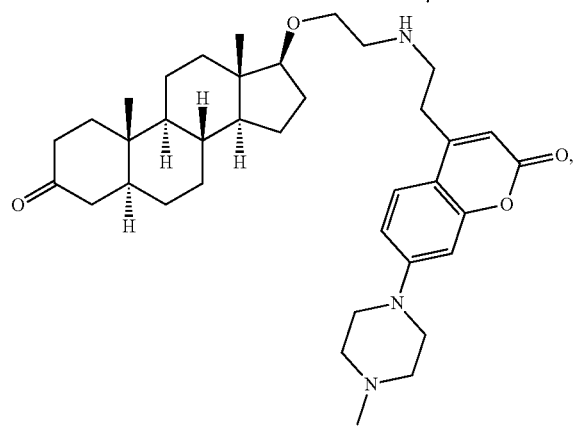
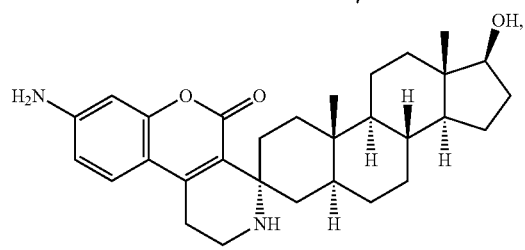
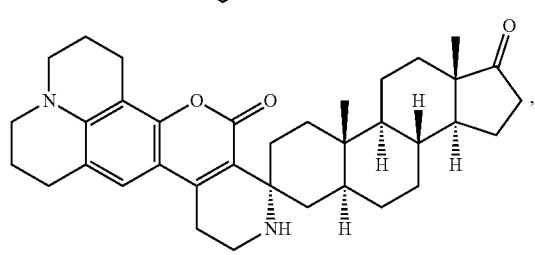

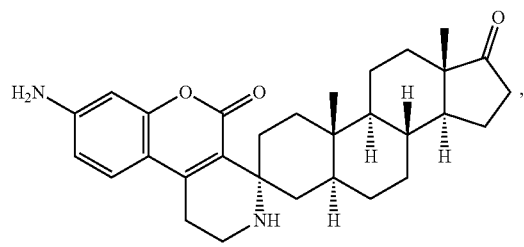
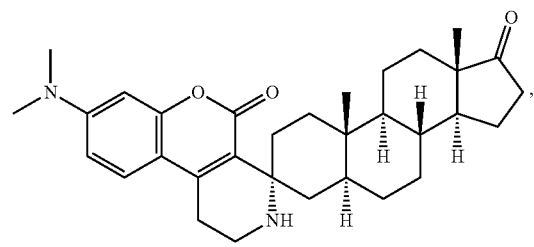
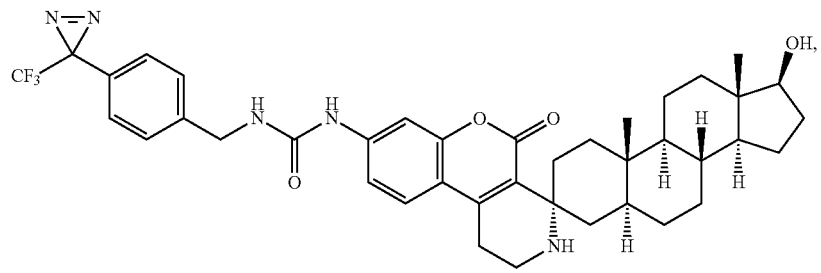
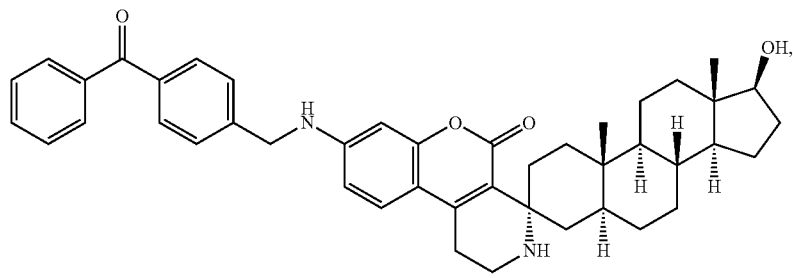
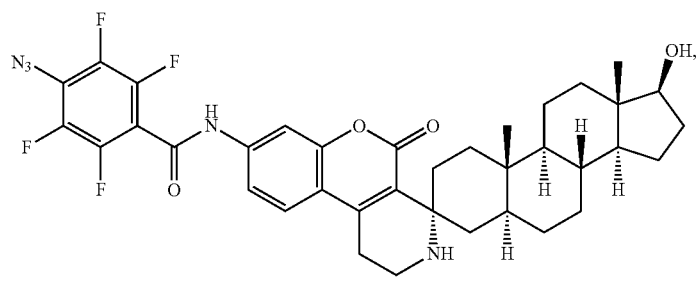
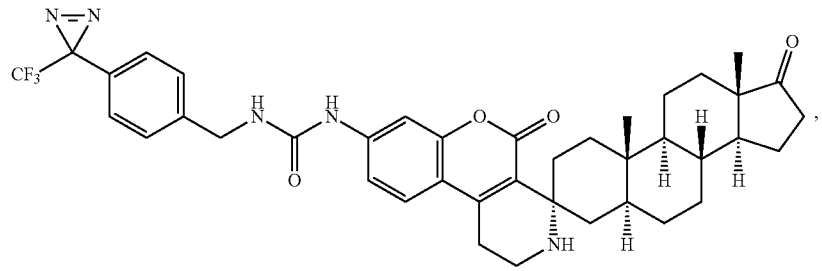
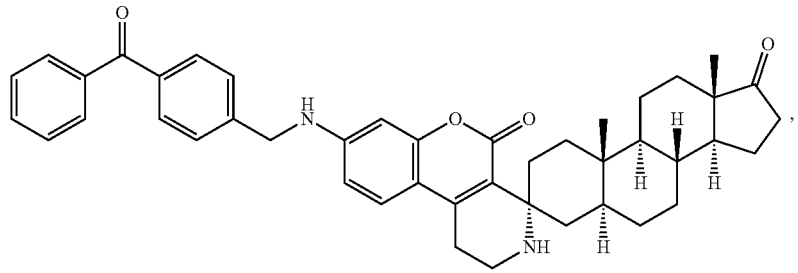

-continued
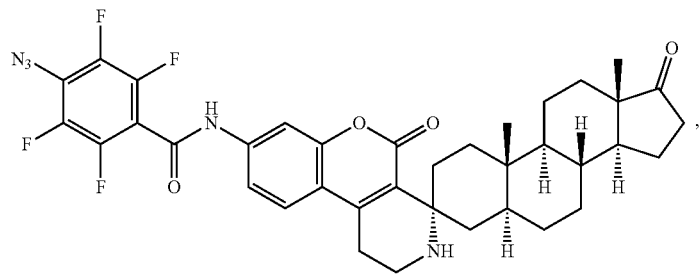
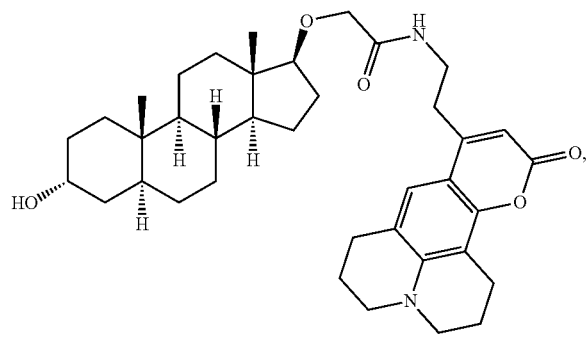
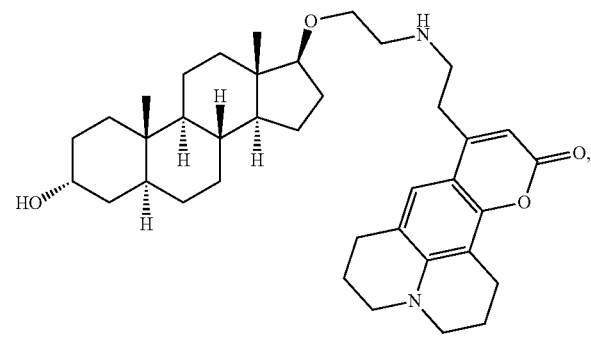
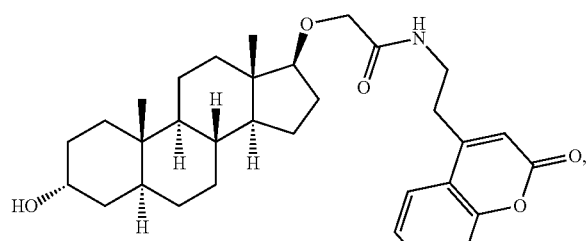
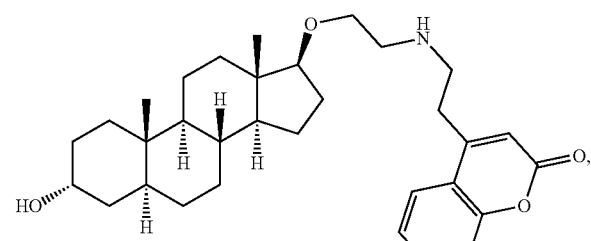
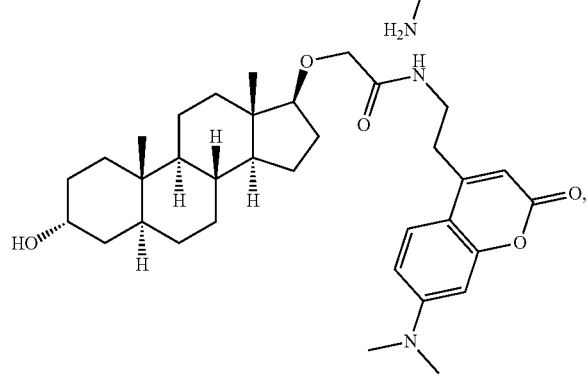
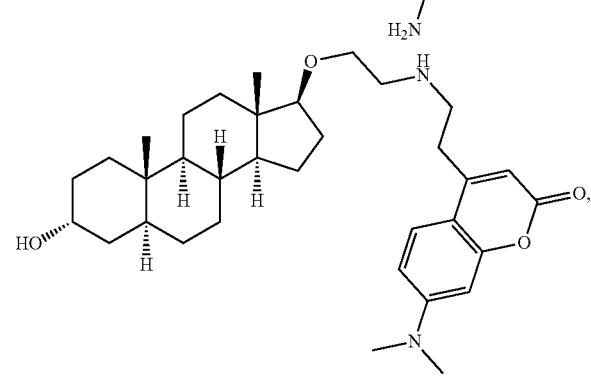
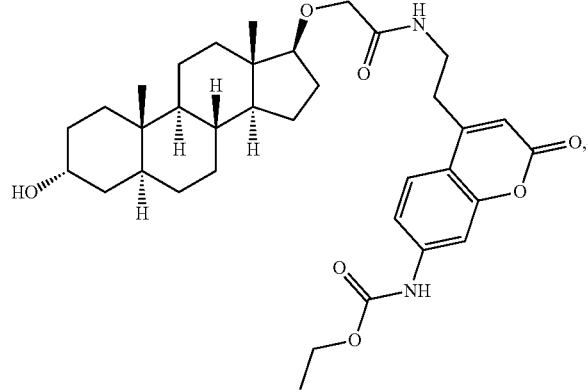
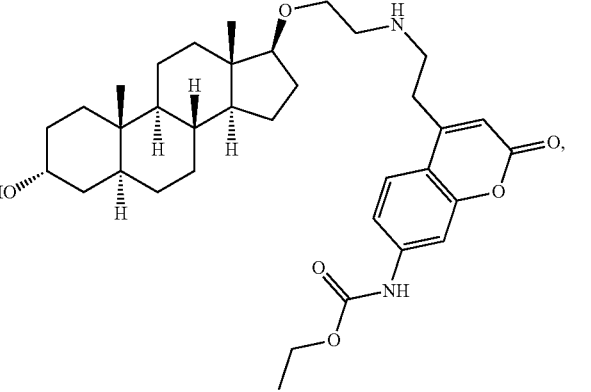

37 38
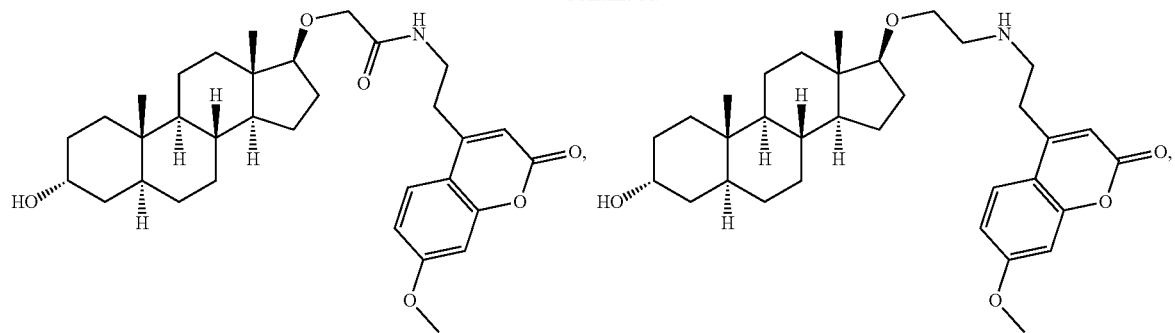
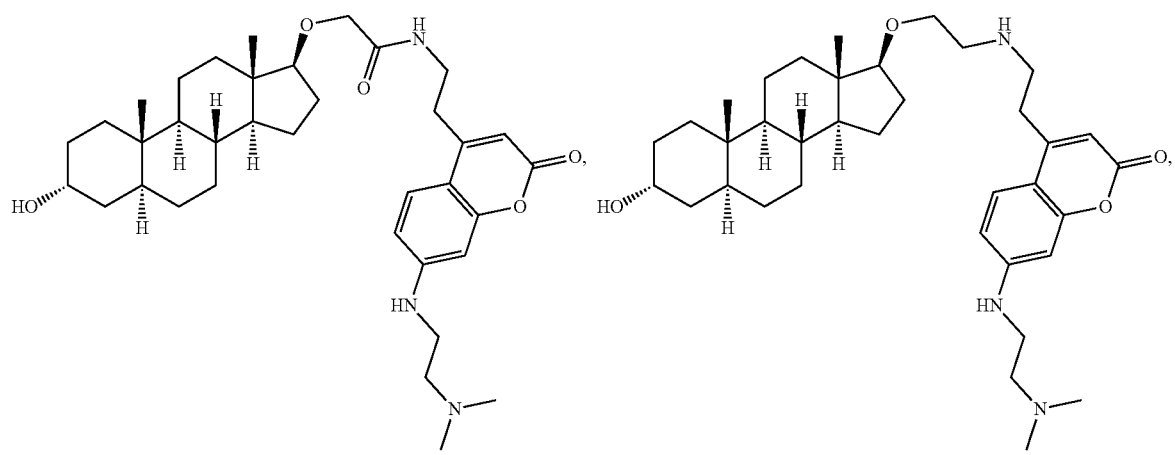
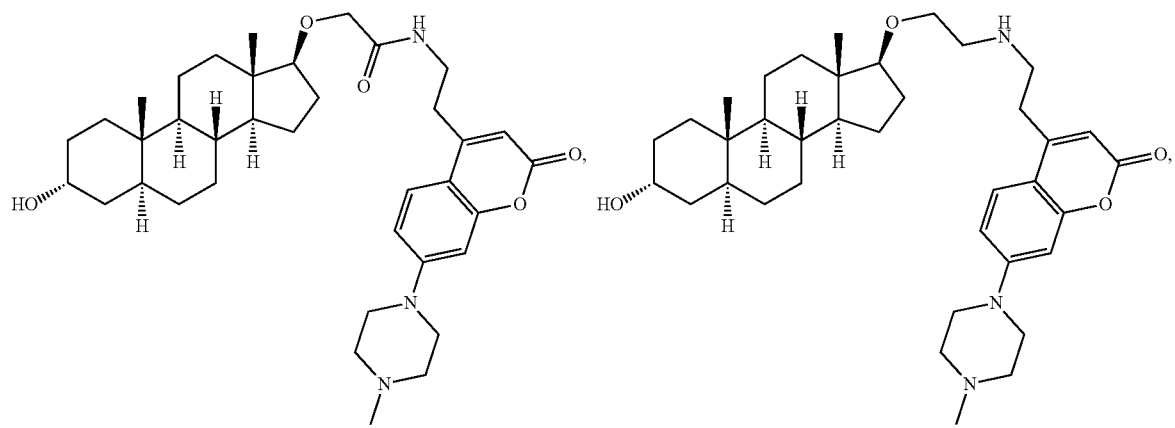
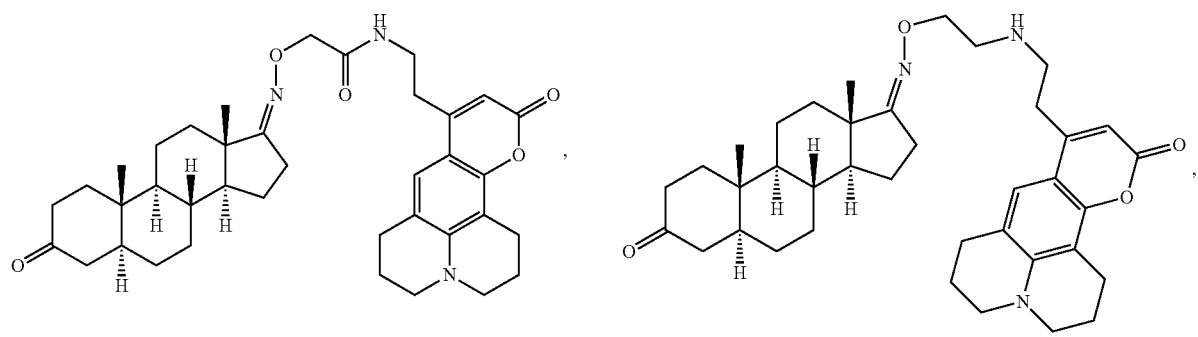

-continued
| 39 | 40 |
|---|---|
| 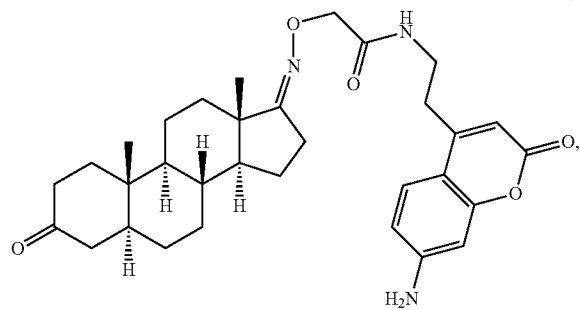 | 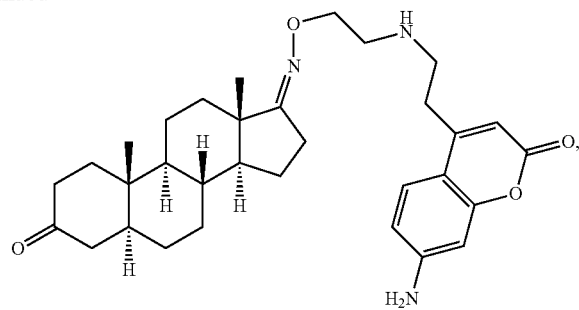 |
| 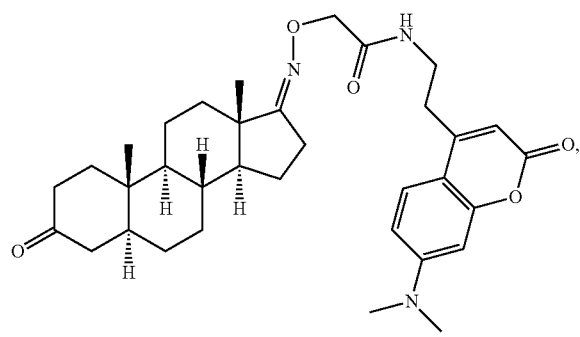 | 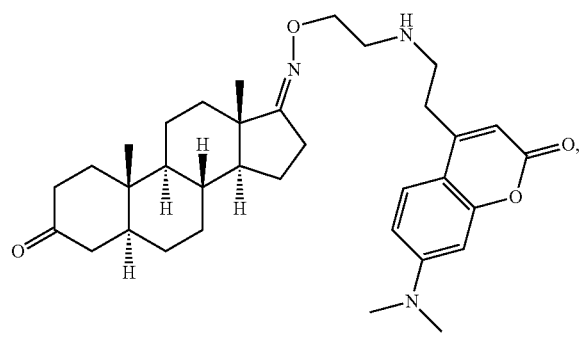 |
| 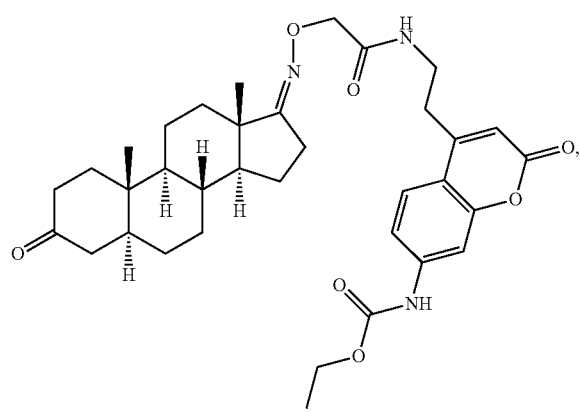 | 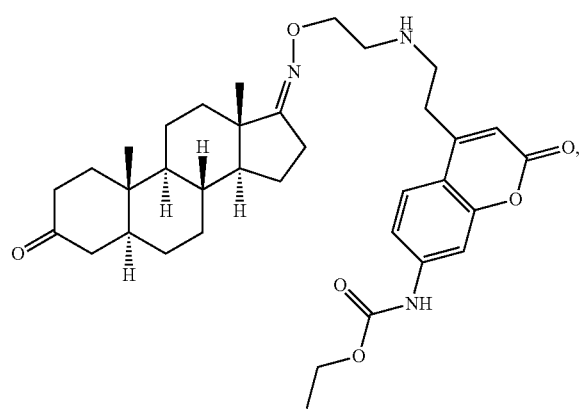 |
| 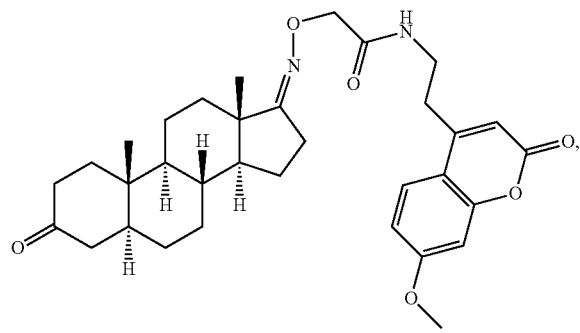 | 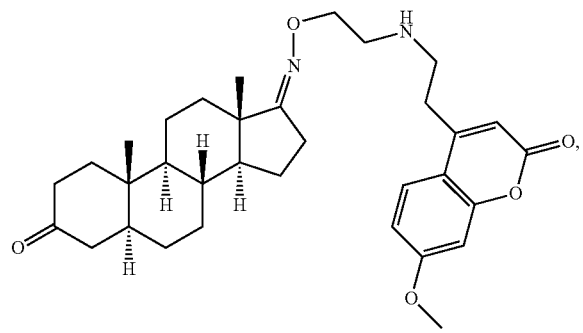 |

41 42
-continued
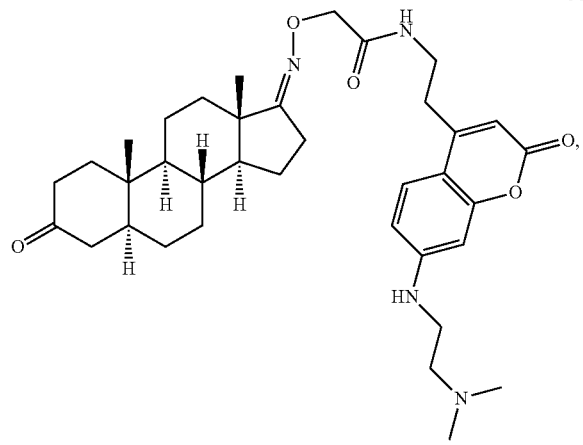
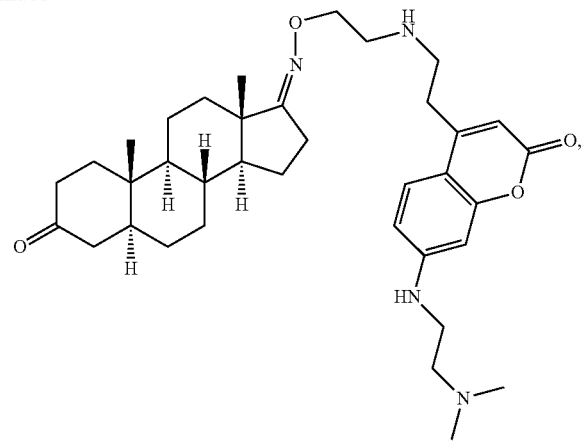
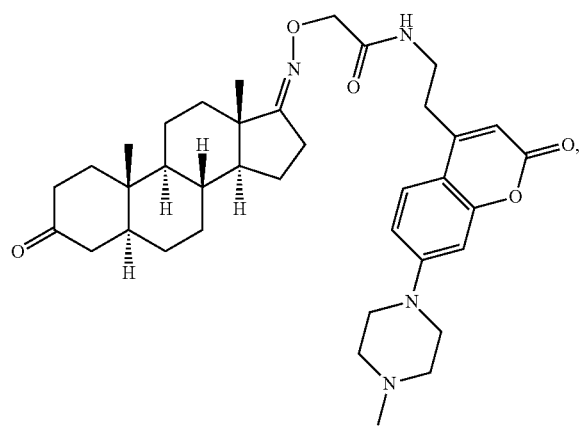
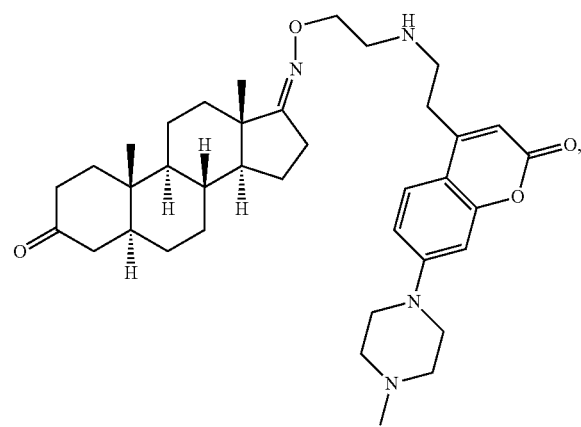
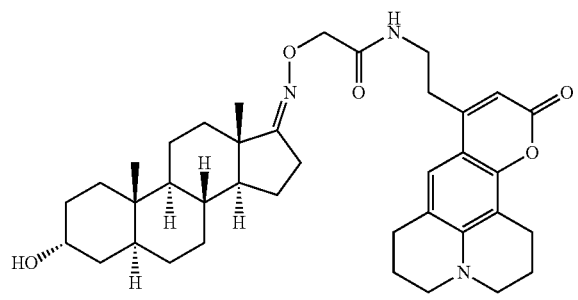
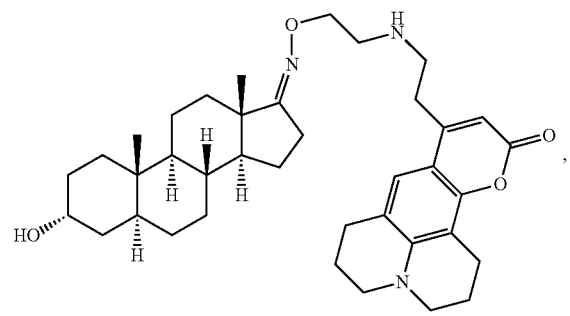
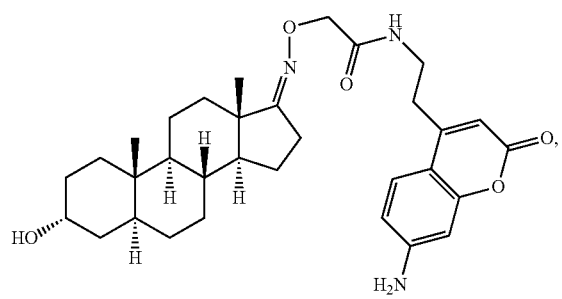
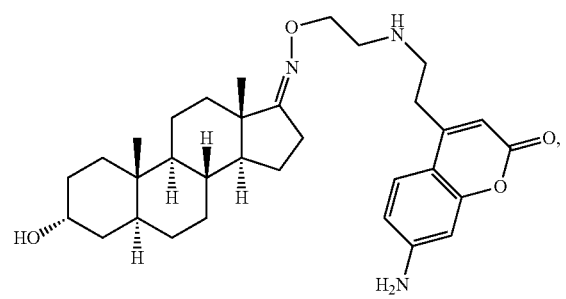

-continued
43 44
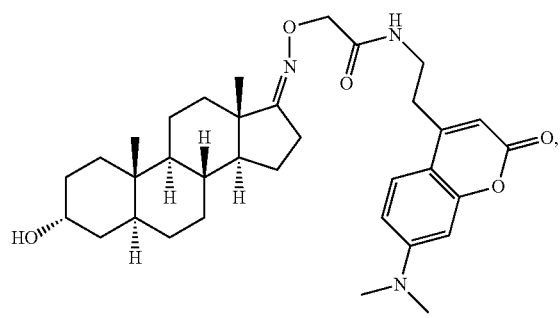
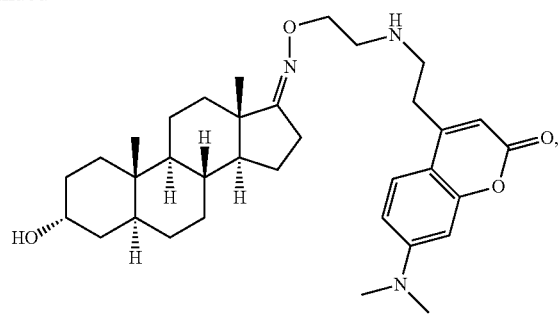
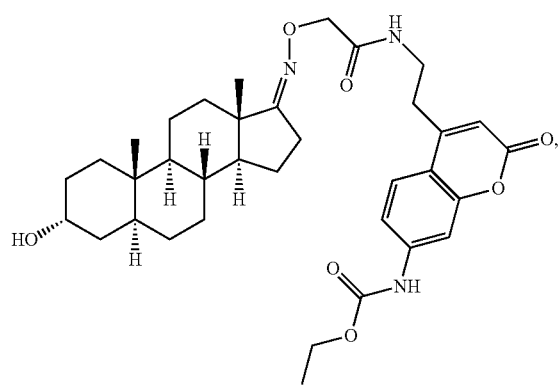
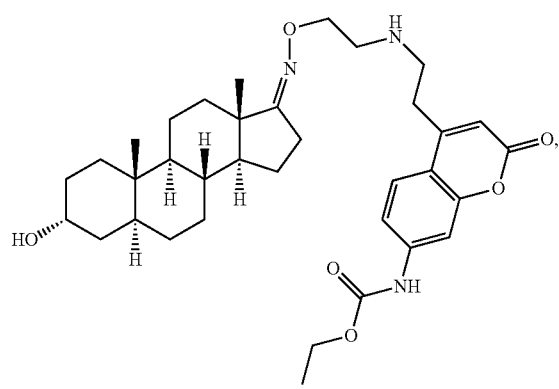
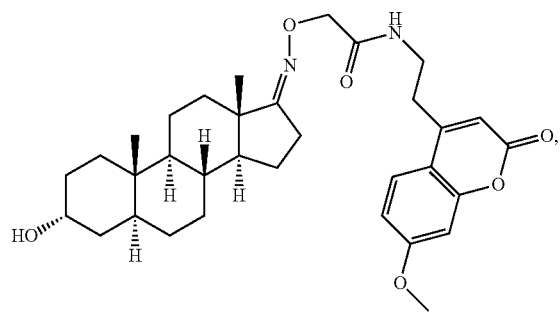
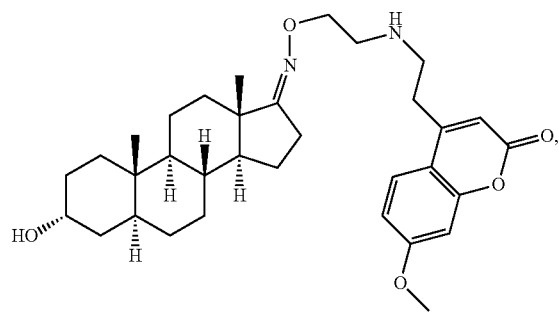
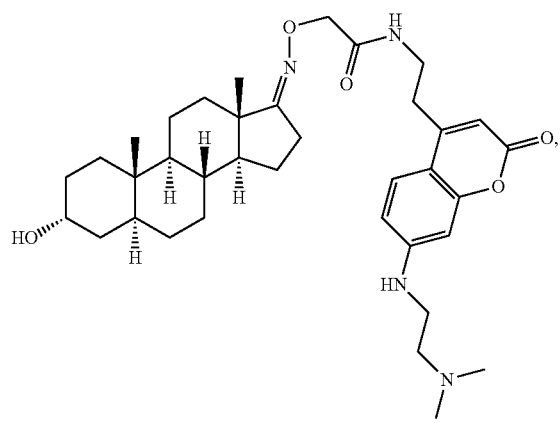
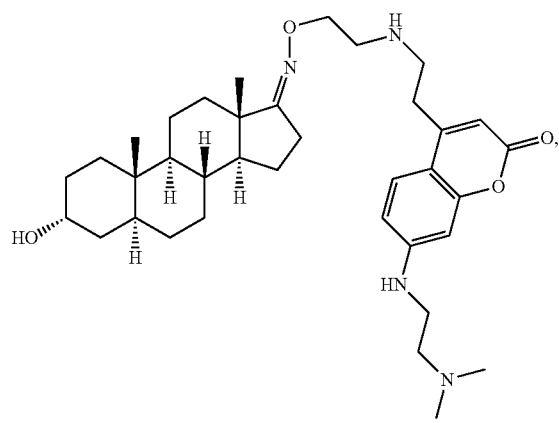

45 46
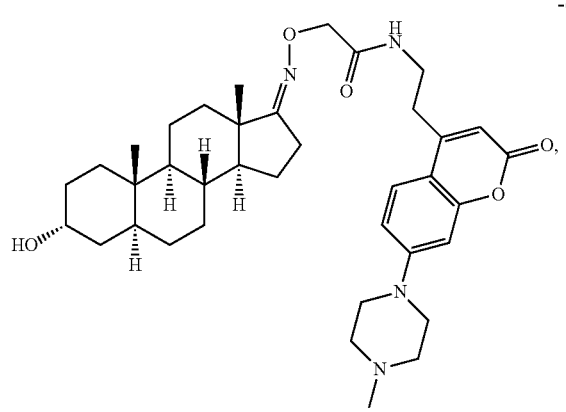 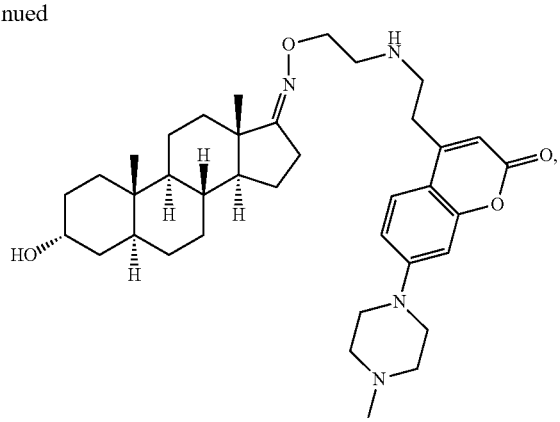
-continued
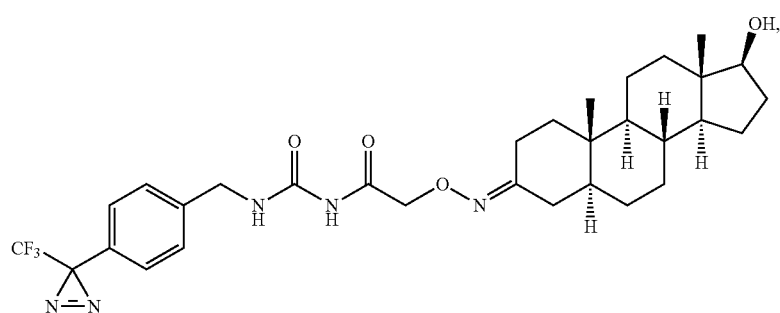
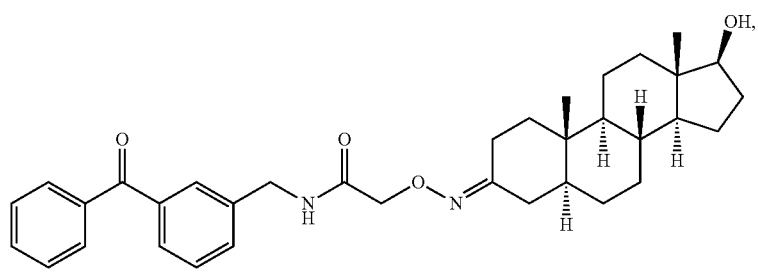
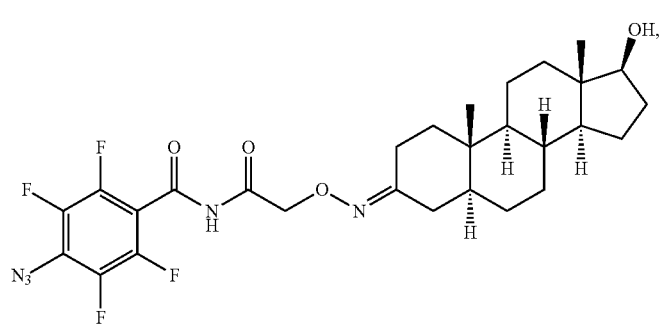
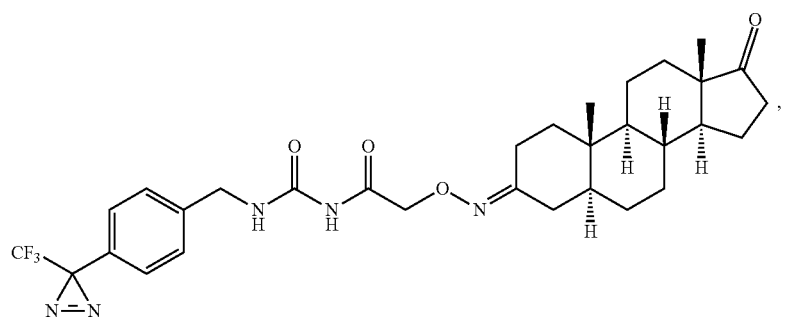

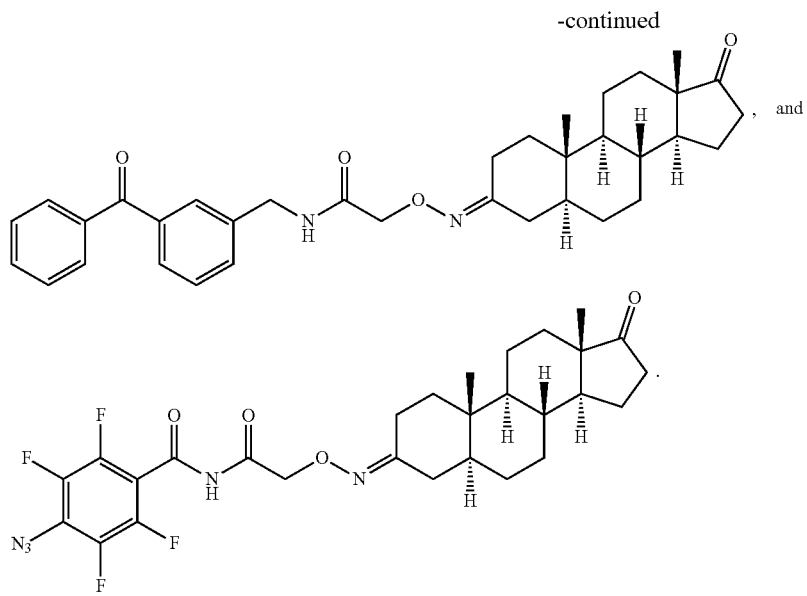

Figure 3:
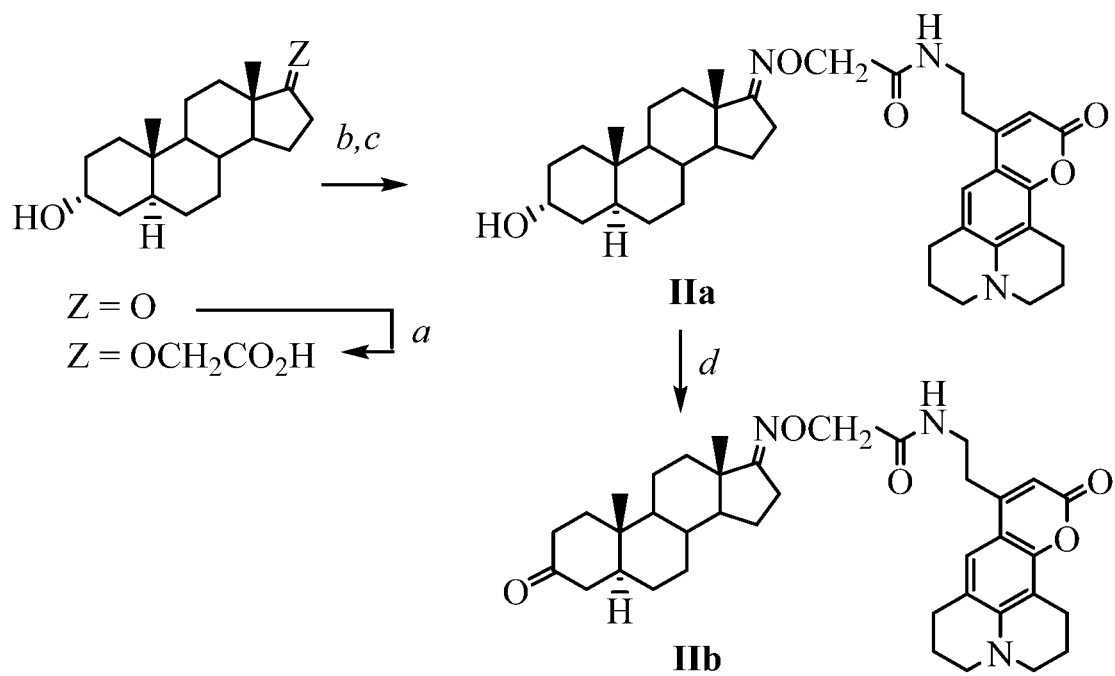
FIG. 3 shows a synthetic route of fluorescent steroids modified at C-17 keto groups. Legend for the reagents used in the synthesis: a, $H_2NOCH_2CO_2Et$; b, NaOH, aq $CH_3OH$; c, N-(3-dimethylaminopropyl)-N'-ethylcarbodiimide hydrochloride (EDC), 1-hydroxybenzotriazole hydrate (HOBt), and 8-(2-aminoethyl)-2,3,4,5-tetrahydro-1H,4H-11-oxa-3α-aza-benzo[de]anthracen-10-one hydrochloride; d, $Py-SO_3$.

Synthesis of compounds of the present disclosure may be from commercially available materials. For example, the present disclosure provides methods of making compounds (I) and (II) from commercially available materials in which a coumarin moiety is attached to the C-3 or the C-17 position of steroids. Non-limiting examples of methods are provided herein. Synthetic routes to these compounds are shown in FIGS. 2, 3, and 4. A compound was be made by a method of the present disclosure and characterized as to structure and purity as follows. Nuclear magnetic resonance spectra were determined on a Varian instrument ($^1$H, 400 or 500 MHz; $^{13}$C, 100 Mz). High resolution electrospray ionization (ESI) mass spectra were recorded on a Q Exactive mass spectrometer (Thermo Fisher Scientific, Waltham, MA, USA). Resolution was set at 100,000 (at 400 m/z). Samples were introduced through direct infusion using a syringe pump with a flow rate of 3 μL/min. Purity of compounds was established using $^{13}$C NMR and exact mass spectra. Compounds were chromatographed on preparative layer Merck silica gel F254 unless otherwise indicated.

In an aspect, the present disclosure provides compositions comprising compounds of the present disclosure. The compositions further comprise one or more pharmaceutically acceptable carrier.

A composition may comprise additional components. For example, the composition comprises a buffer solution suitable for administration to an individual (e.g., a mammal such as, for example, a human or a non-human). An individual may be a subject. The buffer solution may be a pharmaceutically acceptable carrier.

A composition may include one or more standard pharmaceutically acceptable carrier(s). Non-limiting examples of compositions include solutions, suspensions, emulsions, solid injectable compositions that are dissolved or suspended in a solvent before use, and the like. Injections may be prepared by dissolving, suspending or emulsifying one or more of the active ingredient(s) in a diluent. Non-limiting examples of diluents include distilled water for injection, physiological saline, vegetable oil, alcohol, and the like, and combinations thereof. Further, the injections may contain stabilizers, solubilizers, suspending agents, emulsifiers, soothing agents, buffers, preservatives, and the like. Injections may be sterilized in the final formulation step or prepared by sterile procedure. The composition may also be formulated into a sterile solid preparation, for example, by freeze-drying, and can be used after sterilized or dissolved in sterile injectable water or other sterile diluent(s) immediately before use. Non-limiting examples of pharmaceutically acceptable carriers can be found in: *Remington: The Science and Practice of Pharmacy* (2005) 21st Edition, Philadelphia, PA. Lippincott Williams & Wilkins.

In an aspect, the present disclosure provides methods of using one or more compound or composition thereof. The compounds are suitable in methods to treat various diseases. For example, one or more compounds of the present disclosure or a composition of the present disclosure can be used to treat cancer, other diseases, or a combination thereof. Methods of the present disclosure may be used to inhibit cell growth of malignant cells and/or hyperplastic cells and/or induce selective degradation of a target protein and/or for molecular imaging. A method can be carried out in combination with one or more known therapies.

Non-limiting examples of cancers include leukemia, lung cancer (e.g., non-small cell lung cancer), dermatological cancers, premalignant lesions of the upper digestive tract, malignancies of the prostate, malignancies of the brain, malignancies of the breast, solid tumors, and the like, and combinations thereof.

Non-limiting examples of other diseases include infectious diseases, inflammatory diseases, immune disorders, sleep disorders, neurodegenerative disorders, and the like, and combinations thereof.

A method of the present disclosure may be used to treat various types of cancers, such as, for example, hormonal cancers. Non-limiting examples of hormonal cancers include breast cancers, ovarian cancers, uterine or endometrial cancers, prostate cancers, and the like.

A method of the present disclosure may be used to treat CaP (e.g., androgen-stimulated CaP and CRPC) by inhibiting late-stage oxidoreductases in androgen biosynthesis and/or or impairing AR transactivation or AR dimerization. The methods described herein may be used to overcome AR-V7-mediated resistance when treating CRPC. A method of the present disclosure may inhibit growth of CaP cells better than methods comprising treating with enzalutamide alone.

Compounds of the present disclosure may be used in a method for treating diseases associated with malignant cells (for example, CaP) and/or hyperplastic cells (for example, benign prostatic hyperplasia or hypertrophy (BPH)). The compounds described either inhibit terminal-substrate conversion to DHT or impair AR transactivation or AR dimerization. The compounds may be used with or in place of current CaP therapies, such as bicalutamide, enzalutamide, or abiraterone.

In various examples, one or more compounds and/or one or more compositions comprising one or more compounds described herein are be administered to a subject in need of treatment using any known method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration. Topical and/or transdermal administrations are also encompassed.

A method may be carried out in a subject in need of treatment who has been diagnosed with or is suspected of having CaP (e.g., a male subject (e.g., individual) having CaP). A method may also be carried out in a subject who have a relapse or a high risk of relapse after being treated for CaP. The subject may be referred to as an individual.

A method of treating a disease (e.g., cancer, such as, for example, a hormonal cancer, such as, for example, prostate cancer, such as for example, castration-resistant prostate cancer, such as for example, castration-resistant prostate cancer expressing AR-V7) comprises administering to a subject in need of a treatment (e.g., an individual in need of treatment) a therapeutic amount (e.g., an amount of compound or composition sufficient to treat the subject) of a compound or composition of the present disclosure, where the subject's disease is treated.

In various examples, a compound of the present disclosure is used to inhibit the growth of cells (e.g., malignant cells, such as, for example, cancer cells, such as, for example, a hormonal cancer cells, such as, for example, prostate cancer cells, such as for example, castration-resistant prostate cancer cells, such as for example, castration-resistant prostate cancer cells expressing AR-V7 or hyperplastic cell, such as, for example, (e.g., benign prostatic hyperplasia or hypertrophy (BPH) cells)). For example, growth of cancer cells (e.g., prostate cancer cells, such as, for example, castration-resistant prostate cancer cells, such as for example, castration-resistant prostate cancer cells expressing AR-V7) is inhibited by contacting the cancer cells with a compound in an amount (e.g., 1 nM to 1 mM) and time sufficient to cause degradation of androgen receptor (AR) in the cancer cells, where the degradation of AR results in inhibition of growth of the cancer cells. The inhibition of growth may be better than the inhibition of cell growth caused by other compounds/treatments known in the art (e.g., treatment with enzalutamide). Inhibition of cell growth refers to any decrease in growth/reproduction of a cell (e.g., the growth/reproduction of cancer cells).

A method of inhibiting cell growth comprises contacting a cell with a compound of the present disclosure or a composition comprising a compound of the present disclosure.

The present disclosure provides methods to induce selective degradation of a target protein. A method to induce selective degradation of a target protein comprises: i) contacting a cell (e.g., a cell in a subject in need of treatment) with a compound and/or a composition of the present disclosure, where the compound binds to an E3 ligase and to a target protein in a cell.

A subject in need of treatment or individual in need of treatment may be a human or non-human mammal. Non-limiting examples of non-human mammals include cows, pigs, mice, rats, rabbits, cats, dogs, or other agricultural animals, pets, service animals, and the like. In various examples, the subject or individual is a male or has male reproductive organs. In various examples, the subject or individual has a prostate.

Contacting and/or administration methods of the present disclosure may be performed in combination with contacting and/or administration with one or more additional drugs. Additional drugs may be chosen from anti-androgen drugs, 5α-reductase drugs, androgen metabolism inhibitor drugs, and combinations thereof. Non-limiting examples of anti-androgen drugs include flutamide, bicalutamide, enzalutamide, apalutamide, darolutamide, dilutamide, and the like, and combinations thereof. Non-limiting examples of 5α-reductase drugs include finasteride, dutasteride, and the like, and combinations thereof. Non-limiting examples of androgen metabolism drugs include abiraterone acetate, abiraterone acetate fine particle, ketoconazole, and the like, and combinations thereof.

Compounds of the present disclosure may be used as tools for screening small-molecule inhibitors of oxidoreductases or small-molecule anti-androgens that bind to AR.

In an example, the compounds and compositions are suitable in methods involving fluorescence microscopy. Methods involving fluorescence microscopy can be combined with other techniques, such as flow cytometry. Techniques for fluorescence microscopy are known in the art. For example, such techniques can be used to monitor cellular activity (e.g., androgen metabolism).

A method comprising molecular tracking (e.g., intracellular tracking) in a cell (e.g., a prostate cell) comprises contacting the cell (e.g., prostate cell) with a compound of the present disclosure and imaging (e.g., imaging using fluorescence microscopy) the cell (e.g., the prostate cell) at regular intervals (e.g., intervals known in the art) to monitor activity. In an example, activity is androgen metabolism.

In an aspect, the disclosure provides kits. In various examples, a kit comprises a pharmaceutical preparation containing any one or any combination of compounds of the present disclosure. In an example, the instant disclosure includes a closed or sealed package that contains the pharmaceutical preparation. In various examples, the package comprises one or more closed or sealed vials, bottles, blister (bubble) packs, or any other suitable packaging for the sale, distribution, or use of the pharmaceutical compounds and compositions comprising them. The printed material may include printed information. The printed information may be provided on a label, on a paper insert, or printed on packaging material. The printed information may include information that identifies the compound in the package, the amounts and types of other active and/or inactive ingredients in the composition, and instructions for taking the compound and/or composition. The instructions may include information, such as, for example, the number of doses to take over a given period of time, and/or information directed to a pharmacist and/or another health care provider, such as a physician, or a patient. The printed material may include an indication that the pharmaceutical composition and/or any other agent provided therein is for treatment of a subject having CaP and/or other diseases and/or any disorder associated with cancer and/or other diseases. In various examples, the kit includes a label describing the contents of the kit and providing indications and/or instructions regarding use of the contents of the kit to treat a subject having any cancer and/or other diseases.

In various examples, kits comprise materials that can be used for administration to individuals in need of CaP treatment. A kit, for example, can comprise one or more therapeutics that may be in a lyophilized form, optionally reconstitution media, and instructions for administration. A kit can comprise a single dose or multiple doses.

The steps of the method described in the various embodiments and examples disclosed herein are sufficient to carry out the methods of the present disclosure. The methods described in the embodiment are a combination of steps of the disclosed methods. In another embodiment, the method consists of such steps.

The following Statements provide examples of compounds of the present disclosure, methods using compounds of the present disclosure, and uses of compounds of the present disclosure.

Statement 1. A compound having the following structure:

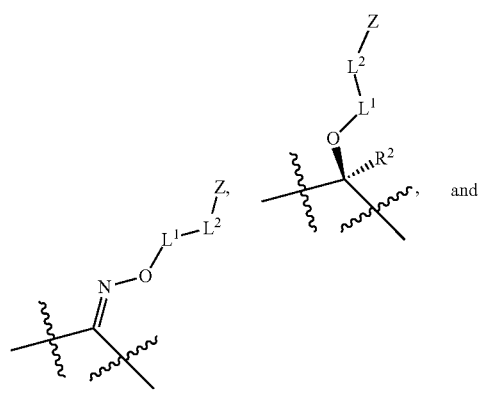

where $R^1$ is hydrogen or an alkyl group (e.g., methyl group, ethyl group, n- and isopropyl group, and the like); $R^3$ is chosen from a carbonyl,

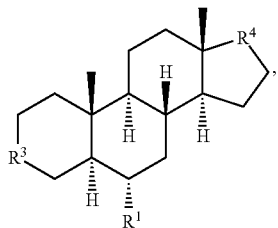

where X is hydroxyl and Y is hydrogen or an alkyl group (e.g., methyl group, ethyl group, n- and isopropyl group, and the like) or X and Y together are a spiro-fused, substituted or unsubstituted coumarin group or coumarin isostere group, and $L^3$ is optional and is a linking group; $R^4$ is chosen from a carbonyl,

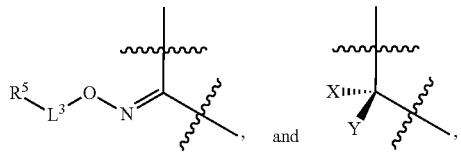

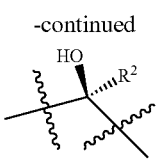

where $L^1$ is a linking group, $L_2$ is optional and is a linking group, Z is an end group comprising a substituted or unsubstituted carbocyclic group or a substituted or unsubstituted heterocyclic group or substituted or unsubstituted coumarin group or substituted or unsubstituted coumarin isostere group, and $R^2$ is an alkyl group or hydrogen; and $R^5$ is a photoactive group, with the proviso that when $R^3$ is a carbonyl or

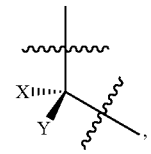

where X is hydroxyl and Y is hydrogen or an alkyl group, that $R^4$ is not

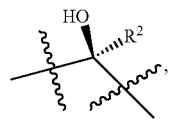

or a carbonyl.

Statement 2. A compound according to Statement 1, where $L^1$ and/or $L^2$ and/or $L^3$ independently are chosen from:

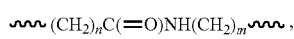

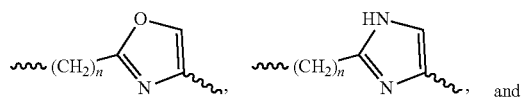

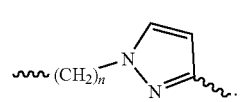

where n is 1, 2, 3, 4, 5, or 6 and m is 1, 2, 3, 4, 5, or 6.

Statement 3. A compound according to Statement 1 or Statement 2, where the compound has the following structure:

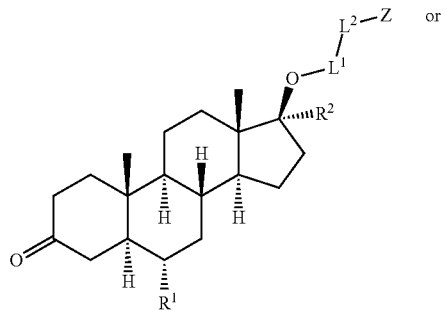
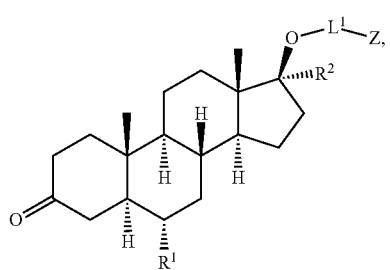
where Z is chosen from:
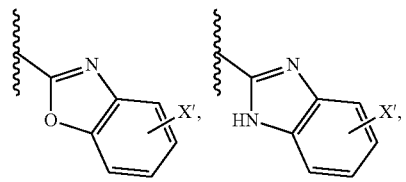
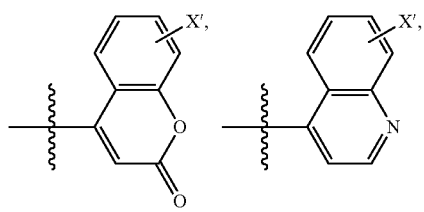
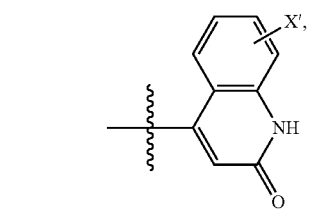
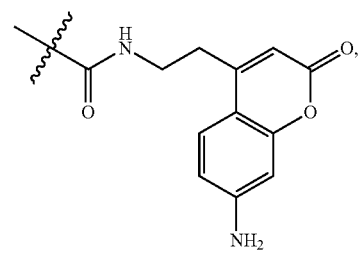
-continued
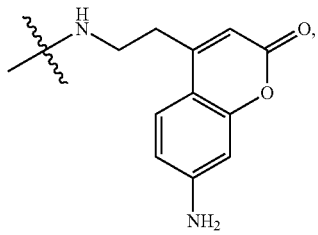
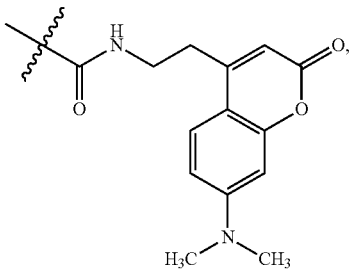
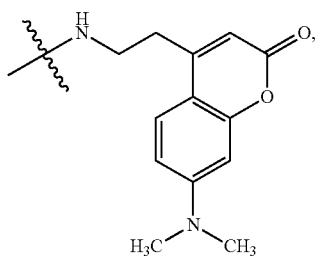
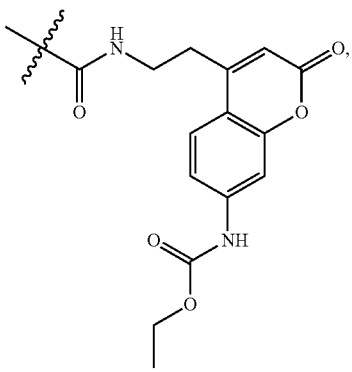
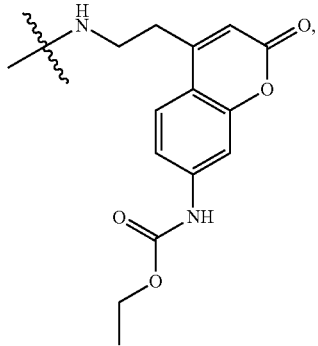

-continued
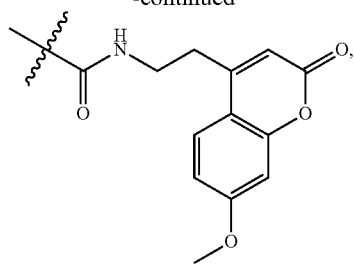
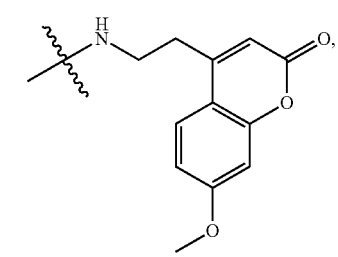
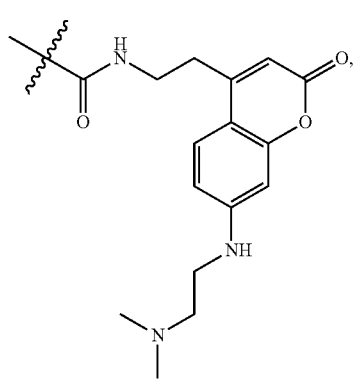
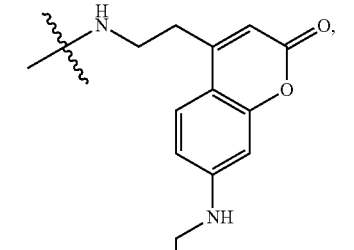
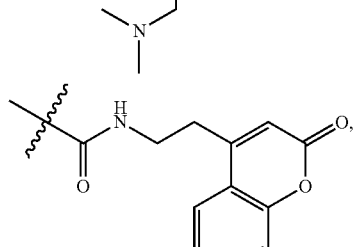
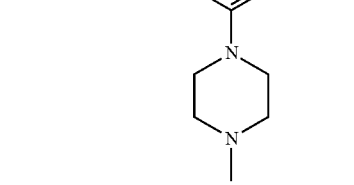
-continued
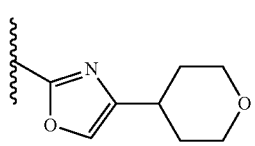
and substituted variants thereof,
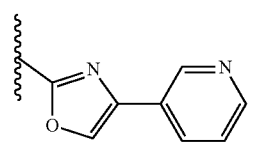 [SMILES: *c1nc(-c2cccnc2)co1]
and substituted variants thereof,
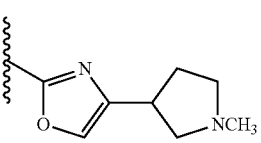
and substituted variants thereof,
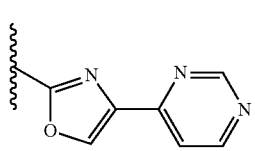 [SMILES: *c1nc(-c2ccncn2)co1]
and substituted variants thereof,
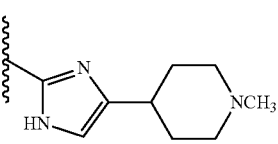 [SMILES: *c1nc(C2CCN(C)CC2)c[nH]1]
and substituted variants thereof,

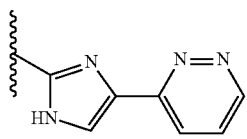 [SMILES: *c1nc(-c2cccnn2)c[nH]1]

and substituted variants thereof,

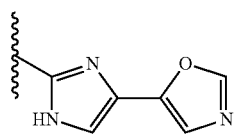

and substituted variants thereof,

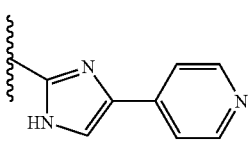 [SMILES: *c1nc(-c2ccncc2)c[nH]1]

and substituted variants thereof, and

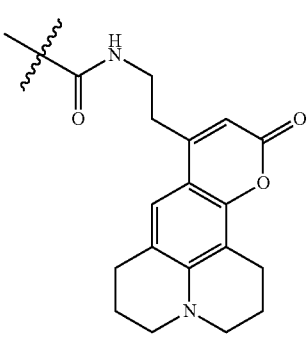 [SMILES: *C(=O)NCCc1cc(=O)oc2c3c4c(cc12)CCCN4CCC3]

and substituted variants thereof,
where X' is independently at each occurrence chosen from hydrogen, alkyl groups, cycloalkyl groups, alkoxy groups, halogens, and combinations thereof.

Statement 4. A compound according to any one of the preceding Statements, where the compound has the following structure:

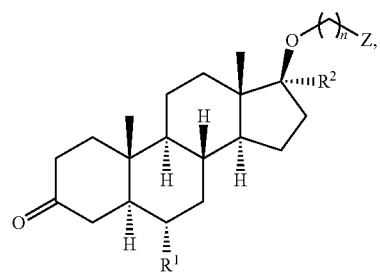

where n is 1, 2, or 3.

Statement 5. A compound according to any one of the preceding Statements, where the compound has the following structure:

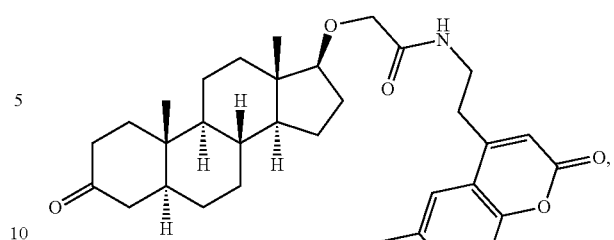

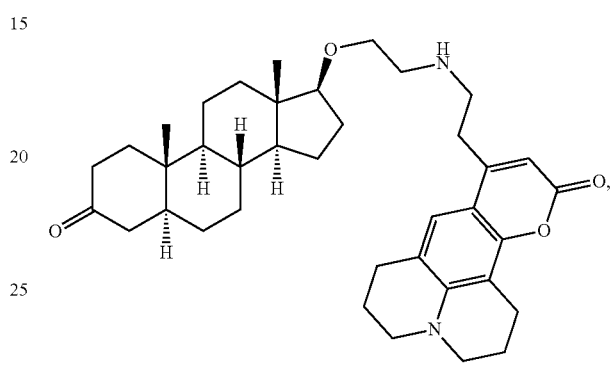

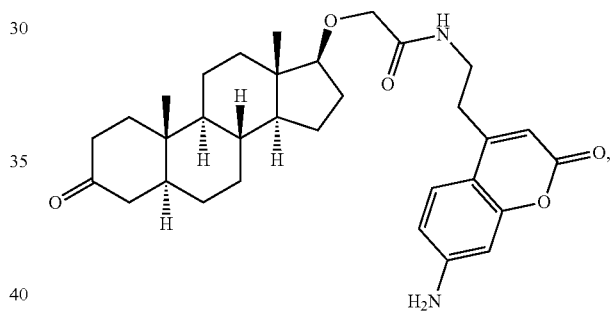

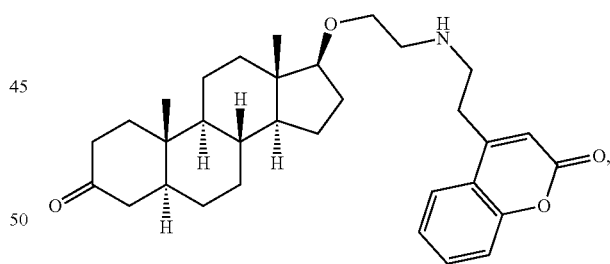

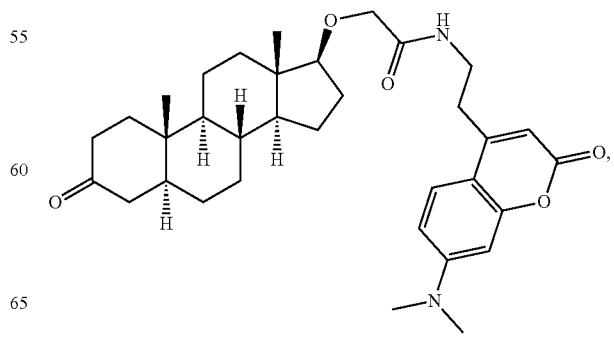

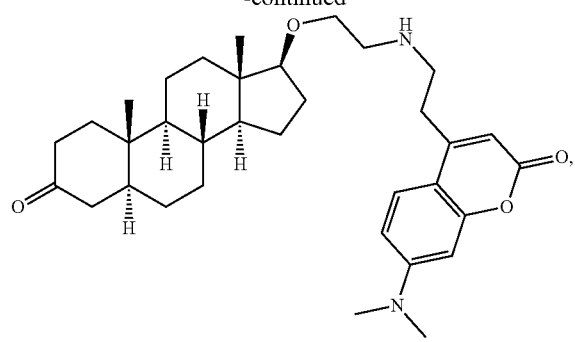
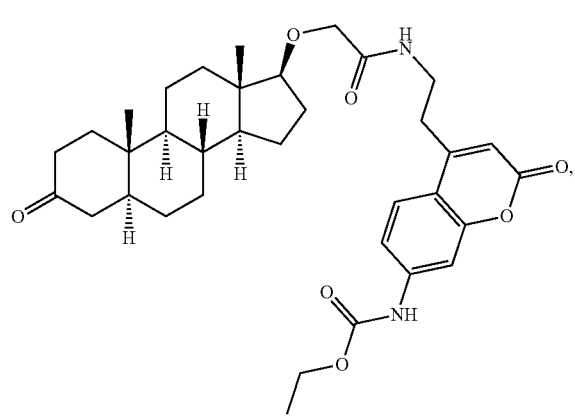
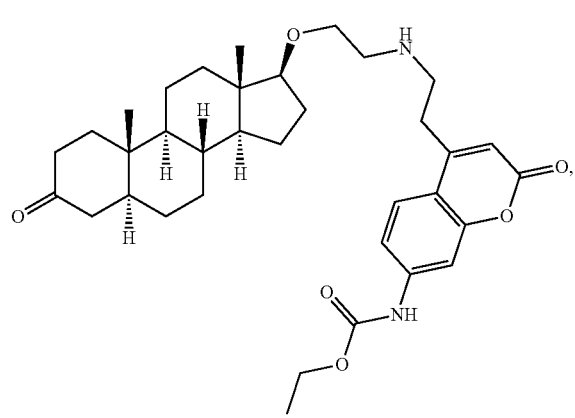
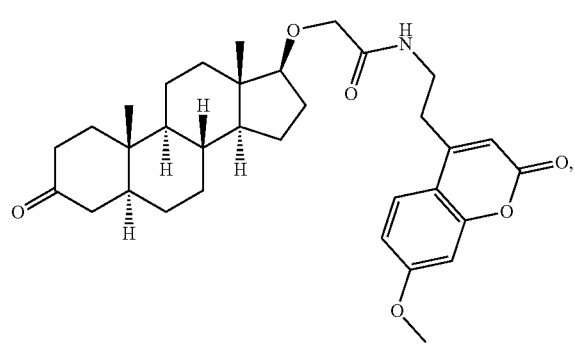
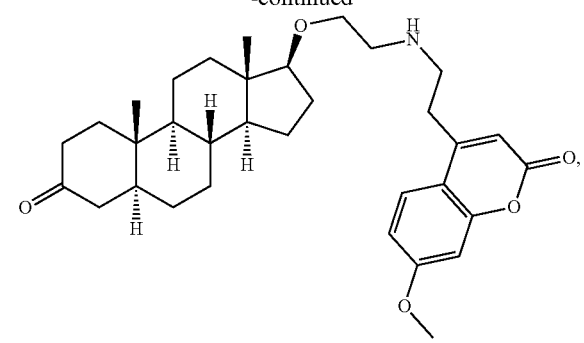
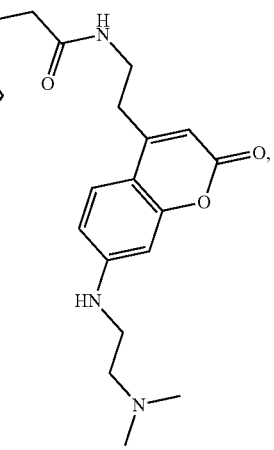
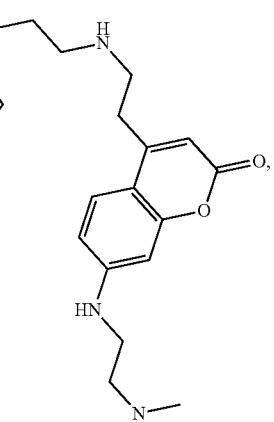
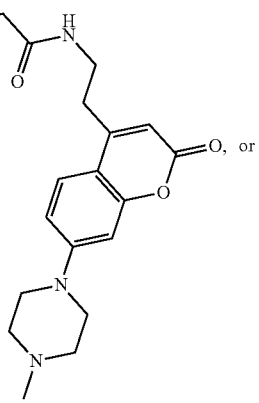

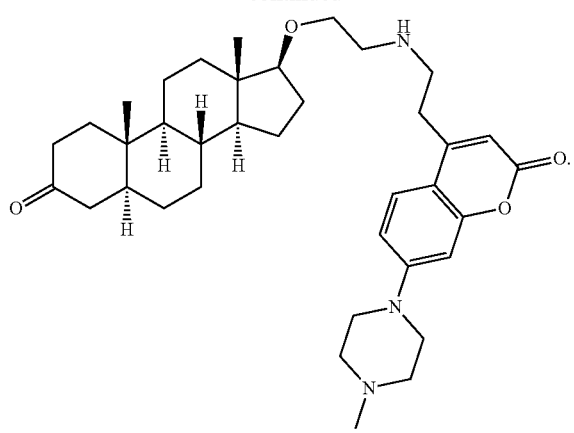

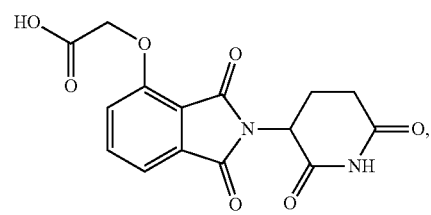

Statement 6. A compound according to Statement 1, where the compound has the following structure:

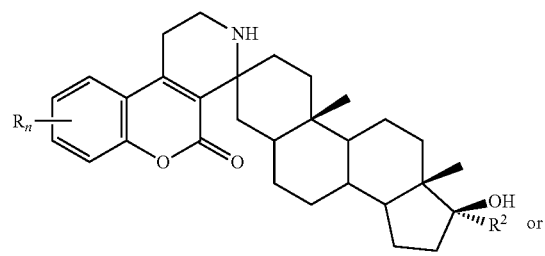

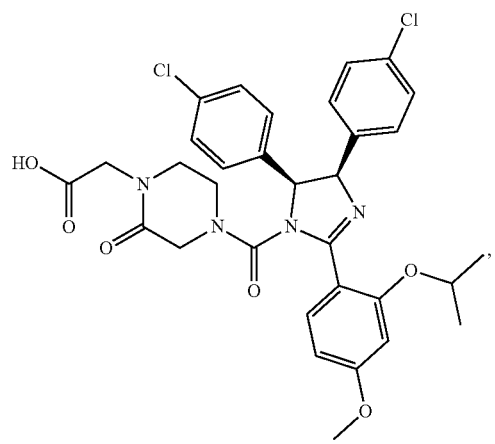

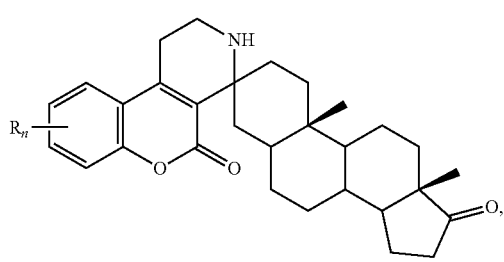

where R is independently chosen from $L^1$-A, $R^5$, —OH, —NH$_2$, —CO$_2$Et, —CN, —CHO, —SO$_3$H, and —CO$_2$H, or three vicinal R groups form a fused cyclic ring system

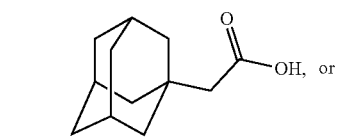

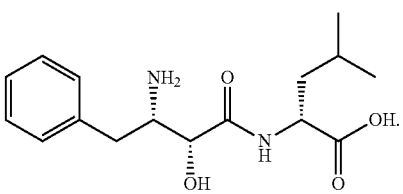

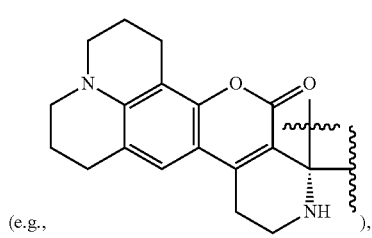

and n is 1, 2, 3, or 4, and $L^1$ is a linking group and A is an E3 ligase recruiter group, where only one R is $L^1$-A.

Statement 7. A compound according to Statement 1 or Statement 6, where A is formed from:

Statement 8. A compound according to Statement 6, where A is formed from ligase recruiter groups that bind cereblon, von Hippel-Lindau (VHL), or Mouse-Double-Minute-2.

Statement 9. A compound according to any one of Statement 1 or Statement 6, where the compound has the following structure:

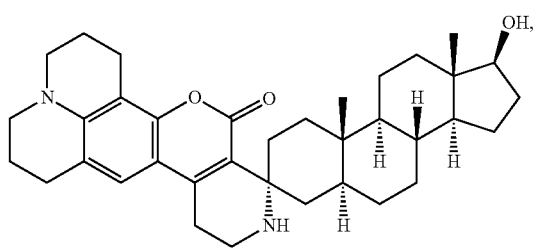
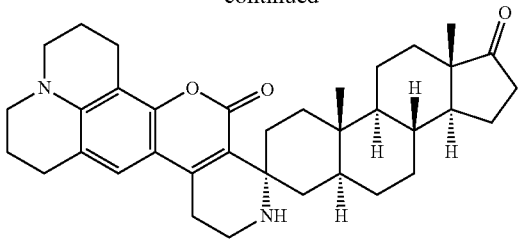
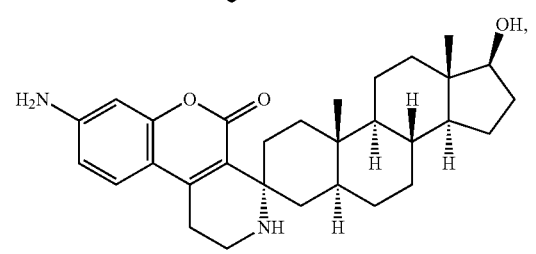
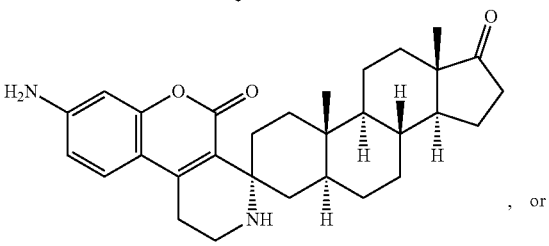
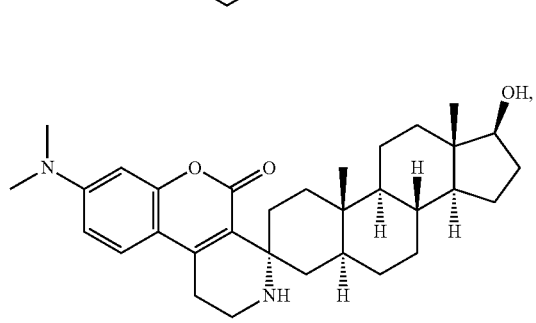
Statement 10. A compound according to Statement 1 or Statement 6, where the compound has the following structure:
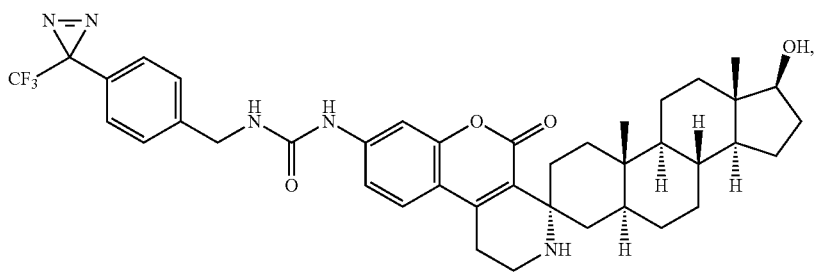
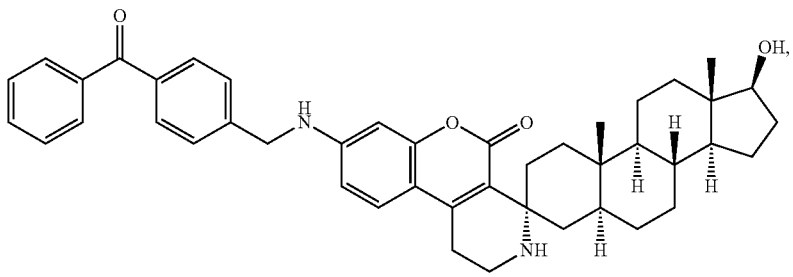
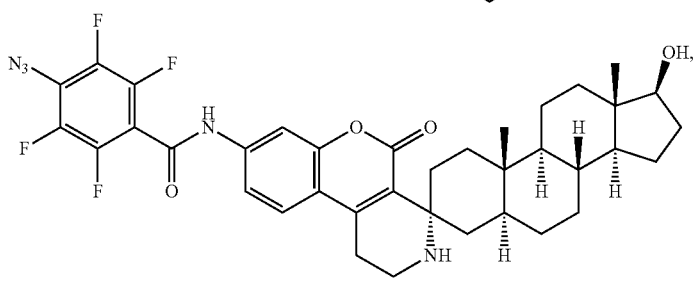

-continued
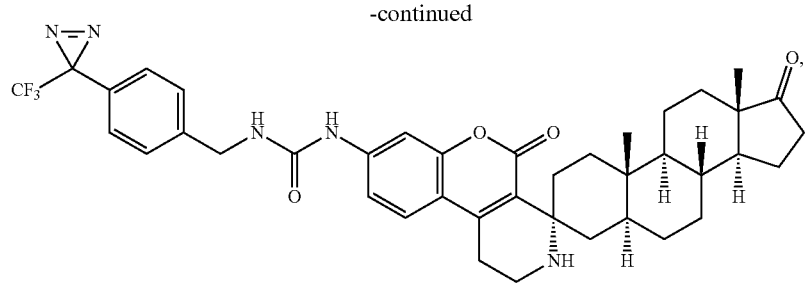
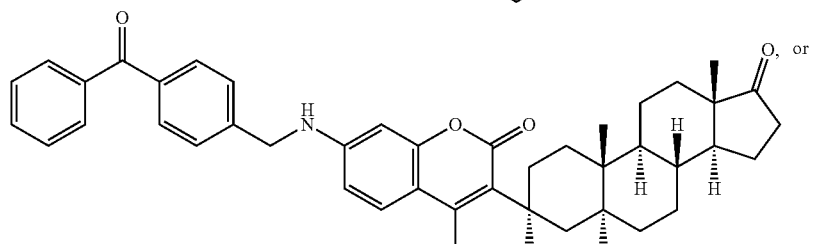
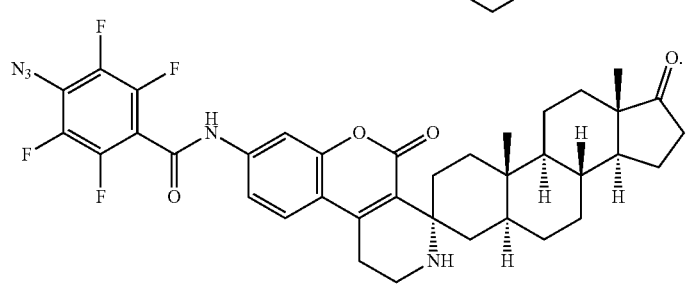
Statement 11. A compound according to Statement 1, where the compound has the following structure:
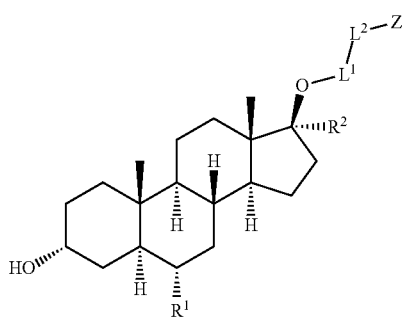
or
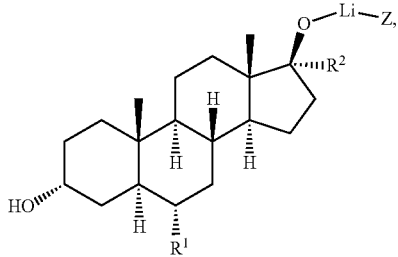
where Z is chosen from:
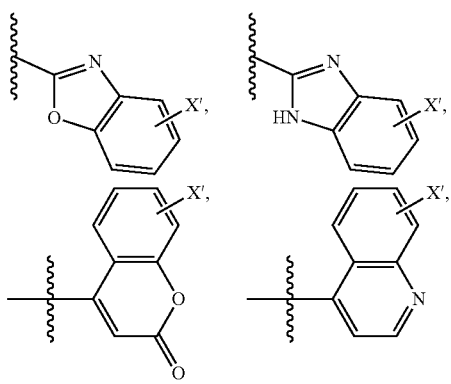
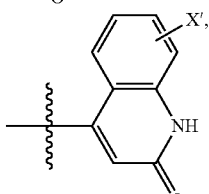
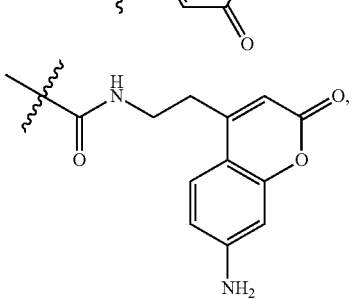

67
-continued
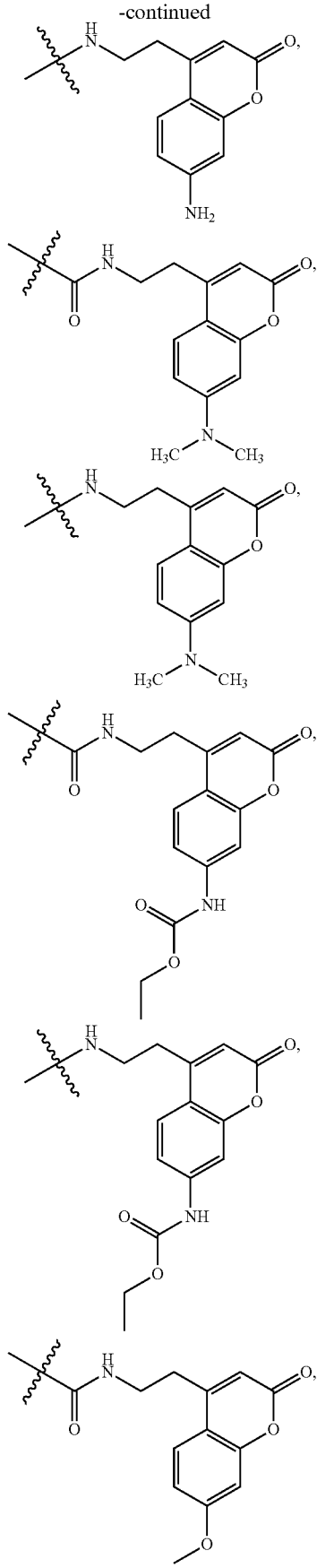
68
-continued
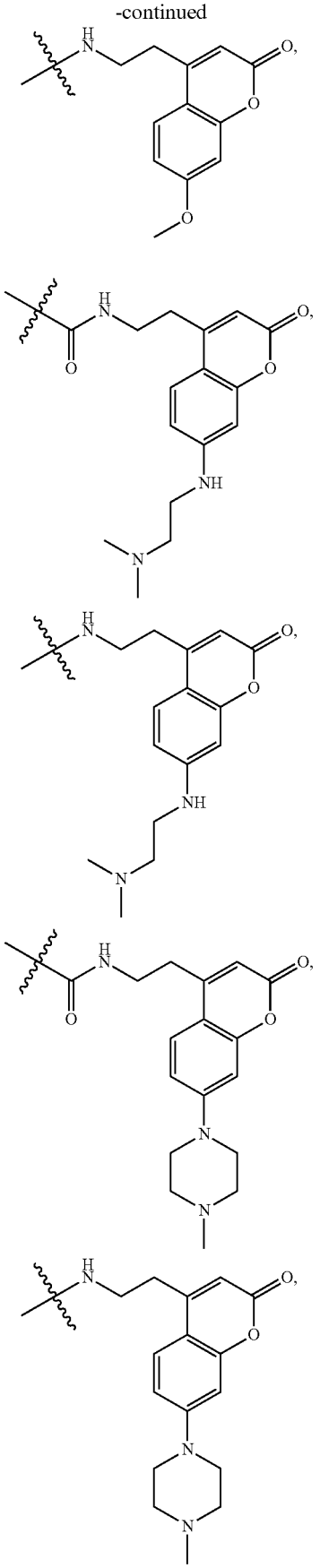

-continued

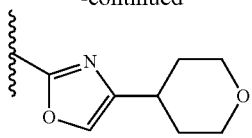

and substituted variants thereof,

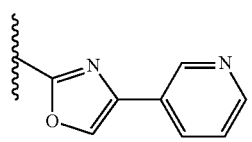

and substituted variants thereof,

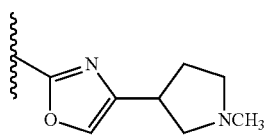 [SMILES: *c1nc(C2CCN(C)C2)co1]

and substituted variants thereof,

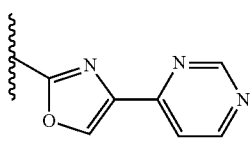 [SMILES: *c1nc(-c2ccncn2)co1]

and substituted variants thereof,

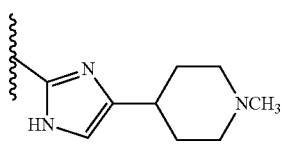 [SMILES: *c1nc(C2CCN(C)CC2)c[nH]1]

and substituted variants thereof,

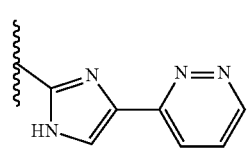 [SMILES: *c1nc(-c2cccnn2)c[nH]1]

and substituted variants thereof,

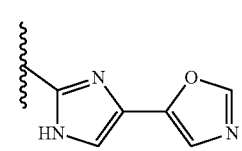 [SMILES: *c1nc(-c2cnco2)c[nH]1]

and substituted variants thereof,

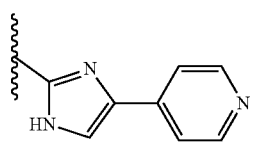 [SMILES: *c1nc(-c2ccncc2)c[nH]1]

and substituted variants thereof, and

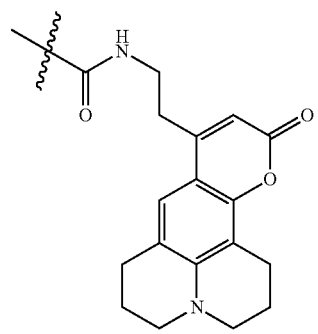 [SMILES: *C(=O)NCCc1cc(=O)oc2c3c4c(cc12)CCCN4CCC3]

and substituted variants thereof, where X' is independently at each occurrence chosen from hydrogen, alkyl groups, cycloalkyl groups, alkoxy groups, halogens, and combinations thereof.

Statement 12. A compound according to Statement 1 or Statement 11, where the compound has the following structure:

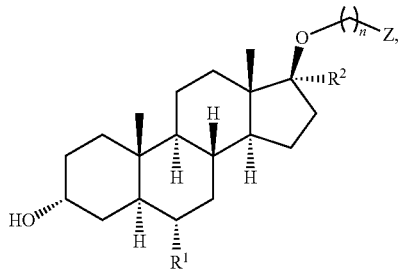

where n is 1, 2, or 3.

Statement 13. A compound according to Statement 1 or Statements 11-12, where the compound has the following structure:

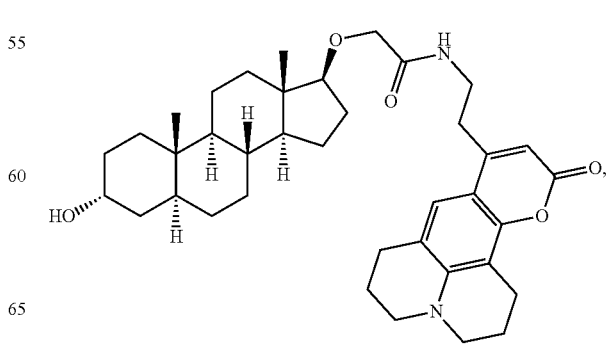

71
-continued
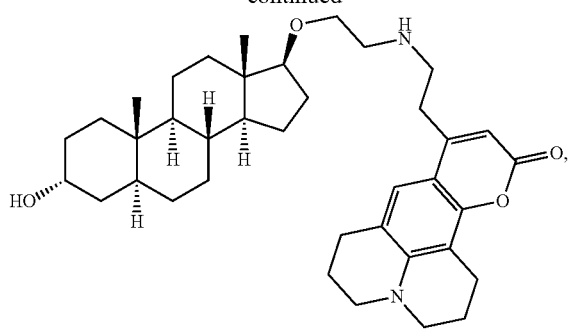
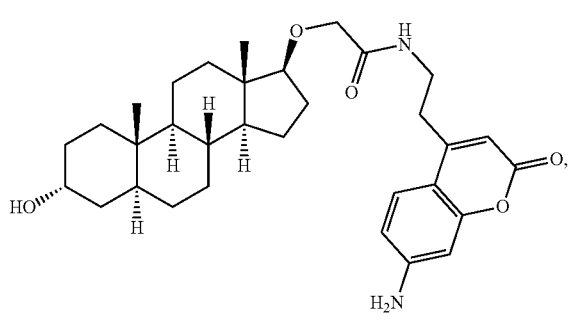
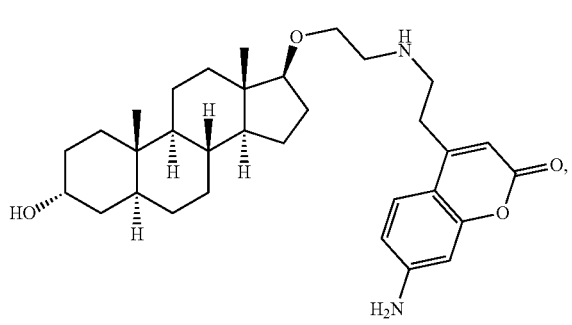
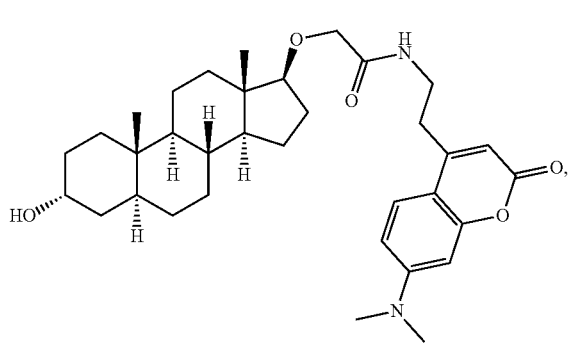
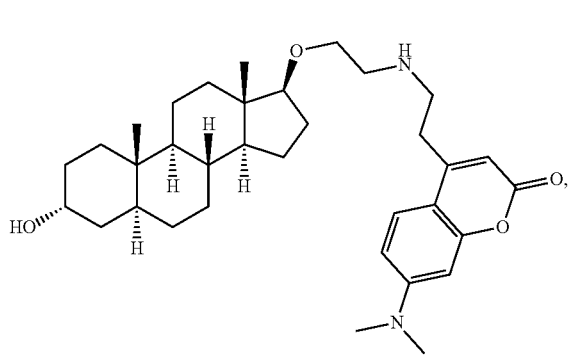
72
-continued
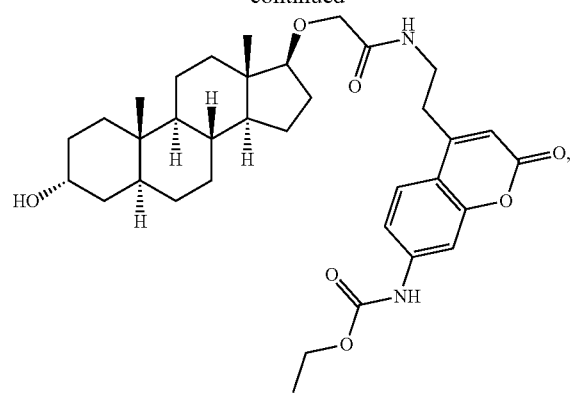
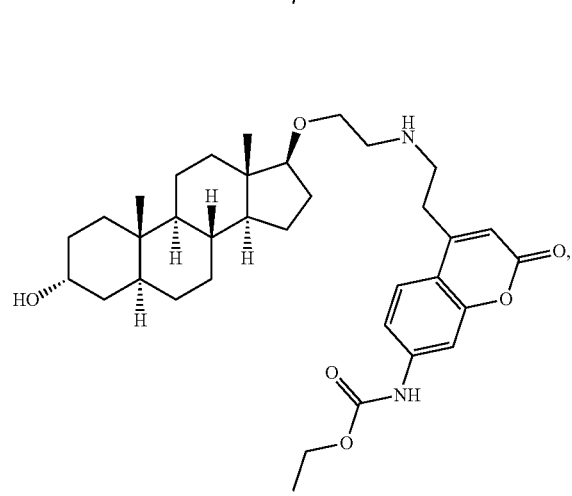
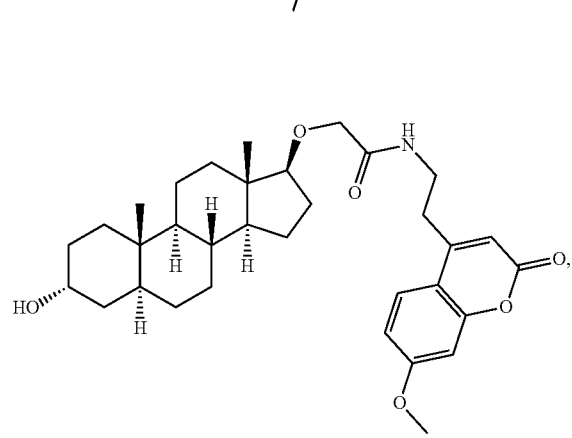
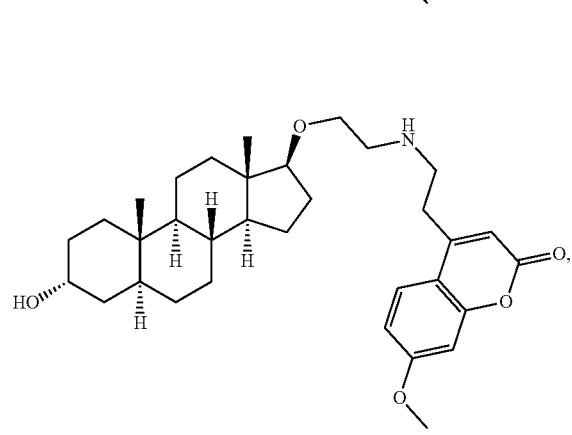

73
-continued
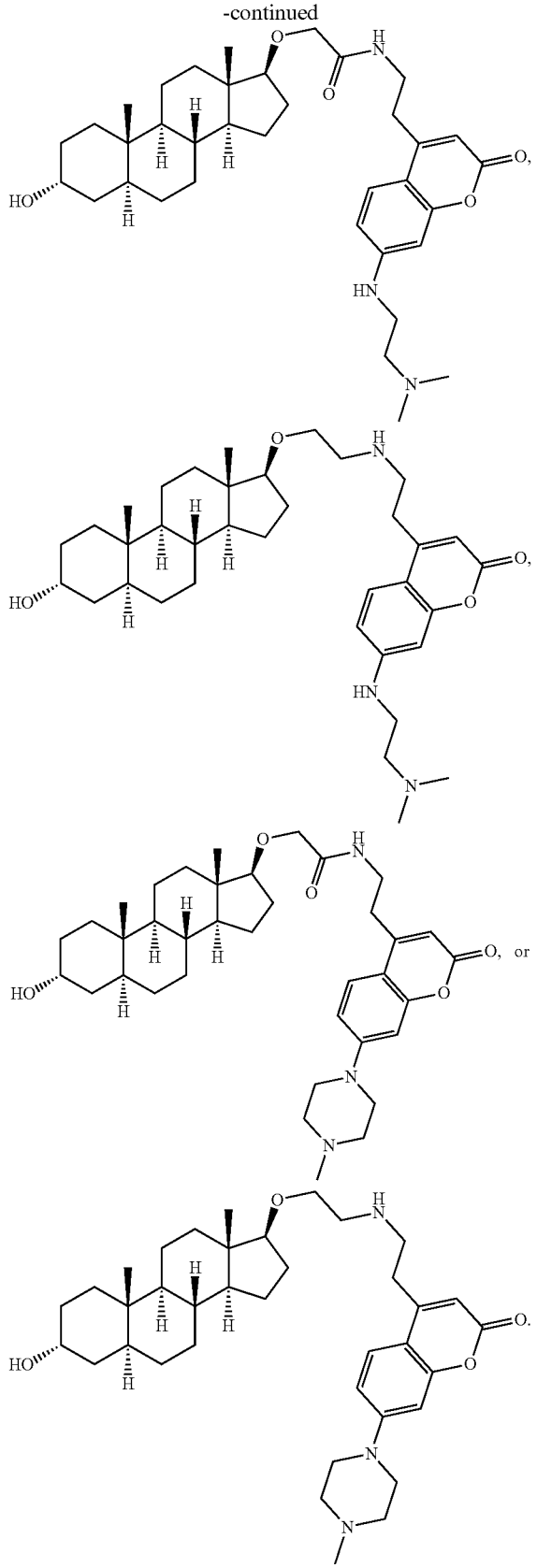
Statement 14. A compound according to Statement 1, where the compound has the following structure:
74
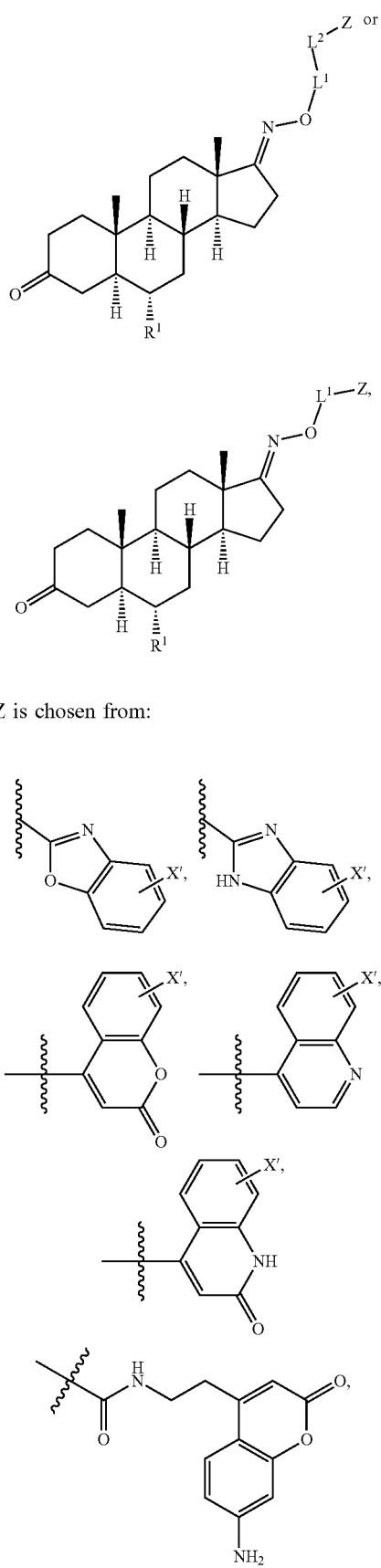
where Z is chosen from:

75
-continued
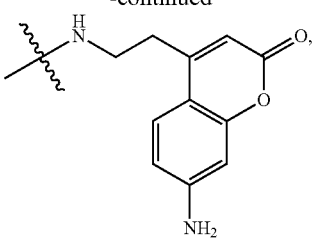
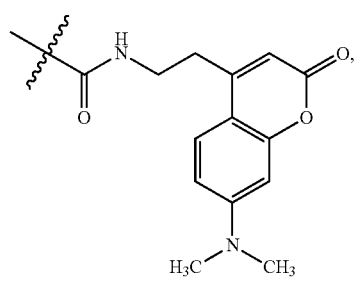
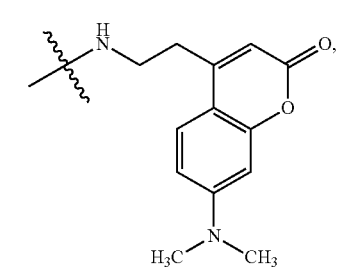
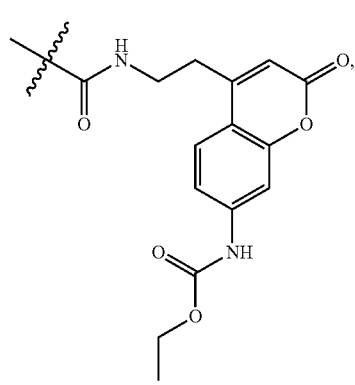
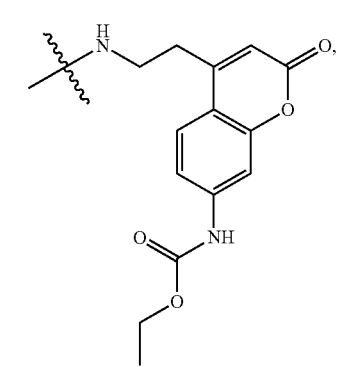
76
-continued
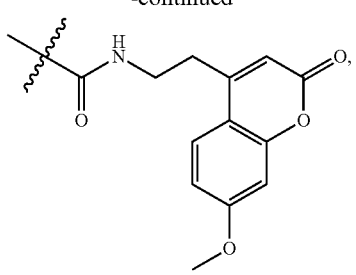
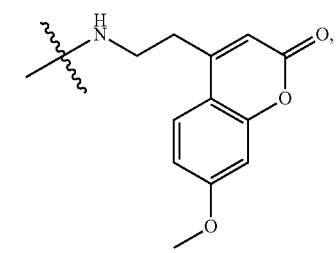
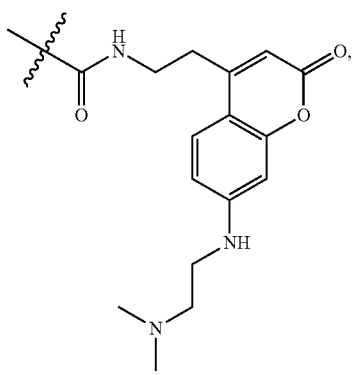
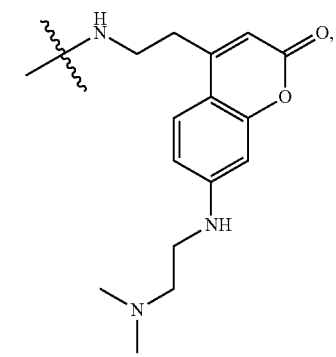
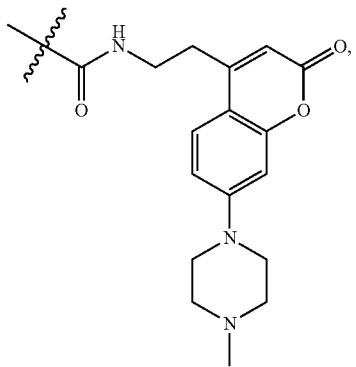

-continued

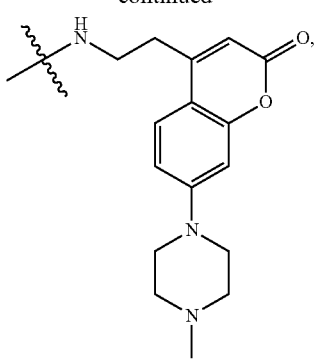

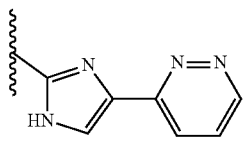 [SMILES: *c1nc(-c2cccnn2)c[nH]1]

and substituted variants thereof,

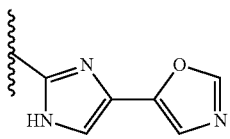 [SMILES: *c1nc(-c2cnco2)c[nH]1]

and substituted variants thereof,

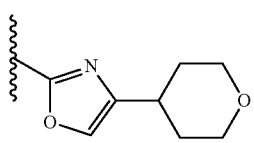

and substituted variants thereof,

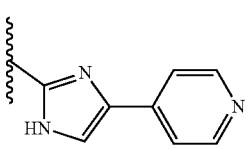 [SMILES: *c1nc(-c2ccncc2)c[nH]1]

and substituted variants thereof,

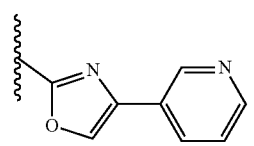

and substituted variants thereof, and

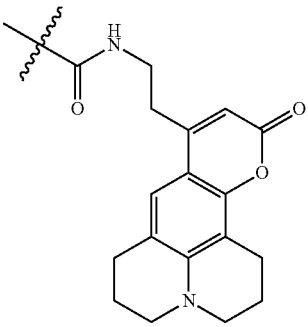 [SMILES: *C(=O)NCCc1cc(=O)oc2c3c4c(cc12)CCCN4CCC3]

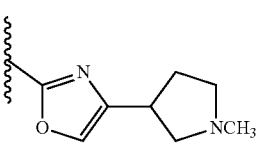

and substituted variants thereof,

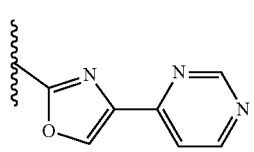

and substituted variants thereof,
where X' is independently at each occurrence chosen from hydrogen, alkyl groups, cycloalkyl groups, alkoxy groups, halogens, and combinations thereof.

Statement 15. A compound according to Statement 1 or Statement 14, where the compound has the following structure:

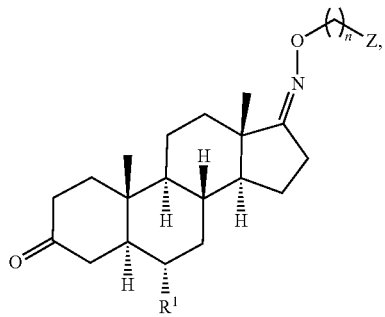

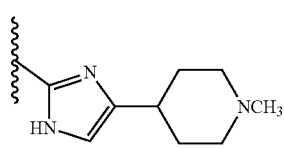

and substituted variants thereof, where n is 1, 2, or 3.

Statement 16. A compound according to Statement 1 or Statements 14-15, where the compound has the following structure:
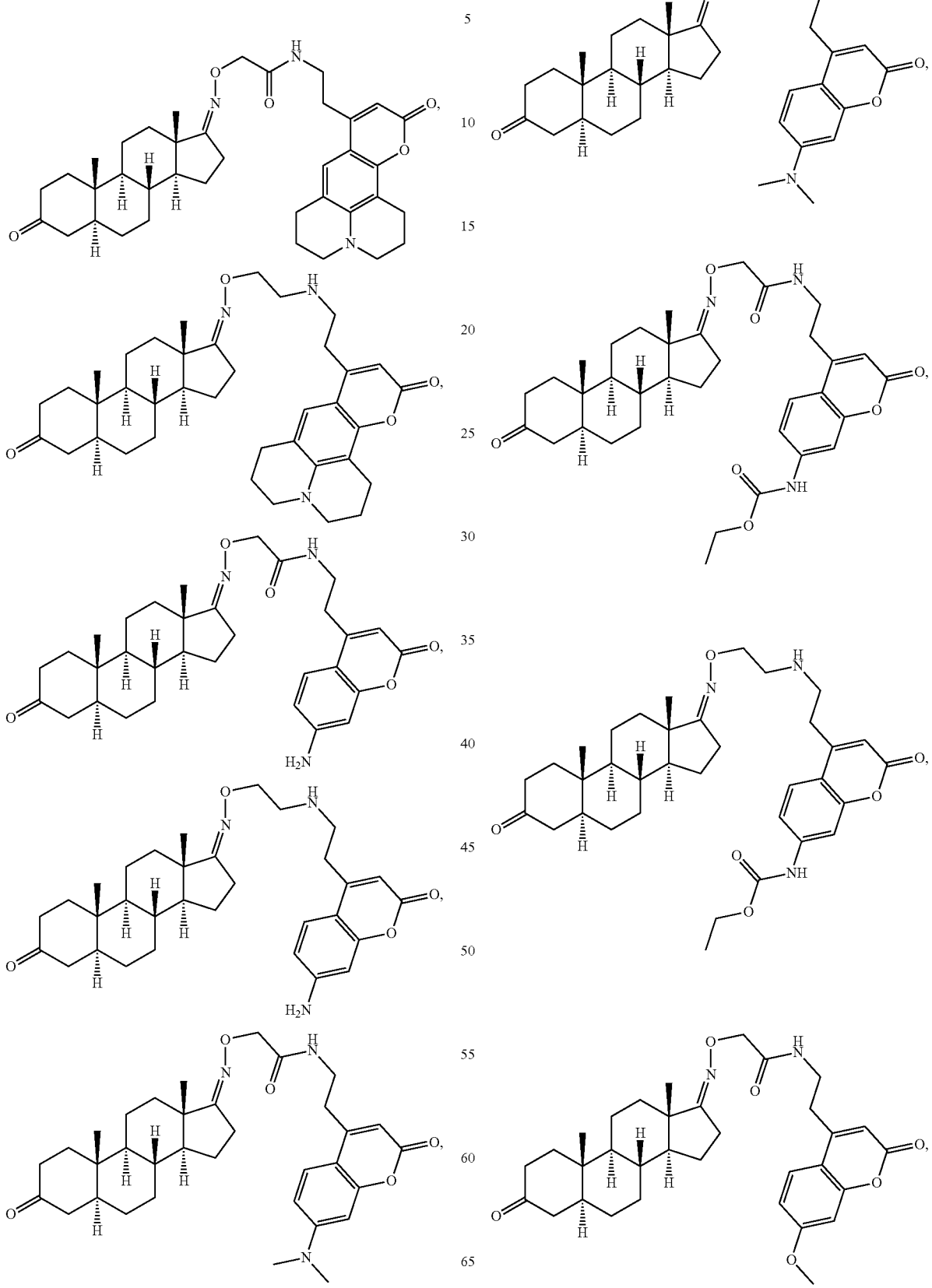

81
-continued
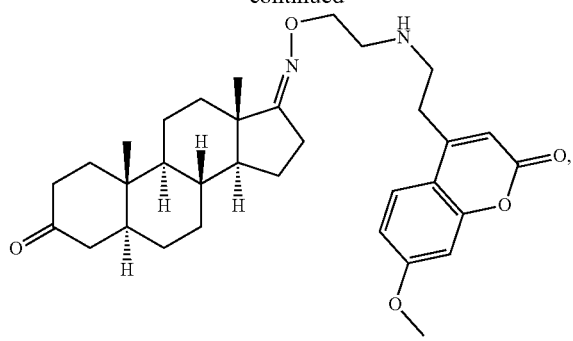
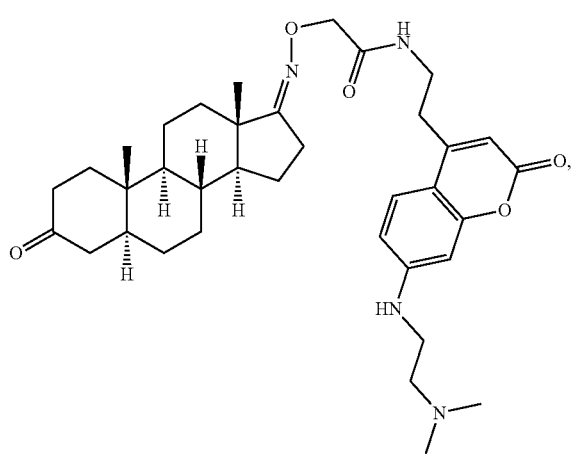
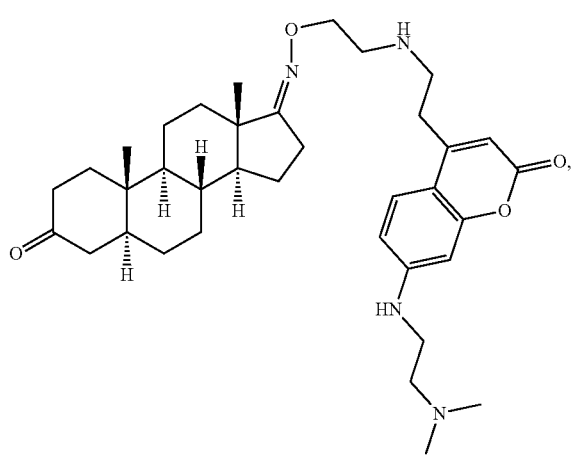
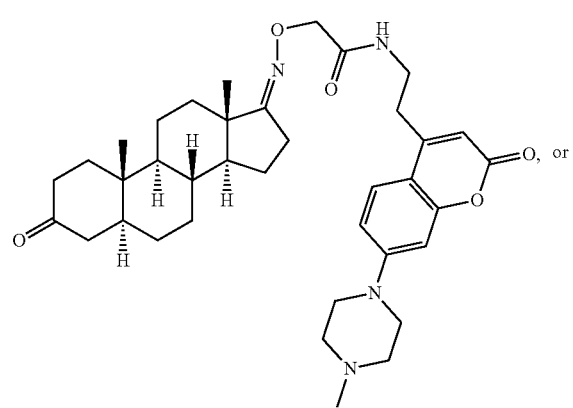
82
-continued
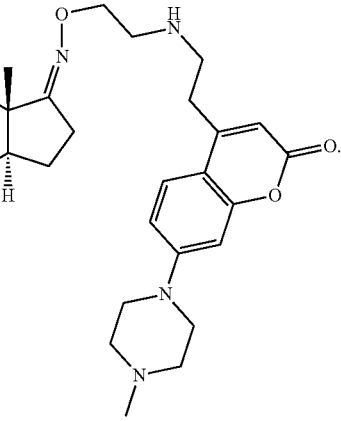
Statement 17. A compound according to Statement 1, where the compound has the following structure:
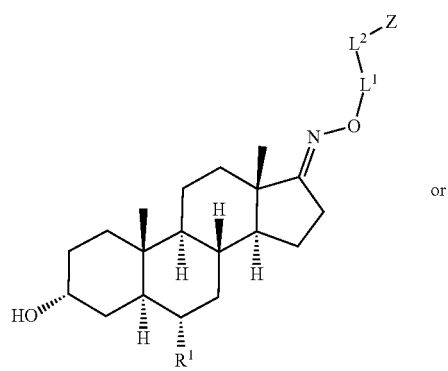
or
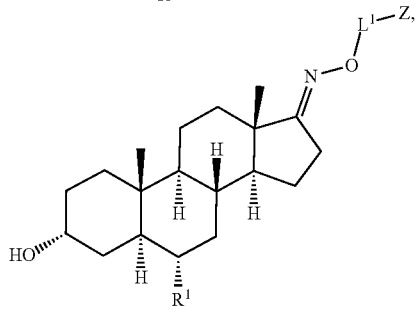
where Z is chosen from:
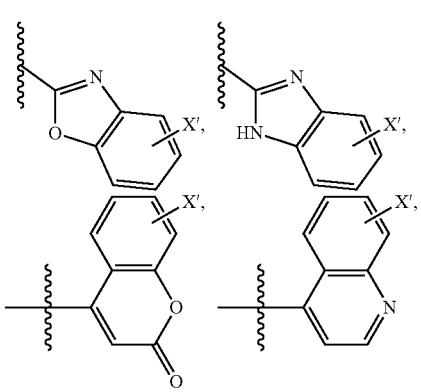

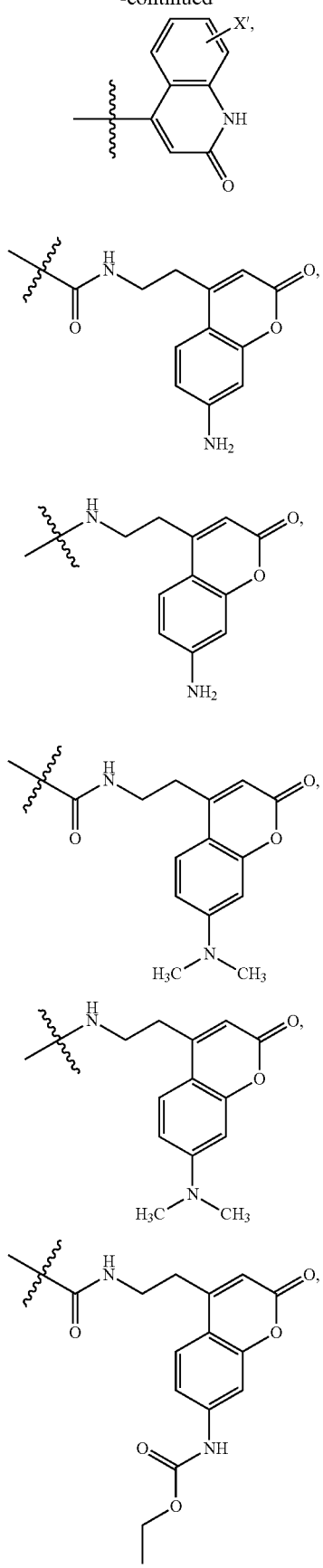
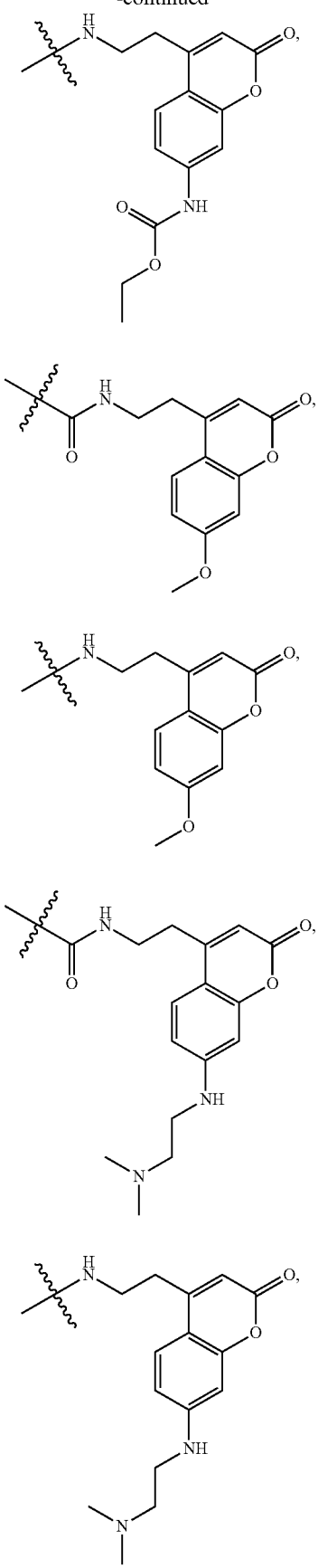

-continued

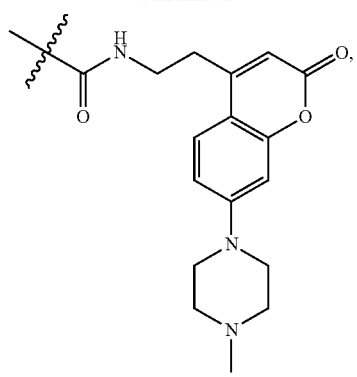

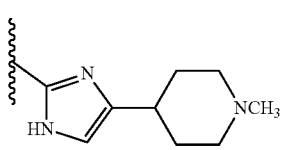

and substituted variants thereof,

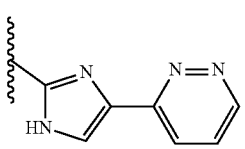

and substituted variants thereof,

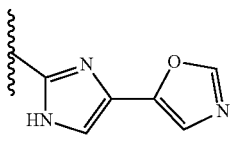

and substituted variants thereof,

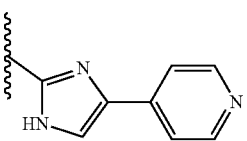

and substituted variants thereof, and

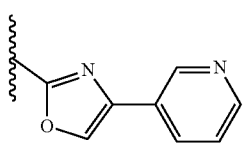 [SMILES: *c1nc(-c2cccnc2)co1]

and substituted variants thereof,

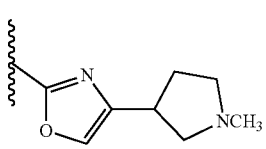 [SMILES: *c1nc(C2CCN(C)C2)co1]

and substituted variants thereof,

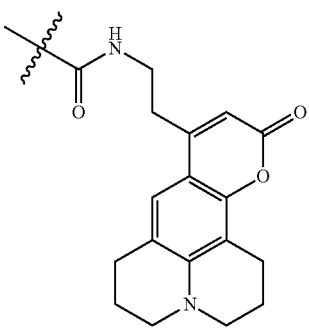 [SMILES: *C(=O)NCCc1cc(=O)oc2c3c4c(cc12)CCCN4CCC3]

and substituted variants thereof, where X' is independently at each occurrence chosen from hydrogen, alkyl groups, cycloalkyl groups, alkoxy groups, and/or halogens.

Statement 18. A compound according to Statement 1 or Statement 17, where the compound has the following structure:

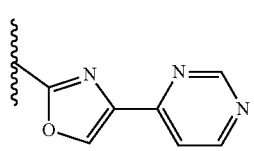

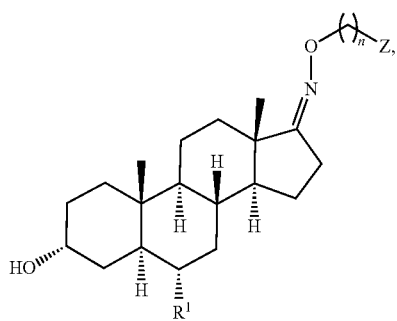
where n is 1, 2, or 3.
Statement 19. A compound according to Statement 1 or Statements 17-18, where the compound has the following structure:
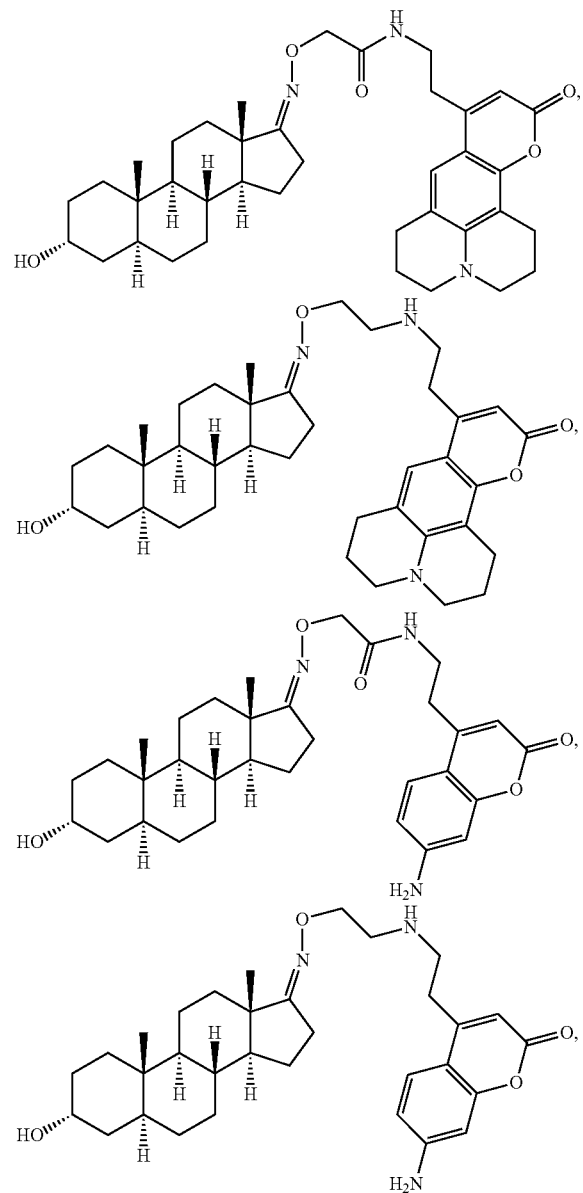
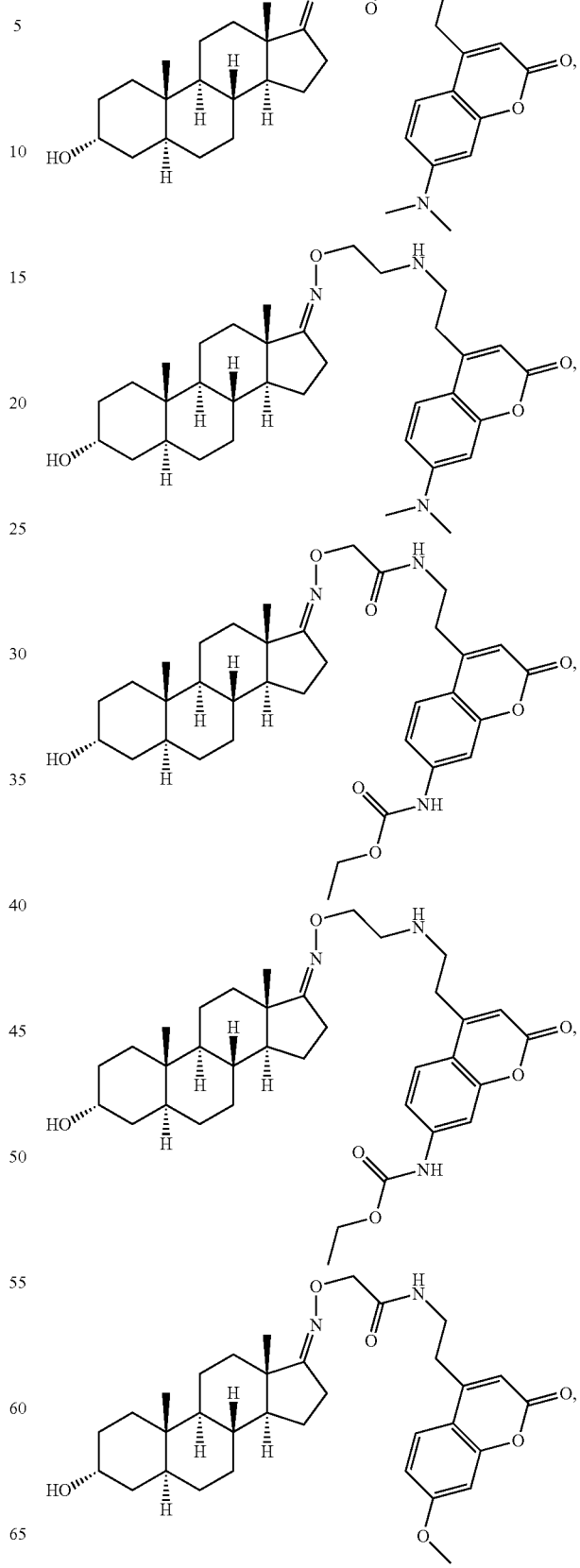

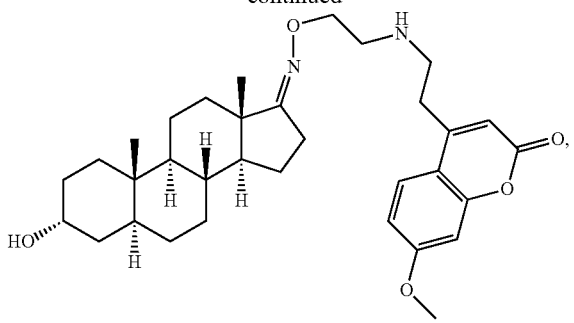
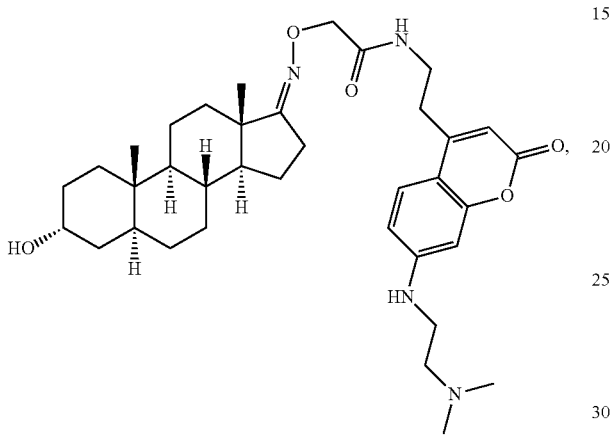
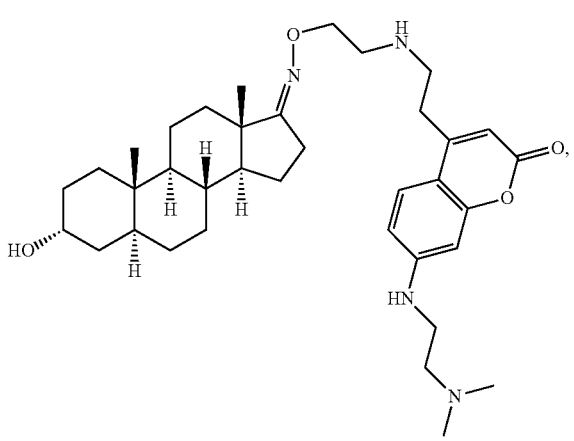
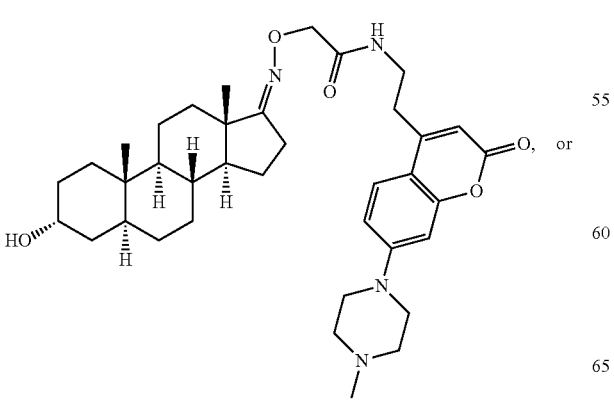
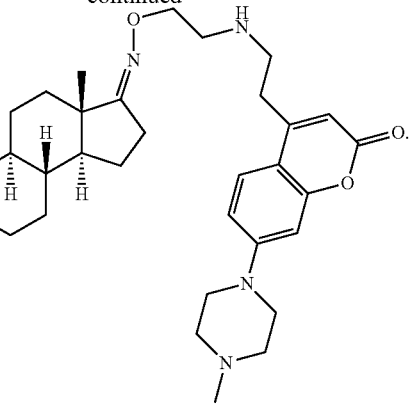
Statement 20. A compound according to 1, where the compound has the following structure:
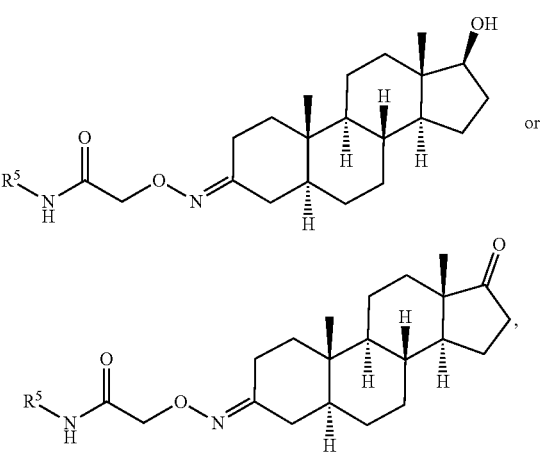
where $R^5$ is chosen from:
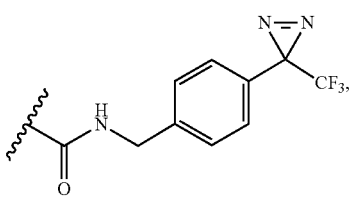
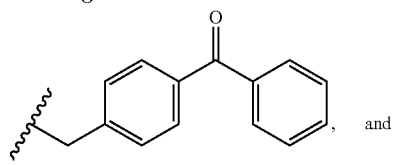
, and
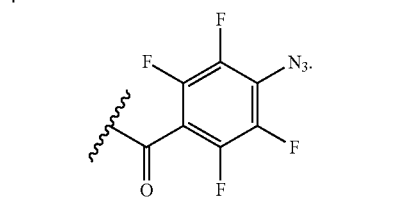
Statement 21. A compound according to Statement 1 or Statement 20, where the compound has the following structure:

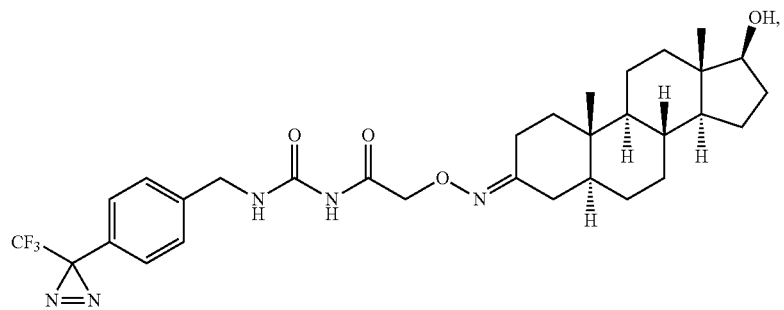
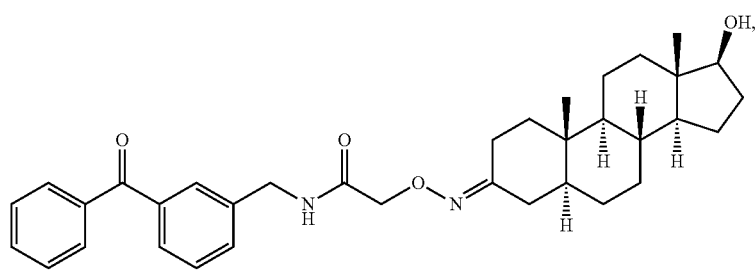
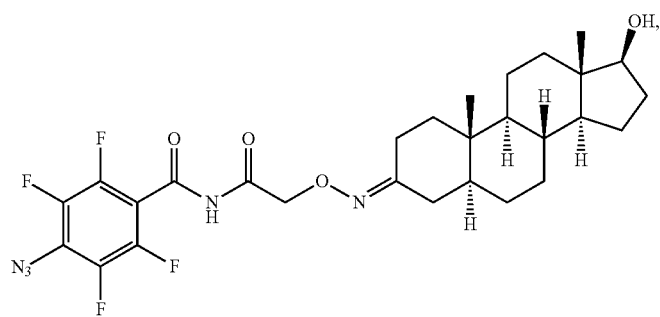
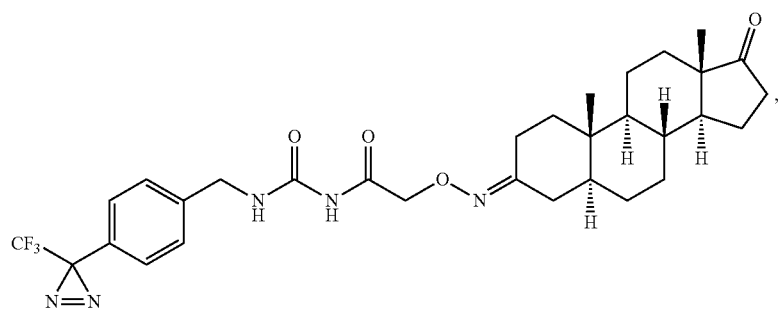
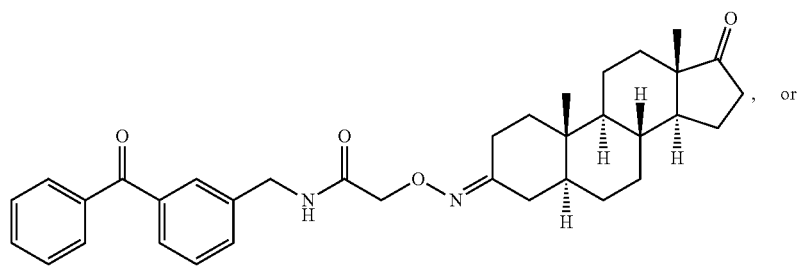
, or

-continued

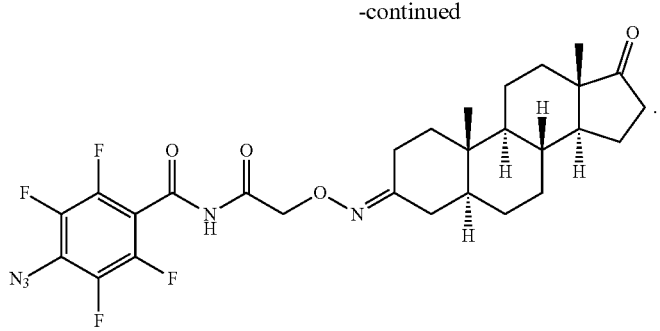

Statement 22. A composition comprising a compound according to any one of the preceding Statements and a pharmaceutically acceptable carrier.

Statement 23. A composition according to Statement 22, further comprising one or more additional drugs.

Statement 24. A composition according to Statement 23, where the one or more additional drugs are chosen from anti-androgen drugs, 5α-reductase drugs, androgen metabolism inhibitor drugs, and combinations thereof.

Statement 25. A composition according to any one of Statements 22-24, where the anti-androgen drugs are chosen from flutamide, bicalutamide, enzalutamide, apalutamide, darolutamide, dilutamide, and combinations thereof and/or the 5α-reductase drugs are chosen from finasteride, dutasteride, and combinations thereof and/or the androgen metabolism drugs are chosen from abiraterone acetate, abiraterone acetate fine particle, ketoconazole, and combinations thereof.

Statement 26. A composition according to any one of Statements 22-25, where the compound has the following structure:

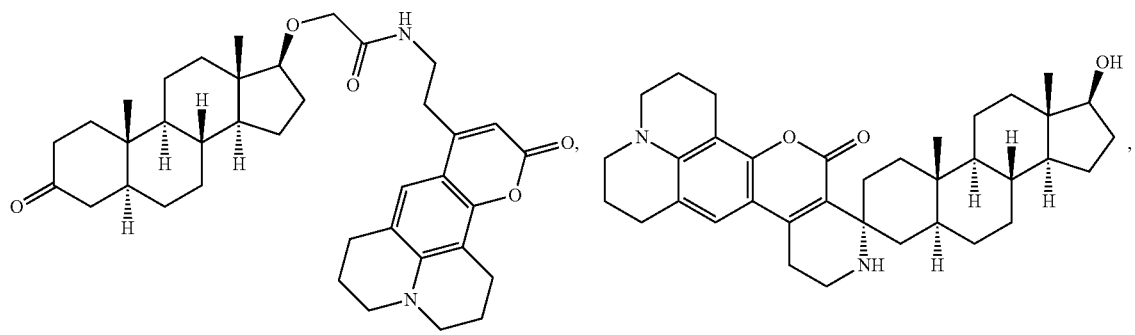

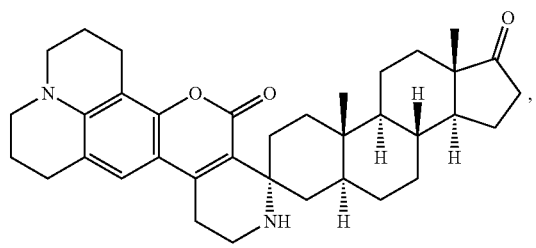

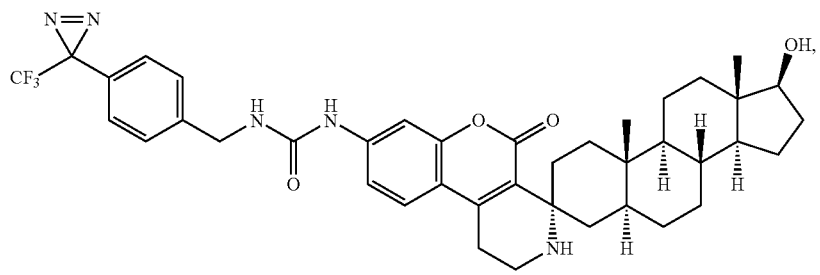

-continued
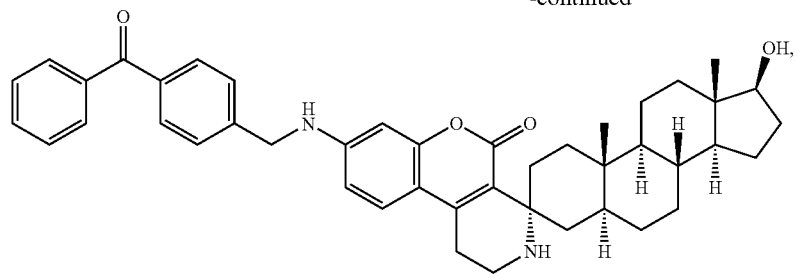
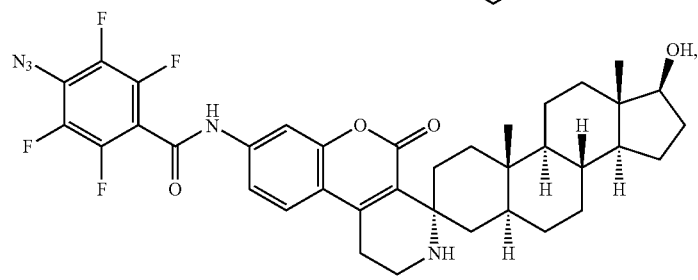
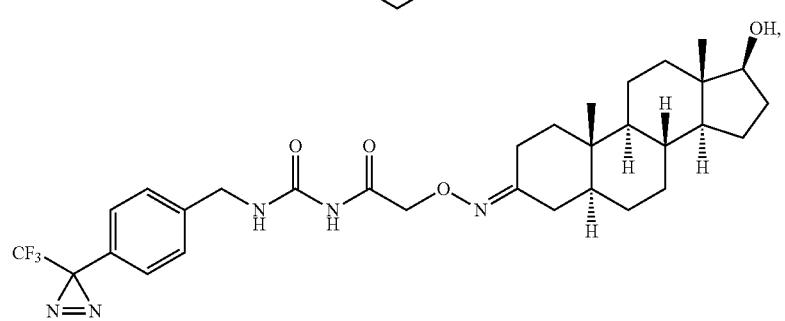
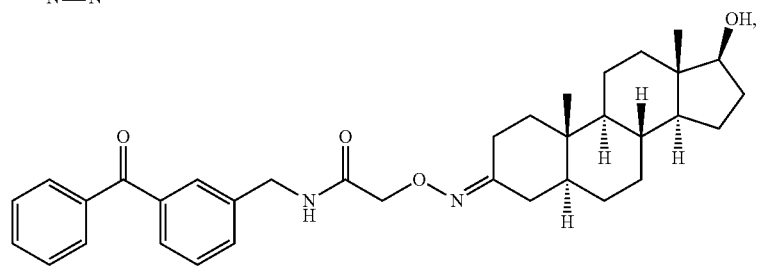
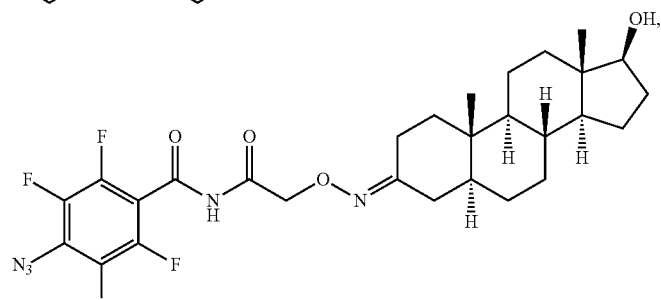
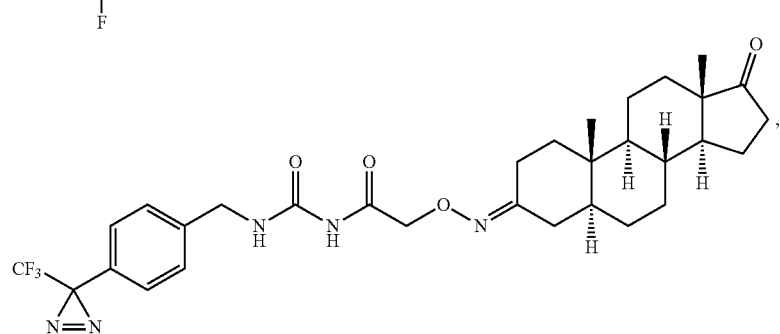

-continued

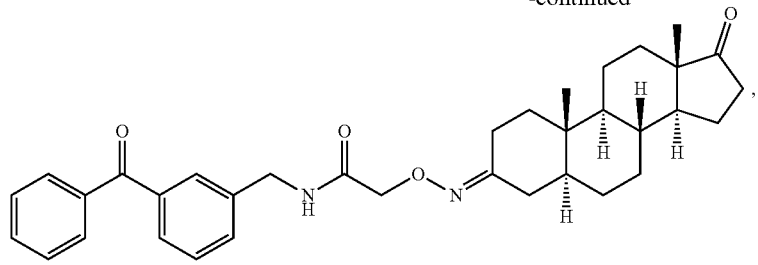

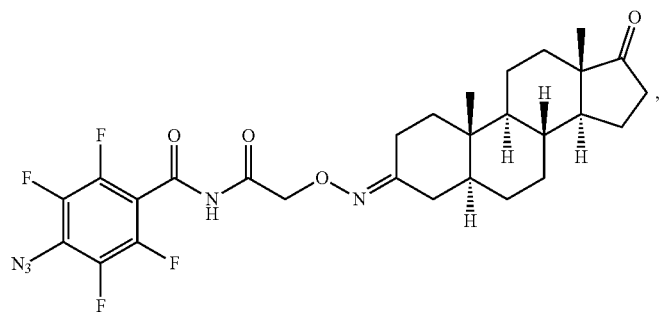

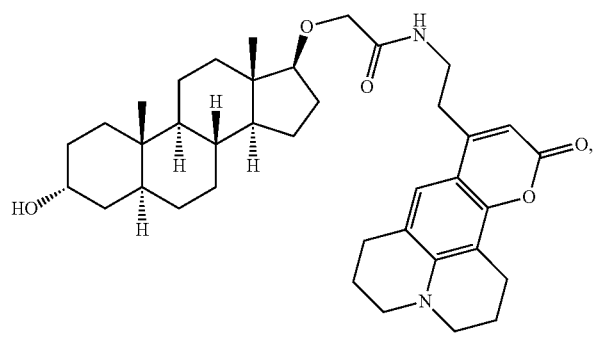

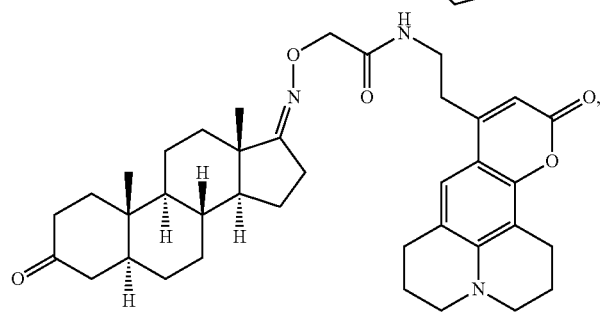

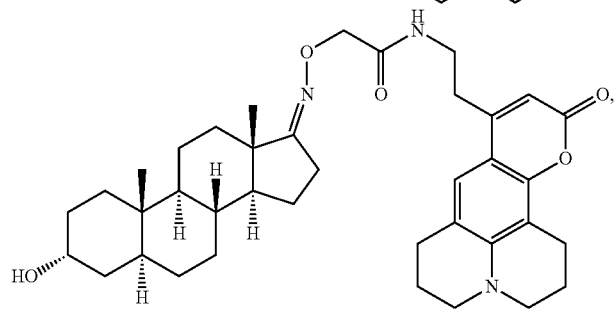

or a combination thereof.

Statement 27. A method of impairing androgen receptor (AR) transactivation and/or androgen receptor dimerization comprising: contacting a cell with a compound according to any one of Statements 1-21 or a composition according to any one of Statements 22-26 in an amount and time sufficient to impair androgen receptor transactivation and/or androgen receptor dimerization.

Statement 28. A method according to Statement 27, further comprising contacting the cell with flutamide, bicalutamide, enzalutamide, apalutamide, darolutamide, dilutamide, finasteride, dutasteride, or a combination thereof.

Statement 29. A method according to Statement 27 or Statement 28, where the compound has the following structure:

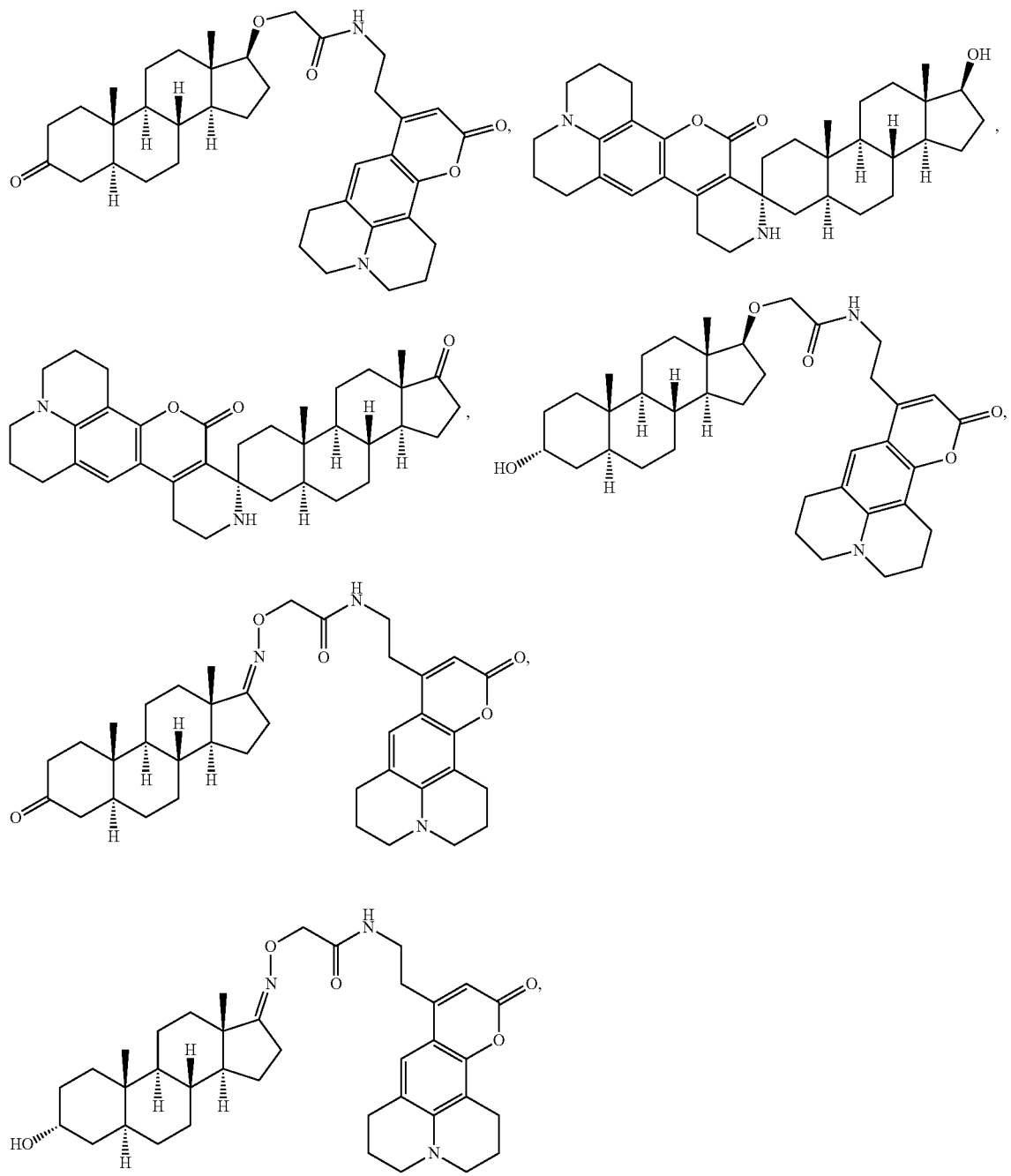

or a combination thereof.

Statement 30. A method of inhibiting cell growth comprising contacting a cell with a compound according to any one of Statements 1-21 or a composition according to any one of Statements 22-26 in an amount and time sufficient to inhibit cell growth.

Statement 31. A method according to Statement 30, further comprising contacting the cell with flutamide, bicalutamide, enzalutamide, apalutamide, darolutamide, dilutamide, finasteride, dutasteride, abiraterone acetate, abiraterone acetate fine particle, ketoconazole, or a combination thereof.

Statement 32. A method according to Statement 30 or Statement 31, where the compound has the following structure:

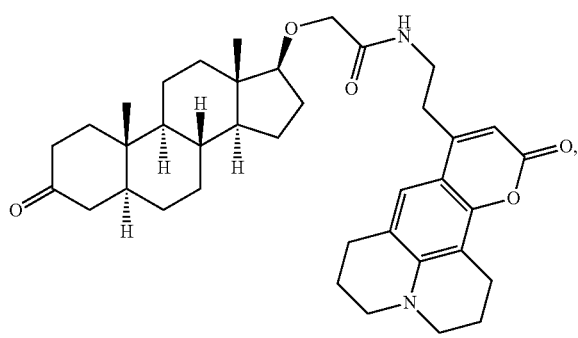
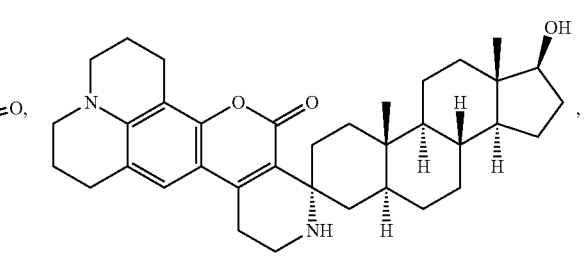
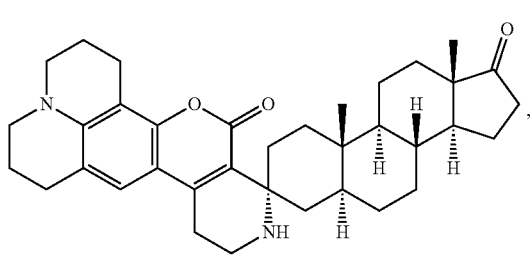
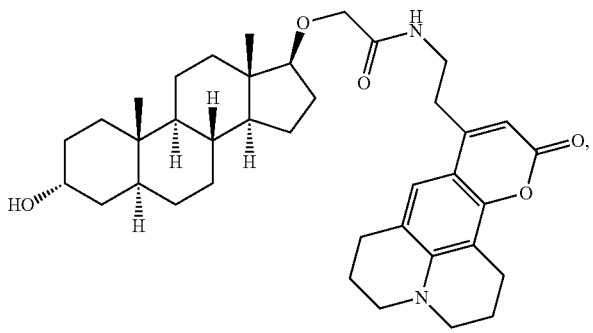
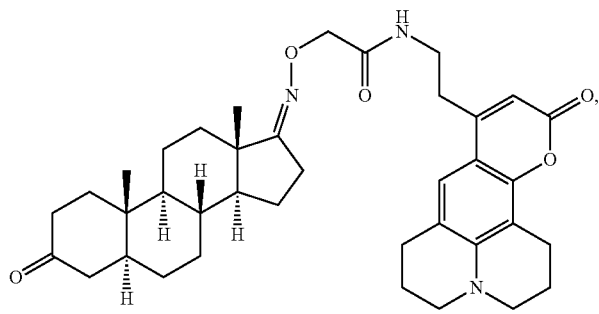
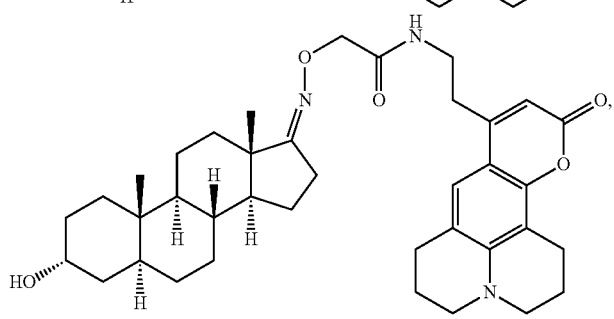

or a combination thereof.

Statement 33. A method according to Statement 31 or Statement 32, where the cell growth inhibited is malignant cell growth and/or hyperplastic cell growth.

Statement 34. A method according to any one of Statements 31-33, where the cell growth (e.g., malignant cell growth and/or hyperplastic cell growth) is cancer cell growth.

Statement 35. A method according to any one of Statements 31-34, where the cell growth (e.g., malignant cell growth and/or hyperplastic cell growth, which may be cancer cell growth) is a hormonal cancer cell growth.

Statement 36. A method according to Statement 35, where the hormonal cancer is chosen from breast cancers, ovarian cancers, uterine or endometrial cancers, prostate cancers, and combinations thereof.

Statement 37. A method according to any one of Statements 31-35, where the cell growth (e.g., malignant cell growth and/or hyperplastic cell growth, which may be cancer cell growth, which may be hormonal cancer cell growth) is prostate cancer cell growth.

Statement 38. A method according to any one of Statement 31-35 or Statement 37, where the cell growth (e.g., malignant cell growth and/or hyperplastic cell growth, which may be cancer cell growth, which may be hormonal cancer cell growth, which may be prostate cancer cell growth) is castration-resistant prostate cancer cell growth.

Statement 39. A method according to any one of Statements 31-35 or Statements 37-38, where the cells (e.g., the malignant cells and/or hyperplastic cells, which may be cancer cells, which may be hormonal cancer cells, which may be prostate cancer cells, which may be castration-resistant prostate cancer cells) express AR-V7.

Statement 40. A method of treating a hyperplastic cell growth disease and/or a malignant cell growth disease in an individual, comprising administering to the individual a compound according to any one of Statements 1-21 or a composition according to any one of Statements 22-26, where the individual's malignant cell growth disease and/or hyperplastic cell growth disease is treated.

Statement 41. A method of according to Statement 40, where the malignant cell growth disease is cancer.

Statement 42. A method according to Statement 40 or Statement 41, where the malignant cell growth disease (e.g., cancer) is a hormonal cancer.

Statement 43. A method according to Statement 42, where the hormonal cancer is chosen from breast cancers, ovarian cancers, uterine or endometrial cancers, prostate cancers, and combinations thereof.

Statement 44. A method according to any one of Statements 40-43, where malignant cell growth disease (e.g., cancer, which may be a hormonal cancer) is prostate cancer.

Statement 45. A method according to any one of Statements 40-44, where the malignant cell growth disease (e.g., cancer, which may be a hormonal cancer, which may be prostate cancer) is castration-resistant prostate cancer.

Statement 46. A method according to any one of Statements 40-45, where the cells of the malignant cell growth disease (e.g., cancer, which may be a hormonal cancer, which may be prostate cancer, which may be castration-resistant prostate cancer) express AR-V7.

Statement 47. A method according to any one of Statements 40-46, where the compound has the following structure:

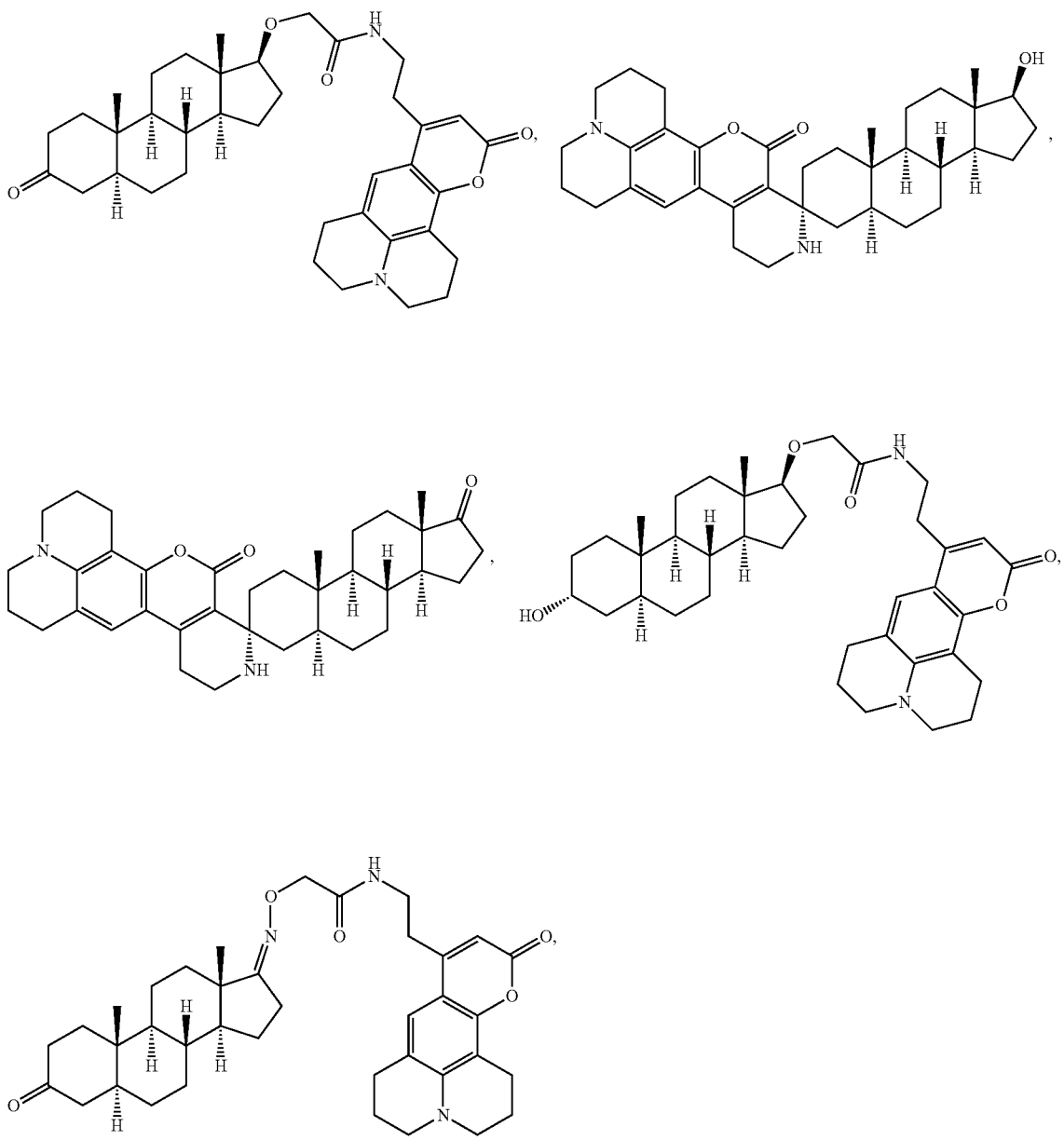

-continued

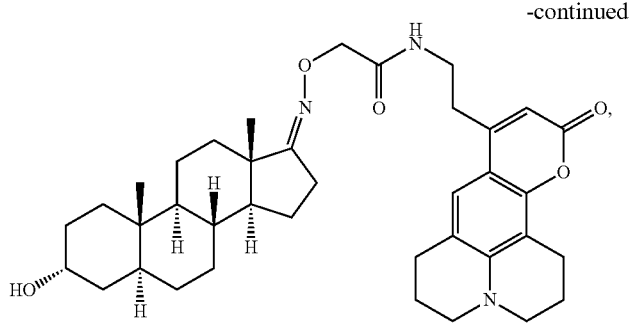

or a combination thereof.

Statement 48. A method of imaging malignant cells and/or hyperplastic cells in an individual, comprising: administering to the individual one or more compounds according to any one of Statements 1 or Statement 6 or Statements 9-10 or Statements 20-21 or a composition according to any one of Statements 22-26, exposing the individual or a portion thereof with electromagnetic radiation, such that the one or more compounds are excited, detecting the one or more excited compounds, and imaging the individual or portion thereof, where the malignant cells and/or hyperproliferative cells are imaged.

Statement 49. A method according 48, where the malignant cells are cancer cells.

Statement 50. A method according to Statement 48 or Statement 49, where the malignant cells (e.g., cancer cells) are hormonal cancer cells.

Statement 51. A method according to Statements 48-50, where the malignant cells (e.g., cancer cells, which may be hormonal cancer cells) are chosen from breast cancer cells, ovarian cancer cells, uterine or endometrial cancer cells, and prostate cancer cells.

Statement 52. A method according to Statements 48-51, where the malignant cells (e.g., cancer cells, which may be hormonal cancer cells) are prostate cancer cells.

Statement 53. A method according to Statements 48-52, where the malignant cells (e.g., cancer cells, which may be hormonal cancer cells, which may be prostate cancer cells) are castration-resistant prostate cancer cells.

Statement 54. A method according to Statements 48-53, where the malignant cells (e.g., cancer cells, which may be hormonal cancer cells, which may be prostate cancer cells, which may be castration-resistant prostate cancer cells) express AR-V7.

Statement 55. A method according to Statements 48-54, where the imaging is repeated such that activity of androgen metabolism may be measured.

Statement 56. A method according to 48-55, where the compound has the following structure:

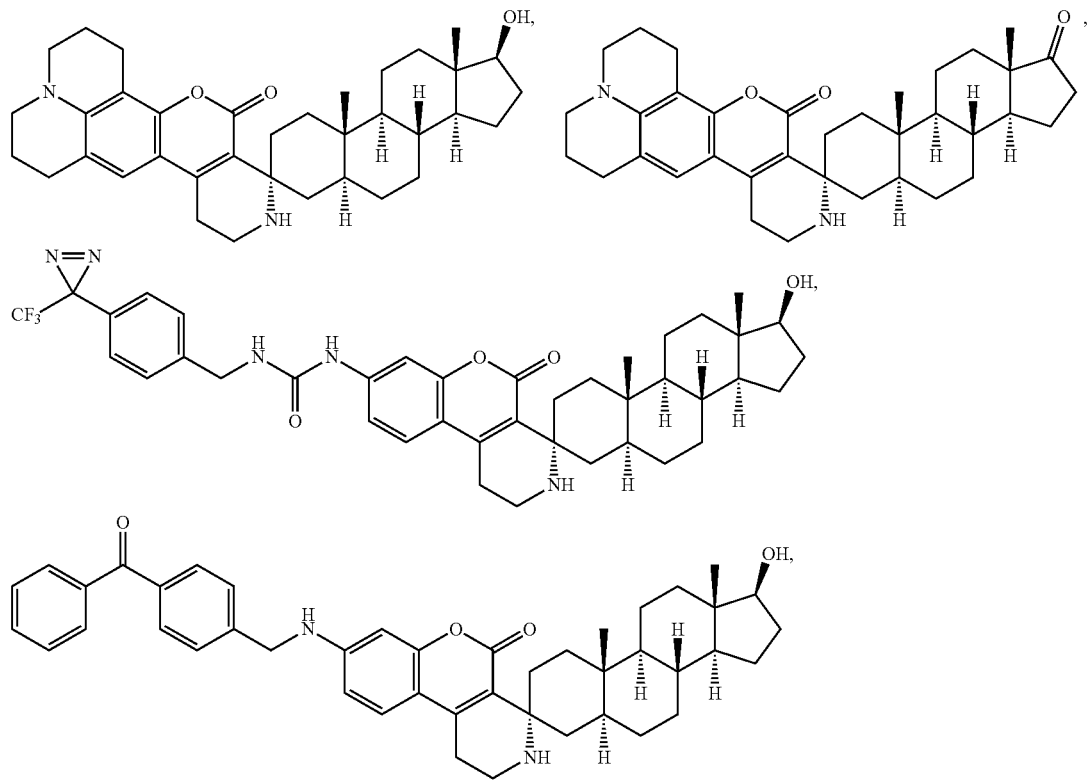

-continued
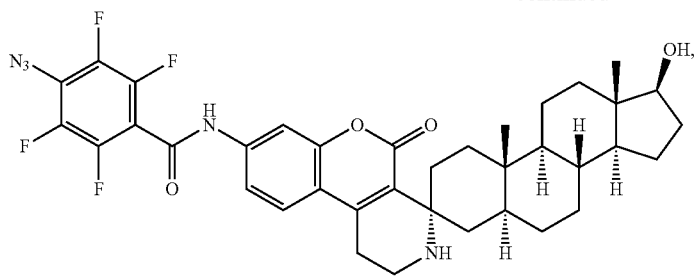
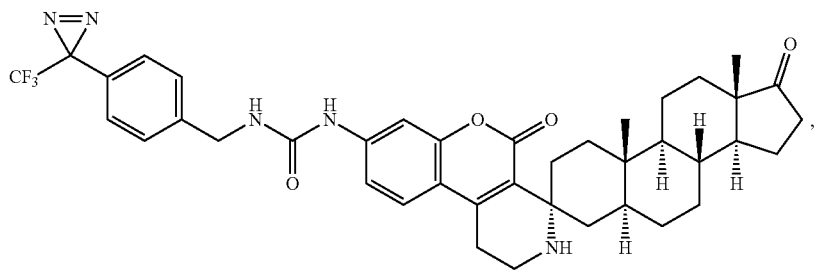
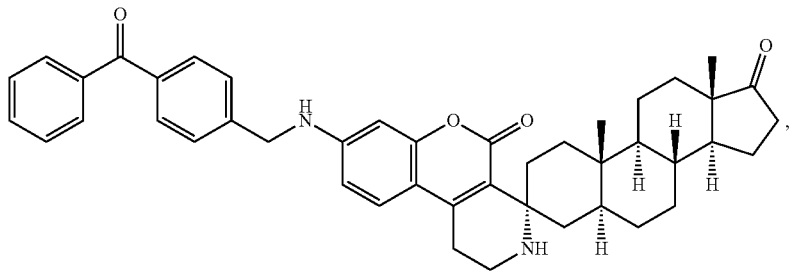
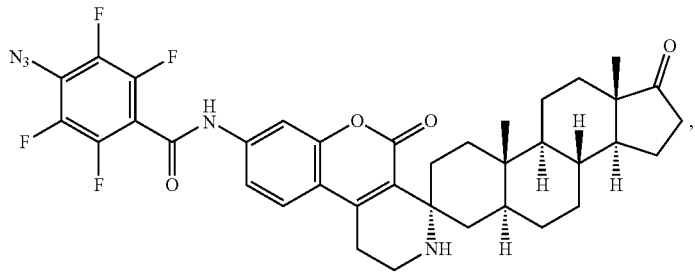
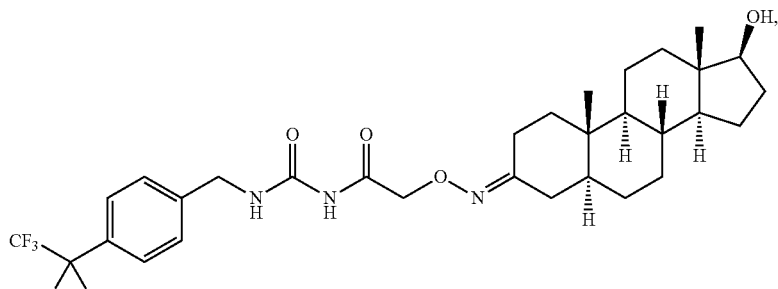
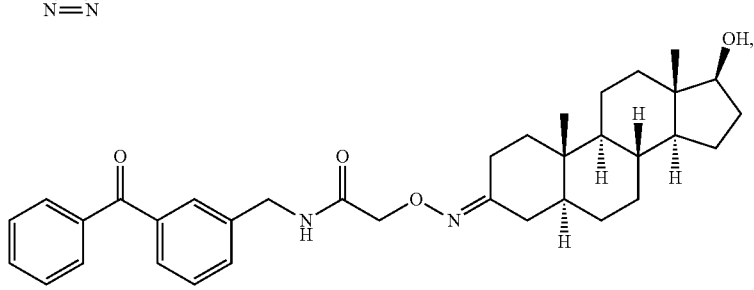

-continued
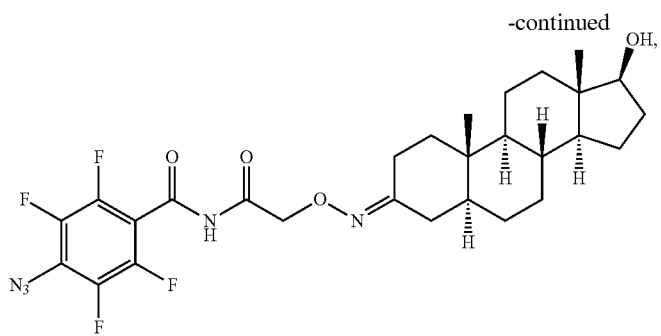
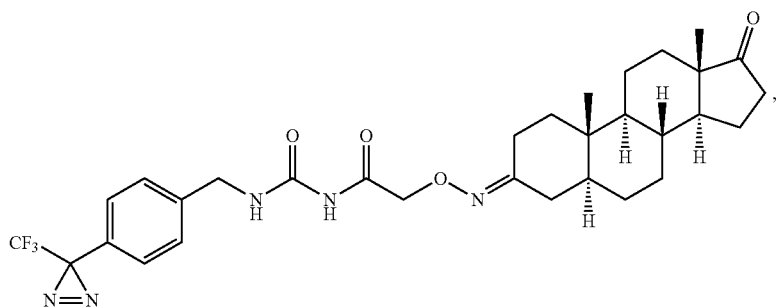
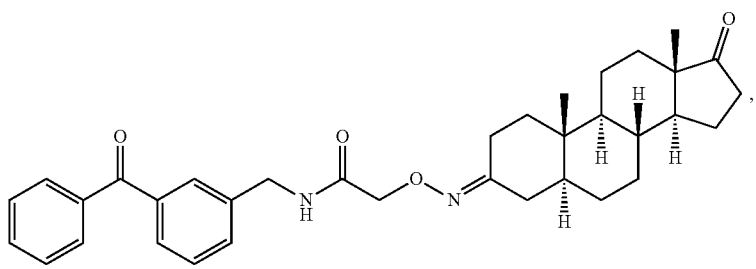
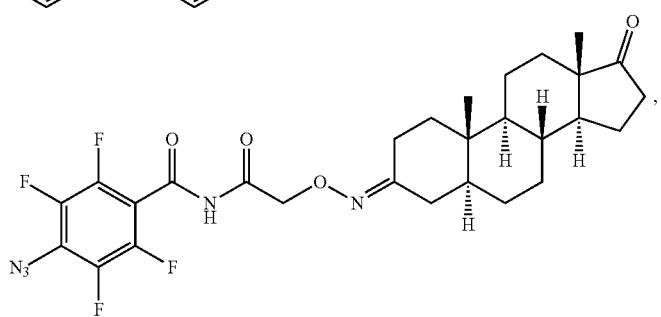
or a combination thereof.
The following examples are presented to illustrate the present disclosure. They are not intended to be limiting in any matter.
Example 1
This example provides a description of compounds of the present disclosure.
Synthesis of compound (Ia aka DIOL-17C) where $R_1$ and $R_2$ are hydrogen as shown below and in FIG. 2:
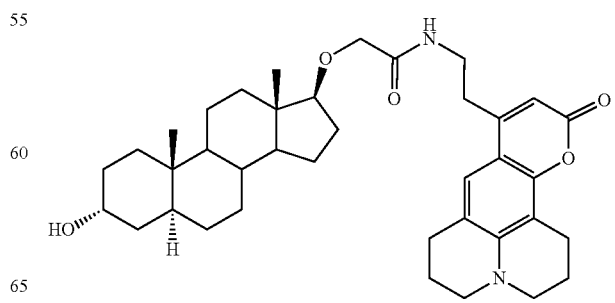
Ia Ethyl (3-Keto-5α-androstan-17β-yl)glycolate. To a suspension of 1 g (3.44 mmol) of androstane-17β-ol-3-one and 95 mg (0.22 mmol, 0.064 eq.) of dirhodium tetraacetate in 10 mL of CH$_2$Cl$_2$ at 0° C. was added dropwise 393 mg (3.44 mmol, 1 eq.) of ethyl diazoacetate with vigorous stirring. After 2 h at 25° C., an additional 393 mg (3.44 mmol, 1 eq) of ethyl diazoacetate was added dropwise, and the mixture was stirred for an additional 2 hours (h). The mixture was diluted with CH$_2$Cl$_2$, washed with water and brine, dried over anhydrous MgSO$_4$, and concentrated. The product was purified by column chromatography using 1:3 EtOAc-hexane to afford 687 mg (53%) of ethyl (3-keto-5α-androstan-17β-yl)glycolate as a semisolid. $^1$H NMR (CDCl$_3$, 500 MHz): δ 4.20 (q, 2H, J=7.2 Hz), 4.09 (s, 2H), 3.40 (t, 1H, J=8.5 Hz), 2.42-2.35 (m, 1H), 2.32-2.24 (m, 2H), 2.11-2.00 (m, 3H), 1.96-1.92 (m, 1H), 1.72-1.68 (m, 1H), 1.58-1.26 (m, 13H), 1.21-1.15 (m, 1H), 1.02 (s, 3H), 1.00-0.83 (m, 2H), 0.82 (s, 3H), 0.75-0.69 (m, 1H). $^{13}$C NMR (CDCl$_3$, 100 MHz): δ 212.22, 171.03, 90.02, 67.80, 60.94, 54.09, 51.12, 46.91, 44.89, 43.28, 38.77, 38.36, 37.90, 35.93, 35.38, 31.43, 28.99, 27.76, 23.48, 21.27, 14.42, 11.86, 11.68. HRMS (ESI) calculated for C$_{23}$H$_{37}$O$_4$ [MH+]: 377.2686. Found: 377.2687.

Ethyl (3β-Hydroxy-5α-androstan-17β-yl)glycolate. To a solution of 300 mg (0.80 mmol) of ethyl (3-keto-5α-androstan-17β-yl)glycolate in 4 mL of THF was added dropwise 2.1 mL (1.04 mmol, 1.3 eq) of lithium tri-tert-butoxyaluminum hydride (0.5 M in bis(2-inethoxyethyl) ether at −20° C. The mixture was stirred for 3 h, quenched with water, extracted with CH$_2$Cl$_2$, dried over anhydrous MgSO$_4$, and concentrated. The product was purified by column chromatography using 1:2 EtOAc-hexane to afford 280 mg (93%) of ethyl (3β-hydroxy-5α-androstan-17β-yl)glycolate as a white solid: mp 72-74° C. $^1$H NMR (CDCl$_3$, 500 MHz): δ 4.20 (q, 2H, J=7.0 Hz), 4.10, 4.06 (ABq, 2H, J$_{AB}$=16.2 Hz), 3.61-3.55 (m, 1H), 3.39 (t, 1H, J=8.2 Hz), 2.05-1.98 (m, 1H), 1.93-1.90 (m, 1H), 1.81-1.77 (m, 1H), 1.72-1.64 (m, 3H), 1.59-1.53 (m, 4H), 1.43-1.36 (m, 2H), 1.32-1.21 (m, 8H), 1.17-1.07 (m, 2H), 0.99-0.82 (m, 3H), 0.81 (s, 3H), 0.79 (s, 3H), 0.65-0.59 (m, 1H). $^{13}$C NMR (CDCl$_3$, 100 MHz): δ 170.89, 89.94, 71.31, 67.60, 60.72, 54.45, 51.12, 44.87, 43.09, 38.18, 37.86, 37.02, 35.55, 35.29, 31.59, 31.50, 28.56, 27.59, 23.27, 20.88, 14.22, 12.34, 11.66. HRMS (ESI) calculated for C$_{23}$H$_{39}$O$_4$ [MH+]: 379.2843. Found: 379.2843.

Ethyl (3α-Benzoyloxy-5α-androstan-17β-yl)glycolate. To a solution of 200 mg (0.53 mmol) of ethyl (3β-hydroxy-5α-androstan-17β-yl)glycolate and 129 mg (1.06 mmol, 2 eq.) of benzoic acid in 3 mL of anhydrous THF was added 214 mg (1.06 mmol, 2 eq.) of diisopropyl azodicarboxylate. The solution was stirred for 12 h at 25° C., quenched with water, extracted with CH$_2$Cl$_2$, washed successively with 10% aqueous K$_2$CO$_3$ solution and water, dried over anhydrous MgSO$_4$, and concentrated. The product was purified by chromatography using 1:5 EtOAc-hexane (R$_f$=0.53) to afford 181 mg (71%) of ethyl (3α-benzoyloxy-5α-androstan-17β-yl)glycolate as a white solid: $^1$H NMR (CDCl$_3$, 400 MHz): δ 8.07-8.05 (m, 2H), 7.58-7.54 (m, 1H), 7.47-7.44 (m, 2H), 5.28 (br s, 1H), 4.20 (q, 2H, J=7.2 Hz), 4.12, 4.07 (ABq, 2H, J$_{AB}$=16.4 Hz), 3.40 (t, 1H, J=8.4 Hz), 2.05-1.98 (m, 1H), 1.95-1.85 (m, 2H), 1.80-1.52 (m, 7H), 1.45-1.14 (m, 12H), 1.03-0.87 (m, 2H), 0.85 (s, 3H), 0.81 (s, 3H), 0.79-0.75 (m, 1H). $^{13}$C NMR (CDCl$_3$, 100 MHz): δ 170.85, 165.87, 132.69, 131.18, 129.53 (two C), 128.32 (two C), 89.97, 70.68, 67.63, 60.70, 54.46, 51.16, 43.10, 40.47, 37.84, 35.97, 35.26, 33.24, 33.00, 31.46, 28.24, 27.59, 26.30, 23.23, 20.47, 14.23, 11.68, 11.43. HRMS (ESI) calculated for C$_{30}$H$_{43}$O$_5$ [MH+]: 483.3105. Found: 483.3108.

N-2'-(2,3,4,5-Tetrahydro-1H,4H-10-keto-11-oxa-3α-azabenzo[de]anthracenyl)ethyl (3α-hydroxy-5α-androstan-17β-yl)glycolamide (Ia aka DIOL-17C). To a solution of 160 mg (0.33 mmol) of ethyl (3α-benzoyloxy-5α-androstan-170-yl)glycolate in 3 mL of methanol was added 0.66 mL (1.33 mmol, 4 eq.) of 2 N aqueous NaOH solution. The suspension was stirred at 50° C. for 12 h, diluted with water, and acidified with 3 N HCl solution to pH 2. The precipitate was collected and dried in vacuum to provide 103 mg (89%) of (3α-hydroxy-5α-androstan-17β-yl)glycolic acid that was sufficiently pure to be used in the next reaction without further purification. To a mixture of 80 mg (0.23 mmol) of this acid and 90 mg (0.25 mmol, 1.1 eq.) of 8-(2-aminoethyl)-2,3,4,5-tetrahydro-1H,4H-11-oxa-3α-azabenzo[de]anthracen-10-one hydrochloride in 2 mL of 1:1 MeOH—CH$_2$Cl$_2$ was added successively 66 mg (0.34 mmol, 1.5 eq.) of EDC, 46 mg (0.34 mmol, 1.5 eq.) of HOBt, and 81 mg (0.80 mmol, 3.5 eq.) of triethylamine. The mixture was stirred for 12 h at 25° C., diluted with water, extracted with CH$_2$Cl$_2$, dried over anhydrous MgSO$_4$, and concentrated. The product was purified by chromatography using 1:10 CH$_3$OH—CH$_2$Cl$_2$ (R$_f$=0.53) to afford 76 mg (54%) of Ia aka DIOL-17C as a yellow foam: $^1$H NMR (CDCl$_3$, 400 MHz): δ 7.12 (s, 1H), 6.74 (t, 1H, J=5.8 Hz), 5.90 (s, 1H), 4.04 (br s, 1H), 3.95, 3.90 (ABq, 2H, J$_{AB}$=15.4 Hz), 3.60 (q, 2H, J=7.2 Hz), 3.28-3.23 (m, 5H), 2.92-2.87 (m, 4H), 2.79 (t, 2H, J=6.2 Hz), 2.00-1.88 (m, 5H), 1.78-1.71 (m, 1H), 1.69-1.16 (m, 17H), 1.08-1.01 (m, 1H), 0.95-0.80 (m, 2H), 0.78 (s, 3H), 0.75-0.70 (m, 1H), 0.68 (s, 3H). $^{13}$C NMR (CDCl$_3$, 100 MHz): δ 170.61, 162.19, 153.65, 151.44, 145.97, 121.67, 118.18, 107.86, 107.71, 106.92, 90.00, 69.21, 66.49, 54.33, 51.06, 49.96, 49.51, 43.00, 39.12, 38.15, 37.77, 36.15, 35.84, 35.21, 32.19, 31.64, 31.49, 29.02, 28.36, 27.79, 27.66, 23.25, 21.54, 20.65, 20.50, 20.36, 11.77, 11.21. HRMS (ESI) calculated for C$_{38}$H$_{53}$N$_2$O$_5$ [MH+]: 617.3949. Found: 617.3940.

Example 2

This example provides a description of compounds of the present disclosure. Synthesis of compound (Id aka DHT-17C) where R$_1$ and R$_2$ are hydrogen as shown in FIG. 2:

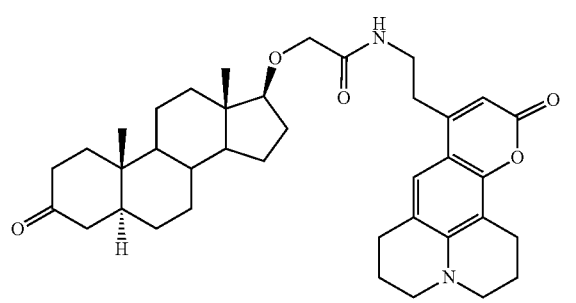

Id

N-2'-(2,3,4,5-Tetrahydro-1H,4H-10-keto-11-oxa-3α-azabenzo[de]anthracenyl)ethyl (3-keto-5α-androstan-17β-yl)glycolamide. To a solution of 100 mg (0.27 mmol) of ethyl (3-keto-5α-androstan-17β-yl)glycolate in 4 mL of THF was added 0.28 mL (0.54 mmol, 2 eq.) of 2 N aqueous NaOH solution. The mixture was stirred for 5 h at 25° C. and concentrated. The residue was diluted with water and acidified with 3 N HCl solution to pH 2 to produce a white precipitate that was collected to afford 83 mg (90%) of (3-keto-5α-androstan-17β-yl)glycolic acid that was used in the next step without further purification. To a mixture of 37 mg (0.11 mmol) of this acid and 42 mg (0.12 mmol, 1.1 eq.) of 8-(2-aminoethyl)-2,3,4,5-tetrahydro-1H,4H-11-oxa-3α-aza-benzo[de]anthracen-10-one hydrochloride in 1 mL of CH$_2$Cl$_2$ were added successively 30 mg (0.16 mmol, 1.5 eq.) of EDC, 24 mg (0.16 mmol, 1.5 eq) of HOBt, and 38 mg (0.37 mmol, 3.5 eq.) of triethylamine. The mixture was stirred for 12 h at 25° C., diluted with water, extracted with CH$_2$Cl$_2$, dried over anhydrous MgSO$_4$, and concentrated. The product was purified by chromatography using 5:1 EtOAc-hexane (R$_f$=0.53 after two developments) to afford 33 mg (51%) of Id (aka DHT-17C) as a yellow foam. $^1$H NMR (CDCl$_3$, 400 MHz): δ 7.10 (s, 1H), 6.72 (t, 1H, J=6.0 Hz), 5.87 (s, 1H), 3.93, 3.89 (ABq, 2H, J$_{AB}$=15.2 Hz), 3.59 (q, 2H, J=6.8 Hz), 3.27-3.22 (m, 5H), 2.91-2.85 (m, 4H), 2.78 (t, 2H, J=6.4 Hz), 2.42-2.21 (m, 3H), 2.09-1.88 (m, 7H), 1.78-1.74 (m, 1H), 1.70-1.64 (m, 1H), 1.59-1.20 (m, 10H), 1.10-1.04 (m, 1H), 0.99 (s, 3H), 0.95-0.80 (m, 2H), 0.73-0.66 (m, 4H). $^{13}$C NMR (CDCl$_3$, 100 MHz): δ 211.90, 170.49, 162.12, 153.61, 151.43, 145.97, 121.65, 118.19, 107.80, 107.72, 106.89, 89.83, 69.19, 53.77, 50.79, 49.95, 49.50, 46.66, 44.66, 42.99, 38.52, 38.13, 38.07, 37.61, 35.70, 35.11, 31.65, 31.17, 28.73, 27.78, 27.65, 23.28, 21.52, 21.01, 20.64, 20.51, 11.76, 11.48. HRMS (ESI) calculated for C$_{38}$H$_{51}$N$_2$O$_5$ [MH+]: 615.3792. Found: 615.3793.

Example 3

This example provides a description of compounds of the present disclosure.

Synthesis of compound (IIa) where R$_1$ is hydrogen as shown in FIG. 3:

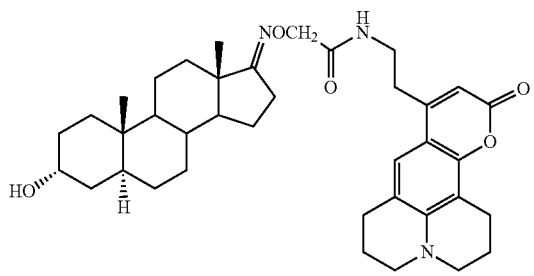

IIa 17-(O-Carboxymethyloximino)-5α-androstan-3α-ol. A mixture of 537 mg (1.85 mmol) of 5α-androstan-3α-ol-17-one and 404 mg (3.7 mmol) of carboxymethoxyamine hemichloride in 20 mL of pyridine was stirred at 80° C. for 15 h. The product was cooled and concentrated. The product was diluted with water and extracted with CH$_2$Cl$_2$. The organic layer was washed with brine and dried over anhydrous MgSO$_4$. The solvent was evaporated, and residue was recrystallized from acetone to afford 652 mg (97%) of a white solid: mp 171-173° C. mp 173-175° C. $^1$H NMR (CDCl$_3$, 400 MHz): δ 4.57 (s, 2H), 4.05 (br s, 1H), 2.54-2.48 (m, 2H), 1.94-0.82 (m, 20H), 0.91 (s, 3H), 0.79 (s, 3H). $^{13}$C NMR (CDCl$_3$, 100 MHz): δ 1743, 172.9, 69.8, 66.4, 54.3, 53.8, 44.5, 39.0, 36.1, 35.7, 34.8, 33.9, 320, 31.4, 30.9, 28.9, 28.2, 26.1, 23.0, 20.2, 17.1, 11.1.

8-Hydroxy-2,3,6,7-tetrahydro-1H,5H-benzo[ij]quinolizine. A mixture of 30 g (0.244 mol) of m-anisidine and 91.7 mL (0.927 mol, 3.8 eq.) of 1-bromo-3-chloropropane was heated 95° C. for 1-2 h at which point an exothermic reaction ensued; heating was discontinued; and the temperature of the mixture peaked at 140-145° C. As the temperature began to decline, heating was resumed. The mixture was heated at 140-145° C. for 48 h and then at 175-180° C. for 21 h. The mixture was cooled, diluted with 370 mL of concentrated HCl, and quenched by the slow addition of 120 mL of water. Once all solids were dissolved, the two phases were separated. The organic layer was washed with 100 mL of 10% HCl and the aqueous solutions were combined. The aqueous solution was extracted with ether to remove unreacted 1-bromo-3-chloropropane. To this acidic aqueous solution was added 200 mL of 25M aqueous NaOH solution. The solution was extracted with toluene until the organic phase was no longer colored. The organic phase was dried over anhydrous MgSO$_4$, and the solvent was removed under reduced pressure to afford 18 g (39%) of a white solid: mp 126-128° C. mp 126-130° C.). $^1$H NMR (400 MHz, DMSO-d$_6$): δ 8.62 (s, 1H), 6.47 (d, 1H, J=8.0 Hz), 5.99 (d, 1H, J=8.0 Hz), 3.01-2.96 (m, 4H), 2.57-2.48 (m, 4H), 1.85-1.79 (m, 4H). $^{13}$C NMR (100 MHz, DMSO-d$_6$): δ 153.0, 143.6, 126.1, 111.9, 107.7, 103.0, 49.6, 49.1, 26.7, 22.1, 21.4, 21.0.

Methyl-5-(benzyloxycarbonylamino)-3-oxopentanoate.
To a solution of 35 mL (30 mmol) of dimethyl malonate in 40 mL of MeOH was added a solution of 17.1 g (30 mmol) of KOH in 70 mL of MeOH dropwise over a 1 h period at 5-10° C. The mixture was stirred at 25° C. for ca. 12 h. The precipitated methyl potassium malonate was collected and washed with cold MeOH. A suspension of 7.42 g (78 mmol, 1.04 eq.) of MgCl$_2$ and 17.6 g (113 mmol, 1.5 eq.) of methyl potassium malonate in 110 mL of anhydrous THE was stirred for 4 h at 50° C. To a solution of 16.7 g (75 mmol, 1 eq.) of N-benzyloxycarbonyl β-alanine in 50 mL of THF at 5° C. in a separate flask was added 14.6 g (90 mmol, 1.2 eq) of 1,1'-carbonyldiimidazole. This imidazolide solution was stirred for 1 h at 25° C. To the methyl magnesium malonate suspension was added the aforementioned imidazolide solution dropwise at 25° C. The mixture was stirred for ca. 12 h, concentrated under reduced pressure, and diluted with ethyl acetate. The ethyl acetate solution was washed successively with aqueous KHSO$_4$ solution, aqueous NaHCO$_3$ solution and brine. The organic layer was dried over anhydrous Na$_2$SO$_4$ and concentrated to afford 18 g (98%) of a yellow oil that was used without further purification. $^1$H NMR (400 MHz, CDCl$_3$): δ 7.34 (br s, 5H), 5.24 (br s, 1H, NH), 5.07 (s, 2H), 3.72 (s, 3H), 3.45 (s, 4H), 2.80 (t, 2H, J=5.2 Hz).

8-(2-Aminoethyl)-2,3,4,5-tetrahydro-1H,4H-11-oxa-3α-aza-benzo[de]anthracen-10-one hydrochloride. To a suspension of 8.33 g (44 mmol) of 8-hydroxy-2,3,6,7-tetrahydro-1H,5H-benzo[ij]quinolizine and 10.8 g (44 mmol) of methyl-5-(benzyloxycarbonylamino)-3-oxopentanoate in 132 mL of toluene was added 88 mL (88 mmol, 2 eq.) of a 1 M solution of tri-isopropoxytitanium chloride in hexane. The mixture was heated at reflux for ca. 12 h. The mixture was diluted with 500 mL of CH$_2$Cl$_2$ and poured into 500 mL of a stirred saturated potassium sodium tartrate solution. The aqueous layer was extracted with CH$_2$Cl$_2$. The combined organic layers were dried over anhydrous Na$_2$SO$_4$. The filtered solution was concentrated, and the residue was dissolved in a mixture of EtOH and hexane. The mixture was stored at 5° C. for 3 days. The resulting precipitate was collected and recrystallized from EtOH to provide 13 g (77%) a 1:9 mixture of the benzyl and isopropyl [2-(10- oxo-2,3,5,6-tetrahydro-1H,4H,10H-11-oxa-3a-aza-benzo[de]anthracen-8-yl)-ethyl]carbamates as a yellow solid. To 5.05 g (13.6 mmol) of this mixture of esters was added 12 mL of concentrated HCl. The solution was heated at 95° C. for 9 h, cooled, and concentrated in vacuo. The residue was suspended in a mixture of MeOH-acetone and was filtered to afford 4.3 g (98%) of 7 as a yellow hydrochloride salt: mp 238-239° C. mp 114-118° C. for free amine). $^1$H NMR (400 MHz, CD$_3$OD): δ 7.25 (s, 1H), 6.00 (s, 1H), 3.36-3.24 (m, 6H), 3.09 (t, 2H, J=7.2 Hz), 2.86 (m, 4H), 2.01 (m, 4H). $^{13}$C NMR (100 MHz, CD$_3$OD): δ 164.2, 154.0, 152.6, 146.7, 123.0, 122.9, 121.5, 109.7, 109.4, 109.1, 109.0, 51.4, 50.9, 39.8, 30.5, 28.6, 22.4, 21.6, 21.5.

N-2'-(2,3,4,5-tetrahydro-1H,4H-10-keto-11-oxa-3a-azabenzo[de]anthracenyl)ethyl 17-(O-carbamidomethyloximino)-5α-androstan-3α-ol (IIa). To a solution of 122 mg (0.38 mmol) of 8-(2-aminoethyl)-2,3,4,5-tetrahydro-1H,4H-11-oxa-3a-aza-benzo[de]anthracen-10-one hydrochloride (7) in 4 mL of 1:3 MeOH—CHCl$_3$ at 0° C. was added successively 75 µL (0.42 mmol, 1.1 eq.) of N,N-diisopropylethylamine, 139 mg (0.38 mmol) of (6), 206 mg (1.5 mmol, 4 eq.) of 1-hydroxybenzotriazole hydrate (HOBt) and 205 mg (1.07 mmol, 2.8 eq.) of N-(3-dimethylaminopropyl)-N'-ethylcarbodiimide hydrochloride (EDC). The EDC was added 30 min apart in two equal portions. The mixture was stirred for 1 h at 0° C., concentrated and chromatographed using 1:10 MeOH—CH$_2$Cl$_2$ (R$_f$=0.39) to afford 134 mg (56%) of IIa as a yellow foam. $^1$H NMR (CDCl$_3$, 400 MHz): δ 7.13 (s, 1H), 6.6 (t, 1H, J=6.4 Hz), 5.87 (s, 1H), 4.46 (s, 2H), 4.03 (br s, 1H), 3.65-3.59 (m, 2H), 3.28-3.23 (m, 4H), 2.92-2.85 (m, 4H), 2.79 (t, 2H), 2.46-2.33 (m, 2H), 1.99-1.94 (m, 4H), 1.82-0.73 (m, 20H), 0.84 (s, 3H), 0.79 (s, 3H). 13C NMR (CDCl$_3$, 100 MHz): δ 173.3, 170.8, 162.3, 153.9, 151.4, 146.1, 121.8, 118.4, 107.8, 107.4, 106.9, 72.6, 66.3, 54.4, 53.9, 50.0, 49.5, 44.5, 39.1, 38.1, 36.2, 35.9, 34.9, 34.1, 32.1, 31.9, 31.5, 29.0, 28.4, 27.8, 26.1, 23.2, 21.6, 20.7, 20.6, 20.3, 17.3, 11.3. HRMS (ESI) calculated for C$_{38}$H$_{52}$N$_3$O$_5$ [MH+]: 630.3901. Found: 630.3899.

Example 4

This example provides a description of compounds of the present disclosure.

Synthesis of compound (IIb) where R$_1$ is hydrogen as shown in FIG. 3:

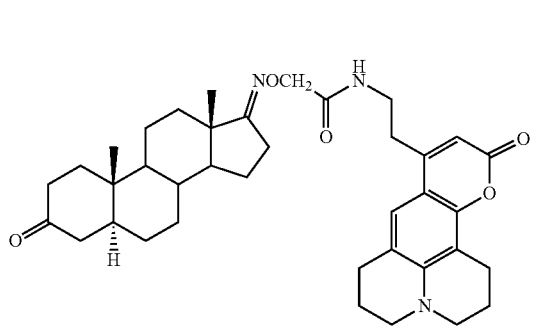

IIb

N-2'-(2,3,4,5-Tetrahydro-1H,4H-10-keto-11-oxa-3α-azabenzo[de]anthracenyl)ethyl 17-(0-carbamidomethyloximino)-5α-androstan-3-one (IIb). To a solution of 30 mg (0.048 mmol) of IIa in 1 mL of 1:1 DMSO:CH$_2$Cl$_2$ was added successively 24 mg (0.24 mmol, 5 eq.) of triethylamine and 23 mg (0.14 mmol, 3 eq.) of SO$_3$-pyridine complex. The mixture was stirred for 5 h at 25° C., diluted with CH$_2$Cl$_2$, washed with brine and water, dried over anhydrous MgSO$_4$, and concentrated. The product was purified by chromatography on silica gel using 1:10 CH$_3$OH—CH$_2$Cl$_2$ (R$_f$=0.56) to afford 16 mg (54%) of IIb as a yellow foam. $^1$H NMR (CDCl$_3$, 400 MHz): δ 7.10 (s, 1H), 6.46 (t, 1H, J=5.8 Hz), 5.87 (s, 1H), 4.46 (s, 2H), 3.69-3.57 (m, 2H), 3.28-3.23 (m, 4H), 2.91-2.86 (m, 4H), 2.79 (t, 2H, J=6.2 Hz), 2.50-2.24 (m, 5H), 2.11-1.94 (m, 5H), 1.87-1.73 (m, 3H), 1.65-1.60 (m, 1H), 1.57-1.26 (m, 8H), 1.18-1.12 (m, 1H), 1.02-0.92 (m, 4H), 0.88 (s, 3H), 0.83-0.72 (m, 1H). $^{13}$C NMR (CDCl$_3$, 100 MHz): δ 211.69, 172.96, 170.60, 162.09, 153.62, 151.42, 145.99, 121.64, 118.25, 107.67, 107.33, 106.82, 72.55, 53.81, 53.61, 49.94, 49.49, 46.58, 44.63, 44.41, 38.46, 38.11, 37.71, 35.76, 34.74, 33.97, 31.81, 31.11, 28.69, 27.78, 26.09, 23.20, 21.51, 20.92, 20.62, 20.51, 17.22, 11.45. HRMS (ESI) calculated for C$_{38}$H$_{50}$N$_3$O$_5$ [MH+]: 628.3745. Found: 628.3741.

Example 5

This example provides a description of compounds of the present disclosure.

Synthesis of compound (Ig aka DHT-3C) where R$_1$ and R$_2$ are hydrogen as shown in FIG. 4.

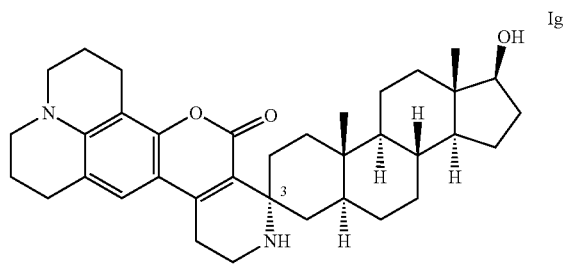

Ig (3R,5S,10S,13S,17S)-17-hydroxy-10,13-dimethyl-1,2,2',3',4,5,6,7,8,8',9,9',10,11,12,12',13,13',14,15,16,17-docosahydro-7'H,11'H-spiro[cyclopenta[a]phenanthrene-3,4'-pyrido[3,2,1-ij]pyrido[4',3':4,5]pyrano[2,3-j]quinolin]-5' (1'H)-one hydrochloride (Ig). To a suspension of 66 mg (0.21 mmol, 1 eq.) of 9-(2-aminoethyl)-2,3,6,7-tetrahydro-1H,5H,11H-pyrano[2,3-j]pyrido[3,2,1-ij]quinolin-11-one hydrochloride in 2 mL of absolute ethanol was added 50 mg (0.17 mmol, 1 eq.) of DHT. To this suspension in a sealed tube was added 0.2 mL of concentrated HCl, and the mixture was stirred under reflux for 48 h. The suspension became a clear solution within the first hour of heating, and a precipitate of the desired product then appeared. The reaction was quenched by the addition of ca. 3 mL of water, and the precipitate was collected by filtration to provide 73 mg (92%) of Ig. Additional purification was achieved by recrystallization from methanol: $^1$H NMR (400 MHz, DMSO-d$_6$) δ 9.41-9.13 (m, 2H), 7.14 (s, 1H), 4.43 (br s, 1H), 3.45 (t, 2H), 3.29-3.22 (m, 4H), 3.12-3 (m, 2H), 2.82-2.64 (m, 4H), 2.57 (t, J=14.2 Hz, 1H), 1.96-1.8 (m, 4H), 1.8-1.7 (m, 2H), 1.7-1.55 (m, 4H), 1.56-1.41 (m, 4H), 1.42-1.3 (m, 3H), 1.28-1.06 (m, 5H), 1.05-0.77 (m, 7H), 0.65 (s, 3H). $^{13}$C NMR (101 MHz, DMSO-d$_6$) δ 158.61, 149.23, 147.42, 145.69, 121.59, 118.47, 114.52, 106.22, 104.7, 80.04, 58.69, 52.91, 50.82, 49.16, 48.65, 42.59 (two C), 36.7, 35.26, 35.05, 34.83, 32.41, 31.64, 31.17, 29.84, 27.47, 27.09, 25.4, 23.05, 22.54, 20.88, 20.12, 19.96, 19.69, 11.42, 11.37. HRMS (ESI) calculated for C$_{36}$H$_{49}$N$_2$O$_3$ [MH+]: 557.3738.

Found: 557.3744. The hydrochloride salt of the desired product was suspended in dichloromethane and washed with an aqueous, saturated solution of NaHCO$_3$. The dichloromethane layer was dried over anhydrous Na$_2$SO$_4$, filtered, concentrated and purified by chromatography on silica gel using 1:10 methanol-dichloromethane (R$_f$=0.55) to afford Ig as a free base: $^1$H NMR (400 MHz, DMSO-d$_6$) δ 7.03 (s, 1H), 4.4 (d, J=4.8 Hz, 1H), 3.48-3.37 (m, 1H), 3.2 (q, J=5.6 Hz, 4H), 2.84 (t, J=5.7 Hz, 2H), 2.7 (q, J=6 Hz, 4H), 2.58 (t, J=5.6 Hz, 2H), 2.52-2.43 (m, 1H), 2.32 (t, J=13 Hz, 1H), 1.95-1.76 (m, 6H), 1.75-1.67 (m, 1H), 1.66-1.54 (m, 2H), 1.54-1.43 (m, 2H), 1.39-1.26 (m, 4H), 1.25-1.03 (m, 5H), 1-0.75 (m, 7H), 0.74-0.64 (m, 1H), 0.62 (s, 3H). $^{13}$C NMR (101 MHz, DMSO-d$_6$) δ 159.5, 149.38, 149.08, 144.58, 122.52, 121.11, 117.68, 108.18, 104.87, 80.11, 53.89, 53.82, 50.79, 49.16, 48.67, 42.59, 39.94, 36.76, 36.13, 35.69, 35.28, 35.25, 33.32, 31.48, 29.88, 28.18, 27.84, 27.13, 26.3, 23.11, 21.16, 20.28, 20.22, 19.88, 11.61, 11.39. HRMS (ESI) Calculated for C$_{36}$H$_{49}$N$_2$O$_3$ [MH+]: 557.3738. Found: 557.3738. Anal. Calculated for C$_{36}$H$_{48}$N$_2$O$_3$: C, 77.66; H, 8.69; N, 5.03. Found: C, 77.53; H, 8.62, N, 4.95. Confirmation of the C-3R stereochemical assignments in the spirocyclic DHT adduct Ig relied on two-dimensional $^1$H-$^{13}$C heteronuclear single quantum coherence (HSQC), gradient-correlation spectroscopy (gCOSY) and 2D rotating frame NOESY (2D ROESY) experiments. The resonance for the protonated amine in the spirocyclic ring system appeared at δ 9.24 ppm in the 2D ROESY spectrum and was the starting point for this stereochemical assignment at C-3. The ammonium group (NH$_2^+$) at C-3 was identified by a D$_2$O exchange experiment in DMSO-d$_6$. Correlations in the ROESY spectrum between this ammonium group and individually the C-1α C-2α, C-4α and C-5α protons (FIG. 5) confirmed the 3α-orientation of the ammonium group in Ig.

Example 6

This example provides a description of compounds of the present disclosure.

Synthesis of compound (Ij) where R$_1$ is hydrogen as shown in FIG. 4.

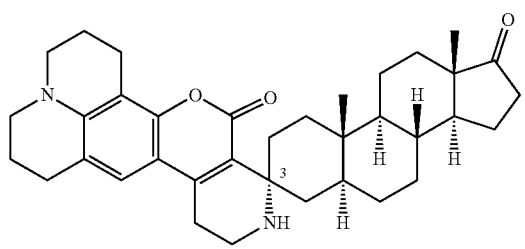

Ij (3R,5S,10S,13S)-10,13-dimethyl-1,2',3',4,5,6,7,8,8',9,9',10,11,12,12',13,13',14,15,16-icosahydro-7'H,11'H-spiro[cyclopenta[a]phenanthrene-3,4'-pyrido[3,2,1-ij]pyrido[4',3':4,5]pyrano[2,3-j]quinoline]-5',17(1'H,2H)-dione. (Ij). The procedure described for the preparation of Ig was repeated using 5α-androstane-3,17-dione to afford Ij (74%) that was purified using hot methanol trituration. $^1$H NMR (400 MHz, DMSO-d$_6$) δ 7.04 (s, 1H), 3.21 (q, J=5.5 Hz, 4H), 2.85 (t, J=5.8 Hz, 2H), 2.71 (q, J=6.1 Hz, 4H), 2.58 (t, J=5.7 Hz, 2H), 2.46-2.30 (m, 3H), 2.08-1.95 (m, 1H), 1.93-1.78 (m, 5H), 1.74 (dd, J=12.7, 3.3 Hz, 1H), 1.7-1.59 (m, 2H), 1.59-1.42 (m, 3H), 1.4-1.32 (m, 2H), 1.31-1.18 (m, 4H), 1.18-1.08 (m, 3H), 1.02-0.96 (m, 1H), 0.95 (s, 3H), 0.79 (s, 3H), 0.79-0.7 (m, 1H). $^{13}$C NMR (101 MHz, DMSO-d$_6$) δ 219.89, 159.52, 149.46, 149.08, 144.61, 122.46, 121.13, 117.71, 108.15, 104.87, 53.87, 53.64, 50.83, 49.16, 48.66, 47.14, 36.12, 35.77, 35.32, 34.63, 33.23, 31.45, 30.65, 28.01, 27.8, 27.12, 26.28, 21.38, 21.15, 20.27, 19.86, 13.49, 11.57.

Example 7

This example provides a description of the biological activity of 2-(((3R,5S,10S,13S,17S)-3-hydroxy-10,13-dimethylhexadecahydro-1H-cyclopenta[a]phenanthren-17-yl)oxy)-N-(2-(11-oxo-2,3,6,7-tetrahydro-1H,5H,11H-pyrano[2,3-j]pyrido[3,2,1-ij]quinolin-9-yl)ethyl)acetamide described as DIOL-17C (aka compound Ia) in the present disclosure.

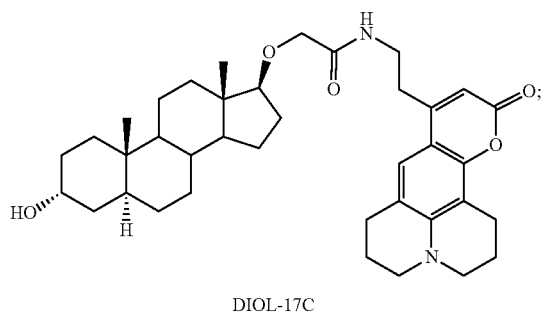

DIOL-17C

Figure 8:
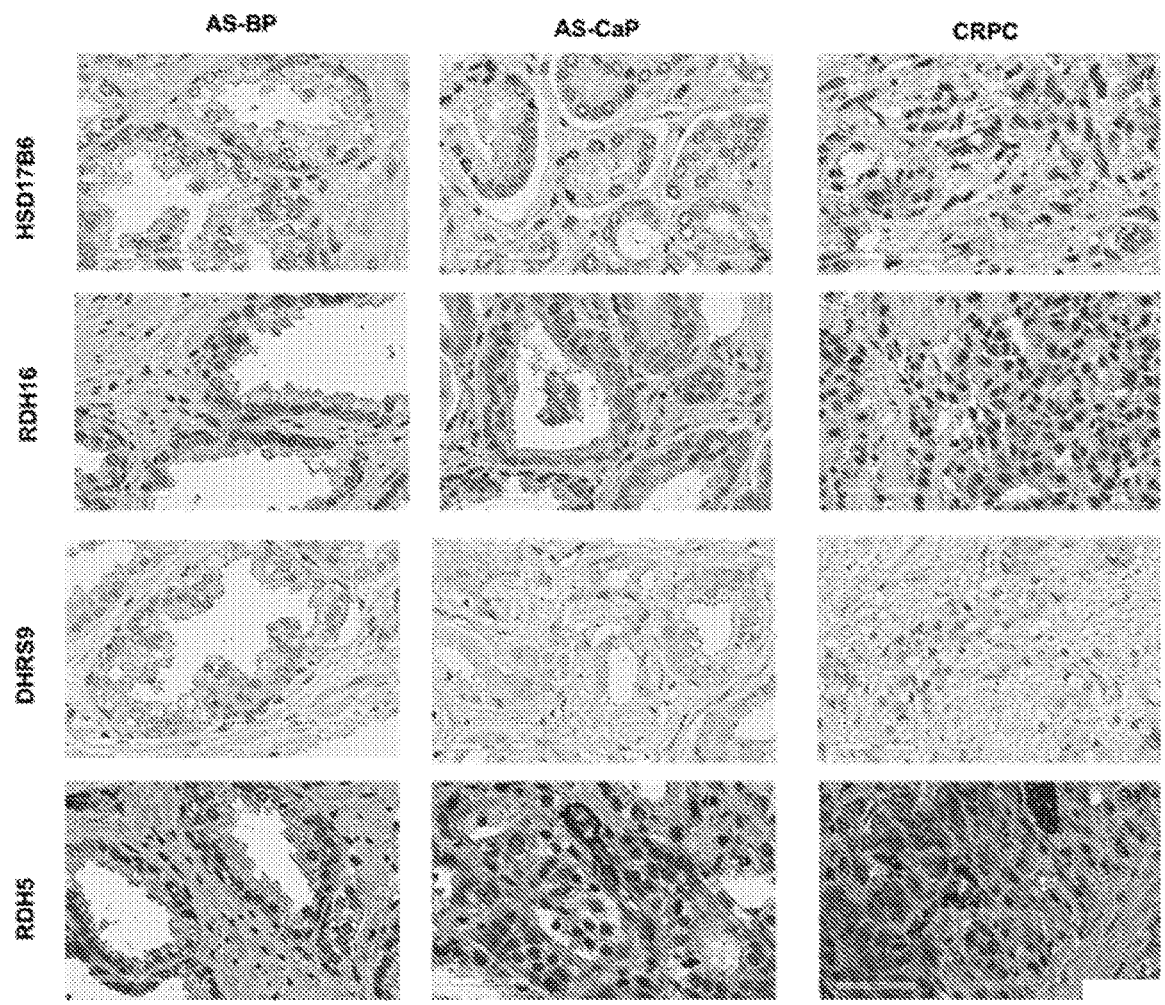
FIG. 8 shows 3α-oxidoreductases are expressed in clinical specimens.
Figure 9:
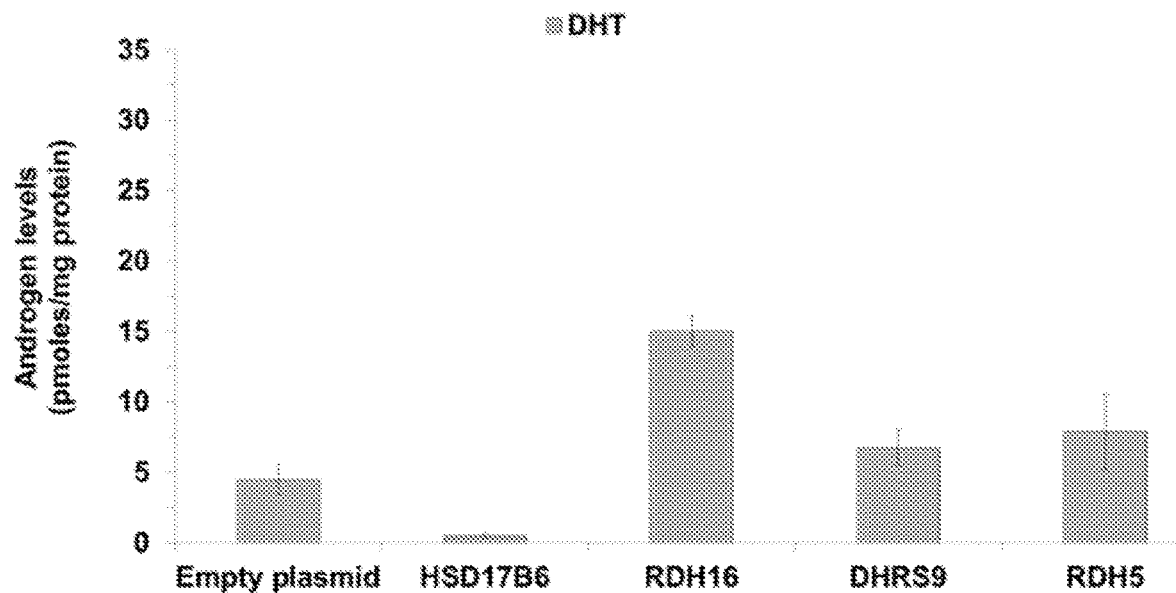
FIG. 9 shows RDH16 expression increased LAPC-4 DHT production.

CaP cells survive ADT and grow because of intratumoral synthesis of DHT and AR hypersensitization. Our group and others previously demonstrated that AR was transactivated by picomolar levels of DHT, CRPC produced sufficient DHT for AR transactivation, and CRPC efficiently metabolized DIOL to DHT. The identification of sufficient tissue levels of DHT for AR transactivation in CRPC led to the repurposing and FDA approval of abiraterone for treatment of advanced CaP. The confluence of front- and backdoor pathways to DHT was appreciated only recently. DIOL is an immediate precursor of DHT in the primary backdoor pathway (FIG. 1), and the preclinical studies unequivocally demonstrated the DIOL to DHT conversion using castration-recurrent CWR-R1 human CaP xenografts. The four 3α-oxidoreductases that metabolize DIOL to DHT were immunostained in tissue microarrays (TMA) constructed from androgen-stimulated benign prostate (AS-BP; n=36) and CaP (AS-CaP; n=36) and CRPC (n=36) (FIG. 8). CaP cell pellets analyzed using LC-MS/MS showed 3α-oxidoreductase expression increased DHT production (FIG. 9).

Figure 10:
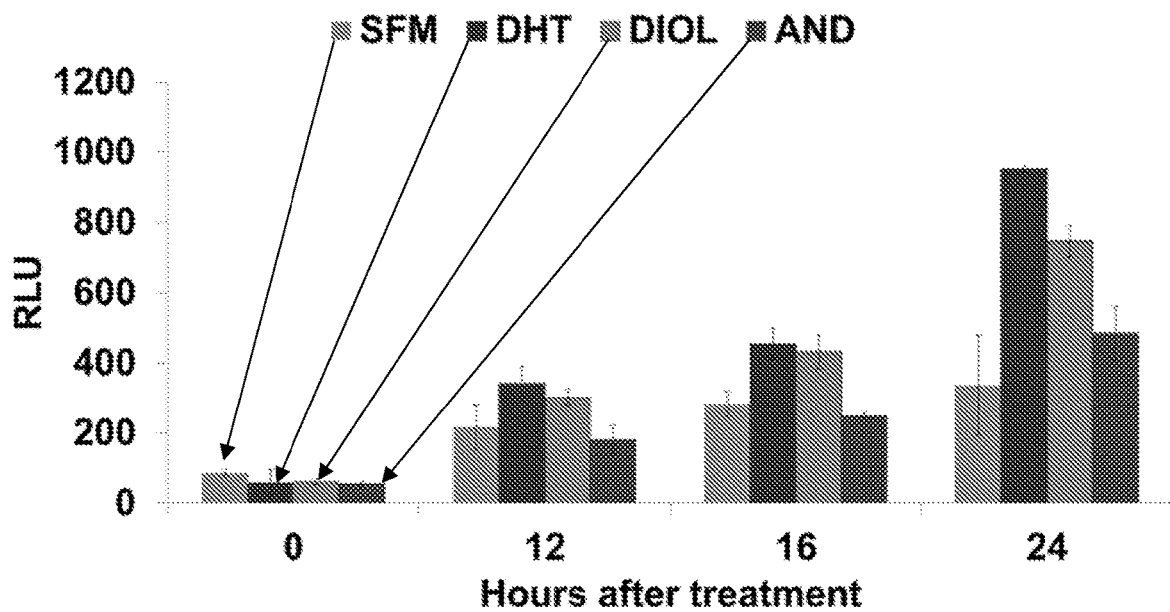
FIG. 10 shows DIOL and DHT treatment produced ARE-luciferase signal. In each series, the columns from left to right are SFM, DHT, DIOL, and androsterone (AND).
Figure 11:
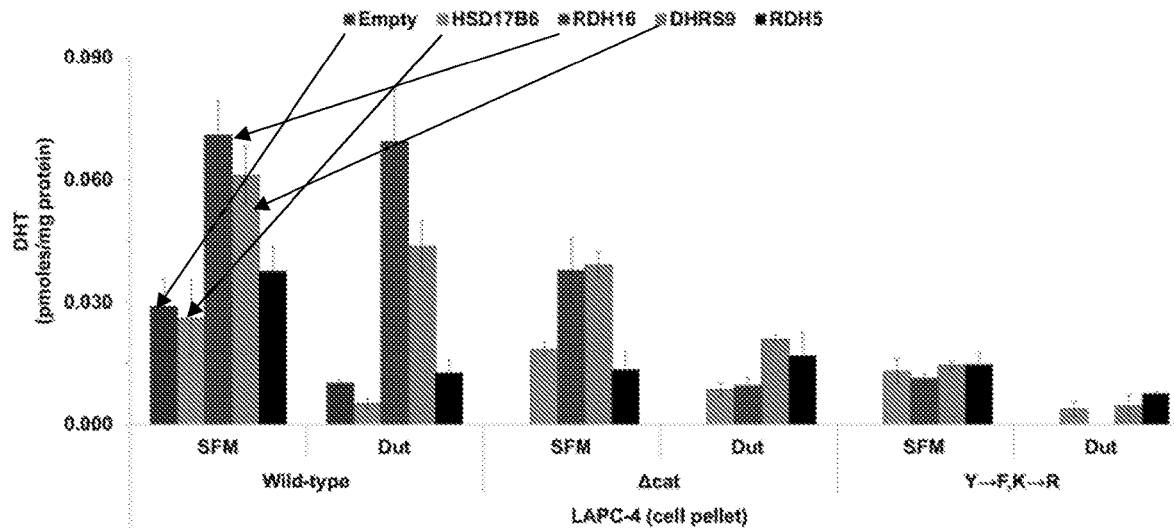
FIG. 11 shows a combination of dutasteride and 3α-oxidoreductase mutants decreased DHT levels better than dutasteride alone. In each series, the columns from left to right are "empty vector", HSD17B6, RDH16, DHRS9, and RDH5.
Figure 12:
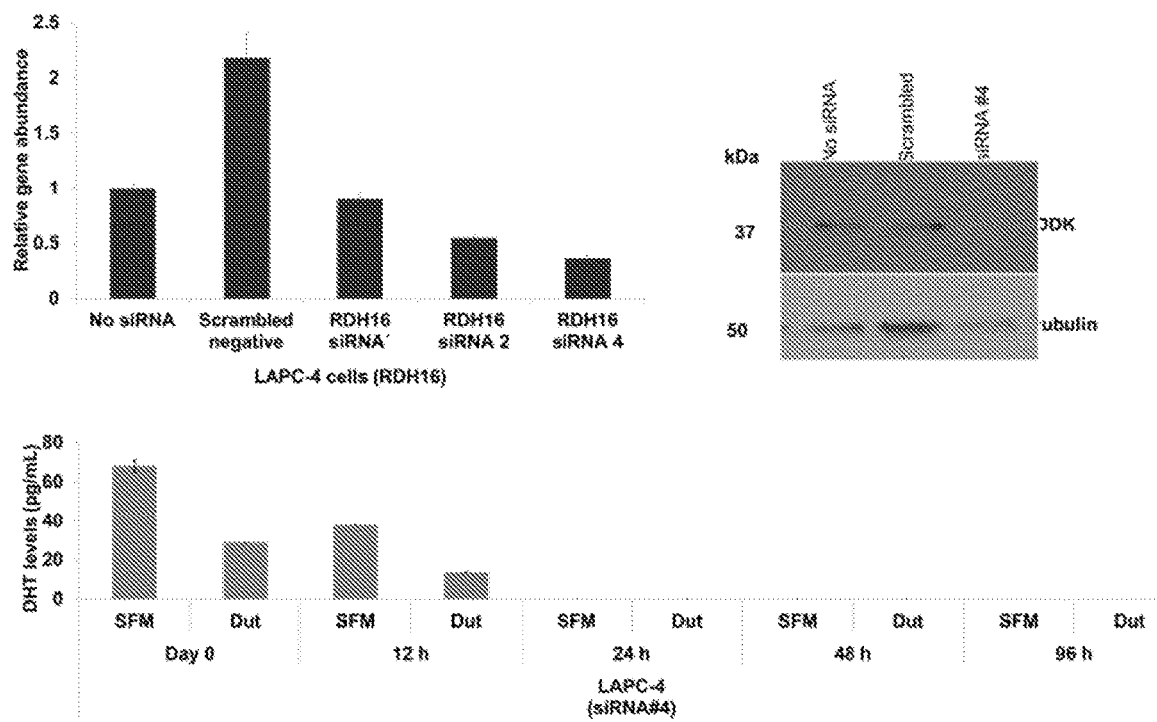
FIG. 12 shows RDH16 knockdown impaired LAPC-4 cell DHT production.
Figure 13:
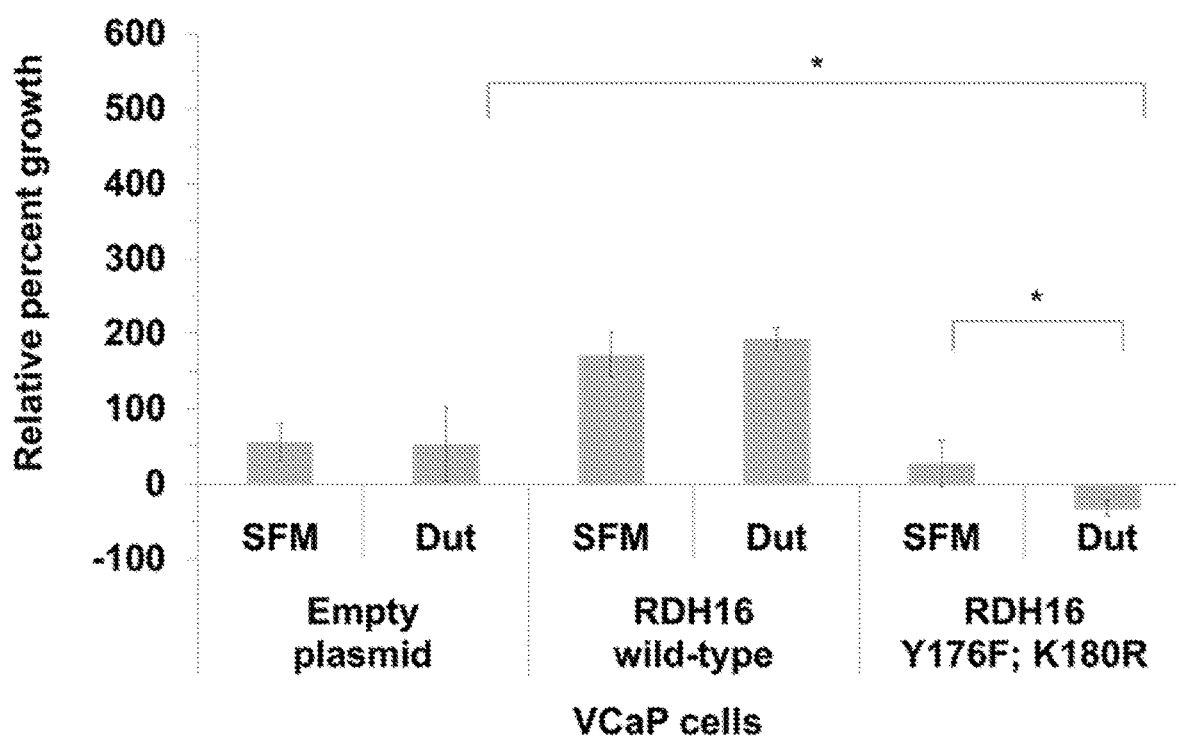
FIG. 13 shows inhibition of frontdoor and primary backdoor DHT synthesis impaired VCaP growth.

Inhibition of DIOL Conversion to DHT by 3α-oxidoreductases: DIOL was converted to DHT in a CRPC xenograft and four 3α-oxidoreductases were present in clinical specimens, which show that DIOL is likely to be metabolized to DHT in patients with advanced CaP or CRPC. In vitro administration leads to AR-luciferase (FIG. 10) transactivation that provides an opportunity to examine inhibitors. Constraint-based Multiple Protein Alignment Tool (COBALT) showed that the four 3α-oxidoreductases share active-site, catalytic amino acids residues. LC-MS/MS confirmed that the four 3α-oxidoreductases convert DIOL to DHT and androsterone to 5α-DIONE. 3α-oxidoreductases catalytic amino acid residues were mutated using site-directed mutagenesis. LC-MS/MS showed that single, double or complete catalytic deletion of the common catalytic amino acids impaired enzyme activity. Furthermore, the impaired catalytic mutants combined with dutasteride decreased CaP cell line DHT levels more than dutasteride alone (FIG. 11). The experiment was repeated using LAPC-4 cells transfected with RDH16 targeted siRNA. DHT ELISA revealed that knockdown of RDH16 expression decreased LAPC-4 DHT levels (FIG. 12). VCaP (FIG. 13) and LAPC-4 cell (data not shown) growth was assessed after expression of the catalytic impaired RDH16 Y176F, K180R mutant and treatment with dutasteride.

Figure 14:
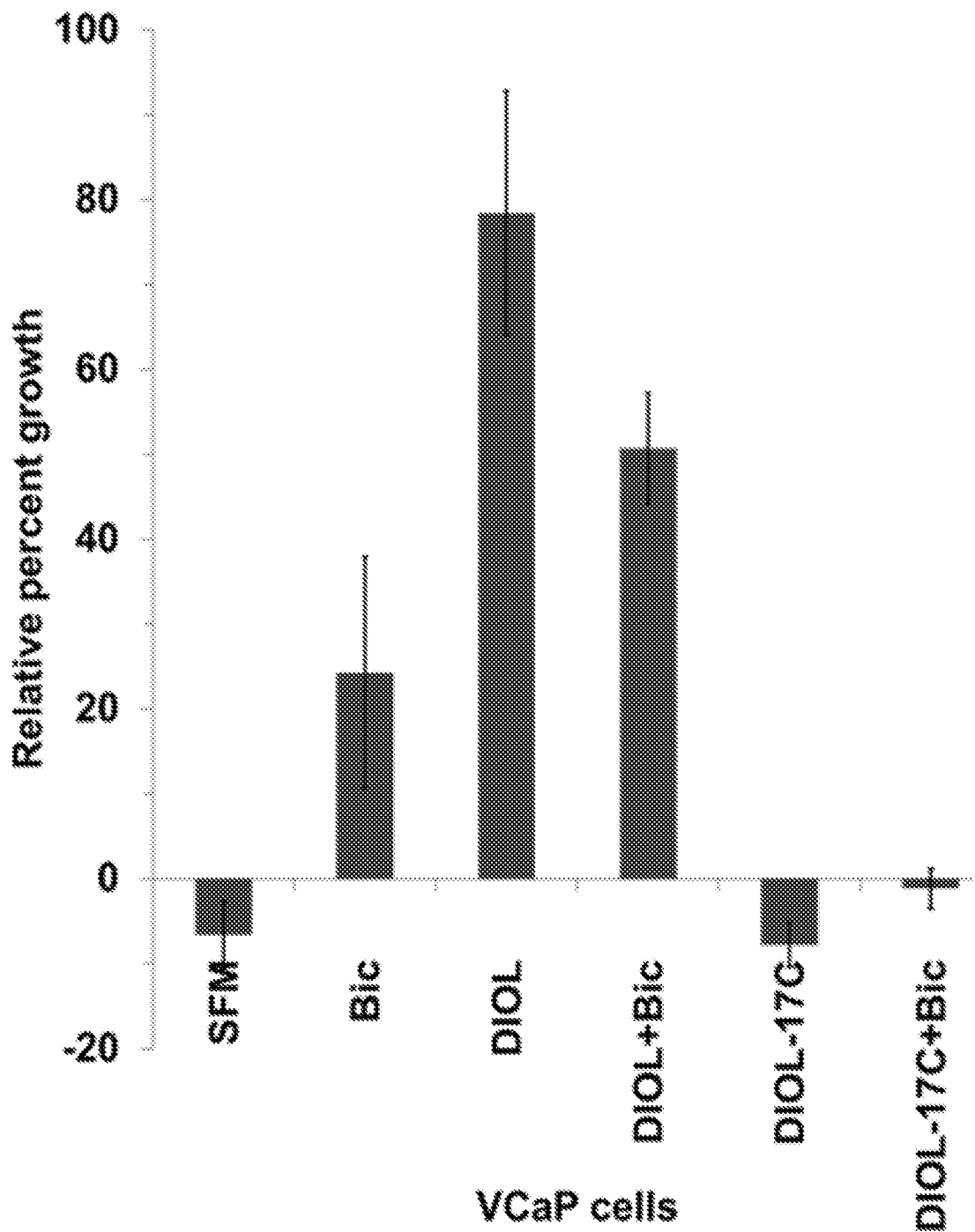
FIG. 14 shows DIOL-17C treatment impaired VCaP cell growth.

Identification of a 3α-oxidoreductase inhibitors: Various non-steroidal compounds were tested for anti-neoplastic activity by screening against PC-3 CaP cells. Coumarin-labeled androgens were developed to track changes in androgen metabolism pathways in response to castration or androgen metabolism inhibition using in vitro and in vivo CaP cell models. Cell viability and AR-regulated gene transcription were assessed using the (3-(4,5-dimethylthiazol-2-yl)-2,5-diphenyltetrazolium bromide (MTT). Data were collected on day 0 and day 6; data were expressed as relative percent growth (average day 6–average day 0 day/average day 0). CaP cell lines were cultured for 6 days in SFM alone or SFM that contained 20 nM DIOL or 20 nM DIOL-17C. MTT showed DIOL-17C treatment impaired CaP cell growth (FIG. 14).

Figure 15:
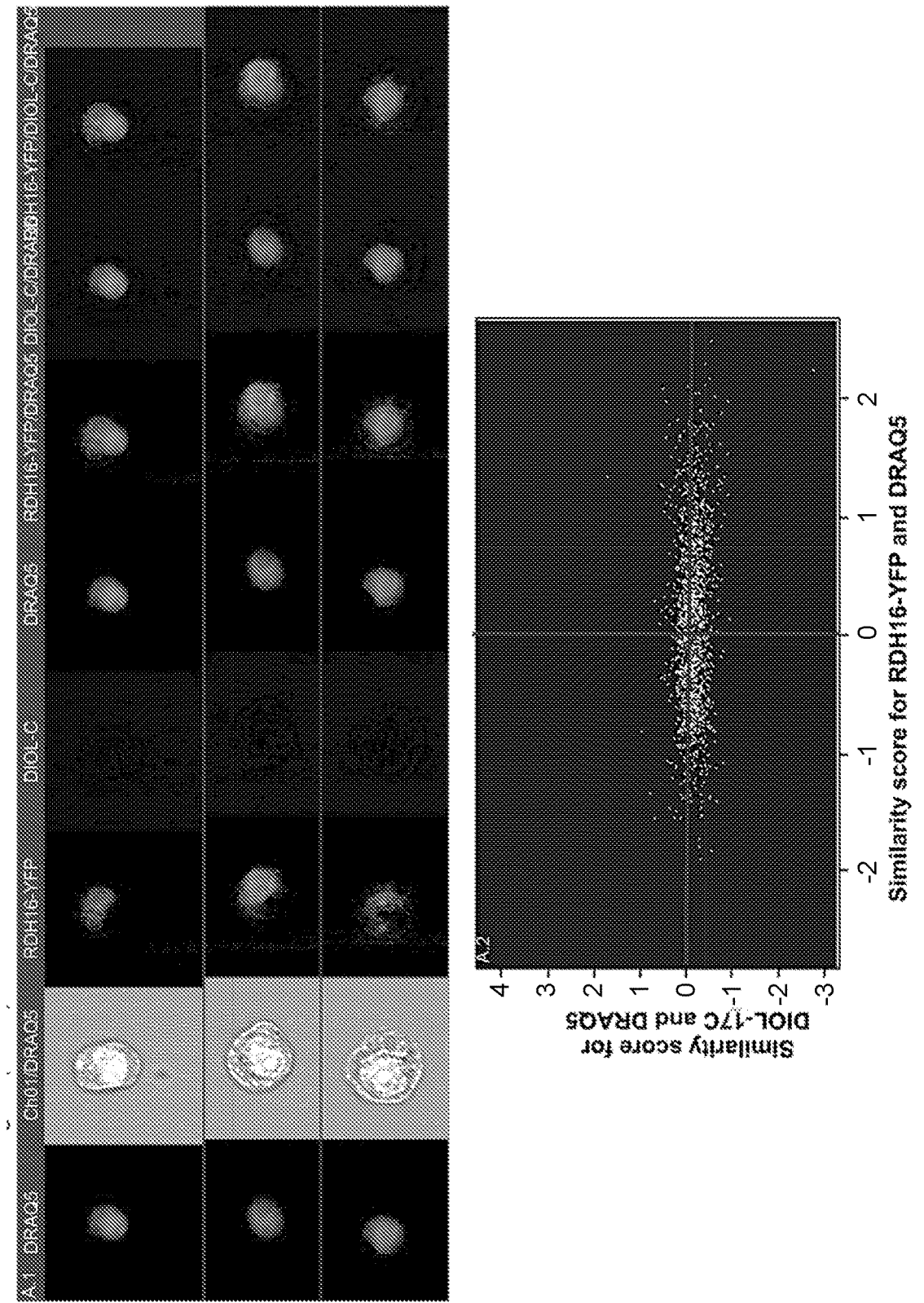
FIG. 15 shows ImageStream RDH16-YFP and DIOL-17C co-localization.
Figure 16:
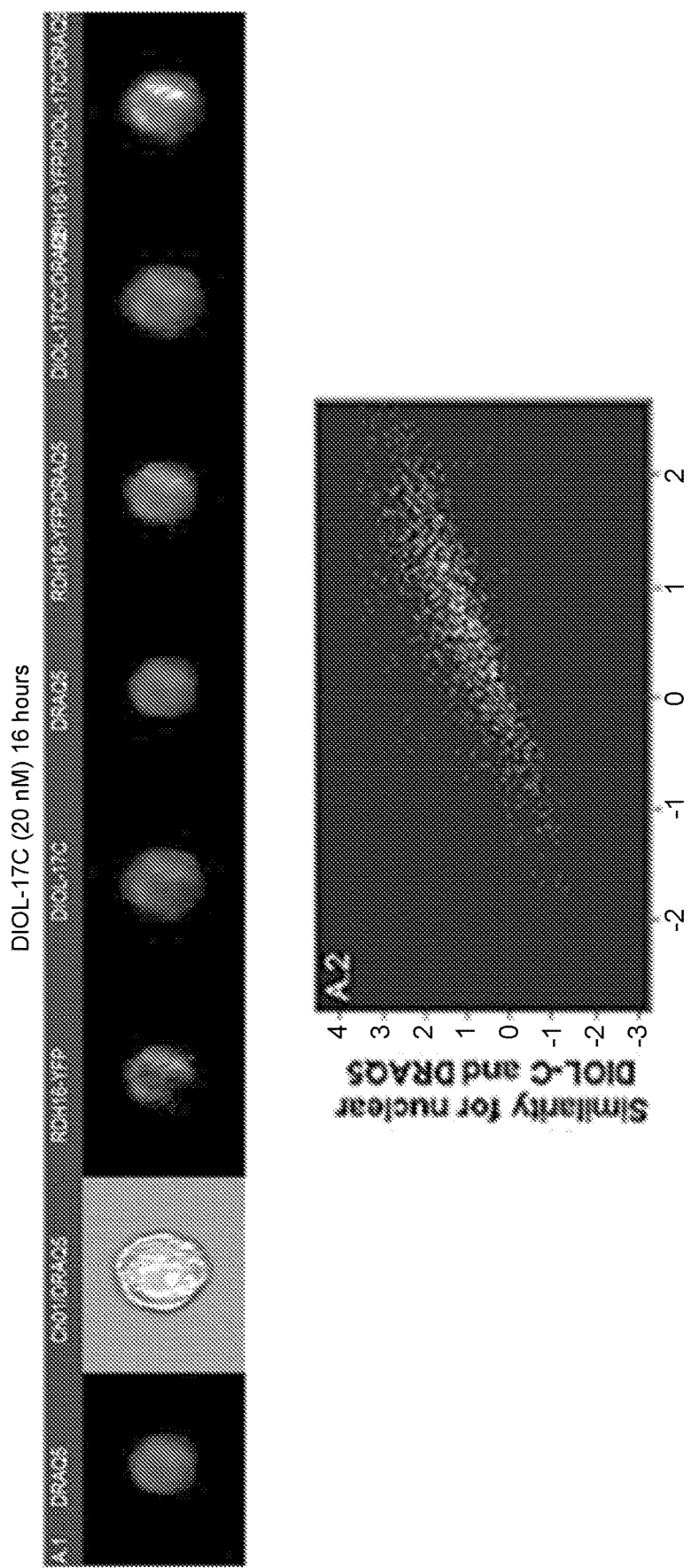
FIG. 16 shows DIOL-17C and DIOL compete for RDH16-YFP.
Figure 16:
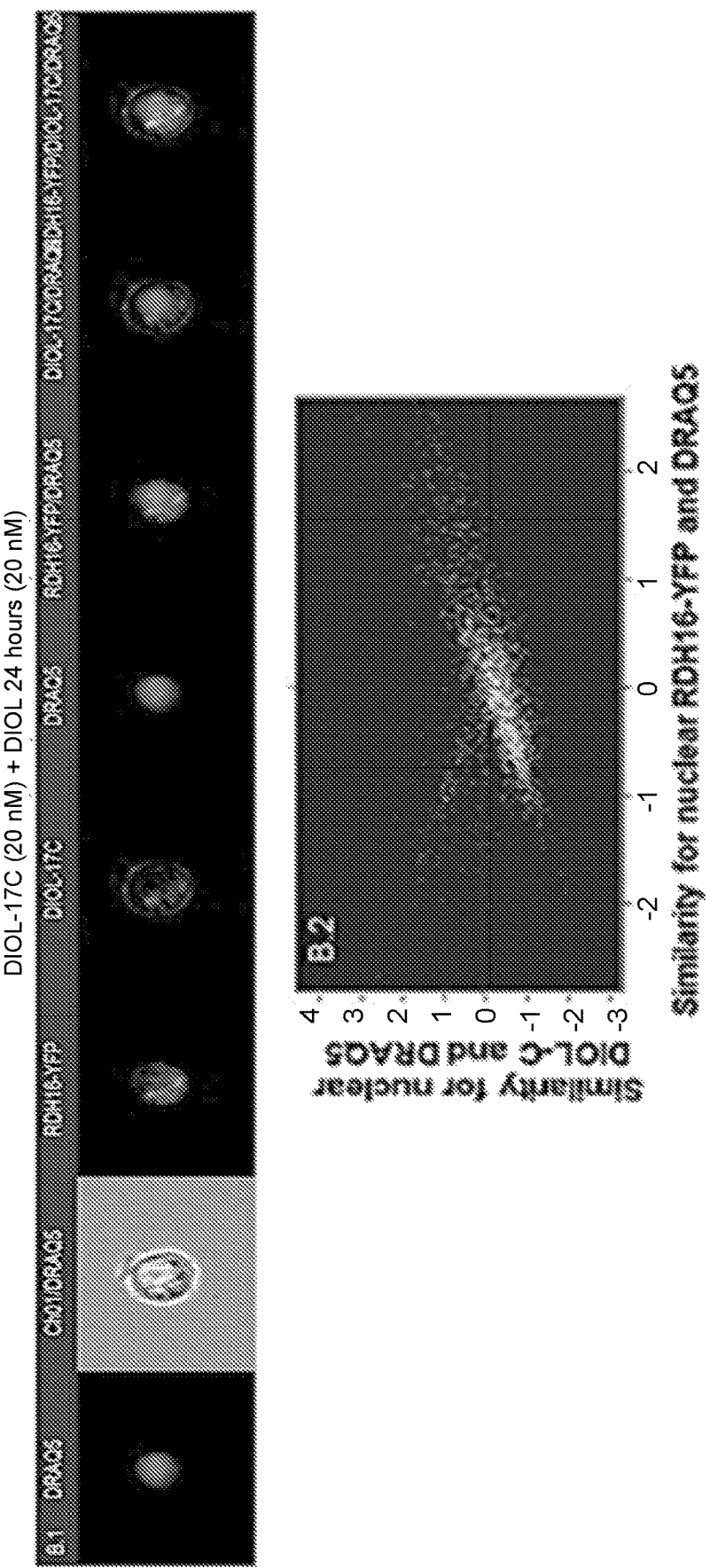

ImageStream (ImageStream$^X$-MKII Flow Cytometer [Amnis, Seattle, WA]) is a hybrid technique that combines the statistical power of flow cytometry and the imaging capability of fluorescence microscopy that was adapted to study simultaneously DIOL-17C compartmental localization and activity. ImageStream data were normalized against single-stained controls and analyzed using Image Data Exploration and Analysis Software (IDEAS; Amnis). The similarity score was measured by comparing two images of the same cell pixel by pixel. If the similarity score was >0, the two objects (RDH16-YFP and DIOL-17C) were co-localized. DIOL-17C (blue) co-localized with RDH16-YFP (color changed to green in IDEA for comparison) and DRAQ5 in the nucleus (white punctate signal) in PC-3-RDH16-YFP cells (FIG. 15A.1 single and merged fluorescent images; 15A.2 high similarity in the upper right quadrant) but not SFM treated PC-3 RDH16-YFP cells (FIG. 15B.1 no punctate signal in the merged images; 15B.2 high similarity in the upper right quadrant). Competition studies using ImageStream demonstrated that DIOL and DIOL-17C compete for RDH16-YFP in PC-3 cells that stably expressed RDH16-YFP (FIG. 16).

Figure 17:
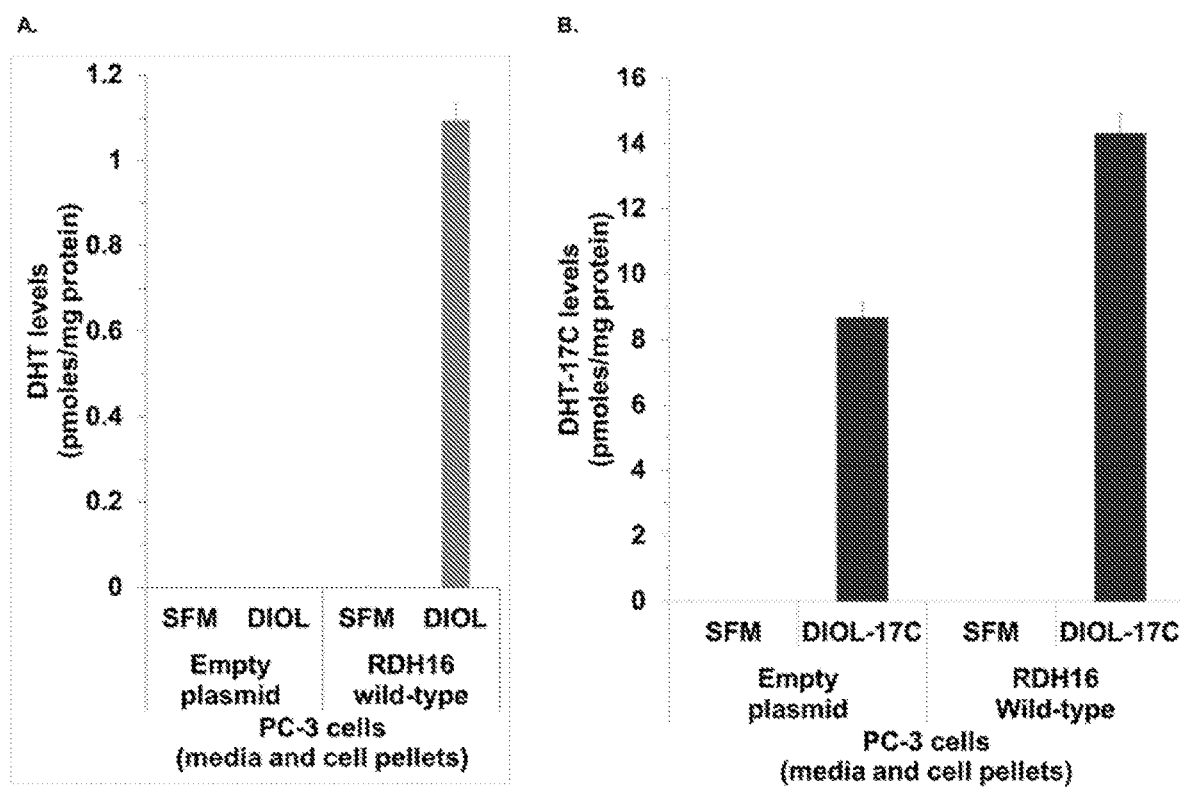
FIG. 17 shows RDH16 metabolized DIOL or DIOL-17C to DHT or DHT-17C, respectively.

LC-MS/MS was performed using CaP cells treated with DIOL-17C to ensure that cells did not produce free DIOL and orphan coumarin. No orphan fluorophores were detected. Addition of coumarin did not impair 3α-oxidoreductase metabolism of DIOL-17C to DHT-17C (FIG. 17).

Example 8

This example provides a description of the biological activity of (((5S,10S,13S,17S)-10,13-dimethyl-3-oxohexadecahydro-1H-cyclopenta[a]phenanthren-17-yl)oxy)-N-(2-(11-oxo-2,3,6,7-tetrahydro-1H,5H,11H-pyrano[2,3-j]pyrido[3,2,1-ij]quinolin-9-yl)ethyl)acetamide described as DHT-17C (aka compound Id) in the present disclosure.

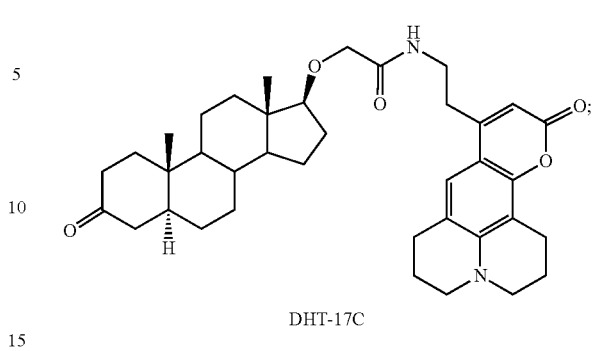

DHT-17C

Androgen-sensitive AR-positive LAPC-4 and VCaP, castration-recurrent and AR-positive CWR-R1 and CWR-22rv1 (22rv1), and AR-negative PC-3 and DU145 cells were transfected with either an empty pCMV expression plasmid (control) or a pCMV plasmid that encoded a wild-type AR tagged with a C-terminal green fluorescent protein (GFP; AR-GFP). AR-positive CaP cell lines were transfected with AR-GFP to assess if DHT-17C or DHT-3C co-localized with AR and translocated to the nucleus. The fluorescencent coumarin moiety was moved from the C-17 to the C-3 position (DHT-3C, aka compound Ig) to test the effect of the coumarin on anti-androgen activity. The data demonstrated that the position of the coumarin moiety on DHT is essential to differentiate DHT-like from anti-androgen-like activities.

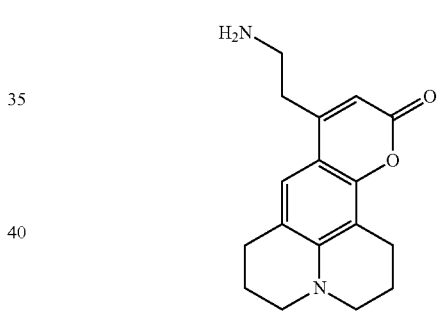

AR positive CaP cell lines were treated for 16 hours with androgen-free, serum-free complete media (SFM) alone, or SFM that contained 20 nM or 50 nM fluorescent-androgens or C alone. The time points were chosen to measure differences in uptake of the fluorescent-androgens and nuclear or cytosolic localization of the fluorescent-androgens and/or AR-GFP. ImageStream analysis demonstrated that DHT-17C and DHT-3C were taken up by VCaP, LAPC-4, CWR-R1, 22Rv1, PC-3, and DU145 cells (data reported for VCaP and PC-3-AR-GFP, which were representative of all cell lines studied). DHT-17C (blue) or DHT-3C co-localized with AR-GFP (green) and the nuclear marker DRAQ5 (red) in the nucleus (white punctate signal) in VCaP-AR-GFP and PC-3-AR-GFP cells (FIG. 18).

Figure 18:
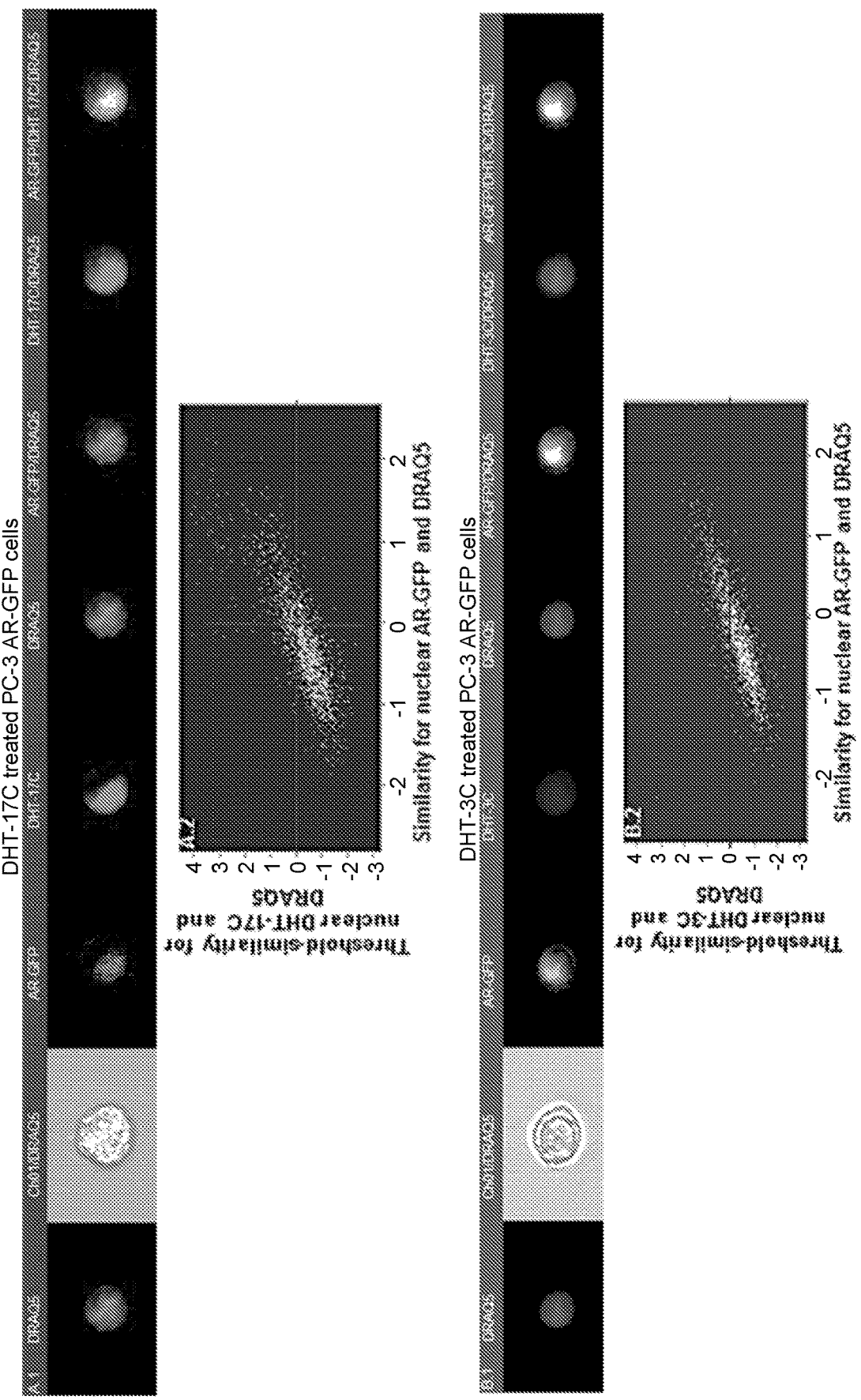
FIG. 18 shows ImageStream data that demonstrated similar AR-GFP co-localization patterns between DHT-17C and DHT-C3. ImageStream also confirmed nuclear co-localization between DHT-17C and AR-V2-GFP.
Figure 18:
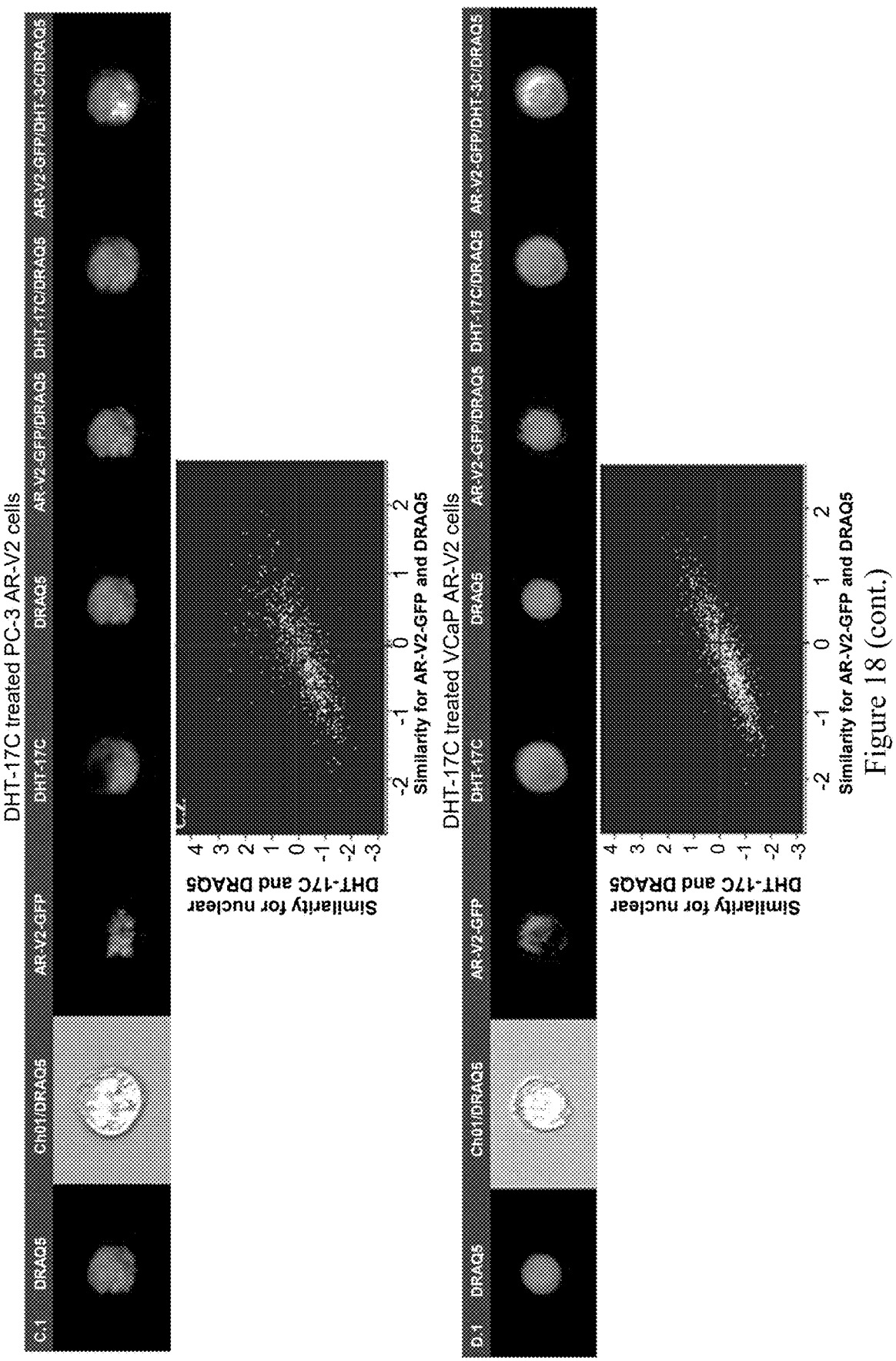

DHT-3C (aka compound Ig) co-localized with AR-GFP and DRAQ5 (FIG. 18). DHT-3C served as a negative control for DHT-17C (aka compound Id) and showed that DHT-17C was an AR-LBD inhibitor in contrast to DHT-3C that retained DHT activity (as described above).

Nuclear localization of DHT-17C or DHT-3C was not observed in AR- or AR-GFP negative PC-3 cells that suggested nuclear localization of DHT-17C or DHT-3C was AR dependent. ImageStream studies were repeated using VCaP and PC-3 cells that stably expressed AR-V2 (splice-variant that lacked the N-terminus) with C-terminal GFP (AR-V2-GFP). ImageStream analysis revealed DHT-17C and DHT-3C co-localized with DRAQ5 and AR-V2-GFP (FIG. 18). ImageStream data was confirmed using immunoprecipitation (IP) studies performed with a DHT-targeted antibody.

Figure 19:
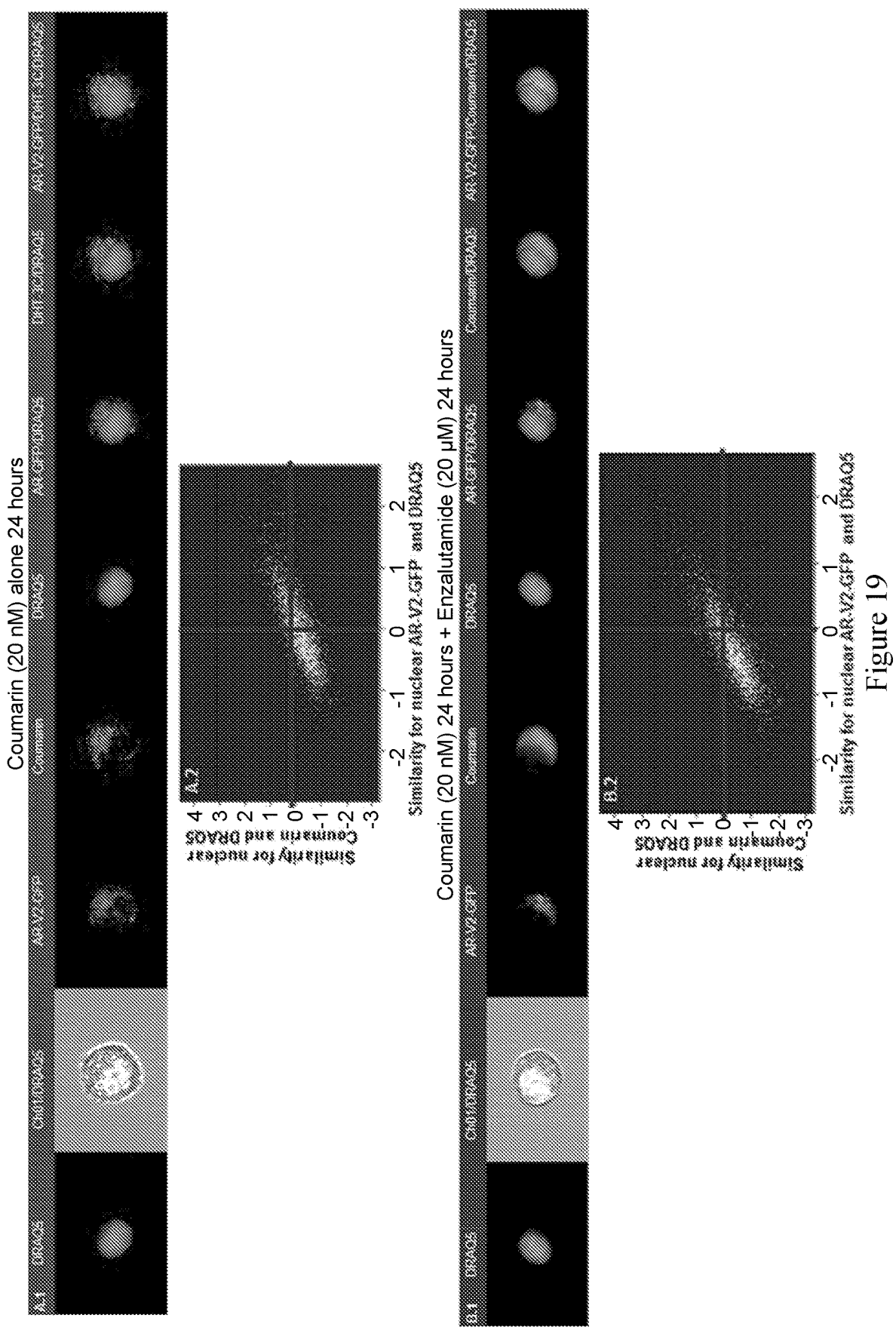
FIG. 19 shows competition data that demonstrated DHT-17C and enzalutamide compete for AR-V2-GFP.
Figure 19:
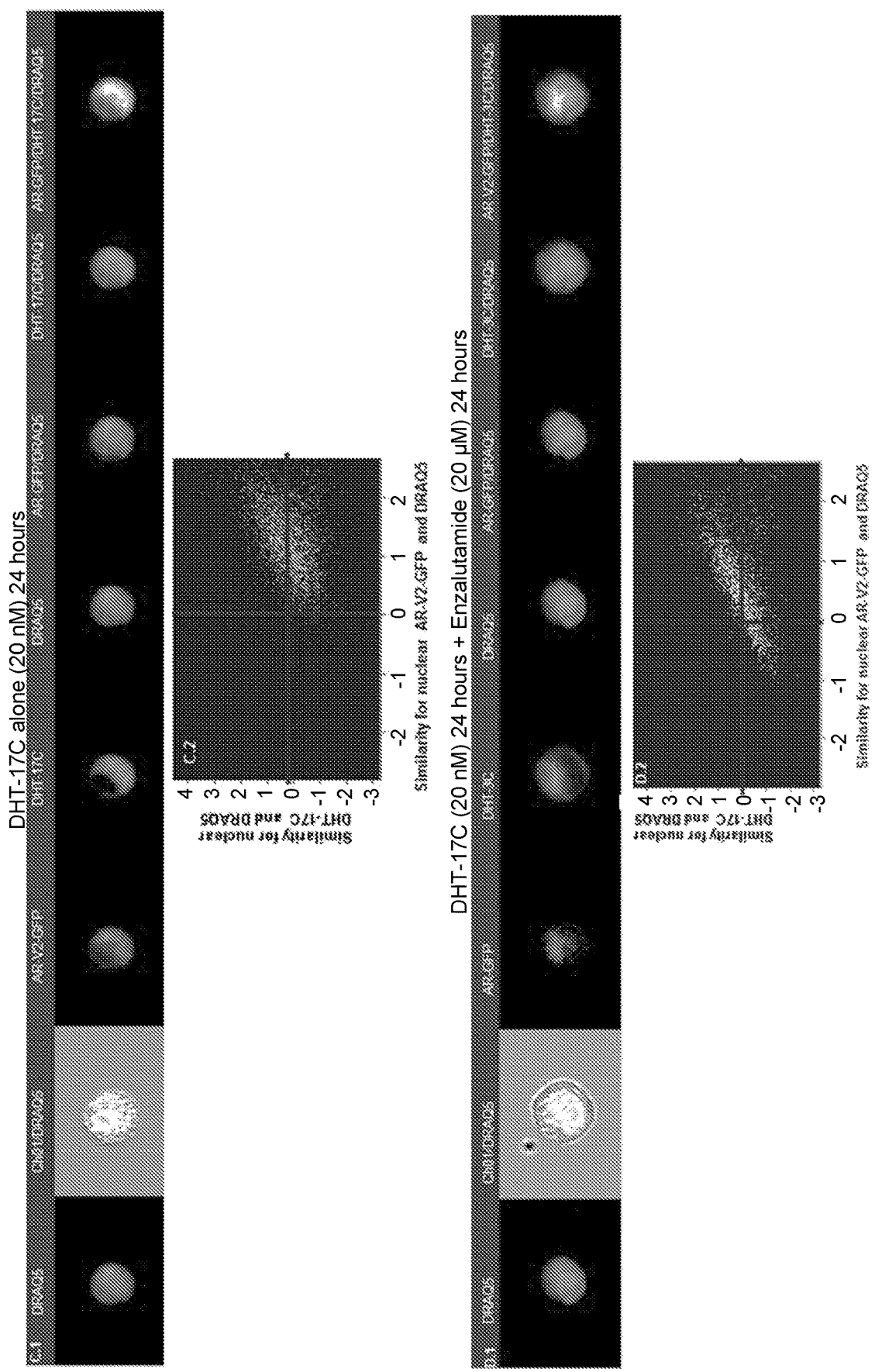

ImageStream was used to perform competition studies between DHT-17C and enzalutamide for AR-GFP or AR-V2 to establish that DHT-17C targets the AR-LBD. ImageStream data confirmed that DHT-17C and enzalutamide compete for the AR-LBD of wild-type AR and AR-V2 (FIG. 19).

Figure 21:
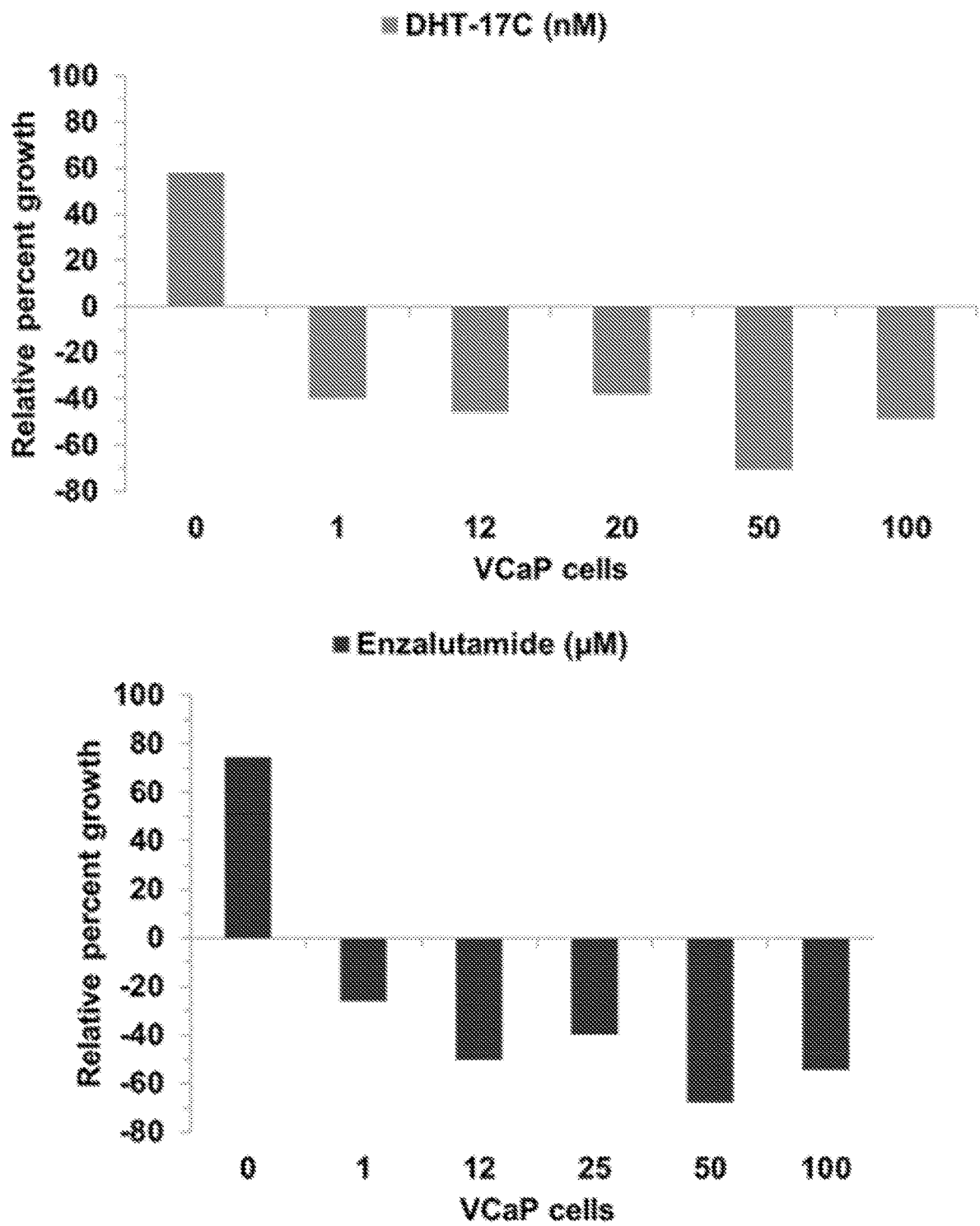
FIG. 21 shows growth data that demonstrated DHT-17C (20 nM) inhibited AR-V7 positive VCaP growth using a 1000× lower dose than enzalutamide (20 μM)
Figure 22:
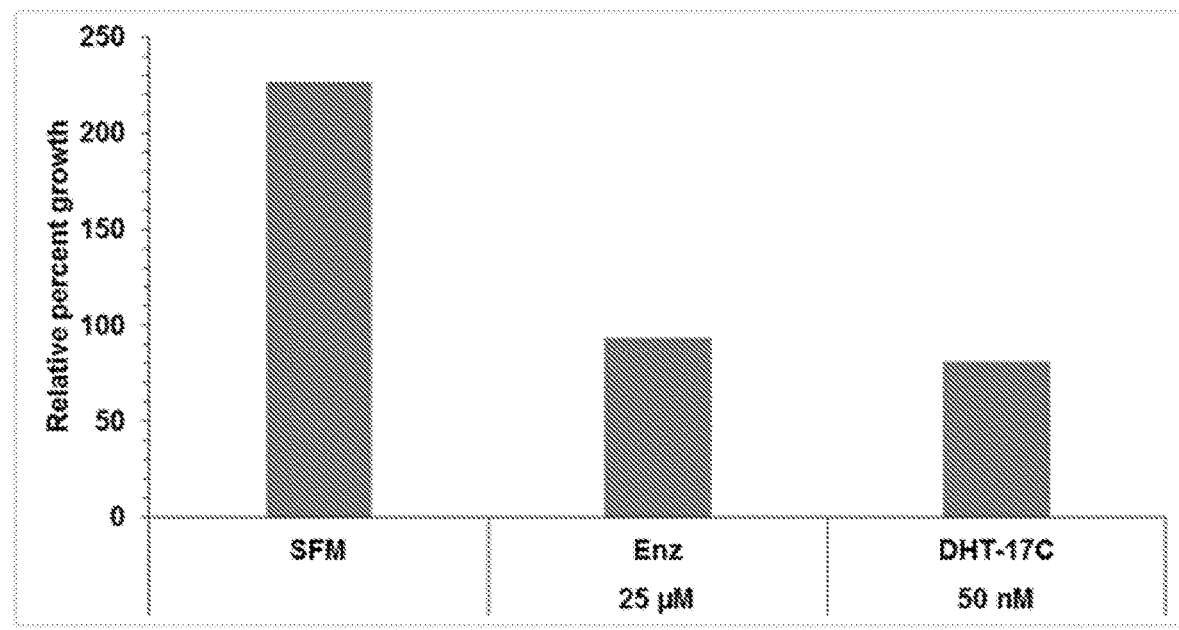
FIG. 22 shows growth data that demonstrated similar growth impairment between DHT-17C (50 nM) and enzalutamide (20 μM) using the castration-recurrent, AR-V7 positive CRPC CWR-R1 cell line.

VCaP, CWR-R1 and PC-3 cells were treated for six days with complete culture media (CM), serum-free culture media (SFM), bicalutamide (Bic) at 10 µM, the coumarin C at 20 µM, DHT at 10 nM, DHT-17C at 20 nM and DHT-3C at 20 nM (FIG. 20). MTT assay analysis revealed that six days of treatment with DHT-3C promoted VCaP, LAPC-4, and LNCaP cell growth, as expected for a surrogate of DHT (data not shown) and CWR-R1 cell growth compared to DHT (FIG. 20). In contrast, DHT-17C treatment impaired VCaP and CWR-R1 cell growth and enhanced the effect of bicalutamide (FIG. 20; p-values<0.05). MTT experiments using LAPC-4, LNCaP and 22Rv1 produced similar responses (data not shown; p-values<0.05). DHT-17C did not impair cell growth in AR-negative PC-3 (FIG. 20), DU145 and non-CaP cell lines (CV-1 monkey kidney and 293 human kidney cell lines). MTT analysis was performed to compare cell growth impairment of VCaP cells treated with DHT-17C versus enzalutamide. Cells were treated with DHT-17C at 1 nM, 12 nM, 20 nM, 50 nM or 100 nM concentrations, or enzalutamide at 1 µM, 12 µM, 20 µM, 50 µM or 100 µM concentrations. DHT-17C at nM concentrations impaired VCaP cell growth to similar extents as enzalutamide at M concentrations (FIG. 21). MTT performed using ezanlutamide (20 uM) or DHT-17C (50 nM) treated mutant AR and AR-V7 positive CWR-R1 cells supported VCaP MTT data (FIG. 22).

Figure 23:
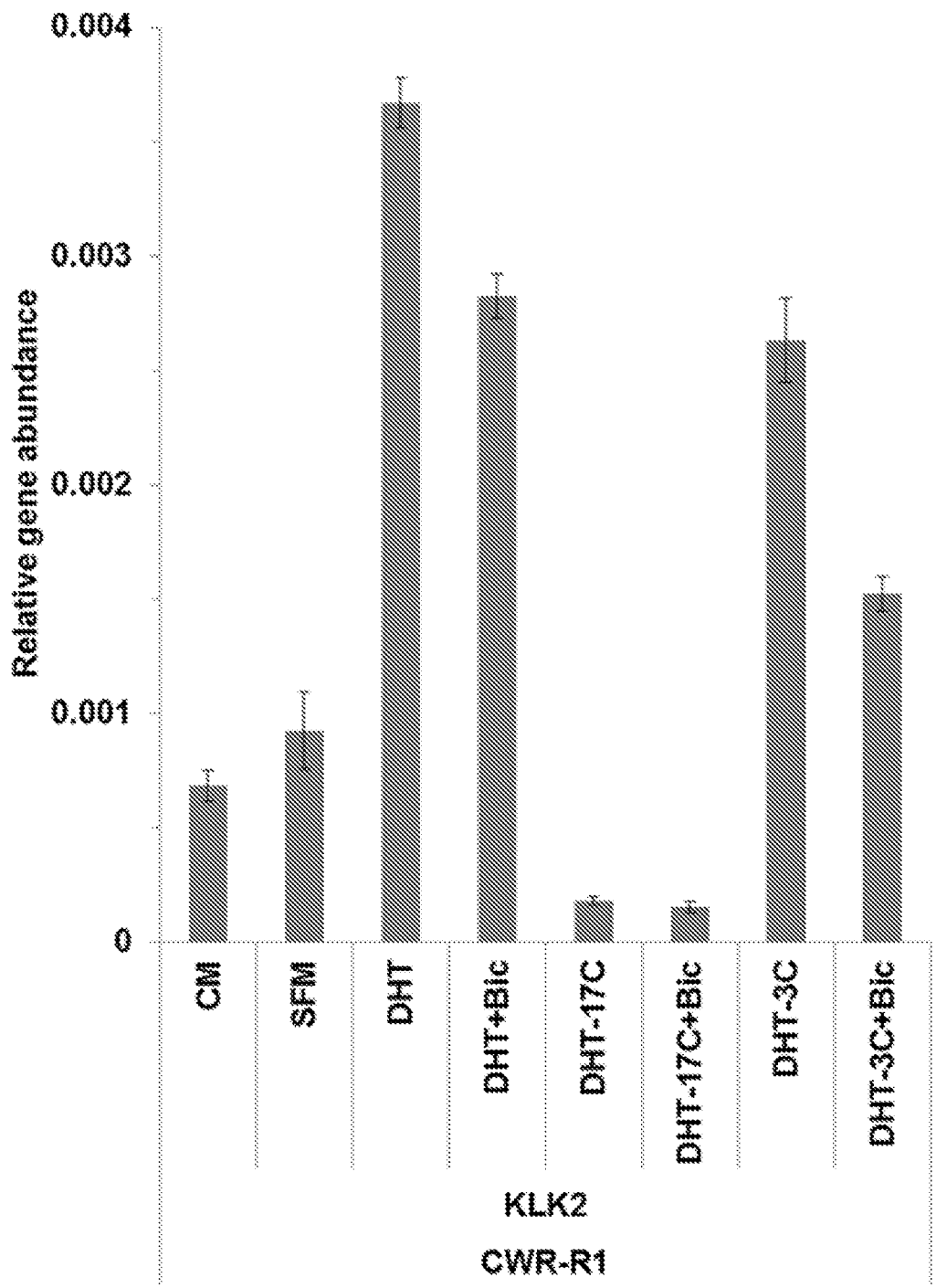
FIG. 23 shows qRT-PCR data that demonstrated DHT-17C treatment of CWR-R1 impaired AR-regulated gene kallikrein-related peptidase 2 (KLK2) transcript induction.

A quantitative real-time-polymerase chain reaction (qRT-PCR) analysis showed that non-transfected VCaP, LAPC-4, LNCaP, CWR-R1 and 22rv1 cells treated 24 hours with DHT, or DHT-3C, produced similar inductions of expression of the AR-regulated gene, KLK2 (FIG. 23; CWR-R1 representative). In contrast, DHT-17C treatment did not induce KLK2 transcript formation in any of the five AR positive CaP cell lines (FIG. 23; CWR-R1 representative) that suggested that the site of fluorophore placement on the DHT molecule and not the presence of C was responsible for a lack of KLK2 induction. Completion of these studies revealed that DHT-17C has anti-androgen-like characteristics but produced another unexpected finding.

Example 9

DHT-3C is a surrogate for DHT that be used as a carrier for molecules that disrupt AR transactivation or even degrade AR.

Figure 24:
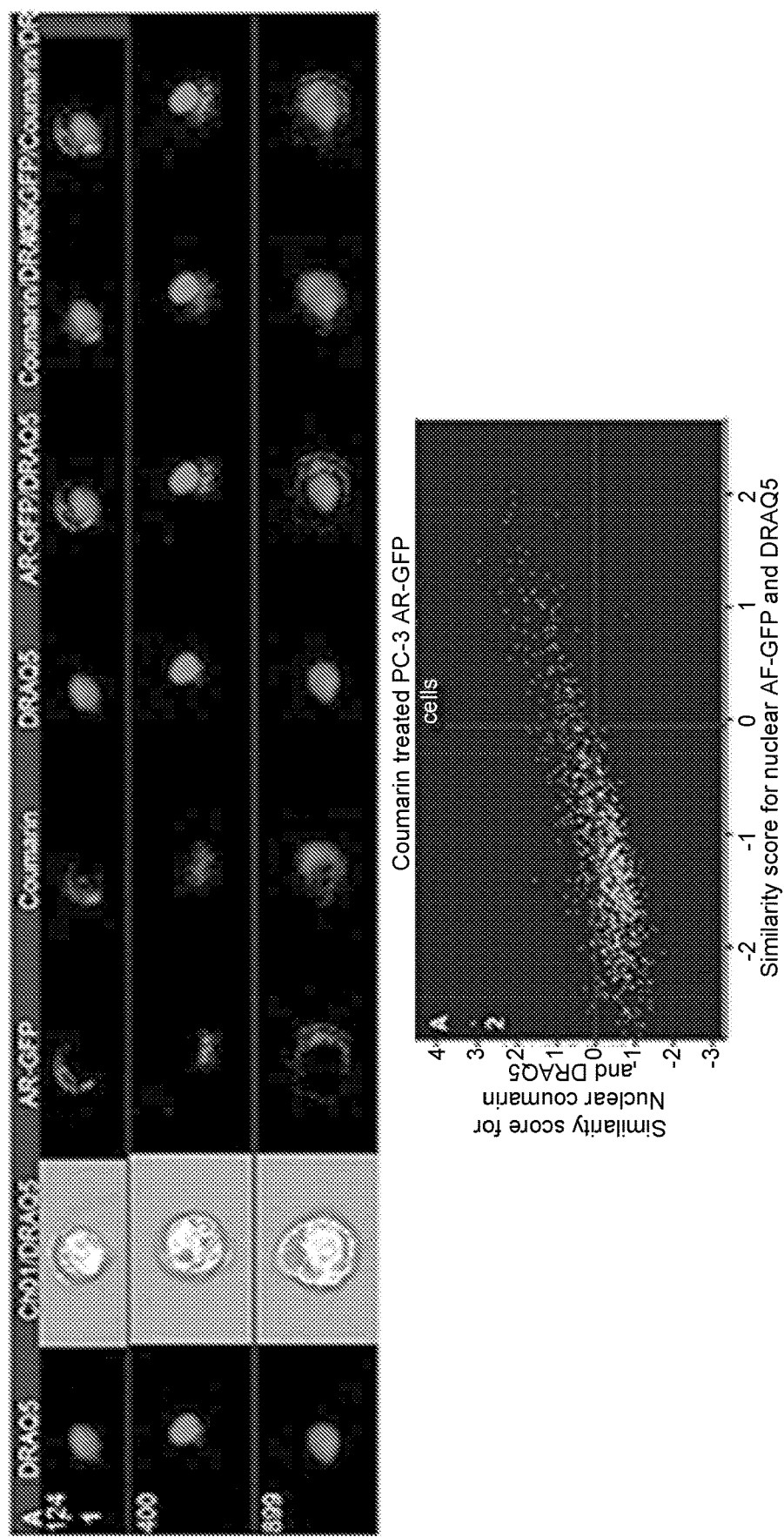
FIG. 24 shows ImageStream data that demonstrated nuclear co-localization between DHT-3C and AR-GFP, but not free coumarin and AR-GFP. AR-GFP studies were confirmed using AR-V2-GFP.
Figure 24:
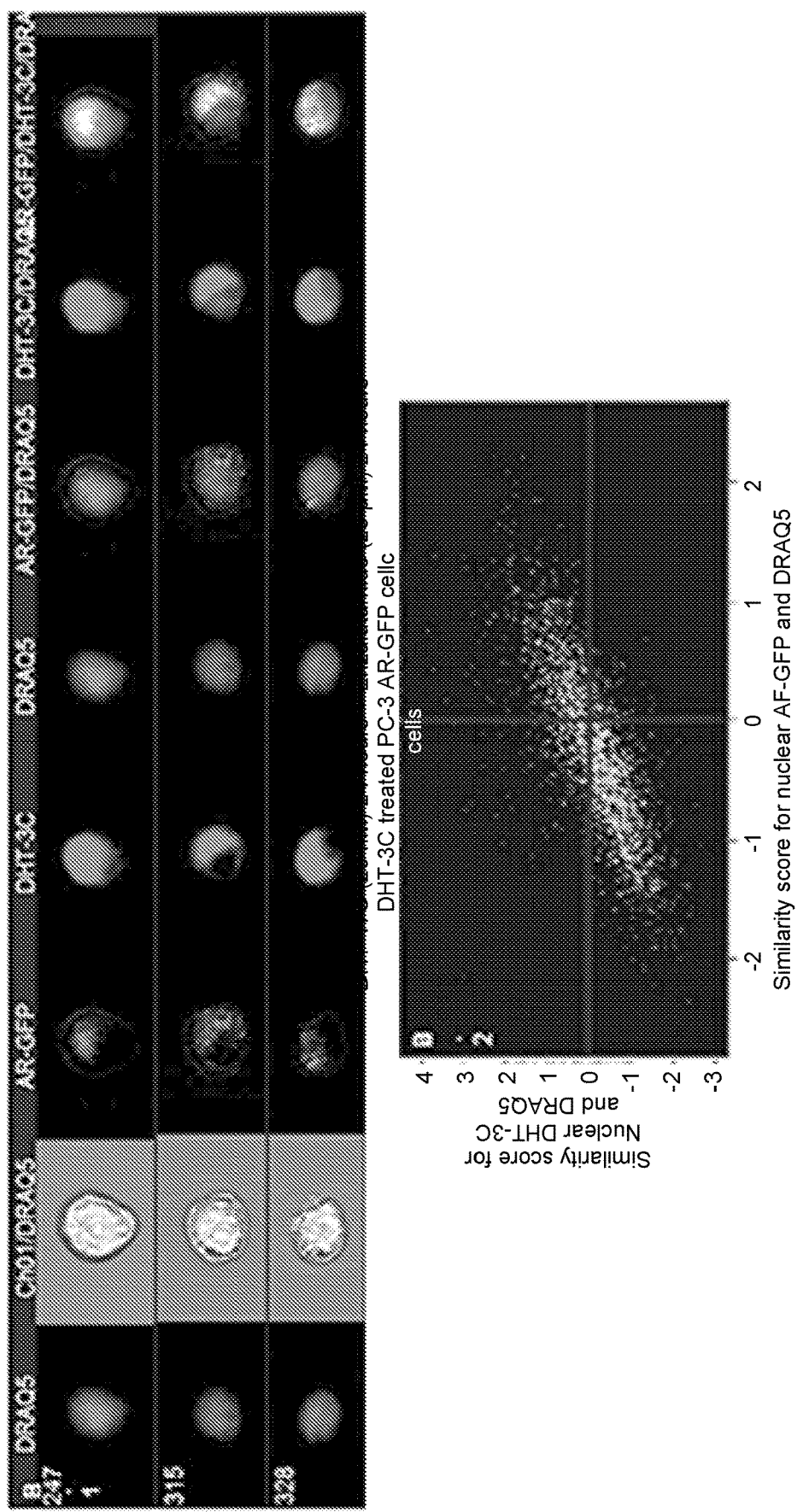
Figure 24:
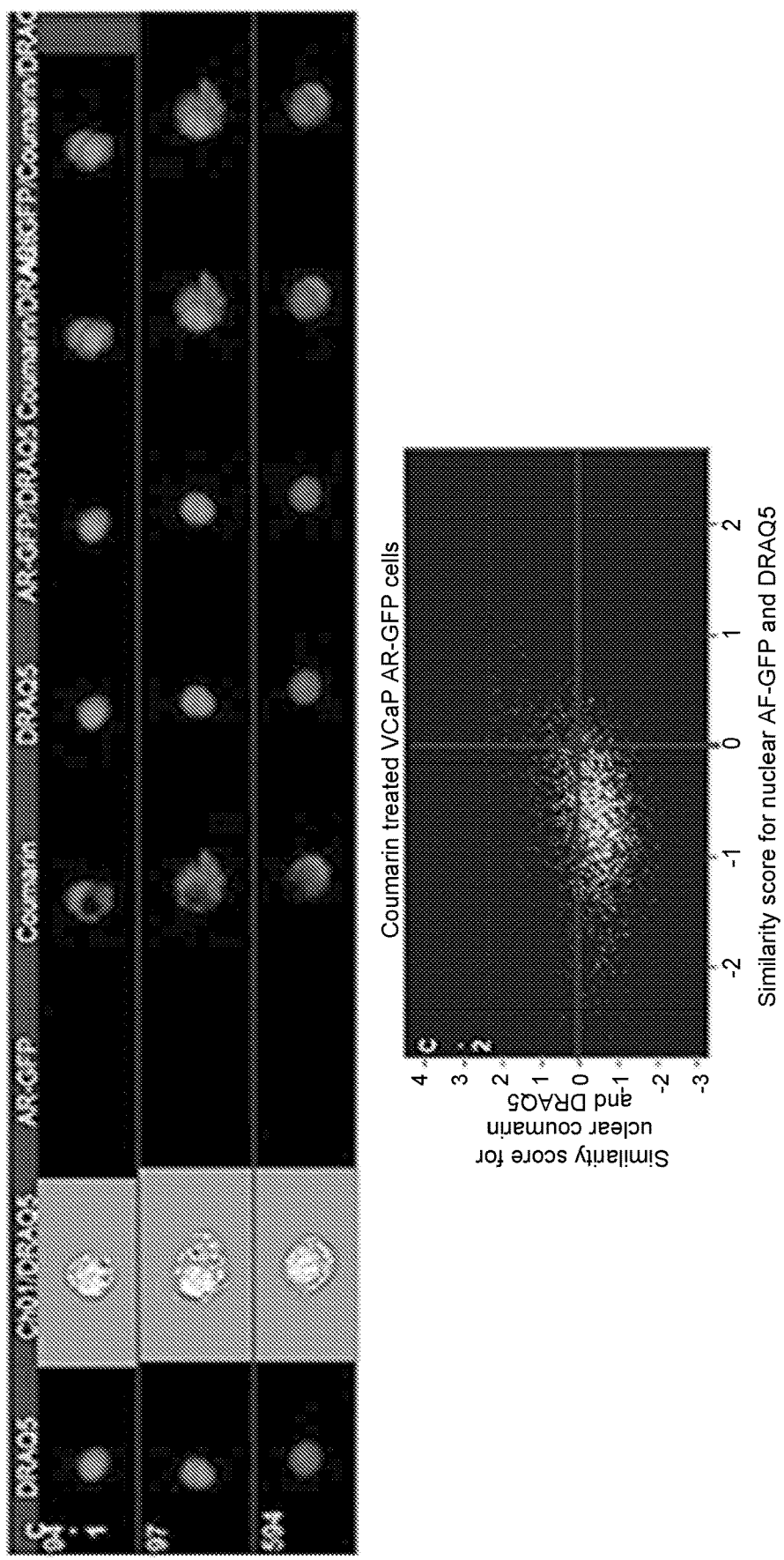
Figure 24:
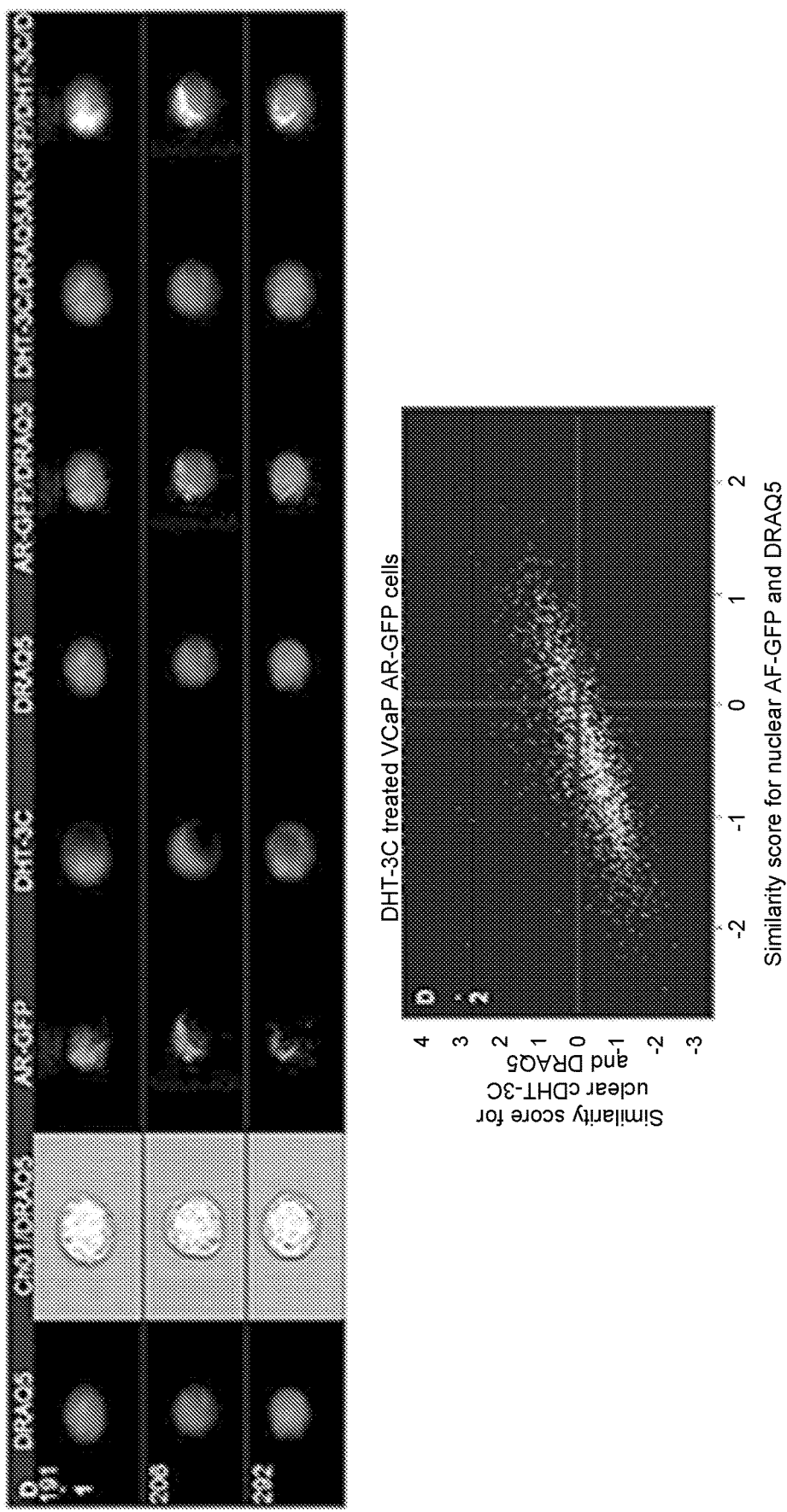
Figure 24:
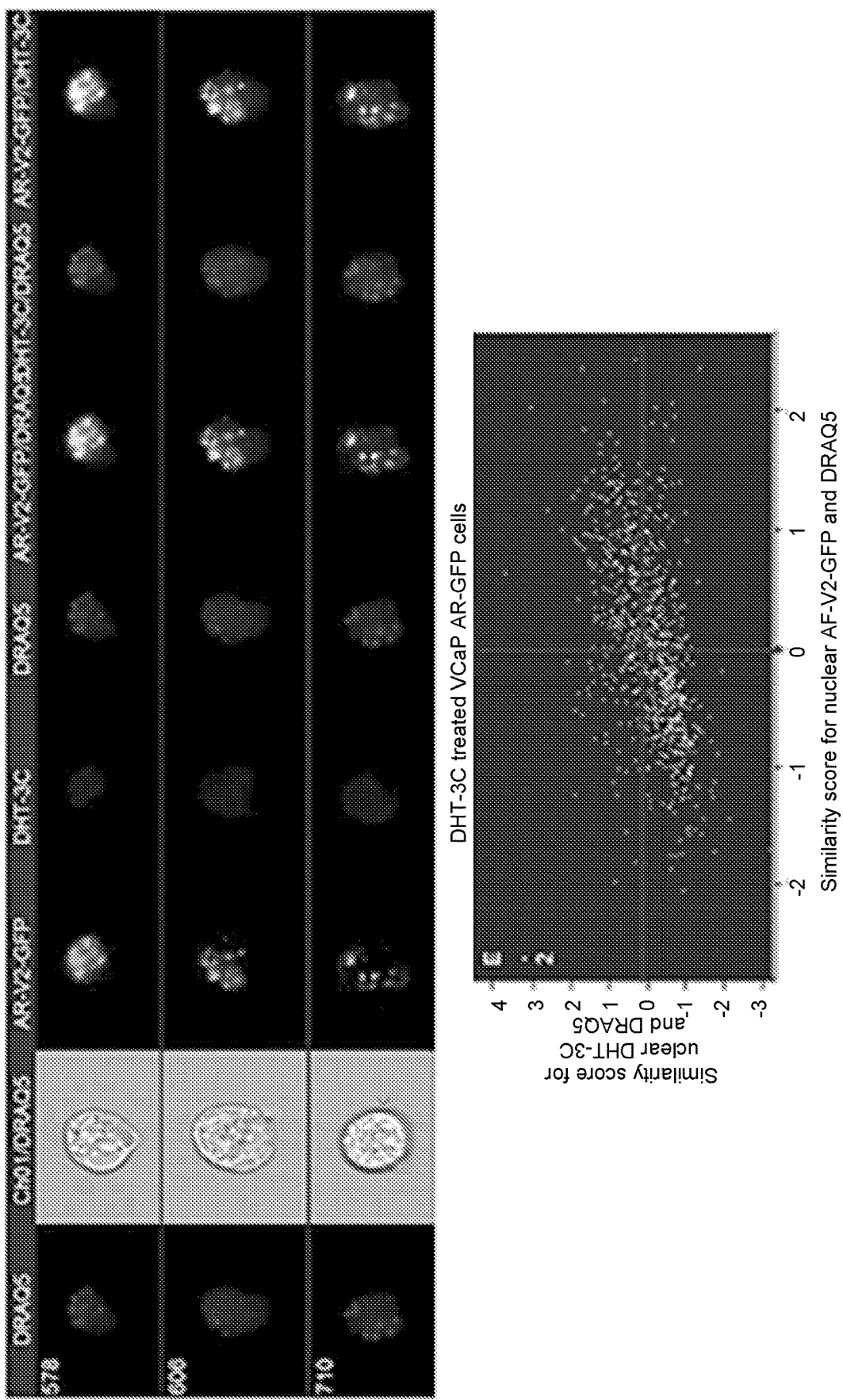

ImageStream was used to evaluate the cellular uptake of DHT-3C (aka compound Ig) in FIG. 4 by AR-negative PC-3 cells with empty plasmid, PC-3 cells that stably expressed AR-GFP (PC-3-AR-GFP), VCaP cells with empty plasmid, VCaP cells that stably expressed AR-GFP (VCaP-AR-GFP), or VCaP that stably expressed AR170 LBD only with splice variant V2 (AR-V2-GFP) to confirm the DHT-like activity exhibited by DHT-3C. Serum-free complete media (SFM)$^2$ was used to androgen deprive cells. PC-3 cells that contained empty plasmid were treated with SFM alone, SFM with C or SFM with DHT-3C. Cells showed minimal auto-fluorescence and did not produce nuclear fluorescence consistent with C or DHT-3C. SFM-treated PC-3 AR-GFP cells showed no auto-fluorescence. SFM with C-treated PC-3 AR-GFP cells demonstrated no nuclear co-localization between C and AR-GFP (FIGS. 24A.1 and A.2). DHT-3C-treated PC-3-AR-GFP showed nuclear co-localization between DHT-3C and AR-GFP (FIGS. 24B.1 and B.2). C-treated VCaP that stably expressed AR-GFP did not produce nuclear co-localization between C and AR-GFP (FIGS. 24C.1 and C.2). DHT-3C treated VCaP that stably expressed AR-GFP demonstrated co-localization between DHT-3C and AR-GFP (FIGS. 24D.1 and D.2). DHT-3C-treated VCaP that stably expressed AR-V2-GFP showed DHT-3C co-localized with the AR LBD (FIGS. 24E.1 and E.2).

Figure 25:
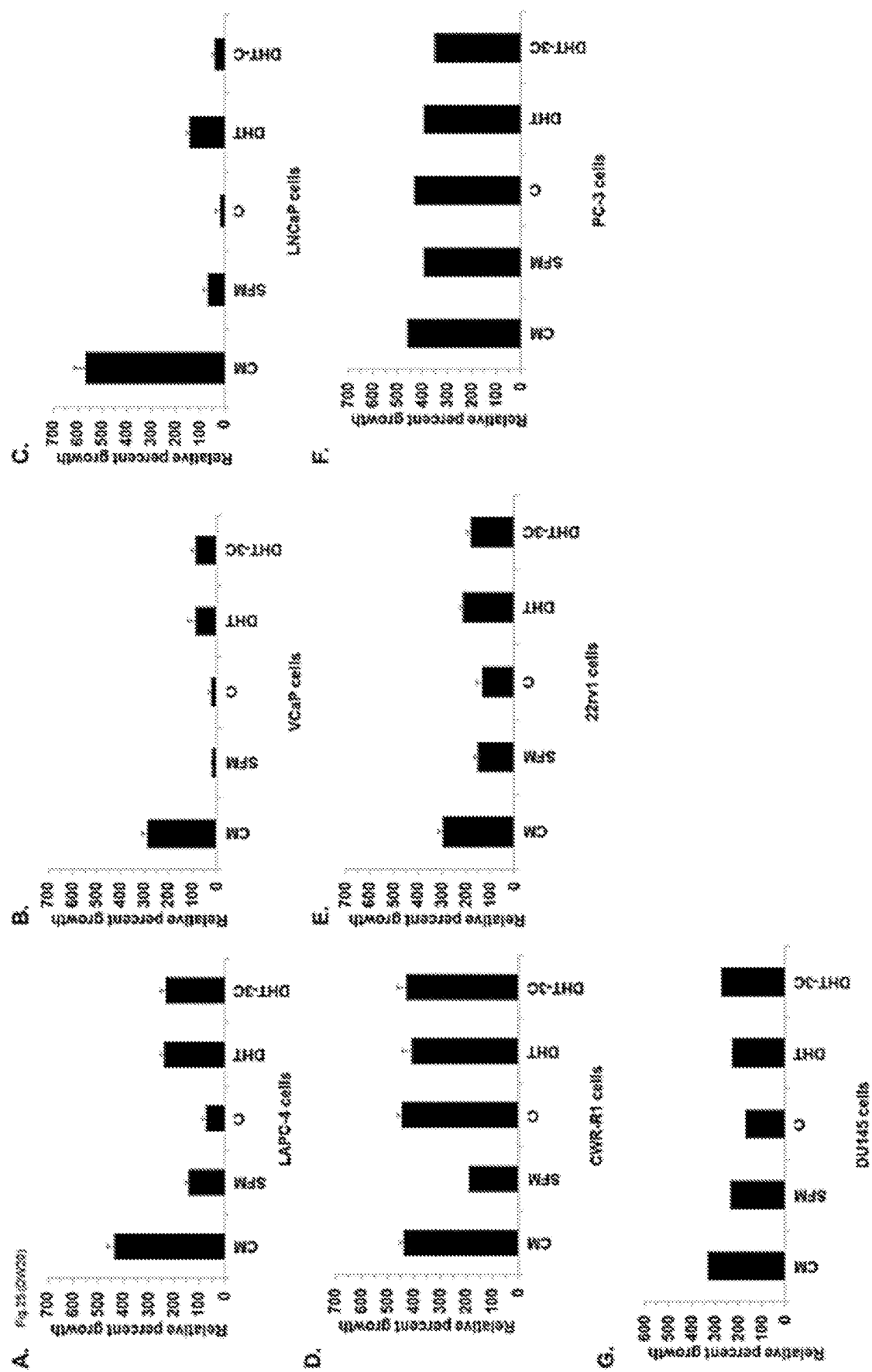
FIG. 25 shows growth data that demonstrated similar growth patterns among AR-Positive CaP cell lines treated with DHT-3C or DHT. The various cell lines are (A) LAPC-4; (B) VCaP; (C) LNCaP; (D) CRW-R1; (E) 22rv1; (F) PC-3; and (G) DU145.

ImageStream data revealed DHT-3C was taken up by CaP cell lines and co-localized with AR in the nucleus. MTT analysis was used to assess if treatment with DHT-3C facilitated CaP cell growth during androgen deprivation. AR positive androgen-sensitive VCaP, LAPC-4 and LNCaP; AR positive castration-recurrent CWR-R1 and CWR22rv1; and AR negative PC-3 and DU145 CaP cell lines were treated for six days under five sets of conditions: complete cell culture media (CM) to establish baseline CaP cell growth; SFM to simulate androgen deprivation; SFM with C alone as the negative control to ensure C alone did not impact CaP cell growth; SFM with DHT as the positive control; and SFM with DHT-3C. SFM with DHT-3C stimulated growth in 3 of 5 cell lines (FIG. 25).

In summary, these data suggested that increased CaP cell growth was AR-dependent and stimulated by either DHT or DHT-3C that functioned as a DHT surrogate.

Figure 26:
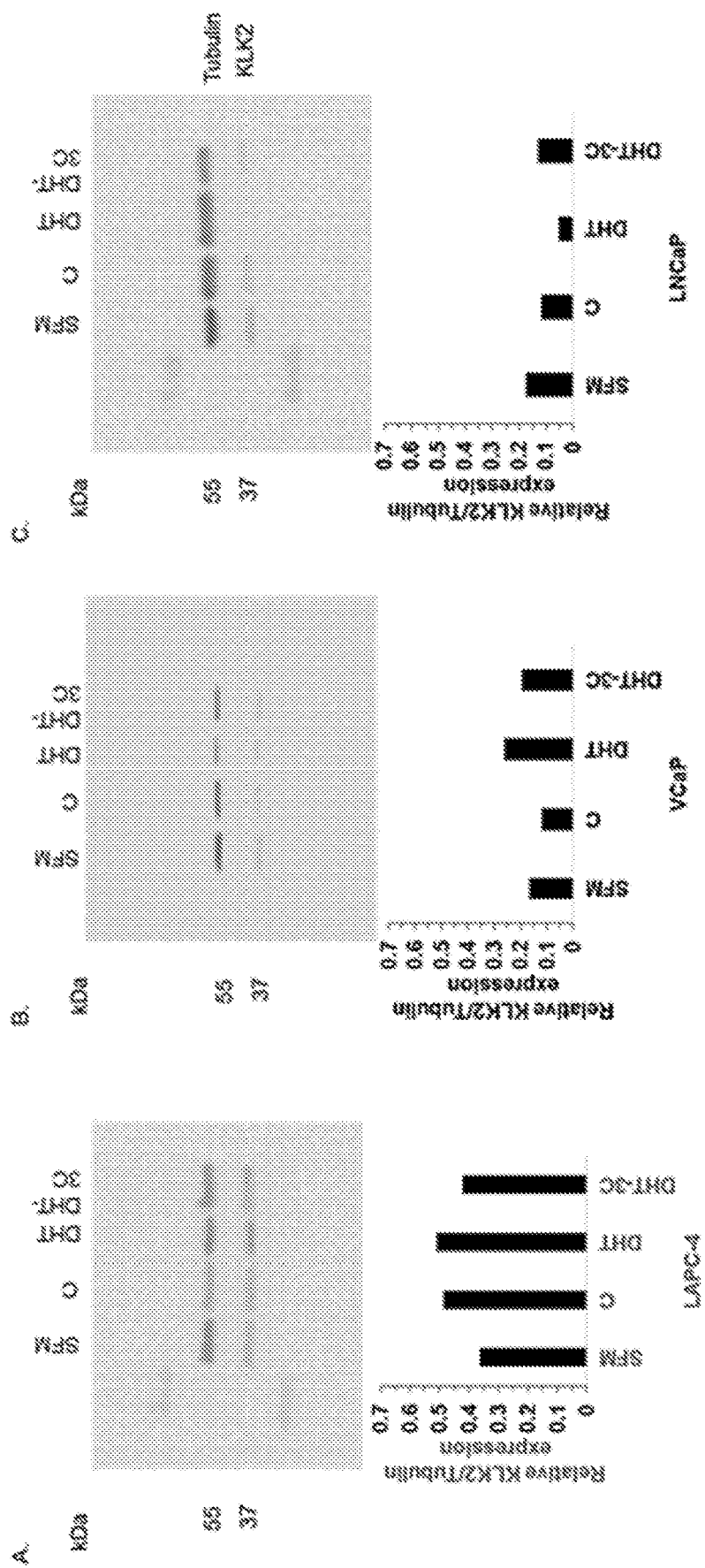
FIG. 26 shows that DHT-3C or DHT treatment of CaP cell lines produced similar AR-regulated gene, KLK2, protein expression levels. The various cell lines are (A) LAPC-4; (B) VCaP; (C) LNCaP; (D) CRW-R1; and (E) 22rv1.
Figure 26:
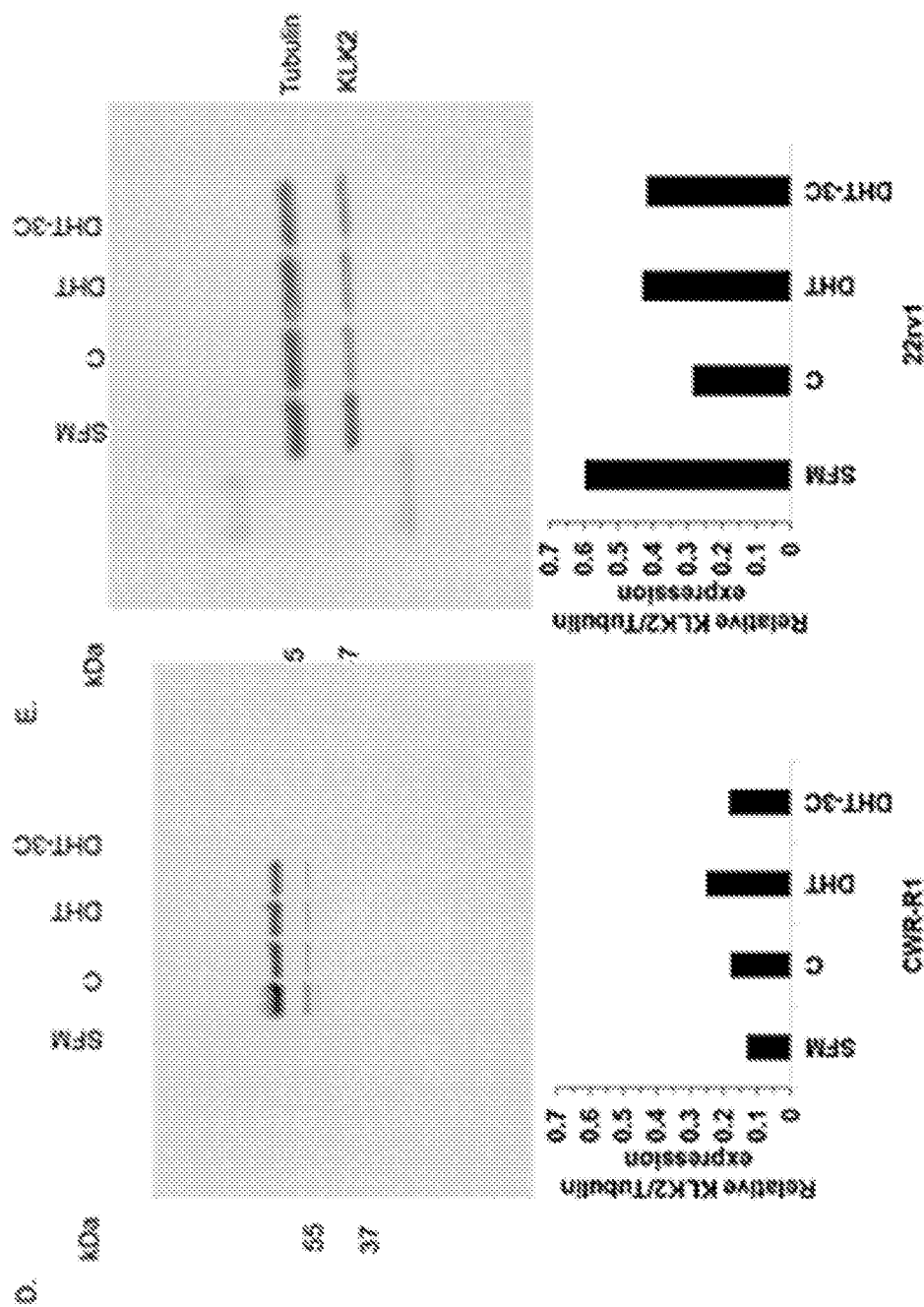
Figure 27:
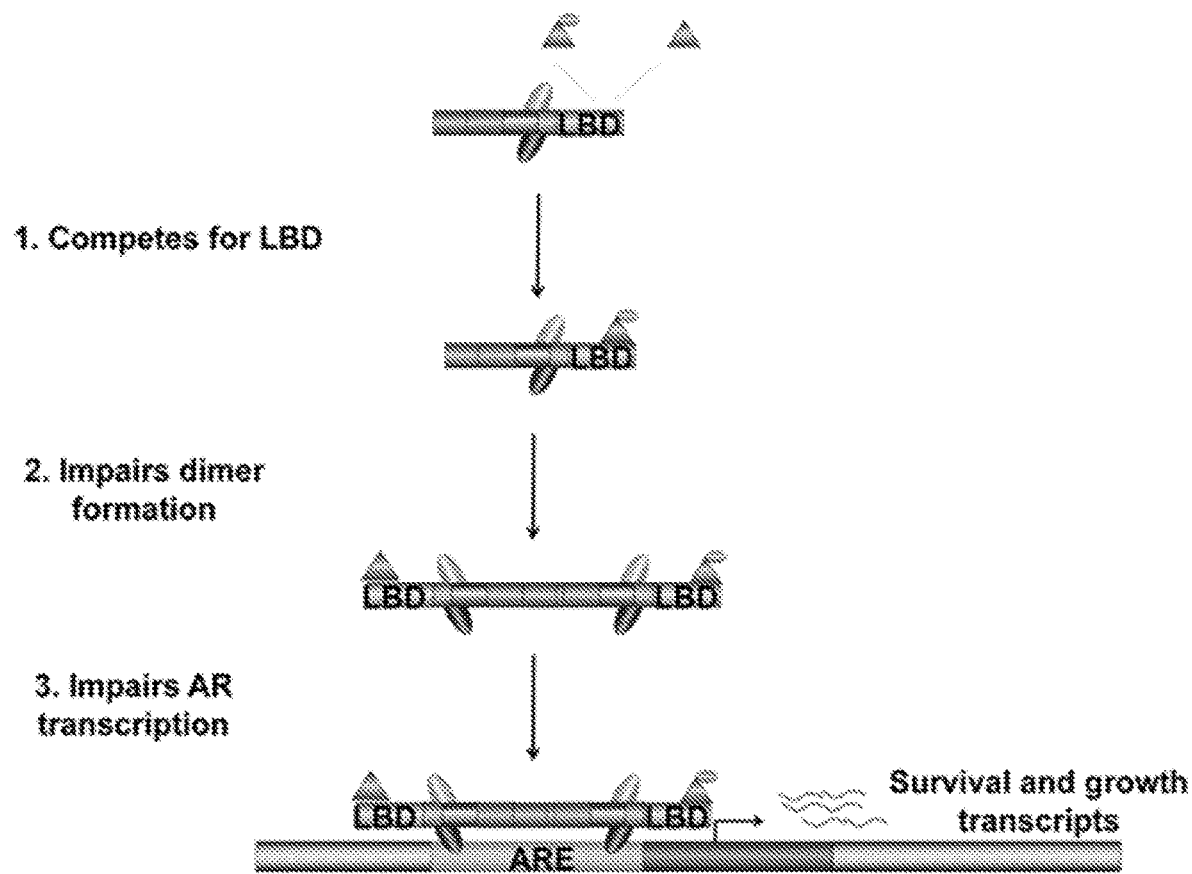
FIG. 27 shows the three-pronged attack against AR ligand binding, AR dimerization and AR transactivation.
Figure 28:
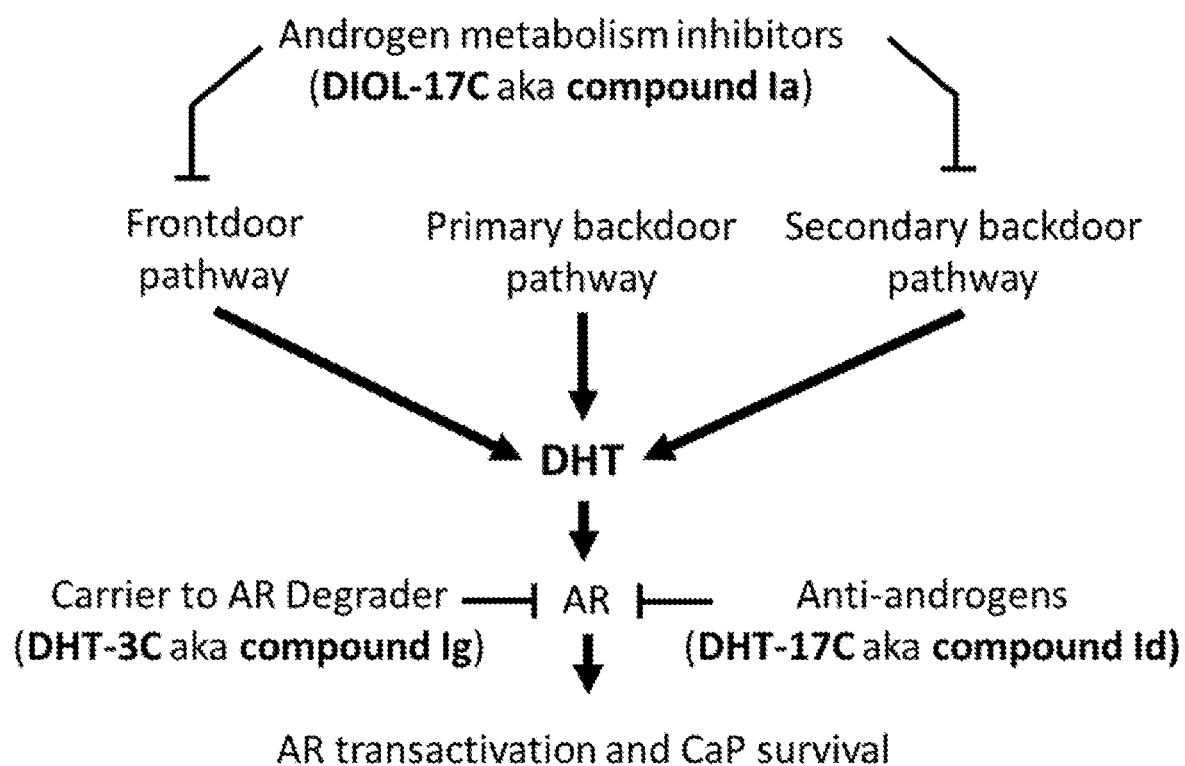
FIG. 28 shows utility of DIOL-17C (compound Ia), DHT-17C (compound Id) and DHT-3C (compound Ig). DIOL-17C inhibits the intratumoral synthesis of DHT by oxidoreductases, DHT-17C competes with DHT for the AR-LBD and may prevent dimerization between AR and AR-V7, and DHT-3C provides a carrier for PROTACS or photo or heat-activated agents to disrupt AR transactivation or even degrade AR.

Additional data showed that DHT-3C, just like DHT itself, impacted AR-regulated gene transcript induction, a finding consistent with C alone having no effect on AR-regulated transcript induction and consistent with computational modeling in which the coumarin moiety in DHT-3C was largely outside of the AR-LBD binding pocket. Western blot analysis confirmed that DHT-3C and DHT treatment produced similar AR-regulated protein expression levels (FIG. 26).

In summary, DHT-3C (aka compound Ig) in FIG. 4 functioned as a true surrogate and its displacement by other ligands provides a means for evaluation of anti-androgens or delivering small molecules to disrupt AR transactivation or even degrade AR.

The use of genetic "knockdown" technologies to down-regulate AR expression was clinically challenging because of low cellular uptake of oligonucleotides and technical difficulties involving delivery to the desired target. In addition, the recently reported development of SNIPER agents as well as of hydrophobic-tagging approach (HyT) for AR degradation represented, in their current manifestation, experimental tools for discovery biology rather than viable therapeutic strategies. There were questions about their reported micromolar efficacy that lies well above the current levels for antineoplastic agents; and there were questions about undesired, off-target effects. On the other hand, a targeted AR protein degradation induced by proteolysis-targeting-chimeras (PROTACs) via the ubiquitin proteasome system (UPS) represented an attractive alternative for which DHT-3C is well designed.

Proteolysis targeting chimera (PROTAC) agents have three components: a ligand that binds to the protein targeted for destruction, an E3 ligase "recruiter" that promotes ubiquitination of the targeted protein, and a spacer that connects the ligand and the recruiter. Several studies described the development of PROTACs to induce AR protein degradation by connecting various ligands for the AR to other ligands that would recruit E3 ubiquitin ligases. For example, one of these studies reported chemical conjugation of a selective AR modulator (SARM) possessing nanomolar affinity for AR to nutlin, a known ligand for MDM2 E3 ligase. This approach generated a SARM-nutlin PROTAC that decreased AR levels in HeLa cells in a proteasome-dependent manner but only at 10 μM concentrations. Two other studies described the development of DHT-based PROTACs by connecting DHT to a ligand for the recruitment of SCFβ-TRCP as well as to the ligand for von Hippel-Lindau (VHL) E3 ligases. The resulting PROTACs showed proteasomal degradation of the AR protein but only at relatively high 10-25 μM concentrations. Moreover, the SCFβ-TRCP-based PROTAC was not cell-permeable and had to be microinjected.

Figure 29:
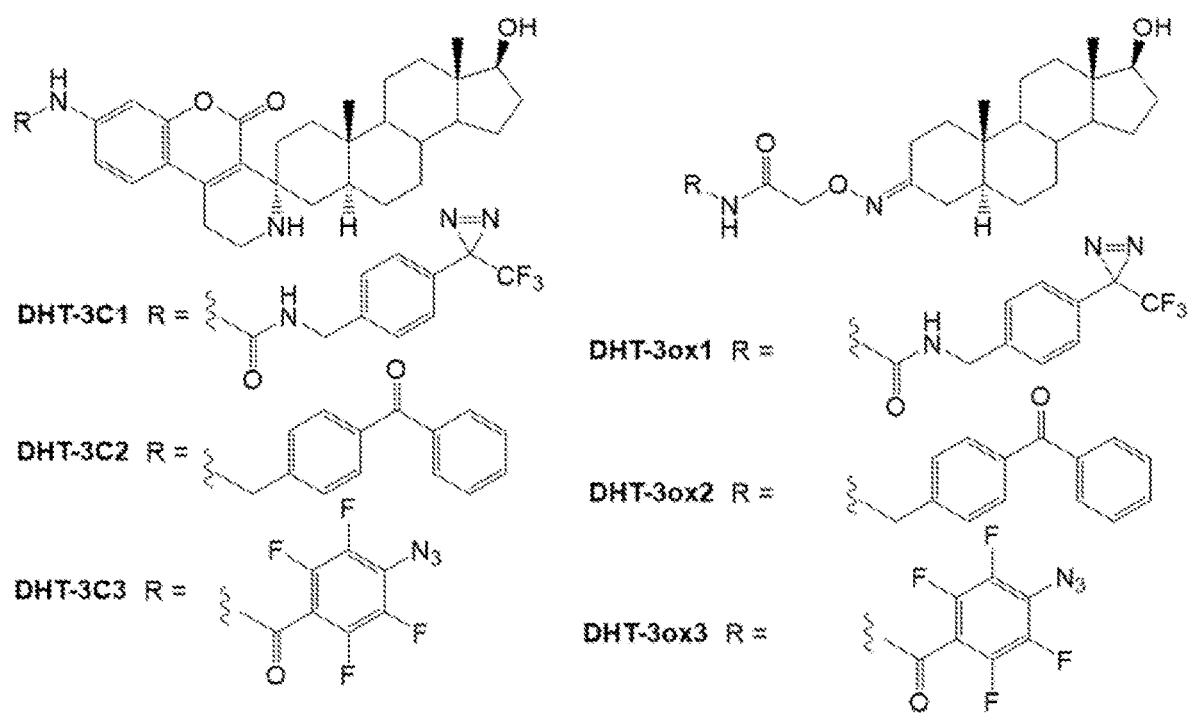
FIG. 29 shows representative photoactive derivatives of DHT-3C or C-3 O-(carboxymethyl)oxime of DHT.
Figure 30:
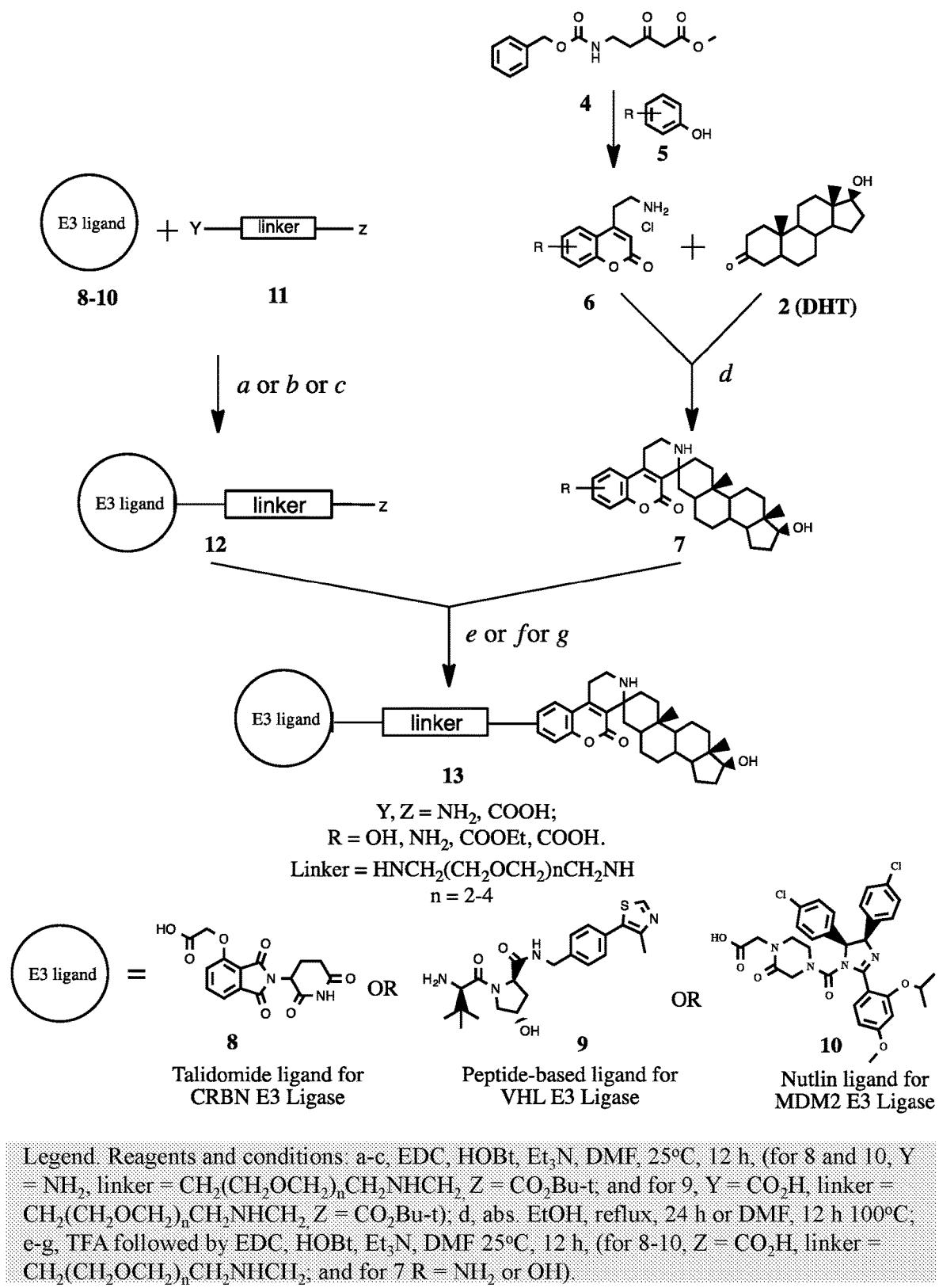
FIG. 30 shows a synthetic route for the synthesis of PROTACs for AR degradation.
Figure 31:
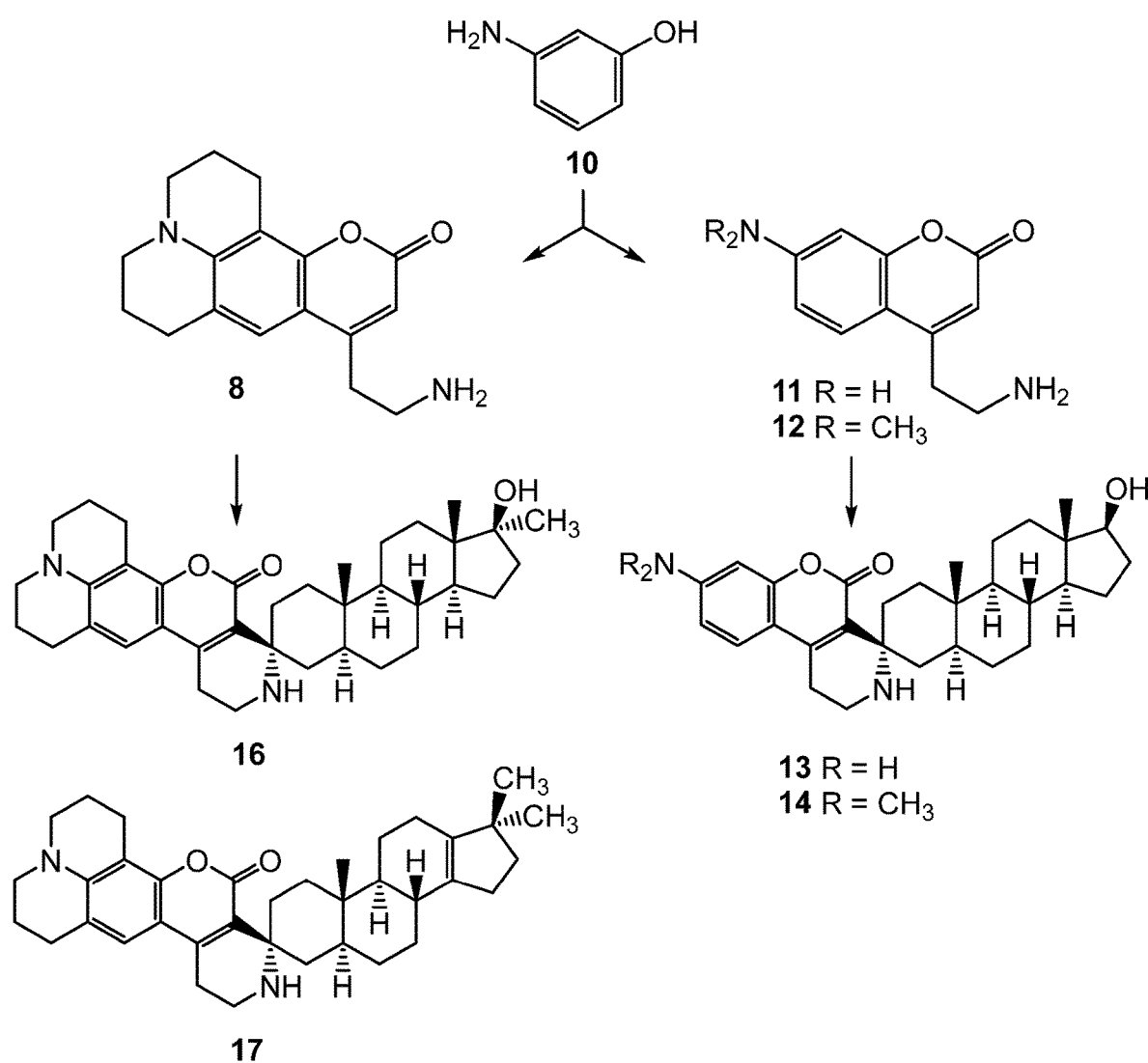
FIG. 31 shows synthesis and Pictet Spengler reactions of various 4-(2-aminoethyl)coumarins with DHT or 17α-methyl-5α-dihydrotestosterone.
Figure 32:
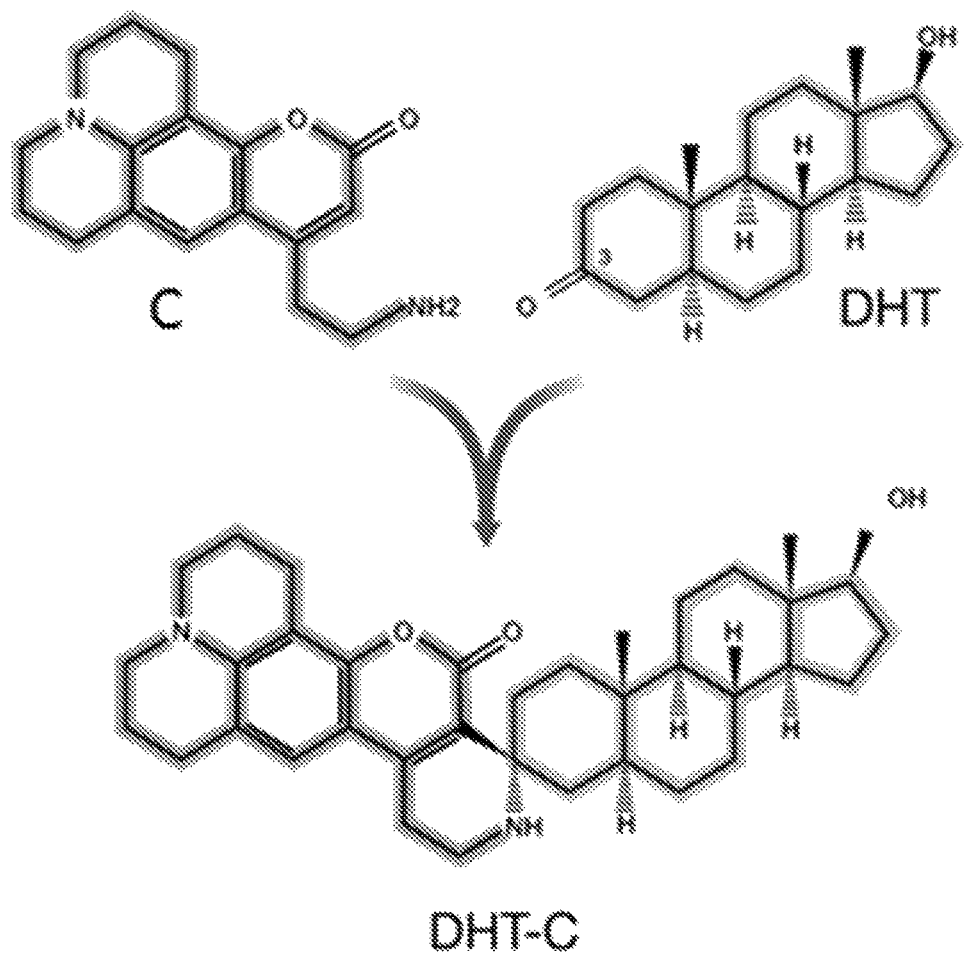
FIG. 32 shows role of fluorescent 5α-dihydrotestosterone surrogate (DHT-C). A. Structure of DHT-C. B. Schematic of DHT-C activation of AR and stimulation of AR-regulated gene transcript induction.
Figure 32:
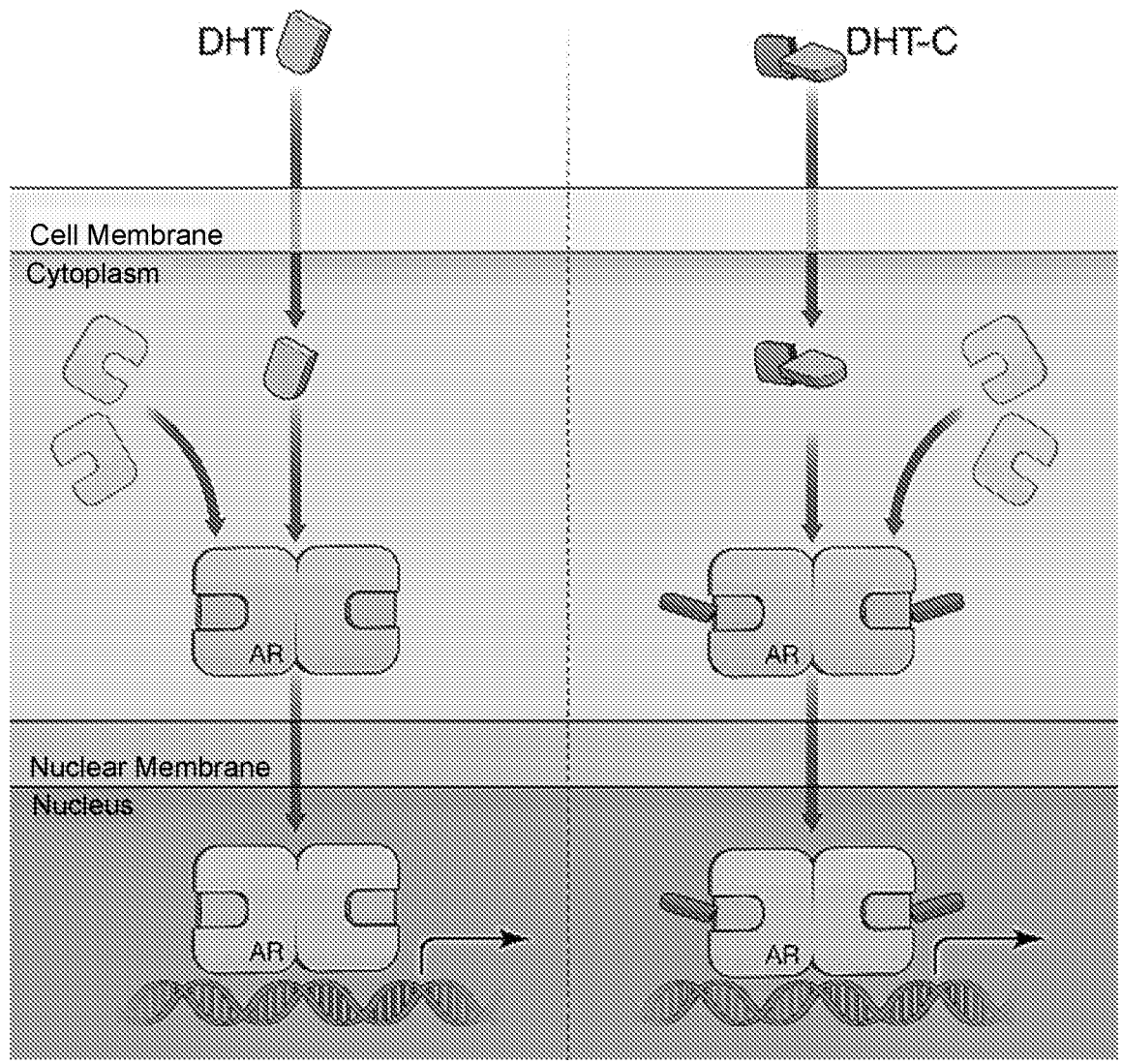
Figure 33:
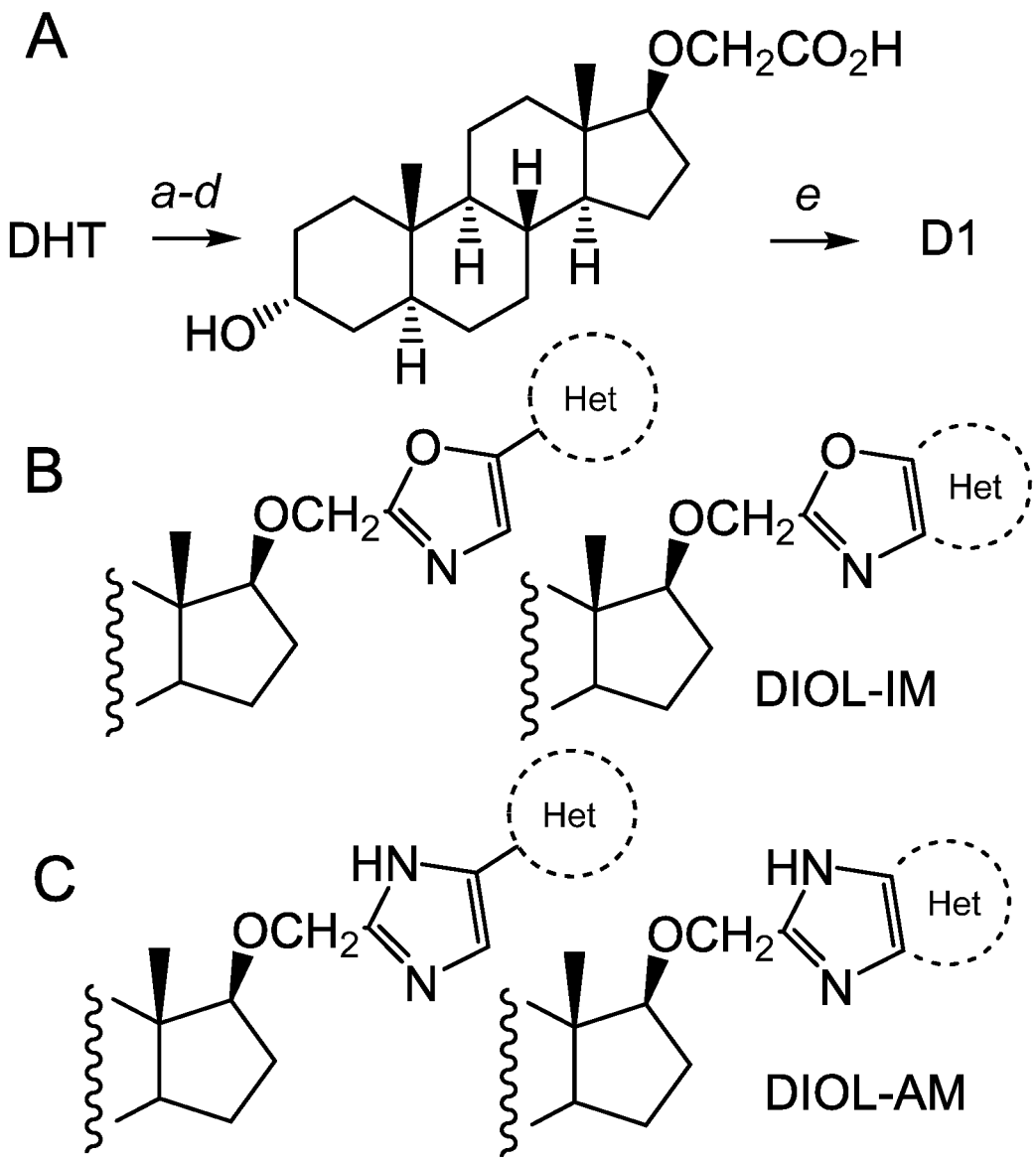
FIG. 33 shows a synthetic route of DIOL-17C and several analogs. (A) Synthesis of DIOL-17C; (B) structures of oxazole and benzoxazole targets; (C) structures of imidazole and benzimidazole targets. Legend: a, $N_2CH_2CO_2Et$, $Rh_2(OAc)_4$, $CH_2Cl_2$; b, $LiAlH(OtBu)_3$; c, $C_6H_5CO_2H$, DIAD; d, NaOH, aq $CH_3OH$; e, EDC, HOBt, aminocoumarin.
Figure 34:
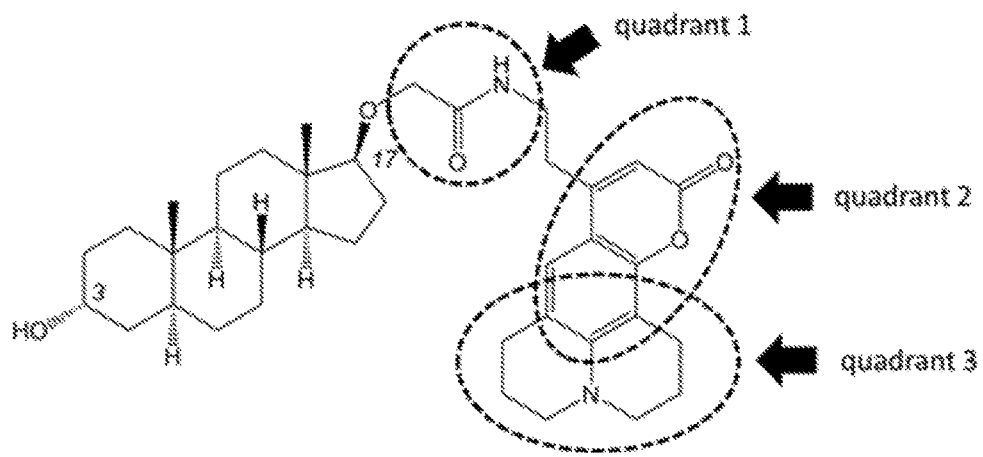
FIG. 34 shows quadrants for DIOL-17C synthetic modification.
Figure 35:
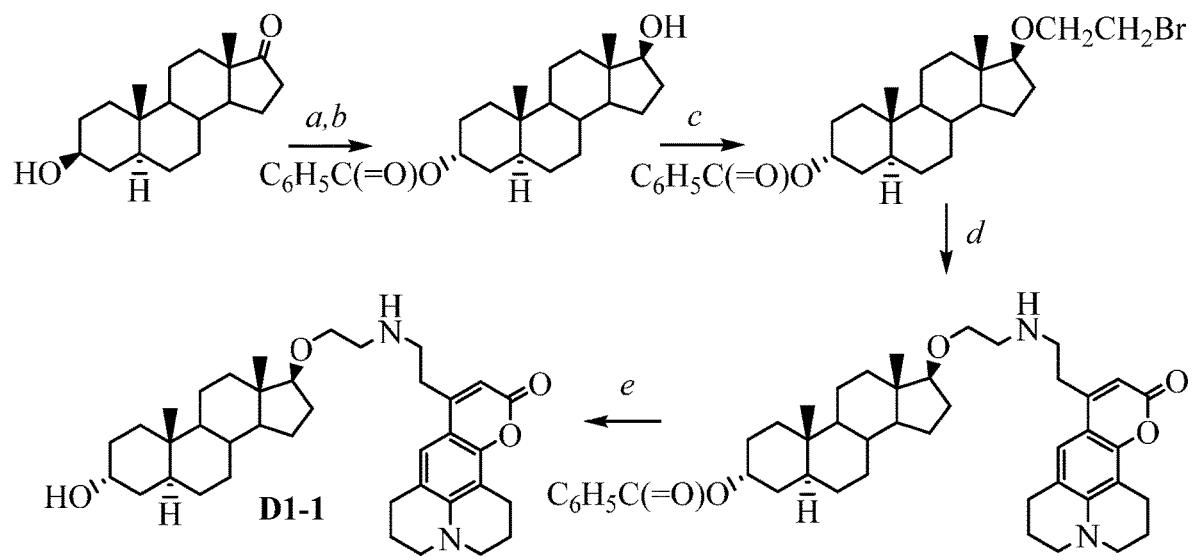
FIG. 35 shows a synthetic route of DIOL-17C. Legend: a, $C_6H_5CO_2H$, DEAD; b, $NaBH_4$; c, NaH, $BrCH_2CH_2Br$; d, 8-(2-aminoethyl)-2,3,4,5-tetrahydro-1H,4H-11-oxa-3a-azabenzo[de]anthracen-10-one hydrochloride, $Et_3N$; e, NaOH, MeOH.
Figure 36:
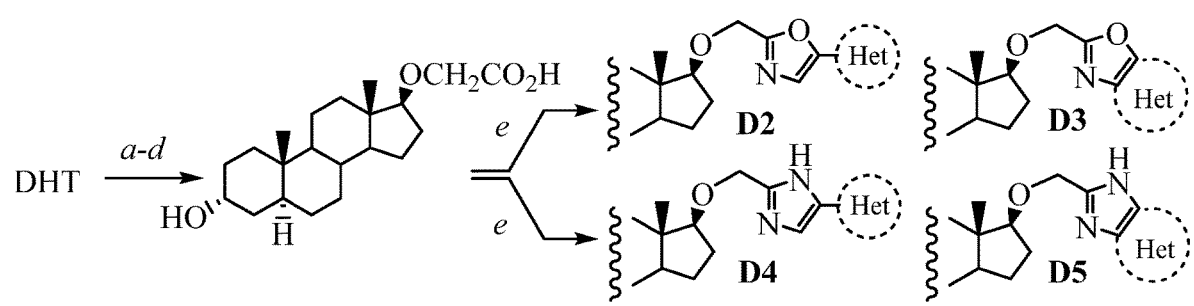
FIG. 36 shows a synthetic route of DIOL-17C analogs with modifications in quadrant 2. Legend: a, $N_2CH_2CO_2Et$, $Rh_2(OAc)_4$; b, $LiAlH(OtBu)_3$; c, $C_6H_5CO_2H$, DIAD; d, NaOH, aq MeOH; e, various standard synthetic reactions.
Figure 37:
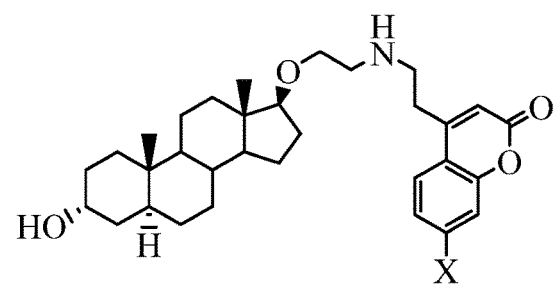
FIG. 37 shows analogs of DIOL-17C in which the amine substituent in the coumarin is modified by a substituent X. Legend: DIOL-17C-2, X=—$NH_2$; DIOL-17C-3, X=—N$(CH_3)_2$; DIOL-17C-4, X=—NHC(=O)O$C_2H_5$; DIOL-17C-5, X=—$OCH_3$; DIOL-17C-6, X=—NH$CH_2CH_2$N$(CH_3)_2$; DIOL-17C-7, X=—N$(CH_2CH_2)_2$N$CH_3$.

In summary, the deficiencies in reported DHT-based PROTACs with respect to potency and cell permeability reside in the nature of the chemical entity used to target the AR, and thus, there exists an ongoing and unmet need for improved PROTAC therapies. DHT-3C, as a potent surrogate for DHT, provides a platform for developing new PROTAC agents. For example, modification of the aniline group in compound Ii with a linker and an appropriate E3 ligase recruiter will provide a new family of potent PROTAC agents. Modification of either the aniline group in compound Ii or a C-3 O-(carboxymethyl)oxime derivative of DHT itself with photoactive groups (FIG. 29), which include diazirines, benzophenones or perfluorinated aryl azides, could provide avenues for unequivocal cross-linking these agents to the AR or a late-stage enzyme in the pathway leading to DHT and new photodynamic/thermal therapies for patients with advanced CaP or CRPC.

Example 10

The following example describes uses for compounds Ij and Ig.

Computational modeling provides information regarding the binding of coumarin-modified androgens either to the active site of late-stage enzymes in the biosynthetic pathways converging on DHT or binding of coumarin modified androgens to the AR-LBD.

Figure 6:
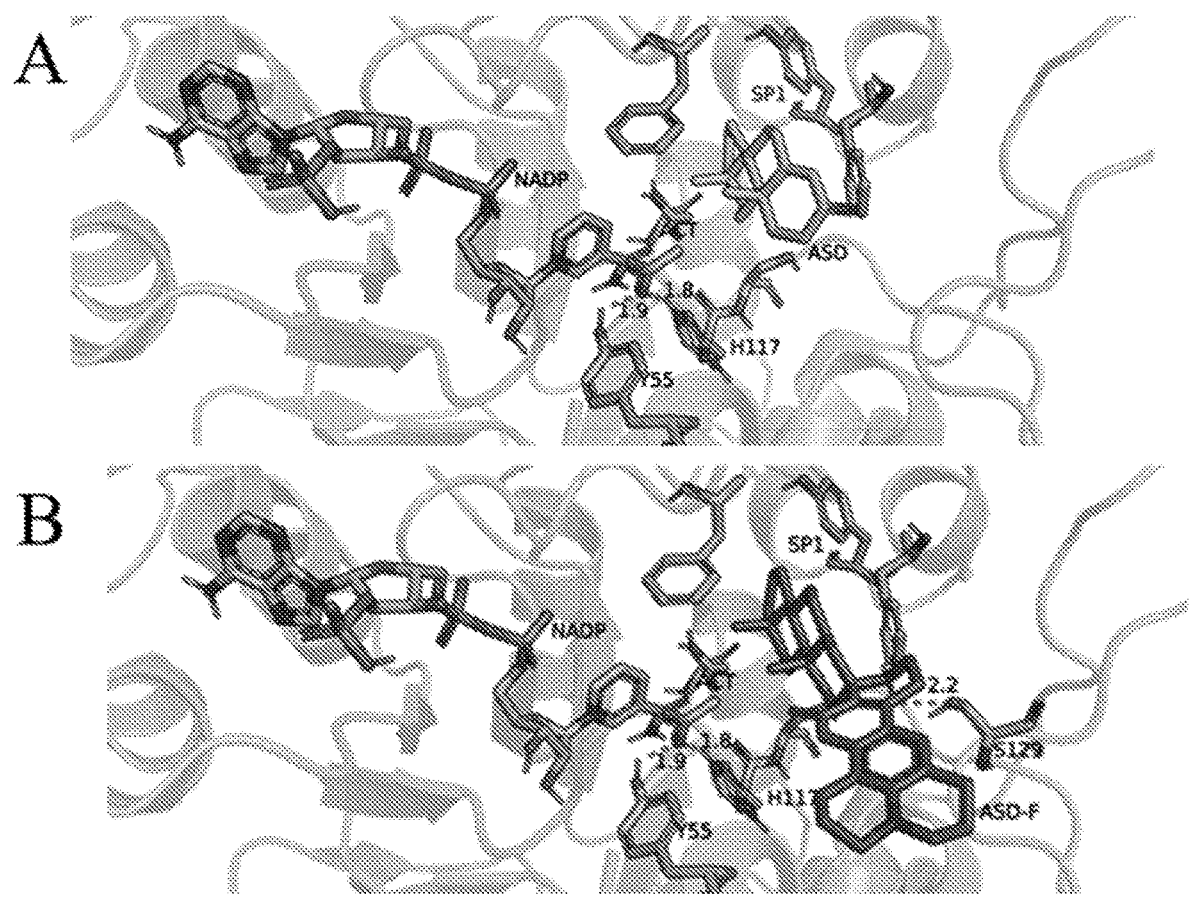
FIG. 6 shows results of computational modeling. Panel A: 5α-DIONE in the SP1 binding site of AKR1C3 (PDB: 1XF0) containing proximal $NADP^+$. Panel B: Compound Ig in the SP1 binding site of AKR1C3 (PDB: 1XF0) containing proximal $NADP^+$.

In the former case, computational modeling of the binding of the compound Ij to AKR1C3 (aka 17β-hydroxysteroid dehydrogenase-5) indicated that the compact nature of this fluorescent androgen Ij did not interfere with binding to the active site (FIG. 6). The X-ray structure of the ligand-binding domain in human AKR1C3 (PDB: 1XF0) with 5α-DIONE (FIG. 6A) was selected as the template to model the binding of the compound Ij aka 5α-DIONE-F (FIG. 6B). The initial enzyme structure was downloaded from the RCSB Protein Data Bank and was prepared for docking using Autodock Tools. The compound Ij was docked using Autodock Vina into the position occupied by 5α-DIONE in AKR1C3. The binding poses of Ij obtained from Vina contained high overlap with that of 5α-DIONE. The binding pose was further refined by performing a series of energy minimization processes. Briefly, the AMBER14SB force field and the second generation of the general AMBER force field (gaff2) were used for the proteins and ligands, respectively. Partial charges for Ij were generated via the Antechamber[9] program in AMBER 18 using the AM1-BCC model. Two courses of minimization were conducted using a hybrid protocol of 2500 steps of steepest descent minimization followed by a conjugate gradient minimization until a maximum 2500 iteration steps was reached or the convergence criterion (the root-mean-square of the energy gradient is less than $1\times10^4$ kcal/mol·Å) was satisfied. During the first step of minimization, a force constant of 100 kcal/mol·Å$^2$ was applied on the protein atoms. The second minimization step consisted of 1,000 steps of steepest descent minimization, followed by 1,500 steps of conjugate gradient minimization, and this course of minimization had no restraints for either the ligand or the protein atoms. In summary, the compound j adopted the same poise as the naturally occurring ligand 5α-DIONE. The BCD rings of compound Ij were inserted into the SP1 binding pocket in an identical fashion as seen for 5α-DIONE, and the C-18 and C-19 angular methyl groups of 5α-DIONE and Ij projected into the oxyanion hole of 17β-HSD5 bounded by Y55, H117 and NADP$^+$. A hydrogen bond with S129 further stabilizes the observed binding mode with Ij. These binding features indicated that the compound Ij possessed a binding mode that matched that of 5α-DIONE itself. In a similar fashion, the compound Ij occupied the same binding pocket seen for a previously described inhibitor, 3-carboxamido-1,3,5-(10)-estratrien-17R-spiro-2-(5,5-dimethyl-6-oxo)tetrahydropyran (EM1404) that bound to AKR1C$_3$ (PDB:1ZQ5).

Figure 7:
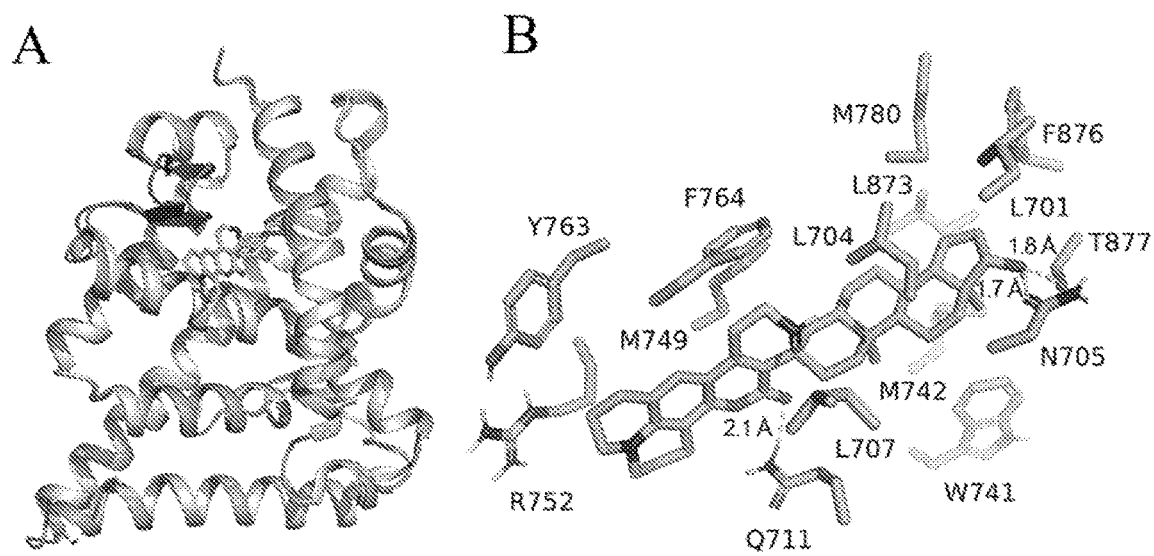
FIG. 7 shows results of computational modeling. Panel A: Computational modeling of the binding of DHT-3C and the AR indicated that the BCD rings of DHT-3C were inserted into the AR-LBD binding pocket. Panel B: Expanded view of DHT-3C binding show interactions with specific residues in the AR and showing that that the hairpin domain (759-771) of AR was "opened" approximately 4.6 Å from its initial position to accommodate DHT-3C.

In the latter case, computational modeling of the binding of compound Ig (aka DHT-3C) and the AR indicated that the BCD rings of compound Ig were inserted into the AR-LBD binding pocket (FIG. 7). The X-ray structure of human AR-LBD in complex with DHT (PDB: 2ama) was selected as the template to model the AR. The initial structure of AR (694-919) was generated using SWISS-MODEL and missing atoms were added. Compound Ig was superimposed to the position of DHT to yield its complex with AR. The complex was refined carefully by performing a series of energy minimization processes and restrained MD simulation. Briefly, The AMBER14SB force field and the second generation of the general AMBER force field (gaff2) were used for the proteins and ligands, respectively. The TIP3P water molecules were added as the solvent and the solute atoms were at least 10 Å away from the boundary of the rectangular box using AmberTools18. The counterions, i.e., chlorine atoms, were added to neutralize the net charge of each system. The long-range electrostatic interactions were handled by the particle mesh Ewald (PME) algorithm, and the non-bonded cutoff for the real-space interactions was set to 10 Å. Two steps of minimization were conducted using a hybrid protocol of 8000 steps of steepest descent minimization followed by a conjugate gradient minimization until a maximum 2000 iteration steps was reached or the convergence criterion (the root291 mean-square of the energy gradient is less than 1 Å~$10^{-4}$ kcal/mol·Å) was satisfied. During the first step minimization, a force constant of 100 kcal/mol·Å$^2$ was applied on the ligand and protein atoms except residues 711, 752 and 759-771; and a force constant of 100 kcal/mol·Å2 was applied on the protein backbone atoms except residues 711, 752 and 759-771 for the second step minimization. The system was heated up from 0 to 303.15 K linearly over a time period of 50 ps with the restraint (force constant of 10 kcal/mol·Å$_2$) on all heavy atoms in the NVT ensemble, followed by equilibrating for 325 ps with a Langevin thermostatis in the NPT (P=1 atm and T=303.15 K) ensemble by gradually decrease the force constant from 10 to 0.2 kcal/mol·Å$_2$. Finally, the 40 ns production run was carried out with Amber12 in the NPT (P=1 atm and T=303.15 K) ensemble with restrain (force constant of 2 kcal/mol·Å$^2$) on the backbone of residues 694-759 and 771-919. The SHAKE algorithm was used to restrain the covalent bonds between heavy atoms and hydrogen atoms, and the time step was set to 2 fs, and the snapshots were saved every 8 ps. The RMSD was well converged in the latter part of the simulation, and the RMSD fluctuation in the last 20 ns are less than 1 Å. Chimera was used to cluster the conformations of the last 20 ns trajectories and the top conformation was selected and subjected to the aforementioned minimization process (step 2). The final conformation was used for further analysis. Modeling revealed that the hairpin domain (759-771) of AR was "opened" approximately 4.6 Å from its initial position to accommodate compound Ig. Compound Ig bound to AR-LBD in a similar binding mode to that of compound Ig. Compound Ig formed two hydrogen bond interactions with N705 and T877 and made favorable van der Waals interactions with residues L701, F876, M780, L873, L704, M742, W741 and L707 (FIG. 7B). Other than these features, the coumarin moiety of compound Ig also formed hydrophobic interactions with F764, M749, Y763 and R752 and formed a hydrogen bond interaction with Q711. These binding features indicated that compound Ig has a more favorable binding mode to AR than DHT.

In summary, computational modeling suggested that successful binding of compounds Ij and Ig would occur to the enzymatic binding pocket of AKR1C3 or AR-LBD respectively, despite the bulky nature of the fluorescent label attached to either 5α-DIONE or DHT. Thus, these fluorescent compounds Ij and Ig are useful tools for screening small-molecule inhibitors of oxidoreductases or small-molecule anti-androgens that bind to AR.

Although the present disclosure has been described with respect to one or more particular examples, it will be understood that other examples of the present disclosure may be made without departing from the scope of the present disclosure.

The invention claimed is:

1. A compound having the following structure:

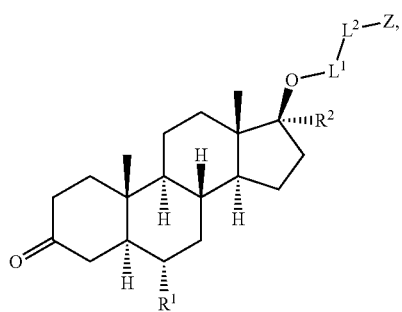

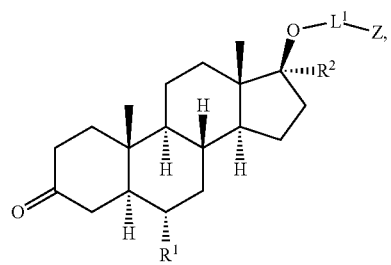

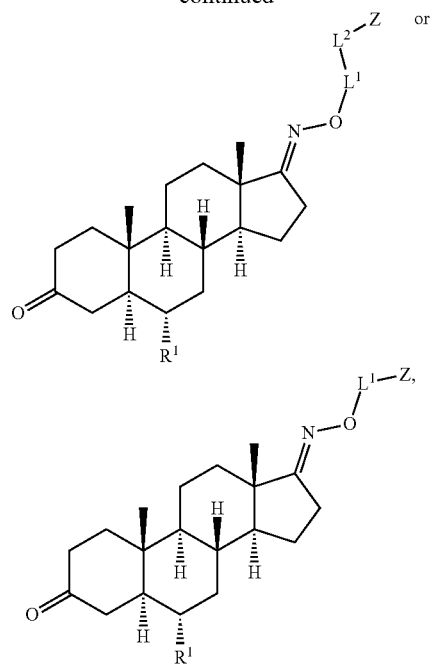

wherein
$R_1$ is hydrogen or an alkyl group;
$L^1$ is a linking group, $L^2$ is optional and is a linking group,
Z is an end group comprising (a) a substituted or unsubstituted coumarin group or
(b)

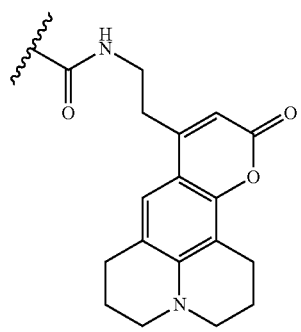 [SMILES: *C(=O)NCCc1cc(=O)oc2c3c4c(cc12)CCCN4CCC3]

or a substituted variant thereof, and $R^2$ is an alkyl group or hydrogen.

2. The compound of claim 1, wherein $L^1$ and/or $L^2$ independently are chosen from:

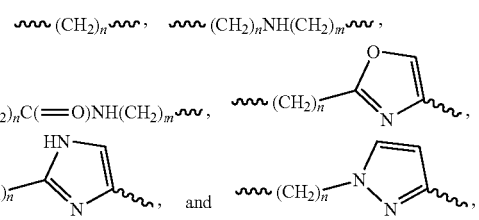

wherein n is 1, 2, 3, 4, 5, or 6 and m is 1, 2, 3, 4, 5, or 6.

3. The compound of claim 1, wherein Z is chosen from:
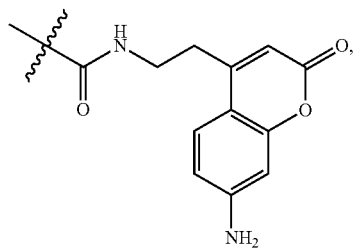
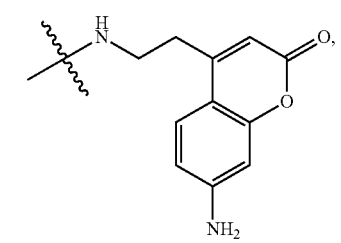
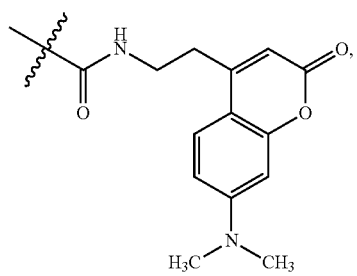
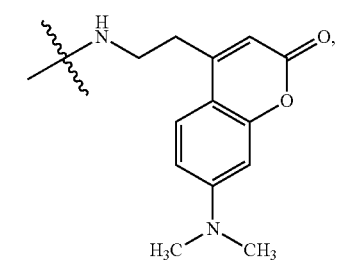
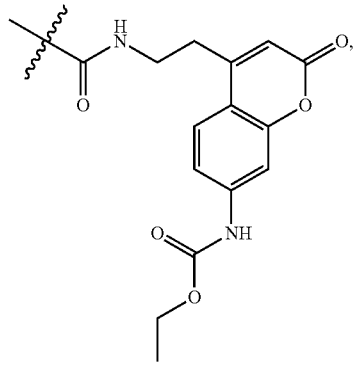
-continued
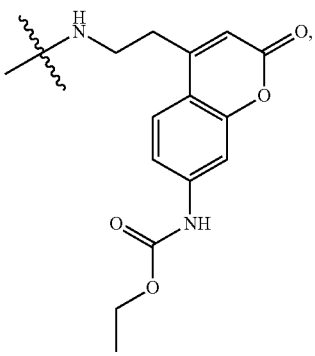
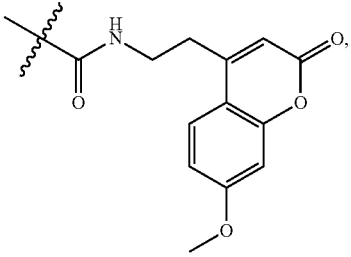
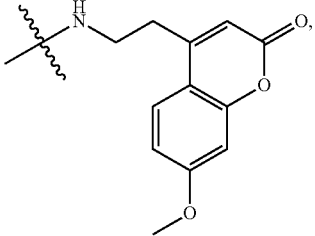
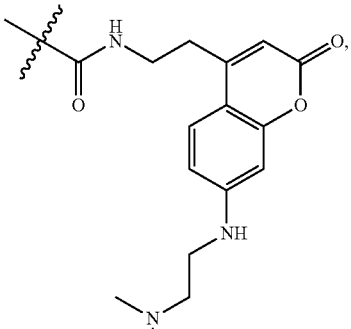
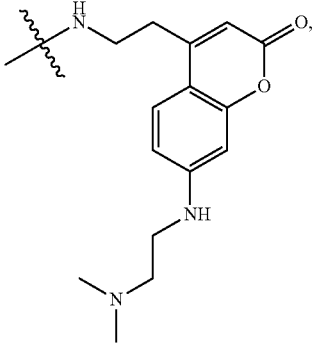

-continued
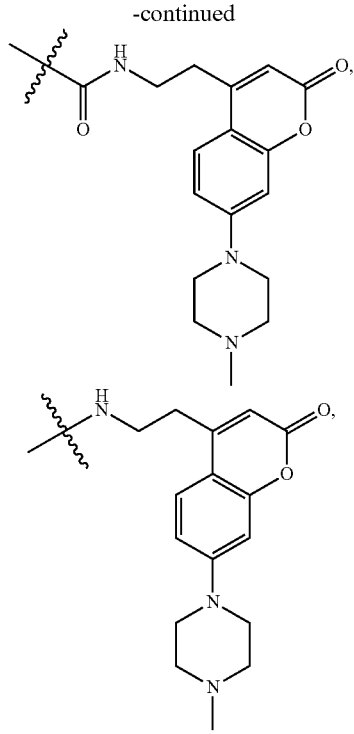
and
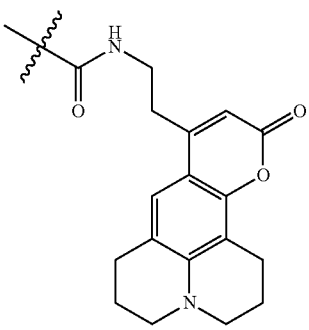 [SMILES: *C(=O)NCCc1cc(=O)oc2c3c4c(cc12)CCCN4CCC3]
or substituted variant thereof,
wherein X' is independently at each occurrence chosen from hydrogen, alkyl groups, cycloalkyl groups, alkoxy groups, halogens, and combinations thereof.
4. The compound of claim 3, wherein the compound has the following structure:
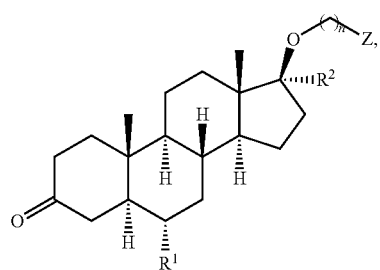
wherein n is 1, 2, or 3.
5. The compound of claim 4, wherein the compound has the following structure:
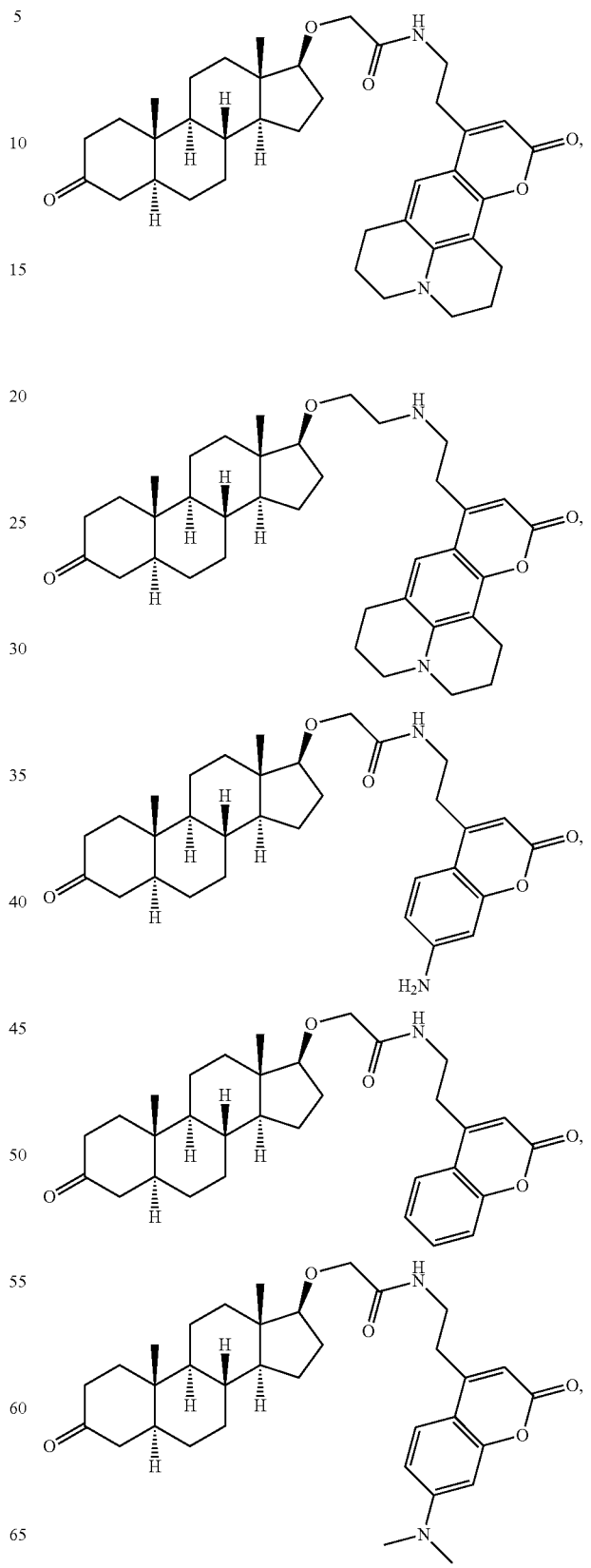

131
-continued
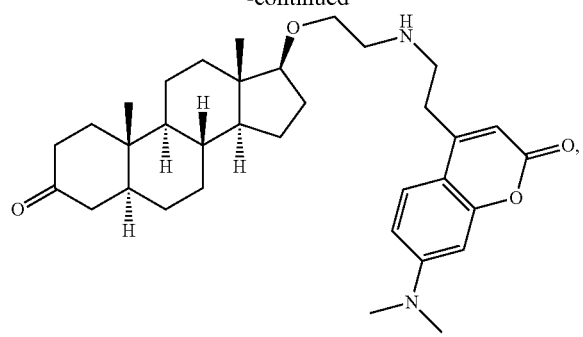
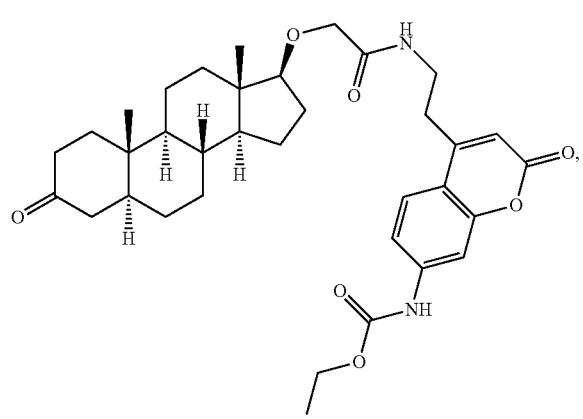
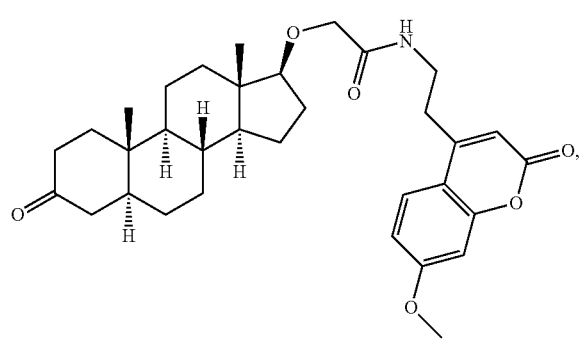
132
-continued
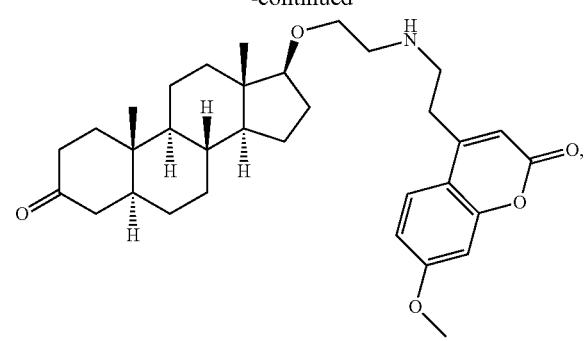
, or
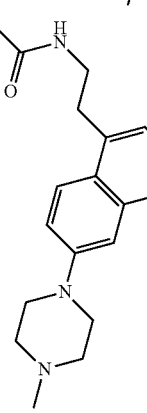

133
-continued
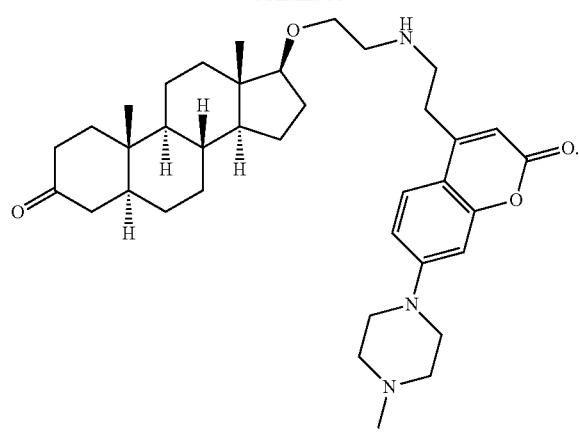
6. The compound of claim 1, wherein the compound has the following structure:
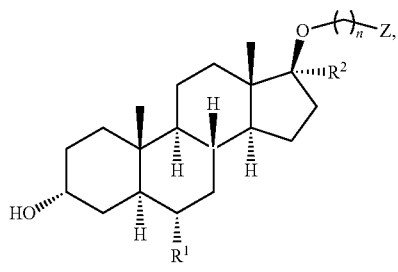
wherein n is 1, 2, or 3.
7. The compound of claim 6, wherein the compound has the following structure:
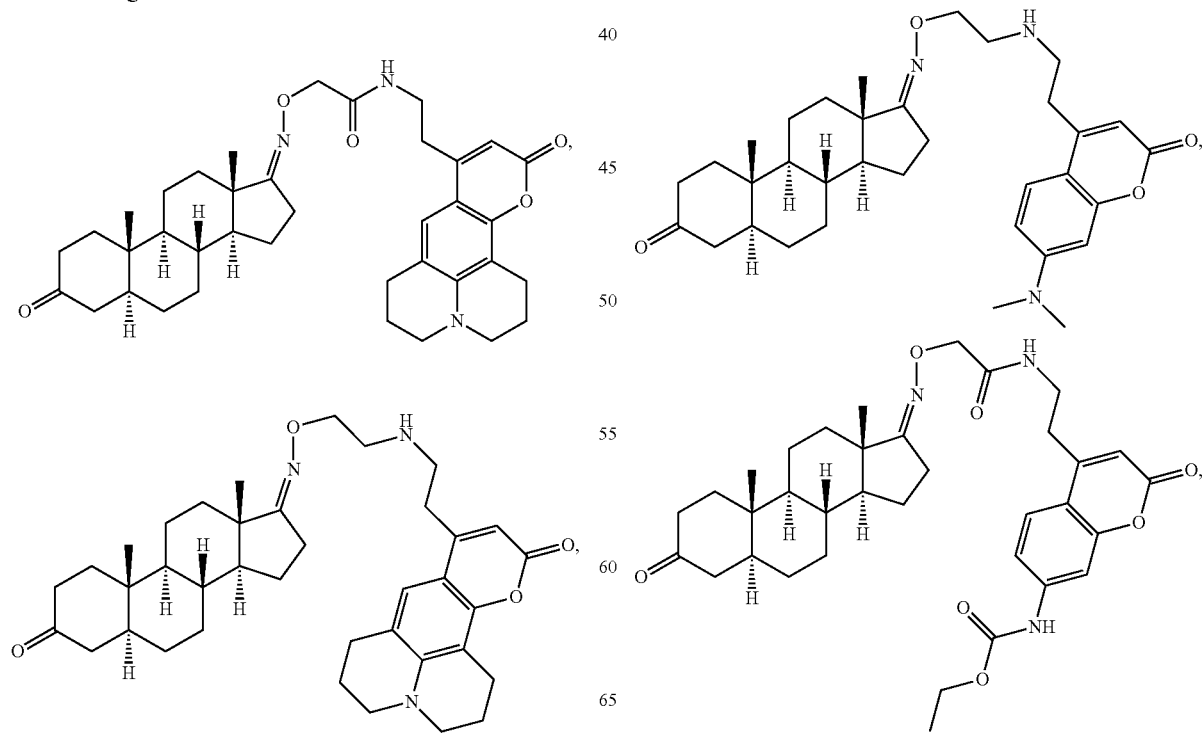
134
-continued
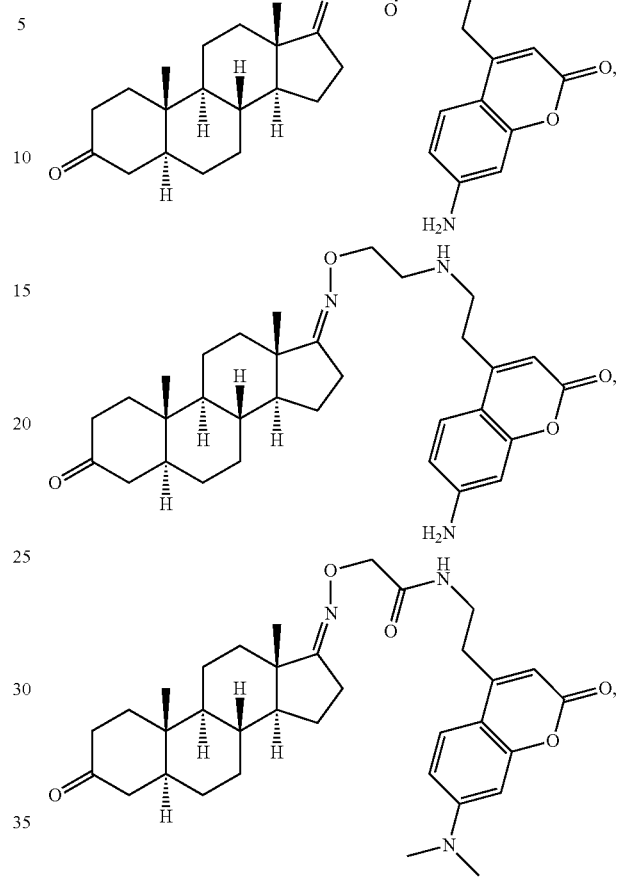

135

-continued

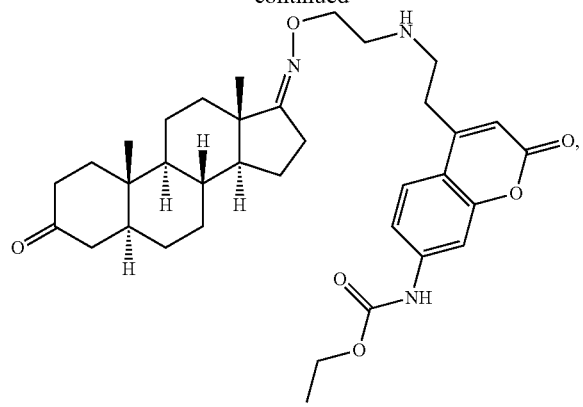

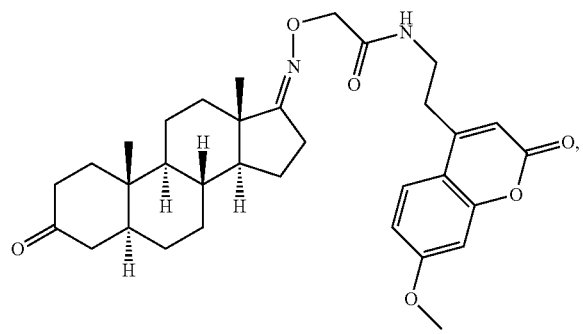

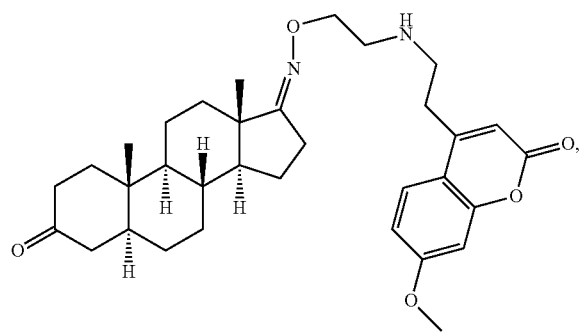

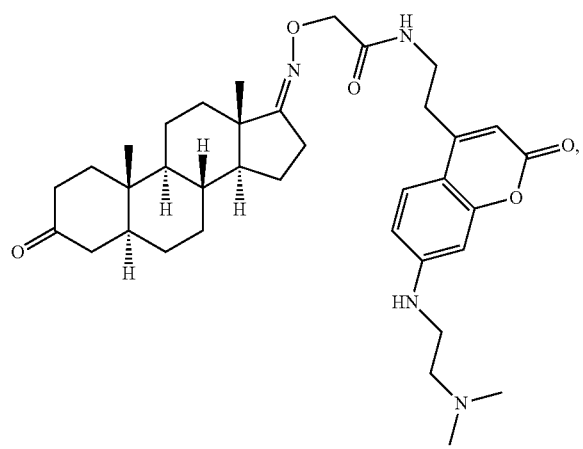

136

-continued

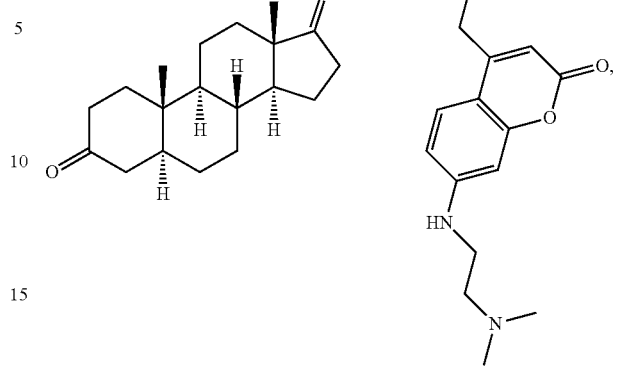

8. A composition comprising a compound of claim 1 and a pharmaceutically acceptable carrier.

9. The composition of claim 8, further comprising one or more additional drugs.

10. The composition of claim 9, wherein the one or more additional drugs are chosen from anti-androgen drugs, 5α-reductase drugs, androgen metabolism inhibitor drugs, and combinations thereof.

11. The composition of claim 10, wherein the anti-androgen drugs are chosen from flutamide, bicalutamide, enzalutamide, apalutamide, darolutamide, dilutamide, and combinations thereof and/or the 5α-reductase drugs are chosen from finasteride, dutasteride, and combinations thereof and/or the androgen metabolism drugs are chosen from abiraterone acetate, abiraterone acetate fine particle, ketoconazole, and combinations thereof.

12. The composition of claim 8, wherein the compound has the following structure:

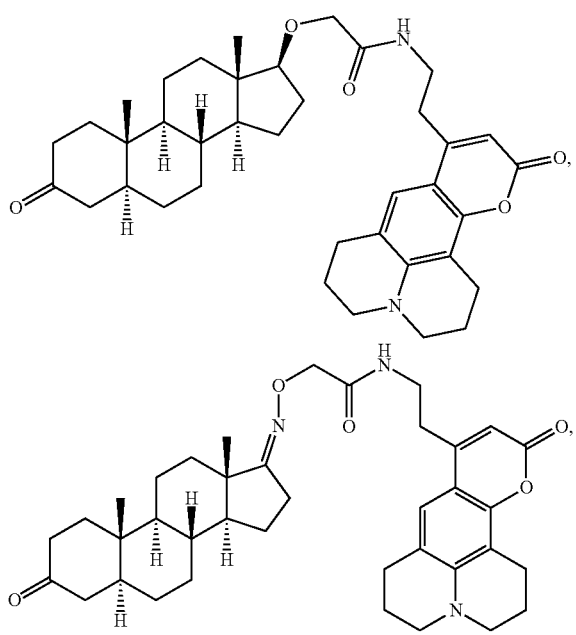

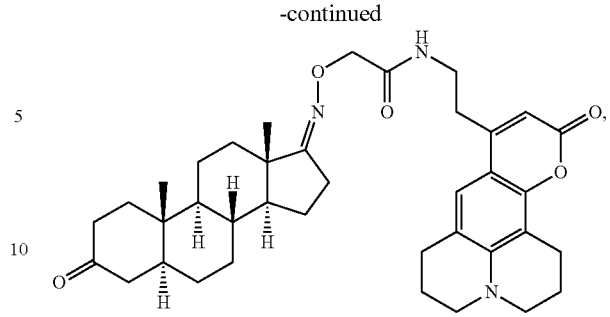

or a combination thereof.

13. A method of treating a malignant cell growth disease and/or a hyperplastic cell growth disease in an individual, comprising administering to the individual a compound of claim 1, wherein the individual's malignant cell growth disease or hyperplastic cell growth disease is treated.

14. The method of claim 13, wherein the malignant cell growth disease is cancer.

15. The method of claim 14, wherein the cancer is a hormonal cancer.

16. The method of claim 15, wherein the hormonal cancer is chosen from breast cancers, ovarian cancers, uterine or endometrial cancers, prostate cancers, and combinations thereof.

17. The method of claim 16, wherein the hormonal cancer is prostate cancer.

18. The method of claim 17, wherein the prostate cancer is castration-resistant prostate cancer.

19. The method of claim 18, wherein the cells of the castration-resistant prostate cancer express AR-V7.

20. The method of claim 13, wherein the compound has the following structure:

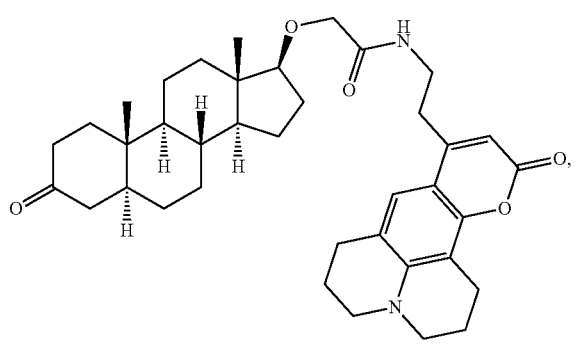

or a combination thereof.

21. A method of impairing androgen receptor (AR) transactivation and/or androgen receptor dimerization in an individual in need of treatment comprising:

administering to the individual in need of treatment a compound of claim 1 or a composition comprising a compound of claim 1, such that the compound contacts one or more cells, wherein androgen receptor transactivation and/or androgen receptor dimerization is impaired in the individual.

22. The method of claim 21, further comprising contacting the cell with flutamide, bicalutamide, enzalutamide, apalutamide, darolutamide, dilutamide, finasteride, dutasteride, or a combination thereof.

23. The method of claim 21, wherein the compound has the following structure:

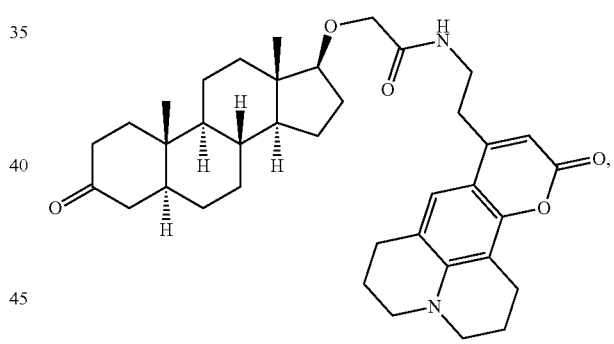

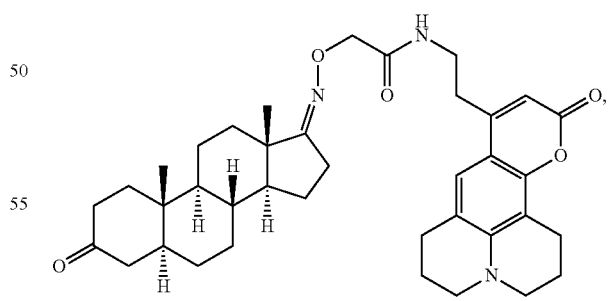

or a combination thereof.

* * * * *